US010624629B2

(12) United States Patent
Nobles et al.

(10) Patent No.: US 10,624,629 B2
(45) Date of Patent: Apr. 21, 2020

(54) SUTURING DEVICES AND METHODS FOR SUTURING AN ANATOMIC VALVE

(71) Applicant: Heartstitch, Inc., Fountain Valley, CA (US)

(72) Inventors: Anthony A. Nobles, Fountain Valley, CA (US); Benjamin G. Brosch, Mission Viejo, CA (US); William Ettlinger Cohn, Bellaire, TX (US)

(73) Assignee: HeartStitch, Inc., Fountain Valley, CA (US)

( * ) Notice: Subject to any disclaimer, the term of this patent is extended or adjusted under 35 U.S.C. 154(b) by 133 days.

(21) Appl. No.: 15/594,412

(22) Filed: May 12, 2017

(65) Prior Publication Data

US 2017/0245853 A1  Aug. 31, 2017

Related U.S. Application Data

(62) Division of application No. 14/111,534, filed as application No. PCT/US2012/033396 on Apr. 12, 2012, now Pat. No. 9,649,106.

(Continued)

(51) Int. Cl.
*A61B 17/04* (2006.01)
*A61B 17/12* (2006.01)
(Continued)

(52) U.S. Cl.
CPC ...... *A61B 17/0483* (2013.01); *A61B 17/0057* (2013.01); *A61B 17/0469* (2013.01);
(Continued)

(58) Field of Classification Search
CPC . A61B 17/04; A61B 17/0469; A61B 17/0482; A61B 17/0483; A61B 17/0493;
(Continued)

(56) References Cited

U.S. PATENT DOCUMENTS

| 118,683 A | 9/1871 | Bruce |
| 1,064,307 A | 6/1913 | Fleming |

(Continued)

FOREIGN PATENT DOCUMENTS

| AU | 2003212025 | 8/2003 |
| AU | 2006251579 | 11/2006 |

(Continued)

OTHER PUBLICATIONS

European Exam Report, re EP Application No. 1277088, dated Sep. 21, 2017.
(Continued)

*Primary Examiner* — Melanie R Tyson
(74) *Attorney, Agent, or Firm* — Knobbe, Martens, Olson & Bear, LLP

(57) ABSTRACT

Suturing apparatuses configured to suture biological tissue, such as an anatomical valve. The suturing apparatuses can comprise an elongate member having a proximal end, a distal end, one or more arms, and one or more needles. A protective member may be used to inhibit contact between a distal end of a needle and surrounding tissue. Methods for suturing bodily tissue such as an anatomical valve may be performed with the suturing apparatuses. The suturing apparatuses may be used to suture adjacent valve leaflets or the base of a valve in order to treat or repair the valve.

15 Claims, 93 Drawing Sheets

Related U.S. Application Data

(60) Provisional application No. 61/476,236, filed on Apr. 15, 2011.

(51) Int. Cl.
*A61B 17/06* (2006.01)
*A61B 17/00* (2006.01)

(52) U.S. Cl.
CPC .... *A61B 17/0482* (2013.01); *A61B 17/06004* (2013.01); *A61B 17/06066* (2013.01); *A61B 2017/00243* (2013.01); *A61B 2017/00575* (2013.01); *A61B 2017/00663* (2013.01); *A61B 2017/00783* (2013.01); *A61B 2017/0406* (2013.01); *A61B 2017/047* (2013.01); *A61B 2017/0472* (2013.01); *A61B 2017/0496* (2013.01); *A61B 2017/061* (2013.01); *A61B 2017/06085* (2013.01)

(58) Field of Classification Search
CPC .......... A61B 17/0057; A61B 17/00234; A61B 2017/047; A61B 2017/0472; A61B 2017/00575; A61B 2017/00663; A61B 2017/00243; A61B 2017/00783
See application file for complete search history.

(56) References Cited

U.S. PATENT DOCUMENTS

| | | | |
|---|---|---|---|
| 1,822,330 | A | 9/1931 | Ainslie |
| 1,989,919 | A | 2/1935 | Everitt |
| 2,348,218 | A | 5/1944 | Karle |
| 2,473,742 | A | 6/1949 | Auzin |
| 2,548,602 | A | 4/1951 | Greenburg |
| 2,637,290 | A | 5/1953 | Sigoda |
| 2,738,790 | A | 3/1956 | Todt, Sr. et al. |
| 2,849,002 | A | 8/1958 | Oddo |
| 2,945,460 | A | 7/1960 | Kagiyama |
| 3,241,554 | A | 3/1966 | Coanda |
| 3,292,627 | A | 12/1966 | Harautuneian |
| 3,394,705 | A | 7/1968 | Abramson |
| 3,664,345 | A | 5/1972 | Dabbs et al. |
| 3,665,926 | A | 5/1972 | Flores |
| 3,774,596 | A | 11/1973 | Cook |
| 3,828,790 | A | 8/1974 | Curtiss et al. |
| 3,831,587 | A | 8/1974 | Boyd |
| 3,842,840 | A | 10/1974 | Schweizer |
| 3,877,434 | A | 4/1975 | Samuels |
| 3,882,852 | A | 5/1975 | Sinnreich |
| 3,882,855 | A | 5/1975 | Schulte et al. |
| 3,888,117 | A | 6/1975 | Lewis |
| 3,903,893 | A | 9/1975 | Scheer |
| 3,946,740 | A | 3/1976 | Bassett |
| 3,946,741 | A | 3/1976 | Adair |
| 3,952,742 | A | 4/1976 | Taylor |
| 3,976,079 | A | 8/1976 | Samuels |
| 4,052,980 | A | 10/1977 | Grams et al. |
| RE29,703 | E | 7/1978 | Fatt |
| 4,107,953 | A | 8/1978 | Casillo |
| 4,119,100 | A | 10/1978 | Rickett |
| 4,164,225 | A | 8/1979 | Johnson et al. |
| 4,230,119 | A | 10/1980 | Blum |
| 4,291,698 | A | 9/1981 | Fuchs et al. |
| 4,299,237 | A | 11/1981 | Foti |
| 4,307,722 | A | 12/1981 | Evans |
| 4,345,601 | A | 8/1982 | Fukuda |
| 4,351,342 | A | 9/1982 | Wiita et al. |
| 4,417,532 | A | 11/1983 | Yasukata |
| 4,423,725 | A | 1/1984 | Baran et al. |
| 4,447,227 | A | 5/1984 | Kotsanis |
| 4,457,300 | A | 7/1984 | Budde |
| 4,484,580 | A | 11/1984 | Nomoto et al. |
| 4,512,338 | A | 4/1985 | Balko et al. |
| 4,546,759 | A | 10/1985 | Solar |
| 4,553,543 | A | 11/1985 | Amarasinghe |
| 4,573,966 | A | 3/1986 | Weikl et al. |
| 4,589,868 | A | 5/1986 | Dretler |
| 4,610,662 | A | 9/1986 | Weikl et al. |
| 4,617,738 | A | 10/1986 | Kopacz |
| 4,662,068 | A | 5/1987 | Polonsky |
| 4,664,114 | A | 5/1987 | Ghodsian |
| 4,734,094 | A | 3/1988 | Jacob et al. |
| 4,744,364 | A | 5/1988 | Kensey |
| 4,750,492 | A | 6/1988 | Jacobs |
| 4,771,776 | A | 9/1988 | Powell et al. |
| 4,774,091 | A | 9/1988 | Yamahira et al. |
| 4,794,928 | A | 1/1989 | Kletschka |
| 4,795,427 | A | 1/1989 | Helzel |
| 4,796,629 | A | 1/1989 | Grayzel |
| 4,824,436 | A | 4/1989 | Wolinsky |
| 4,827,931 | A | 5/1989 | Longmore |
| 4,841,888 | A | 6/1989 | Mills et al. |
| 4,861,330 | A | 8/1989 | Voss |
| 4,898,168 | A | 2/1990 | Yule |
| 4,923,461 | A | 5/1990 | Caspari et al. |
| 4,926,860 | A | 5/1990 | Stice et al. |
| 4,932,956 | A | 6/1990 | Reddy et al. |
| 4,935,027 | A | 6/1990 | Yoon |
| 4,954,126 | A | 9/1990 | Wallsten |
| 4,957,498 | A | 9/1990 | Caspari et al. |
| 4,972,845 | A | 11/1990 | Iversen et al. |
| 4,981,149 | A | 1/1991 | Yoon et al. |
| 4,983,116 | A | 1/1991 | Koga |
| 4,984,564 | A | 1/1991 | Yuen |
| 4,994,070 | A | 2/1991 | Waters |
| 5,002,531 | A | 3/1991 | Bonzel |
| 5,021,059 | A | 6/1991 | Kensey et al. |
| 5,037,433 | A | 8/1991 | Wilk et al. |
| 5,057,114 | A | 10/1991 | Wittich et al. |
| 5,059,201 | A | 10/1991 | Asnis |
| 5,065,772 | A | 11/1991 | Cox, Jr. |
| 5,074,871 | A | 12/1991 | Groshong |
| 5,078,743 | A | 1/1992 | Mikalov et al. |
| 5,090,958 | A | 2/1992 | Sahota |
| 5,100,418 | A | 3/1992 | Yoon et al. |
| 5,104,394 | A | 4/1992 | Knoepfler |
| 5,106,363 | A | 4/1992 | Nobuyoshi |
| 5,108,416 | A | 4/1992 | Ryan et al. |
| 5,108,419 | A | 4/1992 | Reger et al. |
| 5,116,305 | A | 5/1992 | Milder et al. |
| 5,122,122 | A | 6/1992 | Allgood |
| 5,129,883 | A | 7/1992 | Black |
| 5,133,724 | A | 7/1992 | Wilson et al. |
| 5,135,484 | A | 8/1992 | Wright |
| 5,160,339 | A | 11/1992 | Chen et al. |
| 5,163,906 | A | 11/1992 | Ahmadi |
| 5,167,223 | A | 12/1992 | Koros et al. |
| 5,171,251 | A | 12/1992 | Bregen et al. |
| 5,176,691 | A | 1/1993 | Pierce |
| 5,192,301 | A | 3/1993 | Kamiya et al. |
| 5,222,508 | A | 6/1993 | Contarini |
| 5,222,941 | A | 6/1993 | Don Michael |
| 5,222,974 | A | 6/1993 | Kensey et al. |
| 5,224,948 | A | 7/1993 | Abe et al. |
| 5,236,443 | A | 8/1993 | Sontag |
| 5,242,459 | A | 9/1993 | Buelna |
| 5,281,234 | A | 1/1994 | Wilk et al. |
| 5,281,237 | A | 1/1994 | Gimpelson |
| 5,282,827 | A | 2/1994 | Kensey et al. |
| 5,286,259 | A | 2/1994 | Ganguly et al. |
| 5,290,249 | A | 3/1994 | Foster et al. |
| 5,291,639 | A | 3/1994 | Baum et al. |
| 5,300,106 | A | 4/1994 | Dahl et al. |
| 5,304,184 | A | 4/1994 | Hathaway et al. |
| 5,308,323 | A | 5/1994 | Sogawa et al. |
| 5,312,344 | A | 5/1994 | Grinfeld |
| 5,314,409 | A | 5/1994 | Sarosiek et al. |
| 5,320,604 | A | 6/1994 | Walker et al. |
| 5,320,632 | A | 6/1994 | Heidmueller |
| 5,330,446 | A | 7/1994 | Weldon et al. |
| 5,330,497 | A | 7/1994 | Freitas et al. |
| 5,331,975 | A | 7/1994 | Bonutti |
| 5,336,229 | A | 8/1994 | Noda |

(56) References Cited

U.S. PATENT DOCUMENTS

| | | |
|---|---|---|
| 5,336,231 A | 8/1994 | Adair |
| 5,337,736 A | 8/1994 | Reddy |
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |
| 5,350,399 A | 9/1994 | Erlebacher et al. |
| 5,356,382 A | 10/1994 | Picha et al. |
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safar et al. |
| 5,383,896 A | 1/1995 | Gershony et al. |
| 5,383,897 A | 1/1995 | Wholey |
| 5,383,905 A | 1/1995 | Golds et al. |
| 5,389,103 A | 2/1995 | Melzer et al. |
| 5,391,147 A | 2/1995 | Imran et al. |
| 5,391,174 A | 2/1995 | Weston |
| 5,395,383 A | 3/1995 | Adams et al. |
| 5,397,325 A | 3/1995 | Della Badia et al. |
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitefield et al. |
| 5,474,572 A | 12/1995 | Hayburst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,507,754 A | 4/1996 | Green et al. |
| 5,507,755 A | 4/1996 | Gresl et al. |
| 5,514,159 A | 5/1996 | Matula et al. |
| 5,520,609 A | 5/1996 | Moll et al. |
| 5,520,702 A | 5/1996 | Sauer et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,573,540 A | 11/1996 | Yoon |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D+Amnbrosio |
| 5,700,273 A | 12/1997 | Buelna et al. |
| 5,700,277 A | 12/1997 | Nash et al. |
| 5,707,379 A | 1/1998 | Fleenor et al. |
| 5,709,693 A | 1/1998 | Taylor |
| 5,716,329 A | 2/1998 | Dieter |
| 5,720,757 A | 2/1998 | Hathaway et al. |
| 5,722,983 A | 3/1998 | Van Der Weegen |
| 5,728,109 A | 3/1998 | Schulze et al. |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,108 A | 10/1998 | Poncet |
| 5,817,110 A | 10/1998 | Kronner |
| 5,820,631 A | 10/1998 | Nobles |
| 5,836,955 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |
| 5,860,992 A | 1/1999 | Daniel et al. |
| 5,860,997 A | 1/1999 | Bonutti |
| 5,861,003 A | 1/1999 | Latson et al. |
| 5,865,729 A | 2/1999 | Holman et al. |
| 5,868,708 A | 2/1999 | Hart et al. |
| 5,868,762 A | 2/1999 | Cragg et al. |
| 5,871,320 A | 2/1999 | Kovac |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |

(56) References Cited

U.S. PATENT DOCUMENTS

| | | |
|---|---|---|
| 5,908,428 A | 6/1999 | Scirica et al. |
| 5,919,200 A | 7/1999 | Stambaugh et al. |
| 5,919,208 A | 7/1999 | Valenti |
| 5,928,192 A | 7/1999 | Maahs |
| 5,931,844 A | 8/1999 | Thompson et al. |
| 5,935,098 A | 8/1999 | Blaisdell et al. |
| 5,935,149 A | 8/1999 | Ek |
| 5,944,730 A | 8/1999 | Nobles et al. |
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,059,800 A | 5/2000 | Hart et al. |
| 6,066,160 A | 5/2000 | Colvin et al. |
| 6,068,648 A | 5/2000 | Cole et al. |
| 6,071,271 A | 6/2000 | Baker et al. |
| 6,077,277 A | 6/2000 | Mollenauer et al. |
| 6,086,608 A | 7/2000 | Ek et al. |
| 6,099,553 A | 8/2000 | Hart et al. |
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,352,543 B1 | 3/2002 | Cole et al. |
| 6,383,208 B1 | 5/2002 | Sancoff et al. |
| 6,395,015 B1 | 5/2002 | Borst et al. |
| 6,409,739 B1 | 6/2002 | Nobles et al. |
| 6,432,115 B1 | 8/2002 | Mollenauer et al. |
| 6,468,293 B2 | 10/2002 | Bonutti et al. |
| 6,508,777 B1 | 1/2003 | Macoviak et al. |
| 6,527,785 B2 | 3/2003 | Sancoff et al. |
| 6,533,795 B1 | 3/2003 | Tran et al. |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,716,243 B1 | 4/2004 | Colvin et al. |
| 6,726,651 B1 | 4/2004 | Robinson et al. |
| 6,733,509 B2 | 5/2004 | Nobles et al. |
| 6,767,352 B2 | 7/2004 | Field et al. |
| 6,770,076 B2 | 8/2004 | Foerster |
| 6,770,084 B1 | 8/2004 | Bain et al. |
| 6,786,913 B1 | 9/2004 | Sancoff |
| 6,978,176 B2 | 1/2005 | Lattouf |
| 6,855,157 B2 | 2/2005 | Foerster et al. |
| 6,893,448 B2 | 5/2005 | O'Quinn et al. |
| 6,911,034 B2 | 6/2005 | Nobles et al. |
| 6,913,600 B2 | 7/2005 | Valley et al. |
| 6,936,057 B1 | 8/2005 | Nobles |
| 7,004,952 B2 | 2/2006 | Nobles et al. |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |
| 7,220,266 B2 | 5/2007 | Gambale |
| 7,232,446 B1 | 6/2007 | Farris |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,338,502 B2 | 3/2008 | Rosenblatt |
| 7,381,210 B2 | 6/2008 | Zarbatany et al. |
| 7,399,304 B2 | 7/2008 | Gambale et al. |
| 7,435,251 B2 | 10/2008 | Green |
| 7,449,024 B2 | 11/2008 | Stafford |
| 7,491,217 B1 | 2/2009 | Hendren |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |
| 7,879,072 B2 | 2/2011 | Bonutti et al. |
| 7,905,892 B2 | 3/2011 | Nobles et al. |
| 7,918,867 B2 | 4/2011 | Dana et al. |
| 7,931,641 B2 | 4/2011 | Chang et al. |
| 7,993,368 B2 | 8/2011 | Gambale et al. |
| 8,075,573 B2 | 12/2011 | Gambale et al. |
| 8,083,754 B2 | 12/2011 | Pantages et al. |
| 8,105,355 B2 | 1/2012 | Page et al. |
| 8,197,497 B2 | 6/2012 | Nobles et al. |
| 8,202,281 B2 | 6/2012 | Voss |
| 8,246,636 B2 | 8/2012 | Nobles et al. |
| 8,258,005 B2 | 8/2012 | Findlay, III et al. |
| 8,282,659 B2 | 10/2012 | Oren et al. |
| 8,287,556 B2 | 10/2012 | Gilkey et al. |
| 8,298,291 B2 | 10/2012 | Ewers et al. |
| 8,303,622 B2 | 11/2012 | Alkhatib |
| 8,348,962 B2 | 1/2013 | Nobles et al. |
| 8,372,089 B2 | 2/2013 | Nobles et al. |
| 8,398,676 B2 | 3/2013 | Roorda et al. |
| 8,430,893 B2 | 4/2013 | Ma |
| 8,469,975 B2 | 6/2013 | Nobles et al. |
| 8,496,676 B2 | 7/2013 | Nobles et al. |
| 8,500,776 B2 | 8/2013 | Ebner |
| 8,540,736 B2 | 9/2013 | Gaynor et al. |
| 8,568,427 B2 | 10/2013 | Nobles et al. |
| 8,623,036 B2 | 1/2014 | Harrison et al. |
| 8,728,105 B2 | 5/2014 | Aguirre |
| 8,758,370 B2 | 6/2014 | Shikhman et al. |
| 8,771,296 B2 | 7/2014 | Nobles et al. |
| 9,131,938 B2 | 9/2015 | Nobles et al. |
| 9,326,764 B2 | 5/2016 | Nobles et al. |
| 9,332,976 B2 | 5/2016 | Yribarren |
| 9,364,238 B2 | 6/2016 | Bakos et al. |
| 9,398,907 B2 | 7/2016 | Nobles et al. |
| 9,402,605 B2 | 8/2016 | Viola |
| 9,649,106 B2 | 5/2017 | Nobles et al. |
| 10,178,993 B2 | 1/2019 | Nobles et al. |
| 10,182,802 B2 | 1/2019 | Nobles et al. |
| 10,194,902 B2 | 2/2019 | Nobles et al. |
| 10,285,687 B2 | 5/2019 | Nobles et al. |
| 10,420,545 B2 | 9/2019 | Nobles et al. |
| 2001/0031973 A1 | 10/2001 | Nobles et al. |

(56) References Cited

U.S. PATENT DOCUMENTS

| | | |
|---|---|---|
| 2002/0013601 A1 | 1/2002 | Nobles et al. |
| 2002/0045908 A1 | 4/2002 | Nobles et al. |
| 2002/0049453 A1 | 4/2002 | Nobles et al. |
| 2002/0087178 A1 | 7/2002 | Nobles et al. |
| 2002/0096183 A1 | 7/2002 | Stevens et al. |
| 2002/0111653 A1 | 8/2002 | Foerster |
| 2002/0128598 A1 | 9/2002 | Nobles |
| 2002/0169475 A1 | 11/2002 | Gainor et al. |
| 2002/0183787 A1 | 12/2002 | Wahr et al. |
| 2003/0078601 A1 | 4/2003 | Skikhman et al. |
| 2003/0114863 A1 | 6/2003 | Field et al. |
| 2003/0144673 A1 | 7/2003 | Onuki et al. |
| 2003/0204205 A1 | 10/2003 | Sauer et al. |
| 2003/0208209 A1 | 11/2003 | Gambale et al. |
| 2003/0220667 A1 | 11/2003 | van der Burg et al. |
| 2004/0015177 A1 | 1/2004 | Chu |
| 2004/0044365 A1 | 3/2004 | Bachman |
| 2004/0059351 A1 | 3/2004 | Eigler et al. |
| 2004/0102797 A1 | 5/2004 | Golden et al. |
| 2004/0153116 A1 | 8/2004 | Nobles |
| 2004/0236356 A1 | 11/2004 | Rioux et al. |
| 2004/0260298 A1 | 12/2004 | Kaiseer et al. |
| 2005/0033361 A1 | 2/2005 | Galdonik et al. |
| 2005/0070923 A1 | 3/2005 | McIntosh |
| 2005/0149066 A1 | 7/2005 | Stafford |
| 2005/0187575 A1 | 8/2005 | Hallbeck et al. |
| 2005/0203564 A1 | 9/2005 | Nobles |
| 2005/0228407 A1 | 10/2005 | Nobles et al. |
| 2005/0261708 A1 | 11/2005 | Pasricha et al. |
| 2005/0261710 A1 | 11/2005 | Sakamoto et al. |
| 2005/0277986 A1 | 12/2005 | Foerster et al. |
| 2006/0052813 A1 | 3/2006 | Nobles |
| 2006/0064113 A1 | 3/2006 | Nakao |
| 2006/0064115 A1 | 3/2006 | Allen et al. |
| 2006/0069397 A1 | 3/2006 | Nobles et al. |
| 2006/0074484 A1 | 4/2006 | Huber |
| 2006/0095052 A1 | 5/2006 | Chambers |
| 2006/0195120 A1 | 8/2006 | Nobles et al. |
| 2006/0248691 A1 | 11/2006 | Rosemann |
| 2006/0265010 A1 | 11/2006 | Paraschac et al. |
| 2006/0282088 A1 | 12/2006 | Ryan |
| 2006/0282094 A1 | 12/2006 | Stokes et al. |
| 2006/0282102 A1 | 12/2006 | Nobles et al. |
| 2006/0287657 A1 | 12/2006 | Bachman |
| 2007/0010829 A1 | 1/2007 | Nobles et al. |
| 2007/0043385 A1 | 2/2007 | Nobles et al. |
| 2007/0060930 A1 | 3/2007 | Hamilton et al. |
| 2007/0106310 A1 | 5/2007 | Goldin et al. |
| 2007/0118151 A1 | 5/2007 | Davidson |
| 2007/0142846 A1 | 6/2007 | Catanese, III et al. |
| 2007/0213757 A1 | 9/2007 | Boraiah |
| 2007/0219630 A1 | 9/2007 | Chu |
| 2007/0276413 A1 | 11/2007 | Nobles |
| 2007/0276414 A1 | 11/2007 | Nobles |
| 2008/0033459 A1 | 2/2008 | Shafi et al. |
| 2008/0065145 A1 | 3/2008 | Carpenter |
| 2008/0077162 A1 | 3/2008 | Domingo |
| 2008/0114384 A1 | 5/2008 | Chang et al. |
| 2008/0188873 A1 | 8/2008 | Speziali |
| 2008/0228201 A1 | 9/2008 | Zarbatany |
| 2008/0269786 A1 | 10/2008 | Nobles et al. |
| 2008/0269788 A1 | 10/2008 | Nobles |
| 2009/0036906 A1 | 2/2009 | Stafford |
| 2009/0048615 A1 | 2/2009 | McIntosh |
| 2009/0099410 A1 | 4/2009 | De Marchena |
| 2009/0105729 A1 | 4/2009 | Zentgraf |
| 2009/0105751 A1 | 4/2009 | Zentgraf |
| 2009/0118726 A1 | 5/2009 | Auth et al. |
| 2009/0125042 A1 | 5/2009 | Mouw |
| 2009/0287183 A1 | 11/2009 | Bishop et al. |
| 2009/0299409 A1 | 12/2009 | Coe et al. |
| 2009/0312772 A1 | 12/2009 | Chu |
| 2009/0312783 A1 | 12/2009 | Whayne et al. |
| 2009/0312789 A1 | 12/2009 | Kassab et al. |
| 2010/0016870 A1 | 1/2010 | Campbell |
| 2010/0030242 A1 | 2/2010 | Nobles et al. |
| 2010/0042147 A1 | 2/2010 | Janovsky et al. |
| 2010/0063586 A1 | 3/2010 | Hasenkam et al. |
| 2010/0087838 A1 | 4/2010 | Nobles et al. |
| 2010/0094314 A1 | 4/2010 | Hernlund et al. |
| 2010/0100167 A1 | 4/2010 | Bortlein et al. |
| 2010/0179585 A1 | 7/2010 | Carpenter et al. |
| 2010/0210899 A1 | 8/2010 | Schankereli |
| 2011/0190793 A1 | 8/2011 | Nobles et al. |
| 2011/0202077 A1 | 8/2011 | Chin et al. |
| 2011/0224720 A1 | 9/2011 | Kassab et al. |
| 2011/0251627 A1 | 10/2011 | Hamilton et al. |
| 2012/0016384 A1 | 1/2012 | Wilke et al. |
| 2012/0035628 A1 | 2/2012 | Aguirre et al. |
| 2012/0059398 A1 | 3/2012 | Pate et al. |
| 2012/0143222 A1 | 6/2012 | Dravis et al. |
| 2012/0165838 A1 | 6/2012 | Kobylewski et al. |
| 2012/0296373 A1 | 11/2012 | Roorda et al. |
| 2013/0103056 A1 | 4/2013 | Chu |
| 2013/0261645 A1 | 10/2013 | Nobles et al. |
| 2013/0324800 A1 | 12/2013 | Cahill |
| 2014/0163585 A1 | 6/2014 | Nobles et al. |
| 2014/0303654 A1 | 10/2014 | Nobles et al. |
| 2014/0309670 A1 | 10/2014 | Bakos et al. |
| 2014/0379006 A1 | 12/2014 | Sutherland et al. |
| 2015/0126815 A1 | 5/2015 | Nobles |
| 2015/0344351 A1 | 12/2015 | Nobles et al. |
| 2015/0359531 A1 | 12/2015 | Sauer |
| 2016/0007998 A1 | 1/2016 | Nobles et al. |
| 2016/0151064 A1 | 6/2016 | Nobles |
| 2016/0174968 A1 | 6/2016 | Nobles et al. |
| 2016/0302787 A1 | 10/2016 | Nobles |
| 2017/0035425 A1 | 2/2017 | Fegelman et al. |
| 2017/0042534 A1 | 2/2017 | Nobles |
| 2017/0049451 A1 | 2/2017 | Hausen |
| 2017/0296168 A1 | 4/2017 | Nobles et al. |
| 2017/0128059 A1 | 5/2017 | Coe et al. |
| 2017/0303915 A1 | 10/2017 | Nobles |
| 2019/0029672 A1 | 1/2019 | Nobles et al. |
| 2019/0239880 A1 | 8/2019 | Nobles |

FOREIGN PATENT DOCUMENTS

| | | |
|---|---|---|
| AU | 2006262498 | 1/2007 |
| CA | 2323084 | 12/2006 |
| CN | 195341 | 2/2005 |
| CN | 1654016 A | 8/2005 |
| CN | 101027001 | 8/2007 |
| CN | 101242785 A | 8/2008 |
| CN | 101495049 | 12/2010 |
| CN | 101257852 | 8/2011 |
| CN | 102892359 | 1/2013 |
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 0983026 | 3/2002 |
| EP | 1 196 093 | 4/2002 |
| EP | 1 303 218 | 4/2003 |
| EP | 0941698 | 5/2005 |
| EP | 0983027 | 12/2005 |
| EP | 1804677 | 7/2007 |
| EP | 1 852 071 | 11/2007 |
| EP | 1909654 | 4/2008 |
| EP | 1909655 | 4/2008 |
| EP | 1 987 779 | 11/2008 |
| EP | 1570790 | 11/2008 |
| EP | 2011441 | 1/2009 |
| EP | 2134266 | 12/2009 |
| EP | 2291125 | 3/2011 |
| EP | 2528511 | 12/2012 |
| EP | 2 572 649 | 3/2013 |
| FR | 2 701 401 | 8/1994 |
| HK | 1036395 | 5/2005 |
| JP | A 09507398 | 7/1997 |
| JP | 09-266910 A | 10/1997 |
| JP | H10-43192 | 2/1998 |
| JP | 2001-524864 | 12/2001 |

(56) References Cited

FOREIGN PATENT DOCUMENTS

| | | |
|---|---|---|
| JP | 2002-500531 | 1/2002 |
| JP | 2003-139113 A2 | 5/2003 |
| JP | 2003-225241 A | 8/2003 |
| JP | 2007-503870 | 3/2007 |
| JP | 2008-514305 | 5/2008 |
| JP | 2008-541857 | 11/2008 |
| JP | 2008-546454 | 12/2008 |
| JP | 4399035 | 10/2009 |
| JP | 2009-261960 | 11/2009 |
| JP | 2010-522625 | 7/2010 |
| JP | 2011-067251 | 4/2011 |
| JP | 2014-134876 | 6/2014 |
| JP | 5848125 | 12/2015 |
| JP | 6336955 | 5/2018 |
| RU | 2010 125954 | 1/2012 |
| SU | 1560129 A1 | 4/1990 |
| WO | WO 92/05828 A1 | 4/1992 |
| WO | WO 93/01750 | 2/1993 |
| WO | WO 93/07800 | 4/1993 |
| WO | WO 95/12429 A1 | 5/1995 |
| WO | WO 95/17127 A1 | 6/1995 |
| WO | WO 95/25468 | 9/1995 |
| WO | WO 95/25470 | 9/1995 |
| WO | WO 96/03083 | 2/1996 |
| WO | WO 96/29012 | 9/1996 |
| WO | WO 96/40347 | 12/1996 |
| WO | WO 97/03613 A1 | 2/1997 |
| WO | WO 97/07745 A1 | 3/1997 |
| WO | WO 97/12540 A1 | 4/1997 |
| WO | WO 97/20505 A1 | 6/1997 |
| WO | WO 97/24975 | 7/1997 |
| WO | WO 97/27807 | 8/1997 |
| WO | WO 97/40738 A1 | 11/1997 |
| WO | WO 97/47261 A1 | 12/1997 |
| WO | WO 98/12970 | 4/1998 |
| WO | WO 98/52476 A1 | 11/1998 |
| WO | WO 99/40851 | 8/1999 |
| WO | WO 99/42160 | 8/1999 |
| WO | WO 99/45848 A1 | 9/1999 |
| WO | WO 00/002489 | 1/2000 |
| WO | WO 01/001868 | 1/2001 |
| WO | WO 01/95809 | 12/2001 |
| WO | WO 2002/24078 A1 | 3/2002 |
| WO | WO 04/012789 | 2/2004 |
| WO | WO 04/096013 | 11/2004 |
| WO | WO 2006/127636 A1 | 11/2006 |
| WO | WO 2007/001936 A1 | 1/2007 |
| WO | WO 07/016261 | 2/2007 |
| WO | WO 2008/121738 A1 | 10/2008 |
| WO | WO 09/081396 | 7/2009 |
| WO | WO 2009/137766 A1 | 11/2009 |
| WO | WO 2011/094619 A1 | 8/2011 |
| WO | WO 11/137224 | 11/2011 |
| WO | WO 12/012336 | 1/2012 |
| WO | WO 2012/142338 A1 | 10/2012 |
| WO | WO 13/027209 | 2/2013 |
| WO | WO 13/142487 | 9/2013 |
| WO | WO 2013/170081 A1 | 11/2013 |
| WO | WO 15/002815 | 1/2015 |
| WO | WO 15/085145 | 6/2015 |
| WO | WO 17/180092 | 10/2017 |
| WO | WO 19/035095 | 2/2019 |
| WO | WO 19/051379 | 3/2019 |
| WO | WO 19/055433 | 3/2019 |

OTHER PUBLICATIONS

European Exam Report, re EP Application No. 1277088, dated Feb. 23, 2018.

Advances in Vascular Surgery, by John S. Najarian, M.D. and John P. Delaney, M.D., copyright 1983 by Year Book Publishers, Inc. at pp. 94, 95, 96, and 224.

Cardio Medical Solutions, Inc. brochure titled: "Baladi Inverter for Clamp less Surgery"—Undated.

Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.

Current Therapy in Vascular Surgery, 2nd edition, by Calvin B. Ernst, M.D. and James C. Stanley, M.D., copyright 1991 By B.C. Decker, Inc., at pp. A and 140.

Eskuri, A., The Design of a Minimally Invasive Vascular Suturing Device, Thesis submitted to Rose-Hulman Institute of Technology, Nov. 1999.

International Search Report and Written Opinion of PCT/US2009/043293 (NRMED.052VPC), dated Jul. 1, 2009.

International Search Report and Written Opinion of PCT/US2012/033396, dated Aug. 7, 2012.

International Search Report and Written Opinion of PCT/US2013/040418, dated Jul. 26, 2013.

International Search Report received in PCT/US 11/23033 dated Apr. 11, 2011.

Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.

Nursing the Open-Heart Surgery Patient, By Mary Jo Aspinall, R.N., M.N., copyright 1973 by McGraw-Hill, Inc., at pp. 216 and 231.

Operative Arterial Surgery, by P.R. Bell, M.D., and W. Barrie, M.D., copyright 1981 by Bell, Barrie, and Leicester Royal Infirmary, printed by John Wright & Sons, pp. 16, 17, 104, 105, 112, and 113.

Sinus Venous Type of Atrial Septal Defect with Partial Anomalous Pulmonary Venous Return, by Francis Robicsek, M.D., et al, in Journal of Thoracic and Cardiovascular Surgery, Oct. 1979, vol. 78, No. 4, at pp. 559-562.

Techniques in Vascular Surgery, by Denton A. Cooley, M.D. and Don C. Wukasch, M.D., copyright 1979 by W.B. Saunders Co., at pp. 38, 57, 86, 134, 156, and 184.

The problem: Closing wounds in deep areas during laparoscopic operations The solution: REMA-Medizintechnik GmbH (no date).

Vascular Access, Principles and Practice, 3rd edition, by Samuel Eric Wilson, M.D., copyright 1996, 1988, 1980 by Mosby-Year Book, Inc., pp. 89 and 159.

Vascular and Endovascular Surgery, by Jonathan D. Beard and Peter Gainers, copyright 1998 by W.B. Saunders Co., Ltd, p. 414.

Vascular Surgery, 3rd edition, vol. 1, by Robert B. Rutherford, M.D., copyright 1989, 1984, 1976 By W.B. Saunders Co., at pp. 347, 348, 354, 594, 607, 622, 675, 677, 680, 698, 700, 721, 727, 735, and 829.

Vascular Surgery, 4th edition by Robert B. Rutherford, M.D., copyright 1995, 1989, 1976, by W.B. Saunders Co., vol. 1, at pp. 400-404, 661, and A.

Vascular Surgery, 4th edition, by Robert B. Rutherford, M.D., copyright 1995, 1989, 1984, 1976 by W.B. Saunders Co., vol. 2, at pp. 1318, 1363, 1426, 1564, and 1580.

Vascular Surgery, by Robert B. Rutherford, M.D. copyright 1977 by W.B. Saunders Co., at pp. 334 and 817.

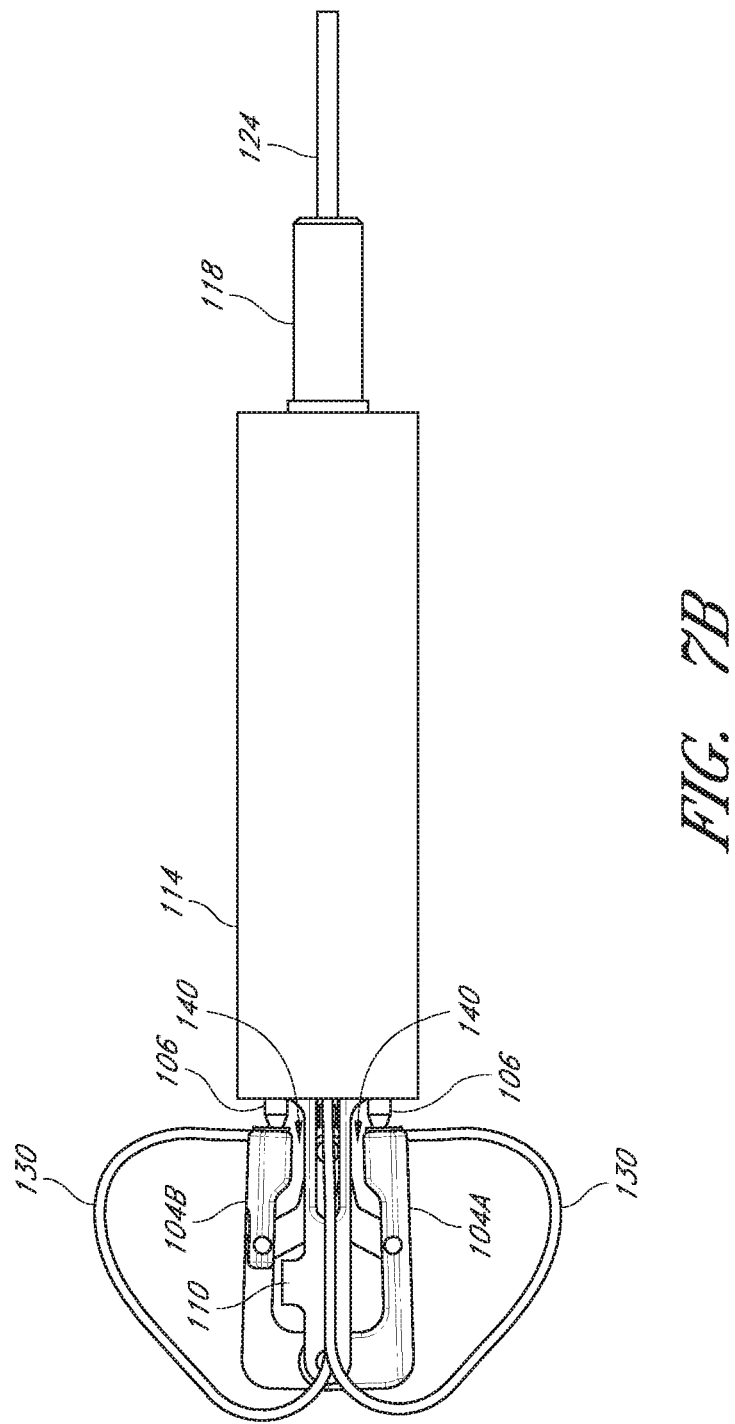

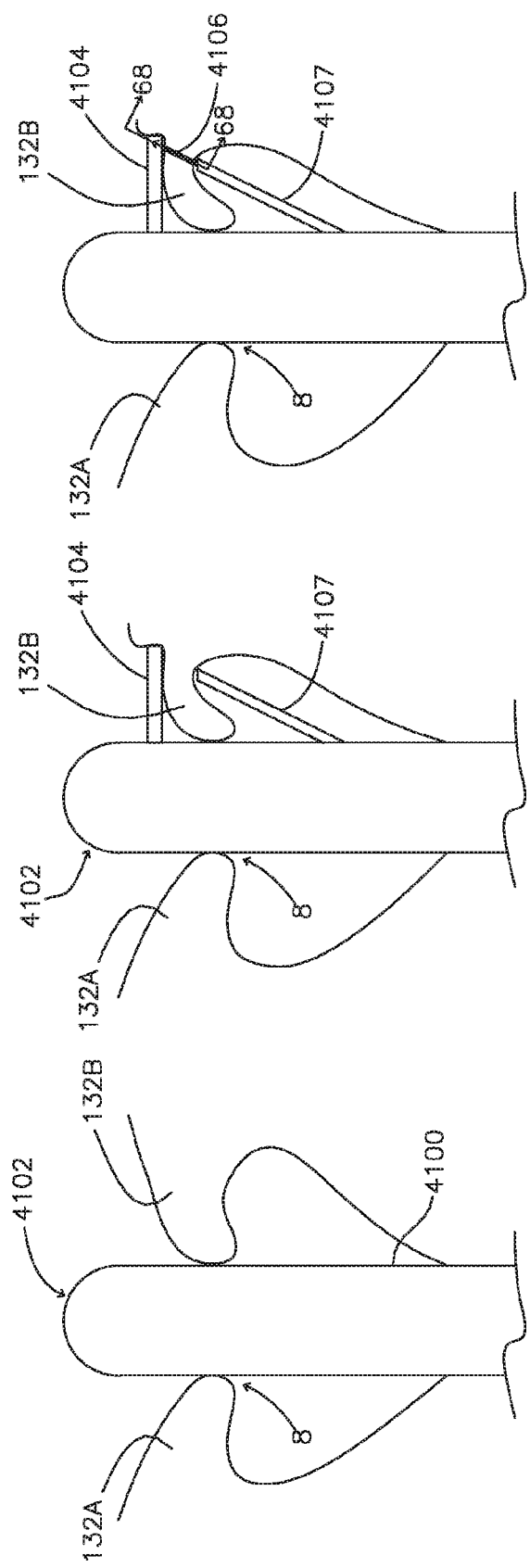

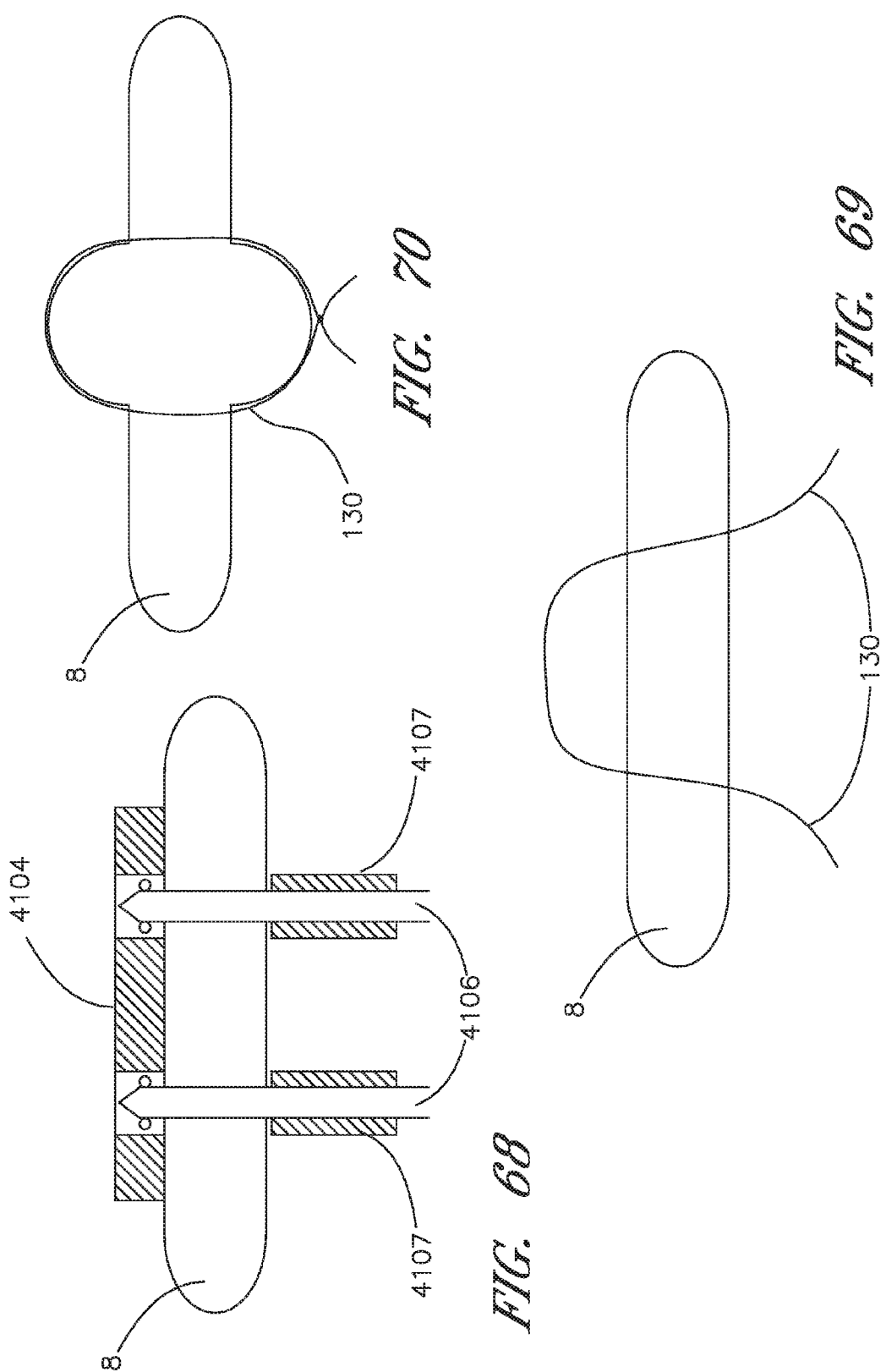

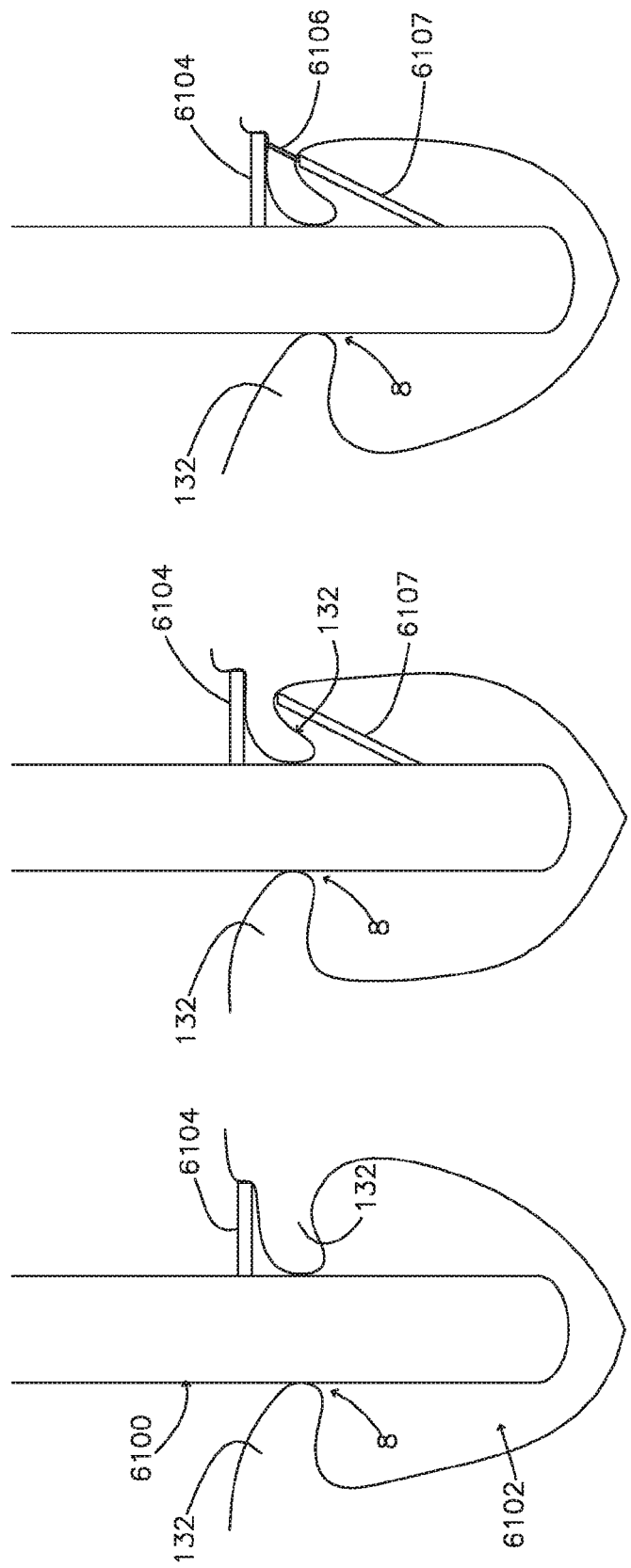

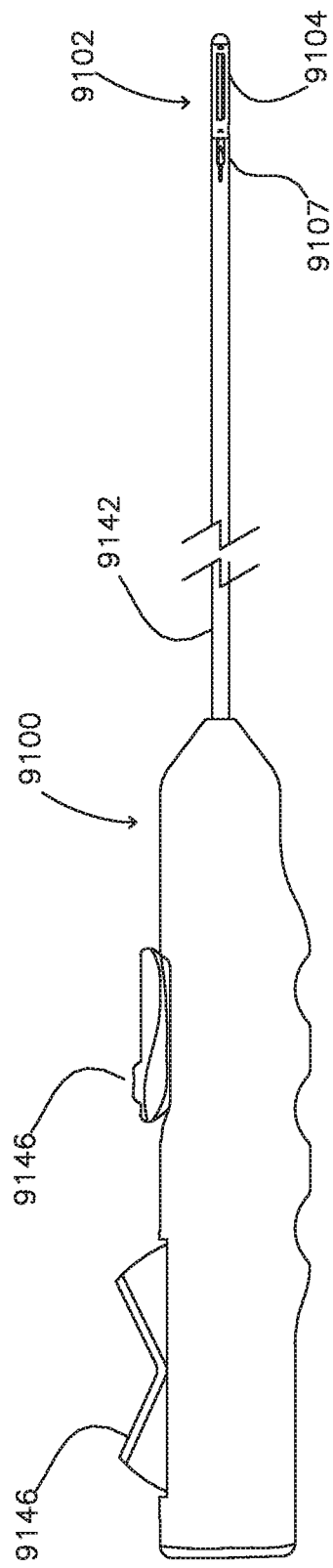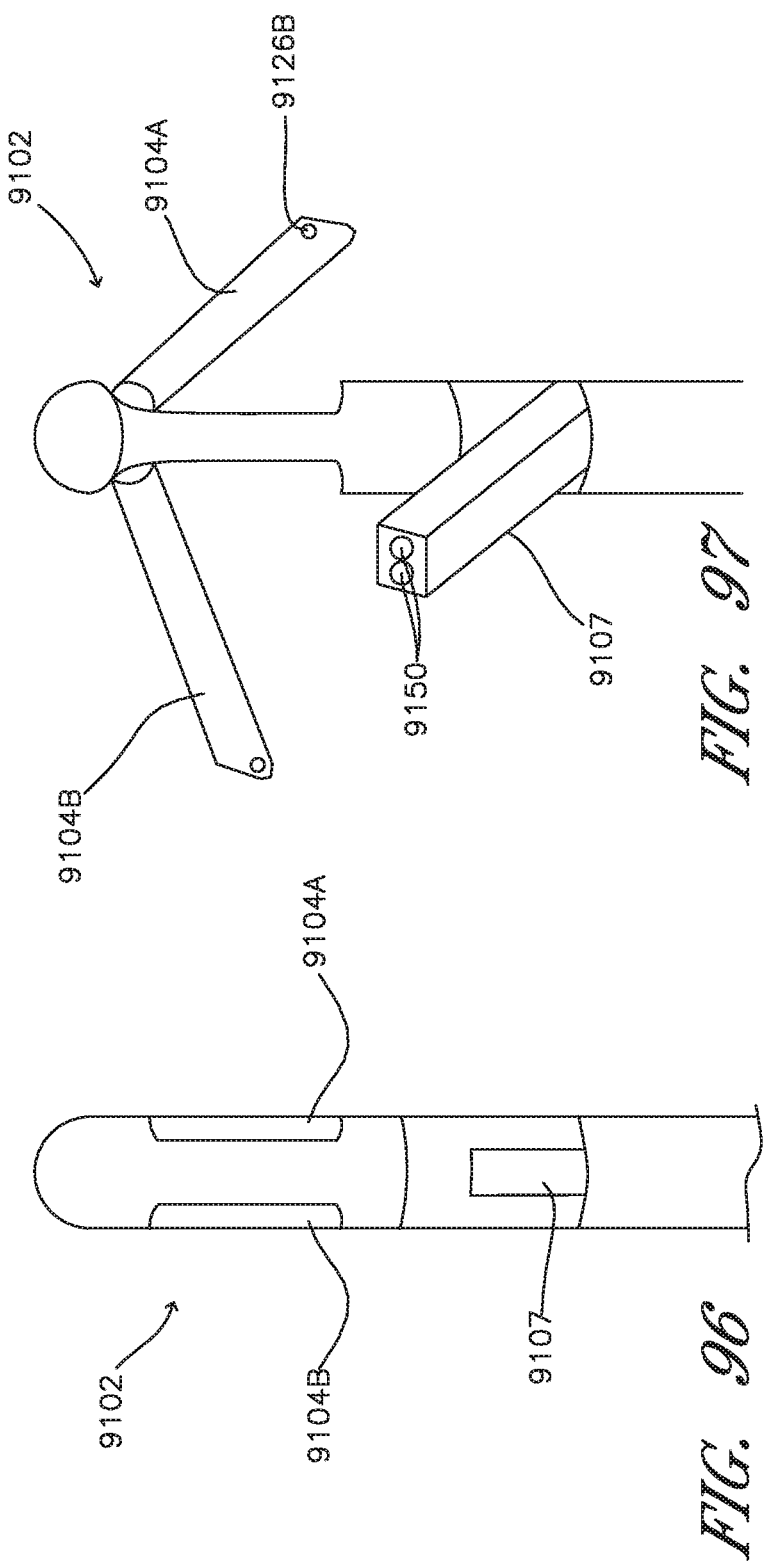

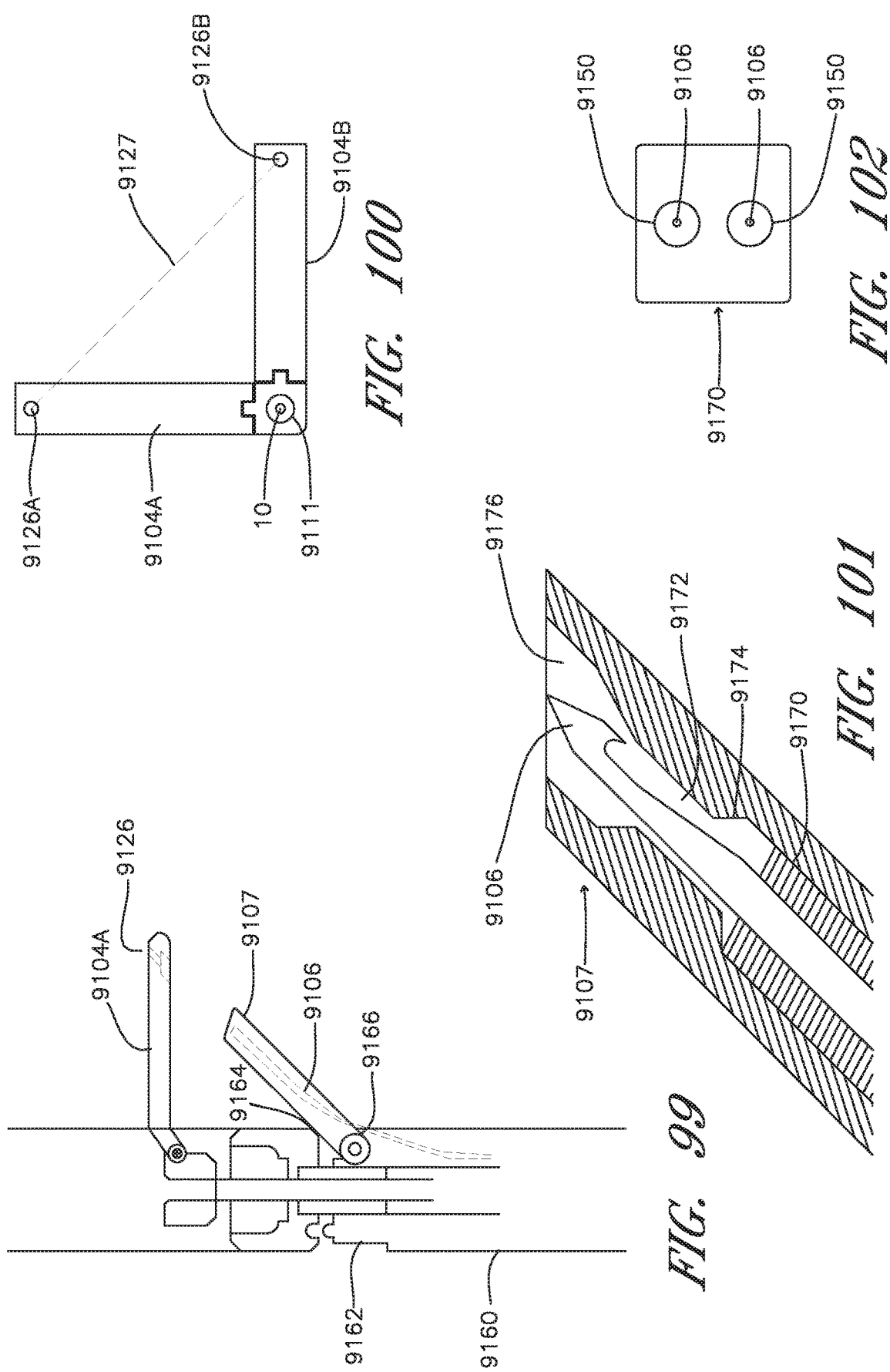

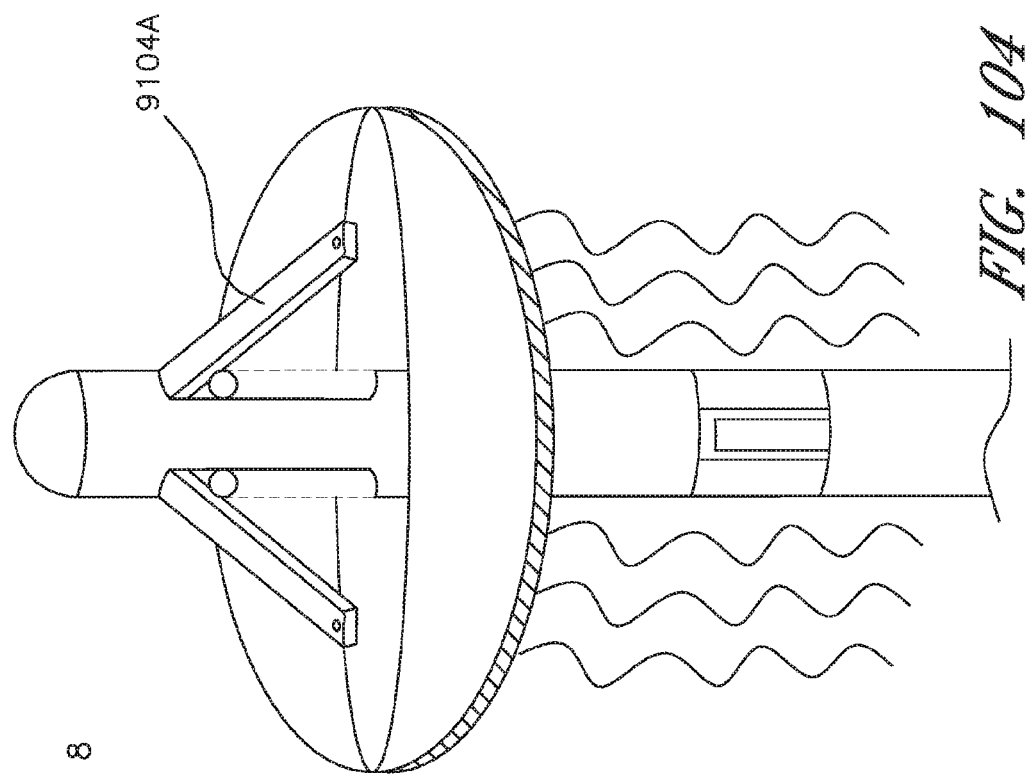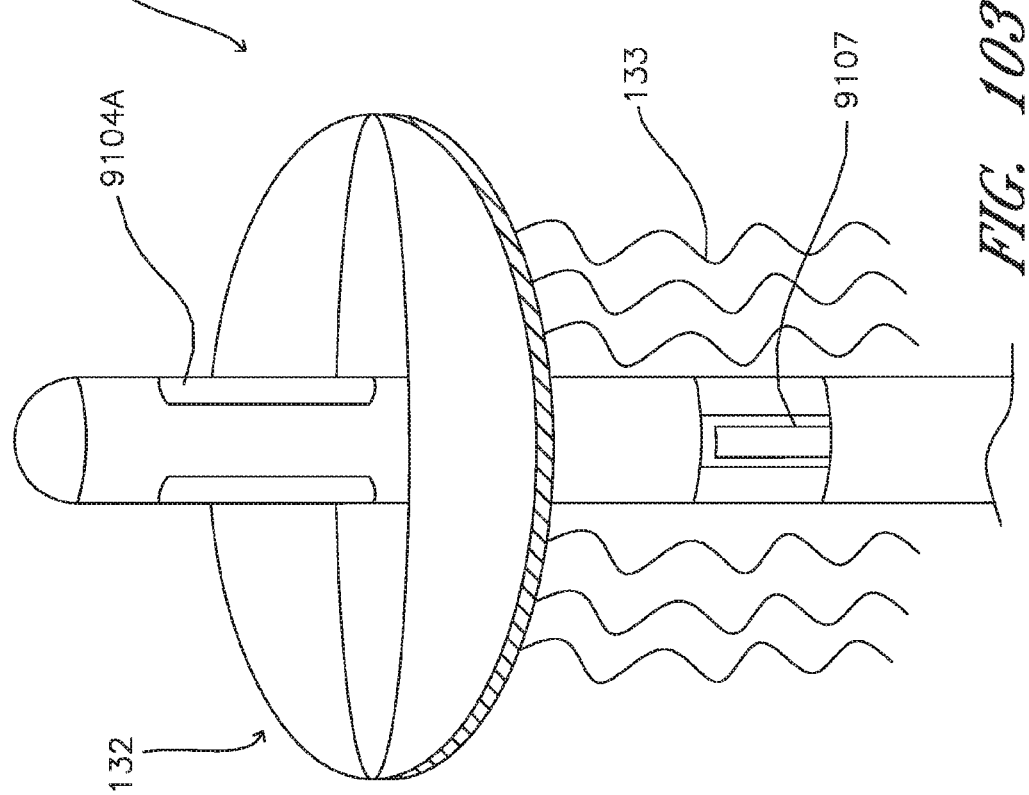

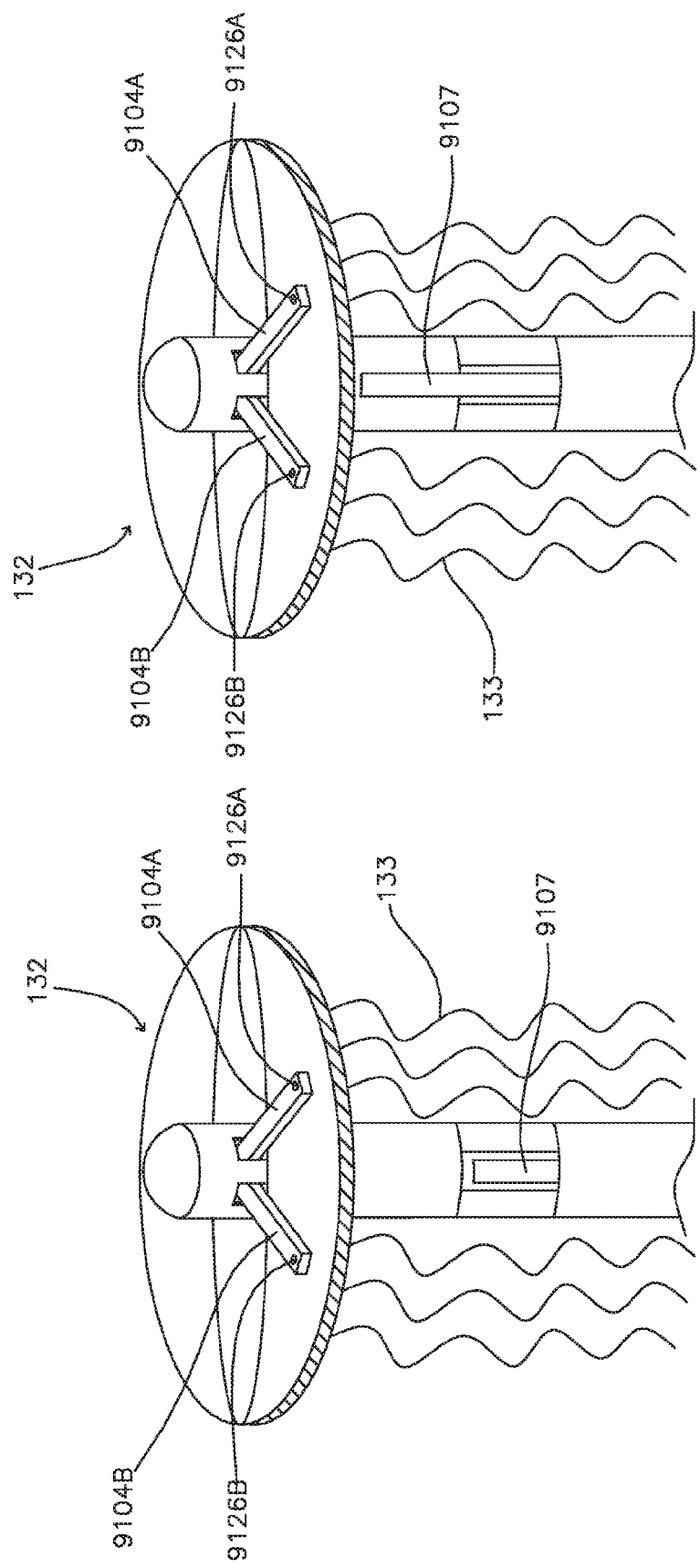

SUTURING DEVICES AND METHODS FOR SUTURING AN ANATOMIC VALVE

CROSS-REFERENCE TO RELATED APPLICATIONS

This application is a divisional of U.S. patent application Ser. No. 14/111,534, filed Feb. 4, 2014, titled "SUTURING DEVICES AND METHODS FOR SUTURING AN ANATOMIC VALVE," which is a U.S. National Phase of International Patent Application No. PCT/US2012/033396, filed Apr. 12, 2012, titled "SUTURING DEVICES AND METHODS FOR SUTURING AN ANATOMIC VALVE", which claims the priority benefit of U.S. Provisional Application No. 61/476,236, filed Apr. 15, 2011, the entirety of which is hereby incorporated by reference.

TECHNICAL FIELD

Embodiments of the present inventions relate to suturing devices and methods. Some embodiments of the present invention relate to suturing devices and methods for suturing an anatomic valve, for example, a heart valve such as a mitral valve, an aortic valve, a tricuspid valve, or a pulmonary valve.

BACKGROUND

Health practitioners frequently use sutures to close various openings such as cuts, punctures, and incisions in various places in the human body. Generally, sutures are convenient to use and function properly to hold openings in biological tissue closed thereby aiding in blood clotting, healing, and prevention of scaring.

There are some circumstances under which it is not feasible to use conventional sutures and suturing methods to close an opening. Additionally, there are some circumstances under which the use of conventional sutures and suturing methods require invasive procedures that subject a patient to risk of infection, delays in recovery, increases in pain, and other complications.

Some heart valves may be weakened or stretched, or may have other structural defects, such as congenital defects, that cause them to close improperly, which can lead to blood flow contrary to the normal flow direction. This condition, referred to as regurgitation, incompetence, or insufficiency, can reduce blood flow in the normal direction. Regurgitation causes the heart to work harder to compensate for backflow of blood through these valves, which can lead to enlargement of the heart that reduces cardiac performance. While the tricuspid valve and the pulmonary valve may present these conditions, the mitral valve and aortic valve more frequently demonstrate these conditions.

A number of procedures have been developed to repair valves that do not close properly. Among these procedures is the Alfieri technique, sometimes called edge-to-edge repair, which involves suturing edges of the leaflets and pulling the leaflets closer together. In another technique, the chordae tendineae are replaced or shortened. A patch is sometimes applied to leaflets that have openings therein. In some instances, leaflets are reshaped by removing a section of the leaflet that is to be treated and the surrounding portion of the leaflet is sutured closed. Some valves are treated by attaching a ring around the outside of the malfunctioning valve. In a mitral valve annuloplasty, for example, a device such as in the shape of a ring or a partial ring may be implanted surrounding the mitral valve to pull the leaflets together. Sutures may be used to attach the annuloplasty ring to the base of the valve. Other valves may be replaced with biological or mechanical replacements. These procedures are frequently performed by highly invasive procedures, which sometimes require opening a patient's chest, stopping the patient's heart and routing blood through a heart-lung machine. Robotically-assisted procedures have been employed to reduce the size of the openings required for such procedures.

SUMMARY OF THE DISCLOSURE

Embodiments of suturing devices and methods for suturing biological tissue are disclosed herein. The suturing devices and their methods of use can be useful in a variety of procedures, such as treating (e.g., closing) wounds and naturally or surgically created apertures or passageways. For example, the suturing devices can be used to treat an anatomical valve, such as a heart valve, including heart valves that may be weakened or stretched, or have other structural defects, such as congenital defects, that cause them to close improperly. In some embodiments, one or more suturing devices can be used to treat or repair valves, such as the tricuspid, pulmonary, mitral, and aortic valves, for example. In some embodiments, one or more suturing devices can be used to perform procedures such as edge-to-edge repair (like an Alfieri technique), annuloplasty (with or without a ring or other implant), suturing of ventricular spaces, suturing of the chordae, suturing in other locations in the heart, replacement of the chordae tendineae, shortening of the chordae tendineae, patch application, leaflet reshaping, and attachment of prosthetics, such as rings and biological or mechanical replacement valves, for example.

In some embodiments, the suturing devices can be used to close or reduce a variety of other tissue openings, lumens, hollow organs or natural or surgically created passageways in the body. In some embodiments, the suturing devices can be used to suture prosthetics, synthetic materials, or implantable devices in the body. For example, the devices can be used to suture pledget within the body.

In some embodiments, a suturing device can comprise an elongate body having a distal end, a single arm, a needle, and a protective member. The single arm can be connected with the elongate body near the distal end for movement between a retracted position and an extended position. The arm can comprise a first suture mount located near a free end of the arm and configured to releasably retain a first suture portion. A needle can be configured to move between a retracted position and a deployed position to retrieve the first suture portion retained in the first suture mount when the first needle is moved from the retracted position to the advanced position and returned to the retracted position. The first protective member can be configured to inhibit contact between a distal end of the first needle and surrounding tissue during at least a portion of the movement of the first needle from its retracted position toward its deployed position.

In some embodiments, a suturing device can comprise an elongate body having a proximal end and a distal end, and a handle at the proximal end. A first arm and a second arm can connect to the elongate body near the distal end, and the first arm and the second arm can be configured to move between a first position, in which the first arm and second arm are retracted within the elongate body, and a second position, in which the first arm and the second arm have free ends extending away from the elongate body. The first arm and the second arm can form an angle between each other and can each have at least one suture mount at their free ends. The suture mounts can be configured to releasably retain a suture portion. A needle arm can connect to the elongate body proximal to the first and second arm, and can extend from a retracted position, in which the needle arm is retracted in the elongate body, to an extended position, in which the needle arm extends distally and outwardly from the elongate body. The needle arm can rotate around the elongate body at least between a first position where the needle arm is aligned with the free end of the first arm and a second position where the needle arm is aligned with the free end of the second arm. The device can also comprise a first needle and a second needle that can have a retracted position in which a distal point of each needle is within the needle arm. The first needle can move from the retracted position to a deployed position in which the distal point of the first needle extends out of the needle arm into the suture mount of the first arm when the needle arm is in the first position. The second needle can move from the retracted position to a deployed position in which the distal point of the second needle extends out of the needle arm into the suture mount of the second arm when the needle arm is in the second position.

Methods of suturing anatomic valves are also described. In some embodiments, an elongate body can be positioned at least partially within the anatomic valve. An arm can be deployed from the elongate body with the first arm releasably holding a first suture portion. A free end of the arm can be positioned at or near a base of the valve. A first needle can be deployed from the elongate body such that the first needle penetrates the valve at a first location and engages the first suture portion. The valve tissue and surrounding anatomy can be protected from a distal end of the first needle as the first needle is deployed to the first location. The first suture portion can be drawing through the leaflet. A second suture portion can be passed through the valve at a second location. The first and second suture portions can be secured together.

In some embodiments, an anatomic valve can be sutured by positioning an elongate body at least partially within the anatomic valve, deploying an arm from the elongate body on a first side of a valve with the first arm releasably holding first and second suture portions. A free end of the arm can be positioned at or near a base of the valve. First and second needles can be deployed from the elongate body on a second side of the valve such that the first needle penetrates the valve at a first location and engages the first suture portion and the second needle penetrates the valve at a second location and engage the second suture portion. The first and second suture portions can be drawn through the valve from the first side to the second side. The first and second suture portions can be secured together.

In some embodiments, an anatomic valve can be sutured by positioning an elongate body at least partially within the anatomic valve and deploying at least two arms from the elongate body with each arm releasably holding a suture portion. A free end of each of the arms can be positioned at or near a base of the valve. Needles can be deployed from the elongate body such that each needle penetrates the valve and engages a corresponding suture portion. The suture portions can be drawn through the leaflet. The suture portions can be secured together in groups of no less than two.

In some embodiments, an anatomic valve can be sutured by positioning a suturing device comprising an elongate body through the valve and extending a plurality of arms from the elongate body of the suturing device, with each of the arms carrying an end of a suture. At least a pair of arms can be positioned at or near a base of the valve. A protection member can be extended from the elongate body toward a first one of the arms positioned at or near a base of the valve. A needle can be advanced through the protection member, through tissue of the valve at a first location, and into contact with a first one of the suture ends carried by the first arm. The needle can be retracted through the tissue of the valve to draw the first suture end through the tissue. The protection member can be rotated along the elongate body such that the protection member extends toward a second one of the arms positioned at or near a base of the valve. A needle can be advanced through the protection member, through tissue of the valve at a second location, and into contact with a second one of the suture ends carried by the second arm. The needle can be retracted through the tissue of the valve to draw the second suture end through the tissue. A distance between the first and second locations can be closed with said suture placed through said locations.

In some embodiments, a mitral valve can be sutured by delivering a suturing device transapically through the heart and into the left ventricle. The suturing device can have a proximal end, a distal end, an elongate body extending between the proximal end and the distal end, and a handle at the proximal end. At least the distal end of the device can be delivered through the mitral valve. A first arm and a second arm can be extended from the elongate body from a first position, in which the first arm and the second arm are retracted into the elongate body, to a second position, in which the first arm and the second arm have free ends extending away from the elongate body. The first arm can carry a first suture end and the second arm can carry a second suture end. The first and second arm can be at or near a base of the valve on the atrial side of the valve.

A needle arm can be extended from a retracted position in which the needle arm is retracted into the elongate body to an initial extended position in which the needle arm is located proximal to the arms. The needle arm in the initial extended position can extend outwardly away from the elongate body in a distal direction on the ventricular side of the valve between adjacent chordae. The needle arm can be rotated toward the first arm with the needle arm remaining on the ventricular side of the valve such that the needle arm extends toward the first arm positioned at or near a base of the valve.

A first needle can be advanced distally out of the needle arm, through tissue of the valve at a first location, and into contact with the first suture end. The first needle can be retracted through the tissue of the valve to draw the first suture end through the tissue, and a first length of suture can run from the first suture end through the tissue. The needle arm can be rotated toward the second arm with the needle arm remaining on the ventricular side of the valve such that the needle arm extends toward the second arm positioned at or near a base of the valve. A second needle can be advanced distally out of the needle arm, through tissue of the valve at a second location, and into contact with the second suture end. The second needle can be retracted through the tissue of the valve to draw the second suture end through the tissue, and a second length of suture can run from the second suture end through the tissue.

The needle arm can be rotated back to the initial extended position. The needle arm can be moved proximally back to the retracted position. The first and second arms can be moved from the second position back to the first position. The suturing device can be withdrawn from the mitral valve, and the first and second lengths of suture can remain within the tissue. A first distance between the first and second locations can be closed to a second distance between the first and second locations.

In some embodiments, tissue can be sutured by delivering a suturing device to a location adjacent the tissue. The suturing device can have a proximal end, a distal end, an elongate body extending between the proximal end and the distal end, and a handle at the proximal end. At least the distal end of the device can be delivered to the location adjacent the tissue. A first arm and a second arm can be extended from the elongate body from a first position, in which the first arm and the second arm are retracted into the elongate body, to a second position, in which the first arm and the second arm have free ends extending away from the elongate body and the first arm and second arm form an angle between each other. The first arm can carry a first suture end and the second arm can carry a second suture end. The first and second arm can be adjacent a first side of the tissue.

A needle arm can be moved from a retracted position in which the needle arm is retracted into the elongate body to an extended position in which the needle arm extends toward the first arm. The needle arm can be located on the opposite side of the tissue from the first arm and the second arm. A first needle can be advanced out of the needle arm, through tissue at a first location, and into contact with the first suture end. The first needle can be retracted through the tissue to draw the first suture end through the tissue, and a first length of suture can run from the first suture end and through the tissue. The needle arm can be rotated toward the second arm such that the needle arm extends toward the second arm. A second needle can be advanced out of the needle arm, through tissue at a second location, and into contact with the second suture end. The second needle can be retracted through the tissue to draw the second suture end through the tissue, and a second length of suture can run from the second suture end and through the tissue.

The needle arm can be moved back to the retracted position. The first and second arms can be moved from the second position back to the first position. The suturing device can be withdrawn from the tissue location, and the first and second lengths of suture can remain within the tissue.

In some embodiments, an anatomic valve can be sutured by positioning an elongate body at least partially within the anatomic valve. A first arm can be deployed from the elongate body, and the first arm can releasably hold a first suture portion at a free end. The free end of the first arm can be positioned at or near an edge of a first leaflet on a first side of the valve. A first needle arm can be deployed from the elongate body on an opposite side of the valve such that the first leaflet is positioned between the needle arm and the first arm. A first needle can be deployed from the first needle arm such that the first needle penetrates the first leaflet at a first location and engages the first suture portion. The first suture portion can be drawn through the first leaflet. A second suture portion can be passed through the second leaflet at a second location, and the two leaflets can be drawn together using a suture placed through the first and second location.

The disclosure describes examples of some embodiments of the inventions. The designs, figures, and description are non-limiting examples of some embodiments of the inventions. Other embodiments of the devices and methods may or may not include the features disclosed herein. Moreover, disclosed advantages and benefits may apply to only some embodiments of the inventions, and should not be used to limit the inventions.

BRIEF DESCRIPTION OF THE DRAWINGS

The above-mentioned and other features disclosed herein are described below with reference to the drawings of specific embodiments. The illustrated embodiments are intended for illustration, but not limitation. The drawings contain the following figures:

FIG. 7B is a plan view as in FIG. 7A, but with the suture clasp arms retracted.

FIG. 65 is a schematic representation of the suturing device of FIGS. 62-64 positioned in a passage through a valve, such as the mitral valve via transapical entry.

FIG. 66 is a schematic representation as in FIG. 65 with the arm extended and the protective member extended.

FIG. 67 is a schematic representation as in FIG. 66 with the needle extended to pierce the valve and engage the arm.

FIG. 68 is a schematic partial cross-sectional view of the arm, needles and valve of FIG. 67, taken along line 68-68.

FIG. 69 is a schematic partial cross-sectional view as in FIG. 68 illustrating suture portions positioned through two locations in the valve.

FIG. 70 is a schematic partial cross-sectional view as in FIG. 69 with the suture portions secured together.

FIG. 77 is a schematic representation of the suturing device of FIG. 76 positioned within a passage of a valve, such as a mitral valve via access through the inferior vena cava and the atrial septum.

FIG. 78 is a schematic representation as in FIG. 77 with the arm extended and a protective member extended.

FIG. 79 is a schematic representation as in FIG. 78 with a needle advanced through the protective member to engage the arm.

FIG. 95 is a plan view of an embodiment of a suturing device.

FIG. 96 is a schematic perspective view of an embodiment of a suturing device.

FIG. 97 is a schematic perspective view of an embodiment of a suturing device with a needle arm and two suture arms in an extended position.

FIG. 99 is a cross sectional view of a section of the device of FIG. 95, showing the needle arm extended and aligned with an extended suture arm.

FIG. 100 is a top view of the device of FIG. 95, with the suture arms extended.

FIG. 101 is a cross sectional view of a distal section of an embodiment of a needle arm.

FIG. 102 is a top view of an embodiment of an extrusion.

FIG. 103 is a schematic representation of the suturing device of FIG. 95 positioned in a passage through a valve, such as the mitral valve via transapical entry.

FIG. 104 is a schematic representation as in FIG. 103 with the arms extended.

FIG. 105 is a schematic representation as in FIG. 104 with the arms positioned against the valve.

FIG. 106 is a schematic representation as in FIG. 105 with the protective member extended.

FIG. 115 is a schematic representation of a cross sectional side view of a valve, showing a tube positioned around a suture passing through the valve.

FIG. 116 is a schematic representation as in FIG. 115 showing two suture ends having been tightened and secured together.

FIG. 117 is a side view of a knot placement device.

FIG. 118 is a cross-sectional view of a knot and knot placement device.

FIG. 119 is a cross-sectional view of an embodiment of a knot and knot placement device.

DETAILED DESCRIPTION OF SPECIFIC EMBODIMENTS

Embodiments of suturing devices and methods for suturing biological tissue are disclosed herein. The suturing devices and their methods of use can be useful in a variety of procedures, such as treating (e.g., closing) wounds and naturally or surgically created apertures or passageways. For example, the suturing devices can be used to treat an anatomical valve, such as a heart valve, including heart valves that may be weakened or stretched, or have other structural defects, such as congenital defects, that cause them to close improperly. In some embodiments, one or more suturing devices can be used to treat or repair valves, such as the tricuspid, pulmonary, mitral, and aortic valves, for example. In some embodiments, one or more suturing devices can be used to perform procedures such as edge-to-edge repair (like an Alfieri technique), annuloplasty (with or without a ring or other implant), suturing of ventricular spaces, suturing of the chordae, suturing in other locations in the heart, replacement of the chordae tendineae, shortening of the chordae tendineae, patch application, leaflet reshaping, and attachment of prosthetics, such as rings and biological or mechanical replacement valves, for example.

In some embodiments, the suturing devices can be used to close or reduce a variety of other tissue openings, lumens, hollow organs or natural or surgically created passageways in the body. In some embodiments, the suturing devices can be used to suture prosthetics, synthetic materials, or implantable devices in the body. For example, the devices can be used to suture a pledget within the body.

Access Methods and Devices

Figure 1:
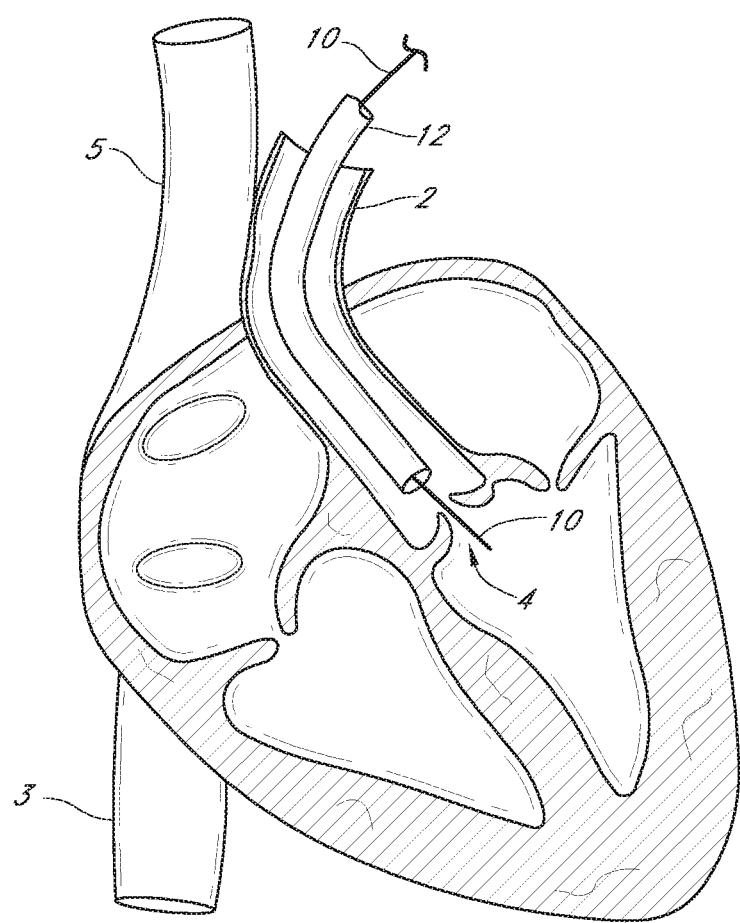
FIG. 1 illustrates a method of providing access to an exemplifying use environment, such as an aortic valve of a heart.

FIG. 1 illustrates an exemplifying use environment for suturing an aortic valve 4. Adaption of the devices and methods disclosed herein for suturing a heart valve may also be made with respect to procedures for suturing other bodily tissue and procedures for suturing prosthetics, synthetic materials, or implantable devices in the body. As depicted by FIG. 1, a guide wire 10 can be advanced through the aorta 2 to a position at or near the aortic valve 4. The guide wire 10 can be advanced into the aorta 2 through a subclavian artery (not shown). It is anticipated that the heart may be accessed through any of a variety of pathways. For example, the heart may be accessed through the inferior vena cava 3, the superior vena cava 5, or other vascular access. With the guide wire 10 in place, the physician can insert a sheath 12 to a position at or near the aortic valve 4. This sheath 12 is typically a single lumen catheter with a valve on its proximal end. The valve can be used, for example, to prevent extraneous bleed back or to introduce medication into the patient's body. A suturing device, such as those described further below, can then be advanced through the lumen of the sheath 12. In an alternative embodiment, the suturing device can be advanced over the guide wire 10 and positioned at or near the aortic valve 4 without the need to insert an introducer sheath 12.

Figure 2A:
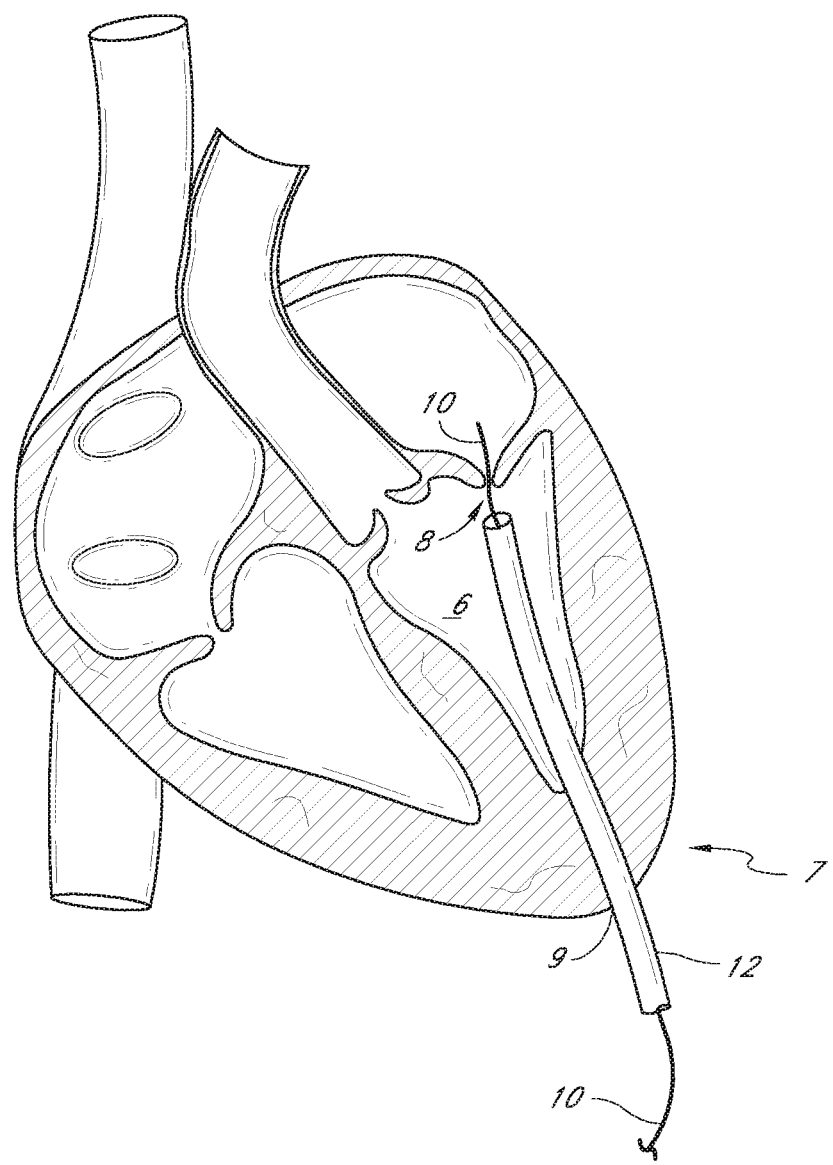
FIG. 2A illustrates a method of providing access to an exemplifying use environment, such as a mitral valve of a heart.

FIG. 2A illustrates another exemplifying use environment for suturing a mitral valve 8. As depicted by FIG. 2A, a guide wire 10 is advanced into the left ventricle 6 of the heart through a puncture or incision 9 near an apex 7 of the left ventricle 6. The heart may be accessed through a limited thoracotomy, small trocar puncture, or small catheter puncture. Other access paths may be used. The guide wire 10 can then be further positioned at or near the mitral valve 8. With the guide wire 10 in place, the physician can insert a sheath 12 to the left ventricle 6. The sheath 12 can be placed at or near the mitral valve 8. The suturing device can then be advanced through the lumen of the sheath 12. In an alternative embodiment, the suturing device can be advanced over the guide wire 10 and positioned at or near the mitral valve 8 without the need to insert an introducer sheath 12.

Figure 2B:
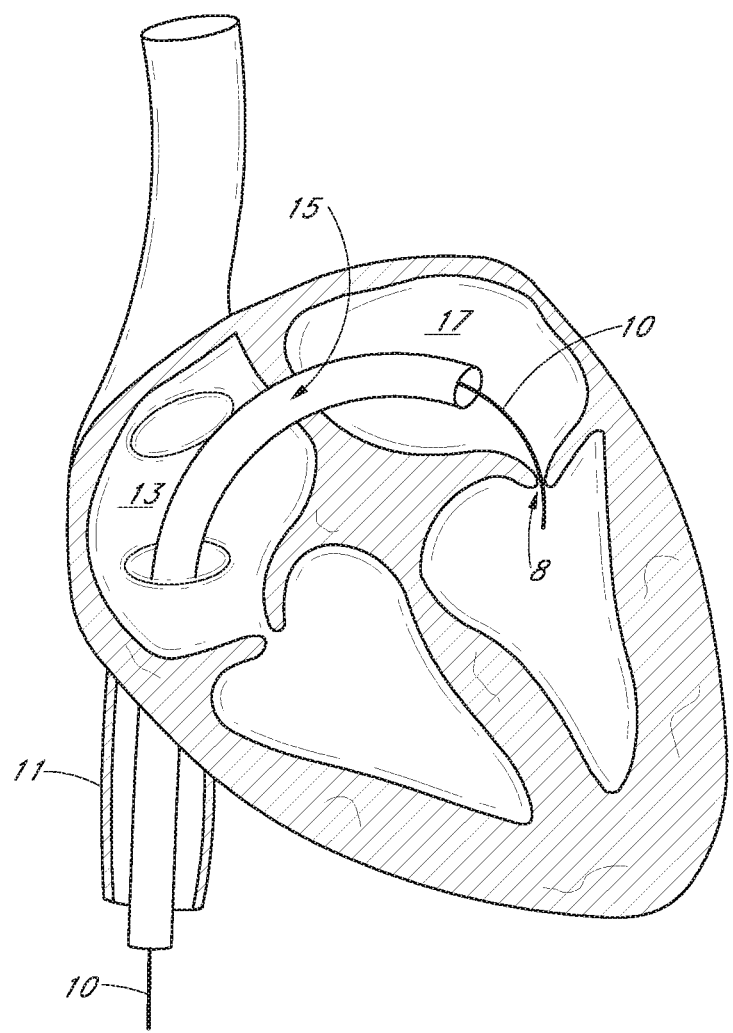
FIG. 2B illustrates a method of providing access to an exemplifying use environment, such as a mitral valve of a heart.

FIG. 2B illustrates another exemplifying access route for suturing a mitral valve 8. As depicted by FIG. 2B, a guide wire 10 is advanced through the inferior vena cava 11 into the right atrium 13 of the heart and through a puncture or an incision near the atrial septum 15 and into the left atrium 17. The guide wire 10 can then be further positioned at or near the mitral valve 8. With the guide wire 10 in place, the physician can insert a sheath 12 to the left atrium 17. The sheath 12 can be placed at or near the mitral valve 8. The suturing device can then be advanced through the lumen of the sheath 12. In an alternative embodiment, the suturing device can be advanced over the guide wire 10 and positioned at or near the mitral valve 8 without the needs to insert an introducer sheath 12. In some embodiments, for any of the access routes discussed above, the device can be inserted without a guide wire.

Embodiments of Suturing Devices and Methods, Such as for Suturing Valve Leaflets FIGS. 3-9 illustrate an embodiment of a suturing device 100 that can be used to suture an anatomical valve, such as a heart valve. While the device 100 will be described with reference to suturing an anatomical valve, such as a heart valve, the device 100 could be used to suture other biological tissue and implantable devices and materials. The suturing device 100 can comprise a distal assembly 102, one or more suture clasp arms 104 (also labeled as 104A, 104B), and one or more suture catch mechanisms 106 (referred to in some embodiments as "needles"). Each arm can have one or more suture portions 130 attached to it. The suturing device 100 can further comprise an elongate body (not shown) to facilitate manipulation of the suture clasp arm(s) 104 and the suture catch mechanism(s) 106 from a remote location. For example, the elongate body can comprise one or more lumens to accommodate a length of suture, or one or more actuator rods for manipulating the suture clasp arm(s) 104 and the suture catch mechanism(s) 106, or both. In some embodiments, the distal assembly 102 can comprise a portion of the elongate body.

Figure 6:
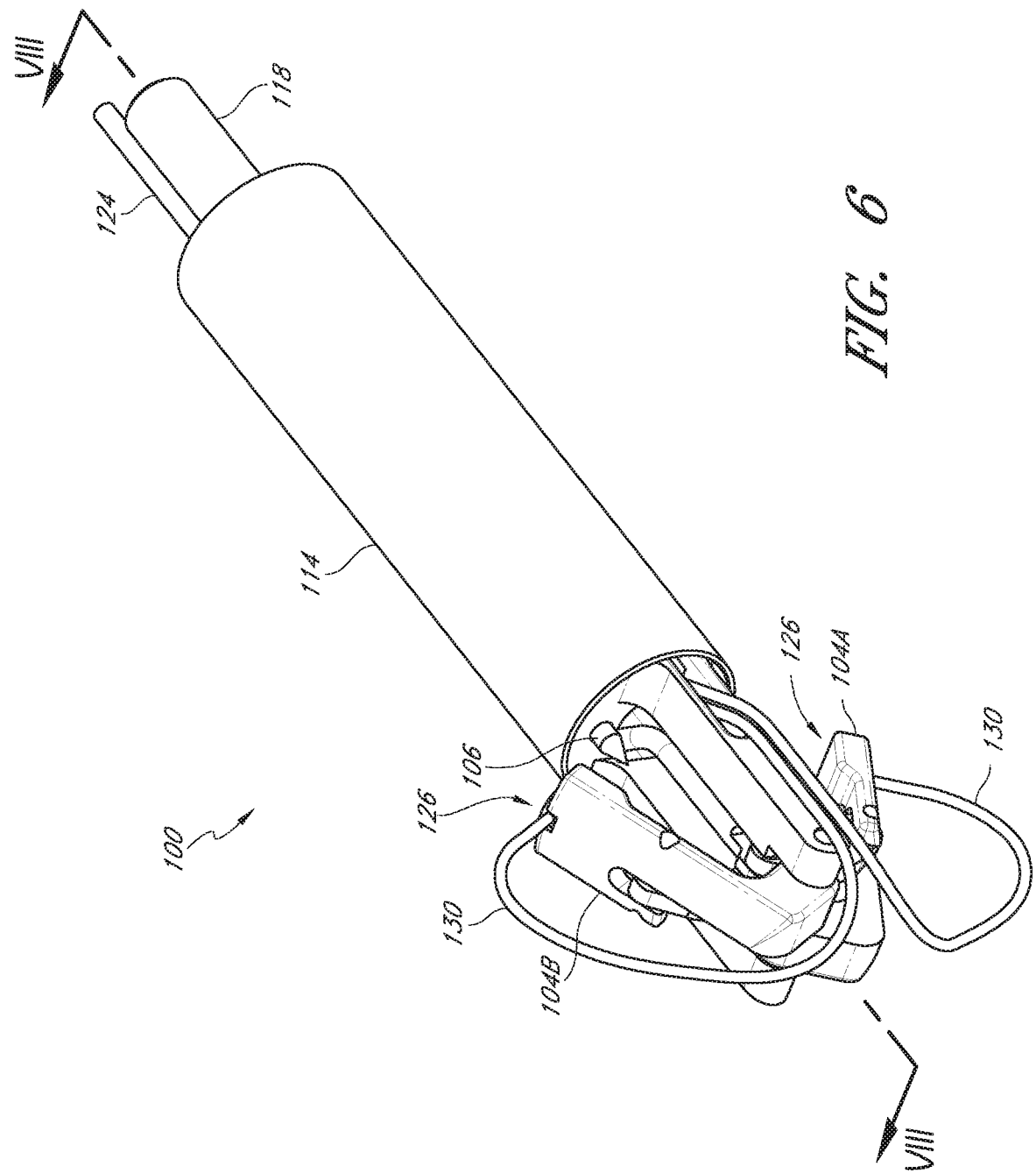
FIG. 6 is a perspective view of the embodiment of FIG. 3, as in FIG. 5, showing a casing attached to the device.
Figure 7A:
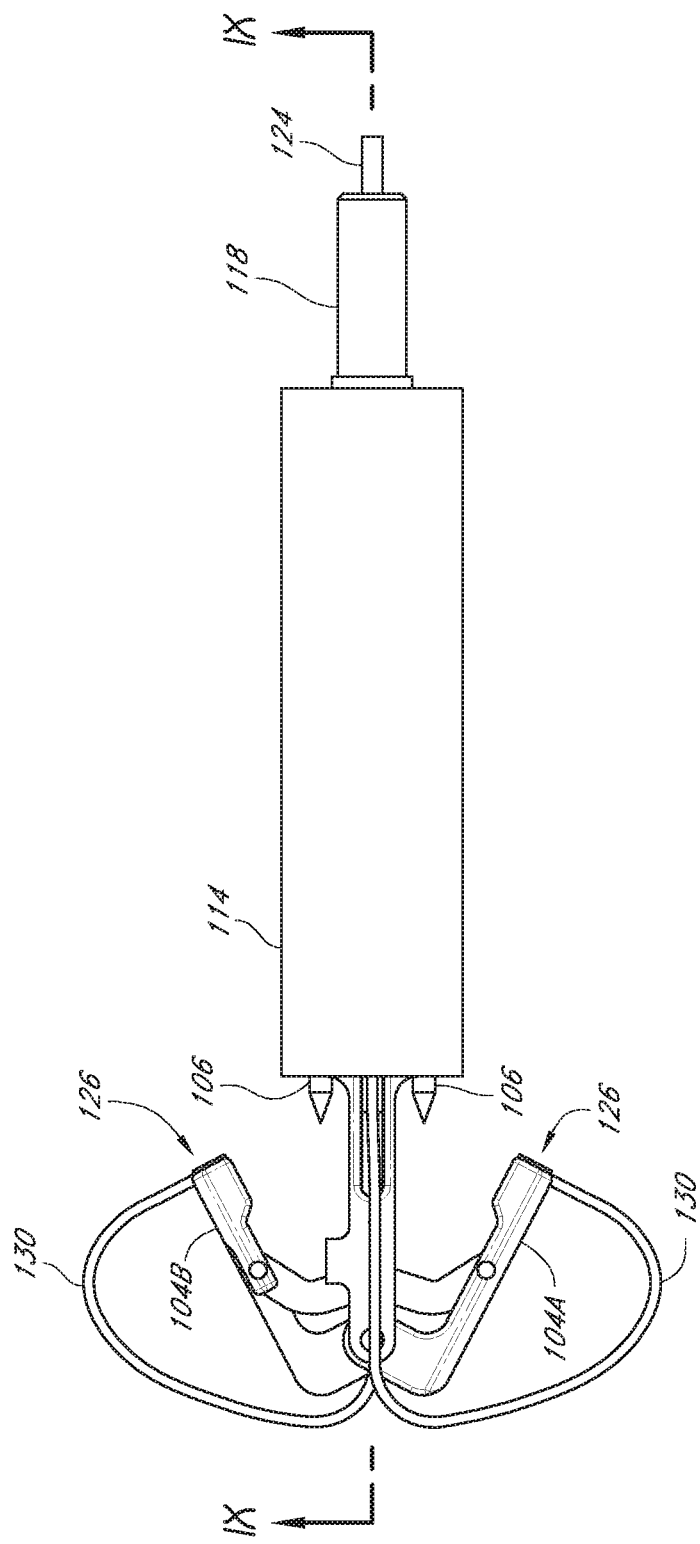
FIG. 7A is a plan view of the embodiment of FIG. 3, with the suture clasp arms in an extended position.
Figure 8:
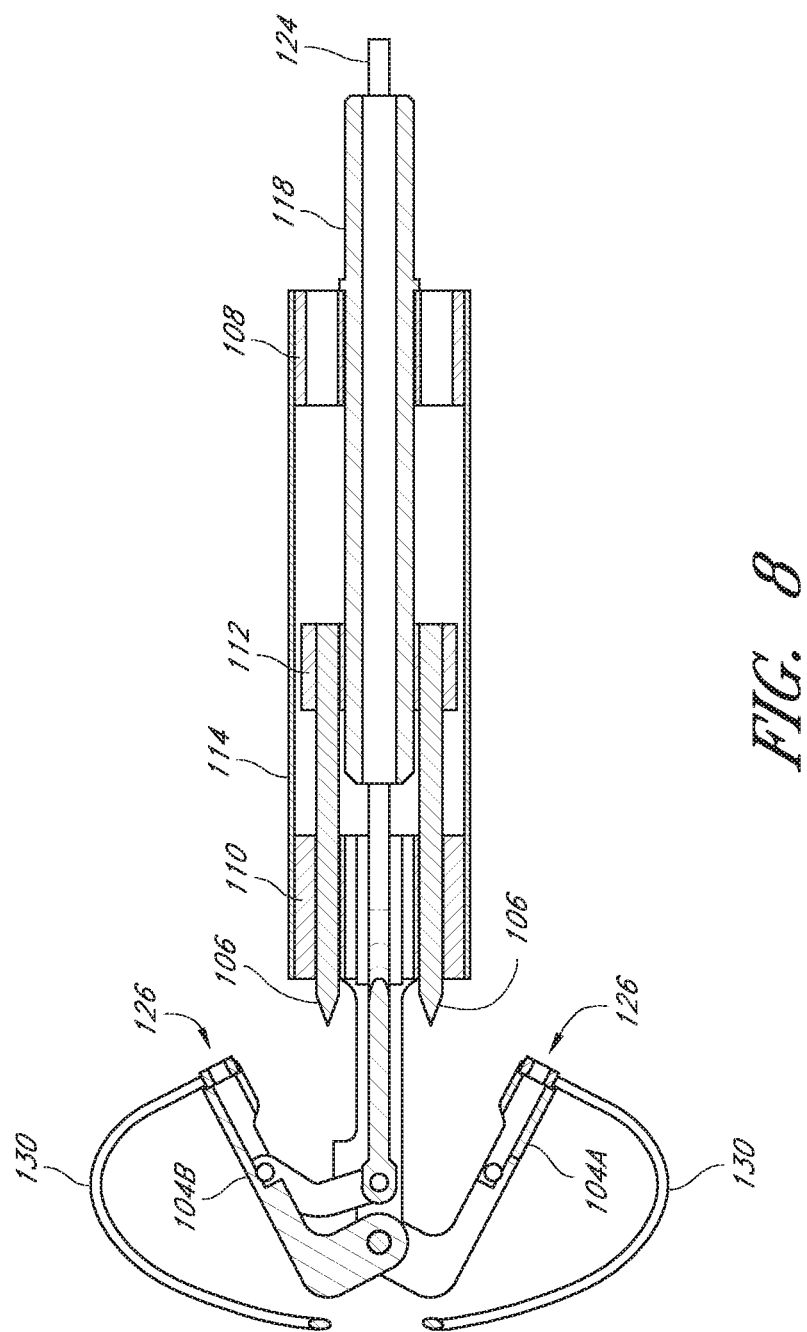
FIG. 8 is a cross-sectional view of the embodiment of FIG. 3, along a line VIII-VIII in FIG. 6.
Figure 9:
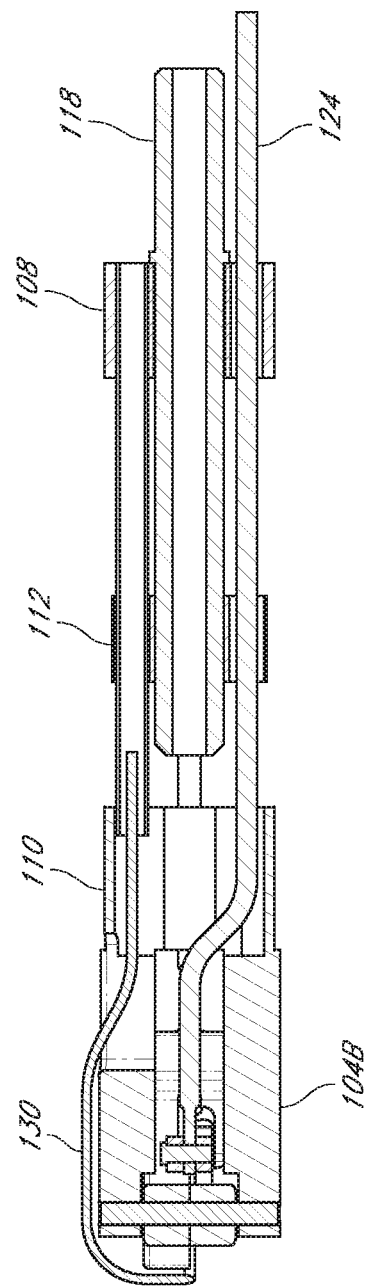
FIG. 9 is a cross-sectional view of the embodiment of FIG. 3, along a line IX-IX in FIG. 7A.

The distal assembly 102 can comprise a proximal mount 108, distal mount 110, a hub 112, and a casing 114 (FIG. 6). The proximal mount 108 can be fixedly connected to the distal mount 110 by the casing 114. The hub 112 can be positioned within the casing 114 for sliding movement between the proximal mount 108 and the distal mount 110.

Figure 5:
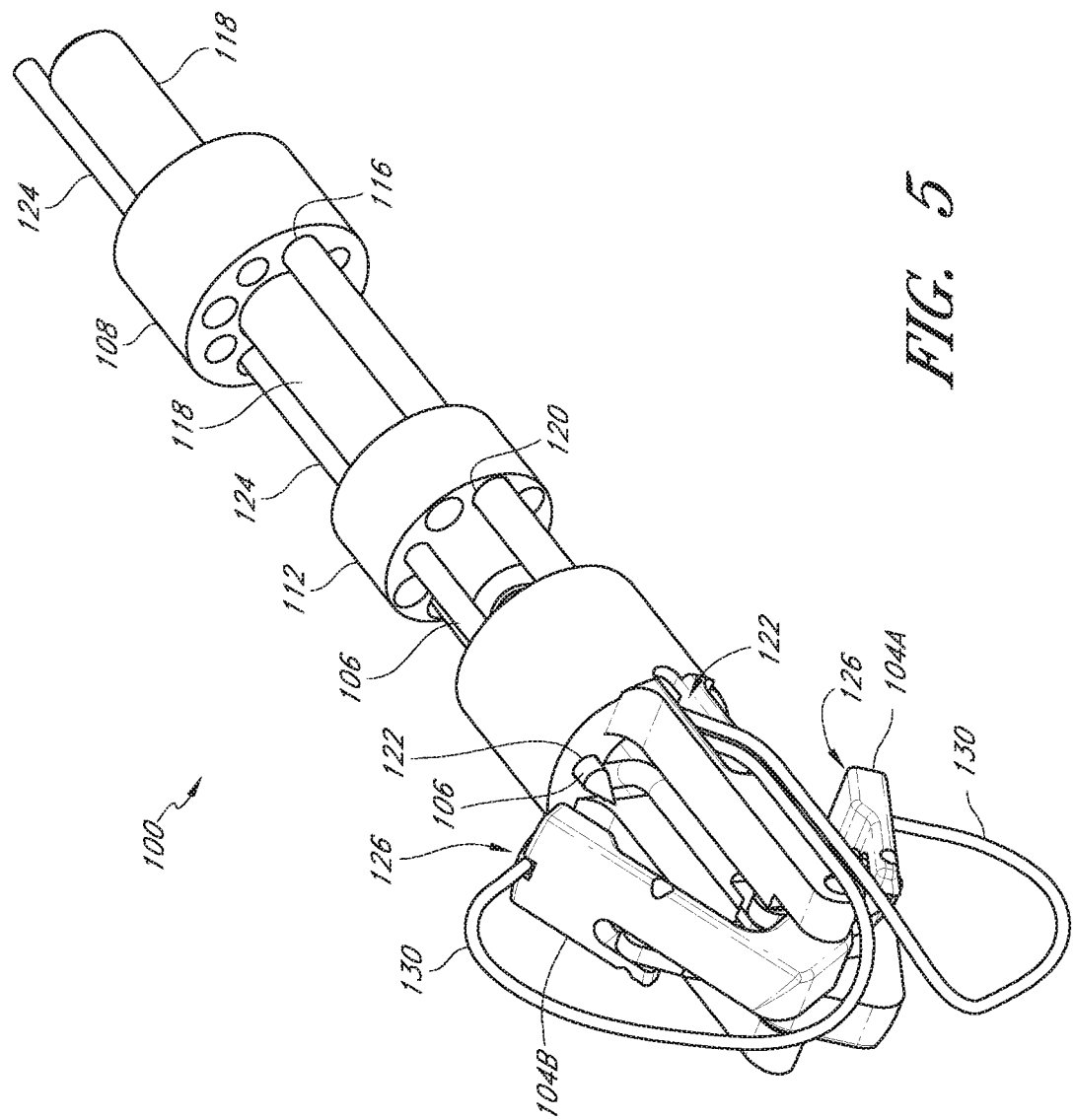
FIG. 5 is a perspective view of the embodiment of FIG. 3, with the suture clasp arms in an extended position and the suture catch mechanisms in a partially advanced position.

The proximal mount 108 can be connected to the elongate body (not shown). Alternatively, a distal end of the elongate body can form or be integrally formed with the proximal mount 108. In some embodiments, the elongate body can comprise the casing 114. The proximal mount 108 can comprise one or more lumens 116, as shown in FIGS. 3 and 5.

The hub 112 can be fixedly connected to the suture catch mechanism(s) 106 and an actuator rod 118. The actuator rod 118 can move through a lumen 116 in the proximal mount 108. Accordingly, distal advancement of the actuator rod 118 causes distal advancement of the suture catch mechanism(s) 106. The hub 112 can comprise one or more lumens 120.

Figure 3:
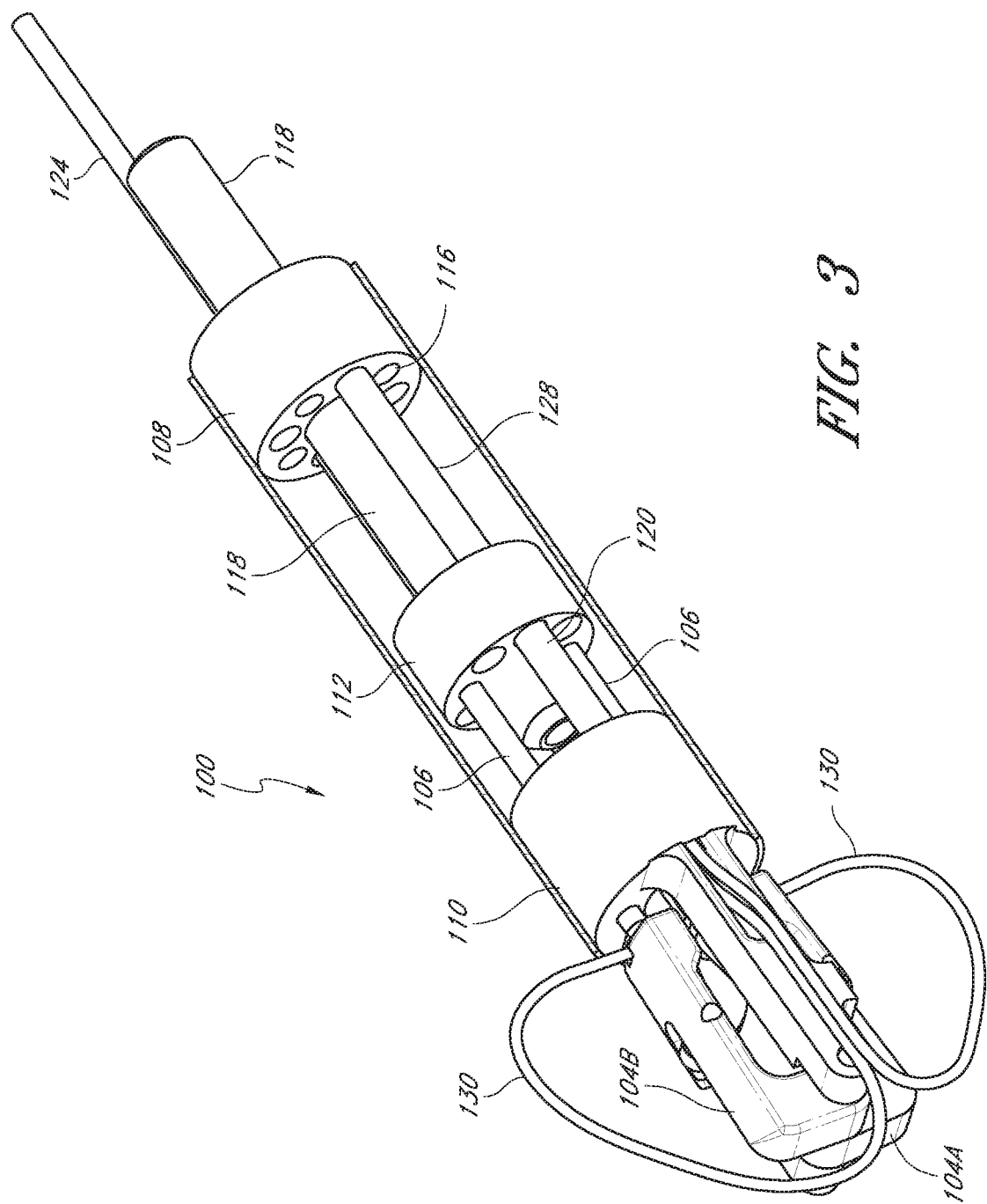
FIG. 3 is a perspective view of an embodiment of a suturing device with suture clasp arms in a retracted position and a casing shown in cross-section.
Figure 4:
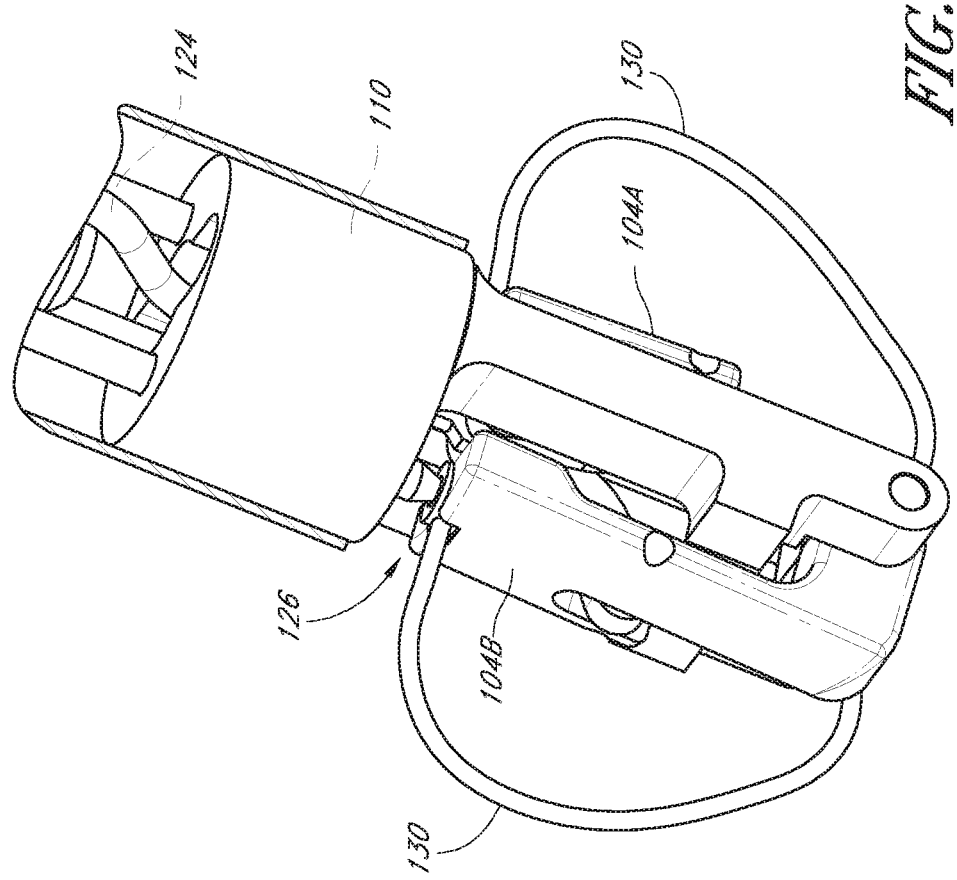
FIG. 4 is an enlarged perspective view of the embodiment of FIG. 3 with the casing shown in cross-section, showing suture catch mechanisms in a partially advanced position.

The suture clasp arm(s) 104 can be pivotally connected to the distal mount 110 such that the suture clasp arm(s) 104 can move between a retracted position, illustrated in FIGS. 3-4, and an extended position, illustrated in FIGS. 5-7A. Although the arms 104 of the device 100 that is illustrated in FIGS. 3-9 pivot about a distal end of the arms 104, the arms 104 can pivot about a proximal end of the arms 104 in other embodiments.

The suture clasp arm(s) 104 can be connected to an actuator rod 124, which can move through a lumen 116 in the proximal mount 108. The arm(s) 104, the distal mount 110, and the rod 124 can be connected such that distal movement of the rod 124 causes the arm(s) 104 extend and proximal movement of the rod 124 causes the arm(s) 104 to retract. In some embodiments, the arm(s) 104 can extend to a position that is substantially perpendicular to their fully-retracted position. In other embodiments, the arm(s) 104 can move less than 90° between the fully-retracted position and the fully-extended position.

The distal mount 110 can comprise one or more lumens 122 (FIG. 5) to allow movement of the suture catch mechanism(s) 106 through the distal mount 110. Additionally or alternatively, the one or more lumens 122 can accommodate a length of suture, the actuator rod 124, or both.

The suture clasp arm(s) 104 can have suture clasps 126 to releasably hold a suture portion 130. The suture catch mechanism(s) 106 can be advanced to engage the suture portion(s) 130 held by the suture clasp arms(s). Once the suture catch mechanism(s) 106 have engaged the suture end portion(s) 130, the suture catch mechanism(s) 106 can be retracted to pull the suture ends from the suture claps 126.

In some embodiments, the suture clasps 126 can be positioned on the suture clasp arm 104 such that the suture catch mechanism 106 retrieves the suture end portion 130 retained in the suture clasp 126 while the suture clasp arm 104 is at least partially retracted from its fully-extended position. In some embodiments, the suture clasps 126 can be positioned on the suture clasp arm 104 such that the suture catch mechanism 106 retrieves the suture end portion 130 retained in the suture clasp 126 while the suture clasp arm 104 is fully retracted. In some embodiments, the suture catch mechanism 106 can be advanced in a continuously longitudinal direction to engage the suture clasp 126 of the suture clasp arm 104 while the suture clasp arm is fully retracted. In some embodiments, the suture clasp 126 can be located on a proximally-facing side of a suture clasp arm 104 that pivots about a distal end of the suture clasp arm. In some embodiments, the suture clasp 126 can be located on a distally-facing side of a suture clasp arm 104 pivots about a proximal end of the suture clasp arm.

In some embodiments, the suture clasp arm 104 can be configured to receive a tissue-piercing portion of the corresponding suture catch mechanism 106. For example, in some embodiments, when the suture catch mechanism 106 is fully advanced, the tissue-piercing portion can be fully received with the corresponding suture clasp arm 104. In some embodiments, the suture clasp arm 104 can receive the tissue-piercing portion of the suture catch mechanism 106 when the arm is at least partially closed. In some embodiments, suture clasp arm 104 can receive the tissue-piercing portion of the suture catch mechanism 106 when the arm is fully retracted.

In some embodiments, the device 100 can comprise a recess 140 between the suture clasp arm 104 and the distal mount 110, or other component of the distal assembly 102, when the suture clasp arm 104 is fully retracted, as illustrated in FIG. 7B. In some embodiments, a tissue portion, such as a valve leaflet, can be received with the recess 140 with the suture clasp arm 104 fully retracted and without damaging the tissue portion. In some embodiments, the tissue portion can be held in the recess 140 by the suture clasp arm 104 while the suture clasp arm is fully retracted. In some embodiments, the tissue portion can be held in the recess 140 by the suture clasp arm 104 while the suture clasp arm is at least partially retracted.

In some embodiments, the recess 140 can have a size and shape to receive a leaflet of a valve between the elongate body and the arm when the arm is at least partially retracted without damaging the leaflet. In some embodiments, the recess 140 can have a size and shape to receive a leaflet of a valve between the elongate body and the arm when the arm is fully retracted without damaging the leaflet. In some embodiments, the recess 140 can have a size and shape to retain the leaflet between the elongate body and the arm when the arm is at least partially retracted without damaging the leaflet. In some embodiments, the recess 140 can have a size and shape to retain the leaflet between the elongate body and the arm when the arm is fully retracted without damaging the leaflet.

Figure 11:
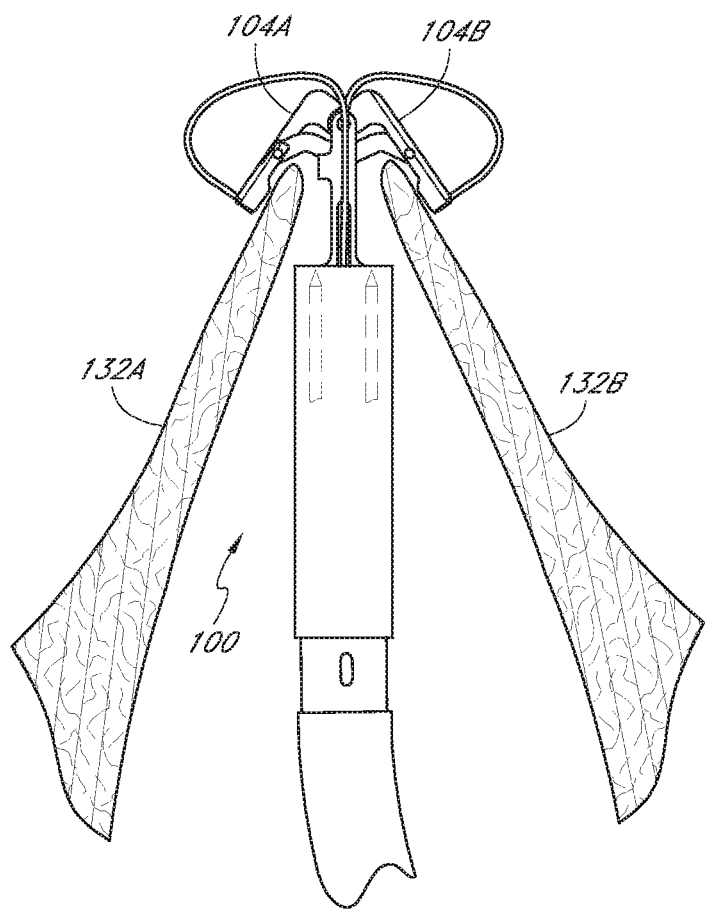
FIG. 11 is a schematic representation as in FIG. 10 with suture clasp arms positioned around first and second leaflets of the valve.

In some embodiments, the device 100 can be manipulated with the suture clasp arm(s) 104 in the extended position to place a tissue portion, such as a leaflet of a valve, between the suture clasp arm 104 and the distal mount 110, as shown, for example, in FIG. 11. In some embodiments, the suture clasp arm 104 can be at least partially closed about the tissue portion. In some embodiments, the suture clasp arm 104 can be fully closed about the tissue portion. In some embodiments, the suture clasp arm 104 can be at least partially retracted to securely hold the tissue portion between the suture clasp arm 104 and the distal mount 110. In some embodiments, the suture clasp arm 104 can be moved to the retracted position to securely hold the tissue portion between the suture clasp arm 104 and the distal mount 110, as shown, for example, in FIG. 12. In some embodiments, the tissue portion is not damaged by closing the suture clasp arm 104 about the issue portion or holding the tissue portion between the suture clasp arm 104 and the distal mount 110.

Figure 13:
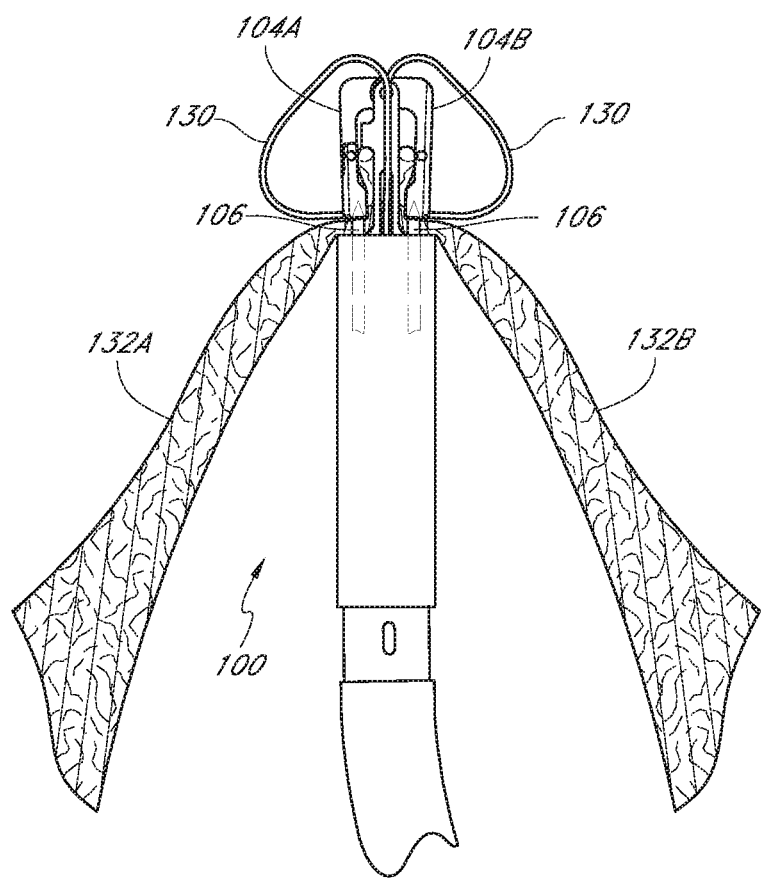
FIG. 13 is a schematic representation as in FIG. 12 showing suture catch mechanisms engaging the suture clasp arms.

With the tissue portion held between the arm 104 and the distal mount 110, the corresponding suture catch mechanism 106 can be advanced to engage the suture portion 130 held by the suture clasp 126 of the arm 104, as shown, for example, in FIG. 13. The suture portion 130 can then be drawn through the tissue portion by the suture catch mechanism 106, as shown, for example, in FIG. 14. In other embodiments, the suture catch mechanism(s) 106 can be advanced toward the suture clasp arm(s) 104 and retrieve the suture ends from the suture clasps 126 when the arm(s) 104 are in the extended position. In some embodiments, the suture catch mechanism can be a needle.

In some embodiments, the distal assembly 102 can comprise a tube or conduit 128 to accommodate a suture and prevent damage to the suture by any component of the device 100. In some embodiments, the conduit 128 extends through a lumen 116 in the proximal mount 108, a lumen 120 in the distal mount 110, and a lumen 122 in the hub 112.

Further details regarding devices, structures, and methods that may be incorporated with the above embodiments are provided in U.S. Pat. No. 7,090,686 and U.S Patent Application Publication No. 2008/0269786, published on Oct. 30, 2008, all of which are hereby incorporated by reference herein in their entireties and are to be included as part of this specification. For example, in some embodiments having a plurality of arms 106 and a plurality of suture catch mechanisms 106, each arm 104 and each suture catch mechanism 106 of the device 100 can be independently actuated to move individually between the retracted position and the extended position.

Figure 10:
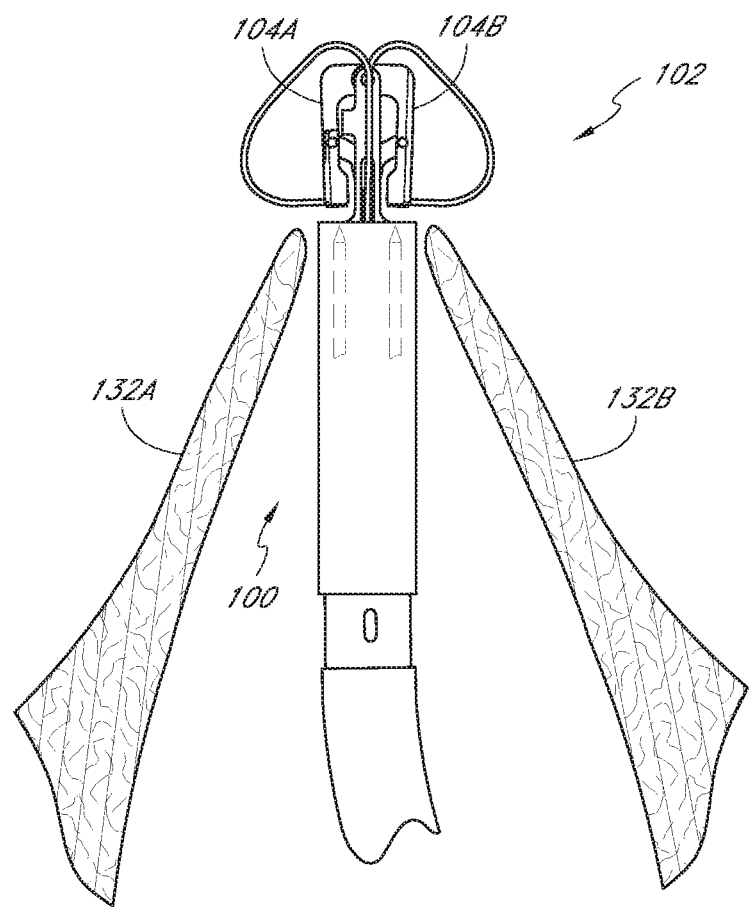
FIG. 10 is a schematic representation an embodiment of a suturing device positioned in a passage through a valve.

FIGS. 10-15 illustrate a method for suturing an anatomical valve according to one embodiment. For example, the method can be used to perform edge-to-edge repair of a mitral valve. The distal end of a suturing device 100 can be positioned between leaflets 132 of a valve, as shown in FIG. 10. The device 100 can be advanced through the vasculature to the desired position using any of the access routes discussed above, and with or without a guide wire. For example, the device 100 can be advanced through the inferior vena cava into right atrium and through the septum and positioned in the passage through the mitral valve 8 (FIG. 2).

The suturing device 100 can be advanced to allow suture clasp arms 104 to extend from the distal assembly 102. The suture clasp arms 104 can then be extended and the device 100 can be retracted until the suture clasp arms 104 extend around a first leaflet 132A and a second leaflet 132B of the valve, as shown in FIG. 11.

Figure 12:
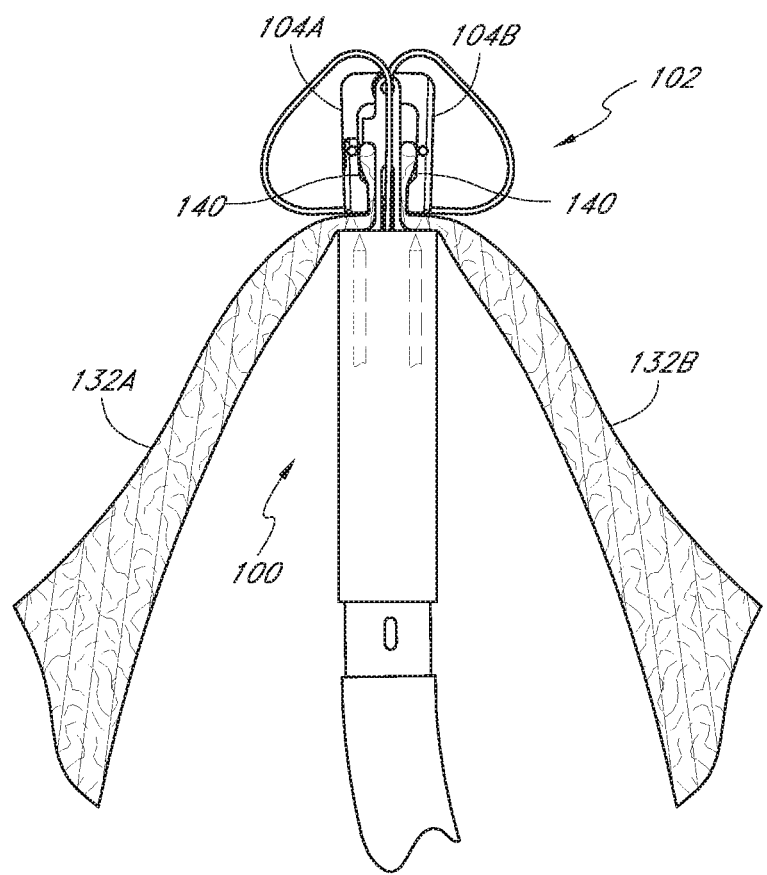
FIG. 12 is a schematic representation as in FIG. 11 with suture clasp arms retracted.

Once the suture clasp arms 104 have been properly positioned around the first and second leaflets 132, the suture clasp arms 104 can be retracted to trap portions of the first and second leaflets 132, for example between the suture clasp arms 104 and the distal mount 110 in the recess 140, as illustrated in FIG. 12.

With the first and second leaflets 132 trapped the suture catch mechanisms 106 can be advanced from the distal assembly 102 to penetrate the first and second leaflets 132 and engage the suture portions 130 held by the suture clasp arms 104, as illustrated in FIG. 13.

Figure 14:
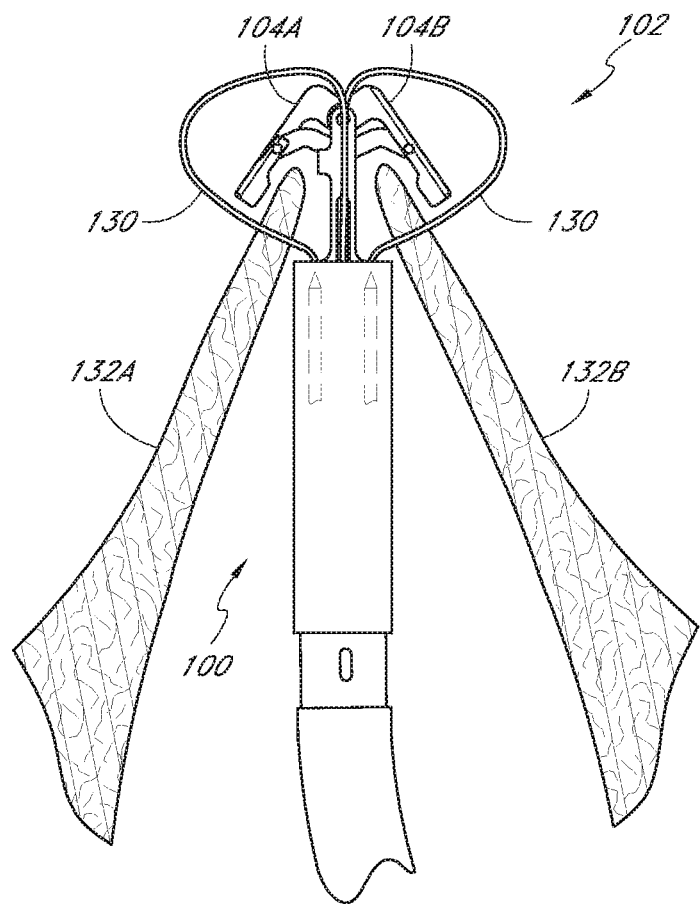
FIG. 14 is a schematic representation as in FIG. 13 showing the suture catch mechanisms and suture portions retracted through the first and second leaflets.

After the suture portions 130 have been engaged, the suture catch mechanisms 106 and engaged suture portions 130 are then retracted through the tissue of the first and second leaflets 132 into the distal assembly 102, as shown in FIG. 14. The suture clasp arms 104 can be extended to release the first and second leaflets 132. After the first and second leaflets have been released, the device 100 can be advanced slightly so that the suture clasp arm 104 can be moved to the retracted position without pinching the leaflets 132. The first suturing device 100 can then be withdrawn from the valve.

Figure 15:
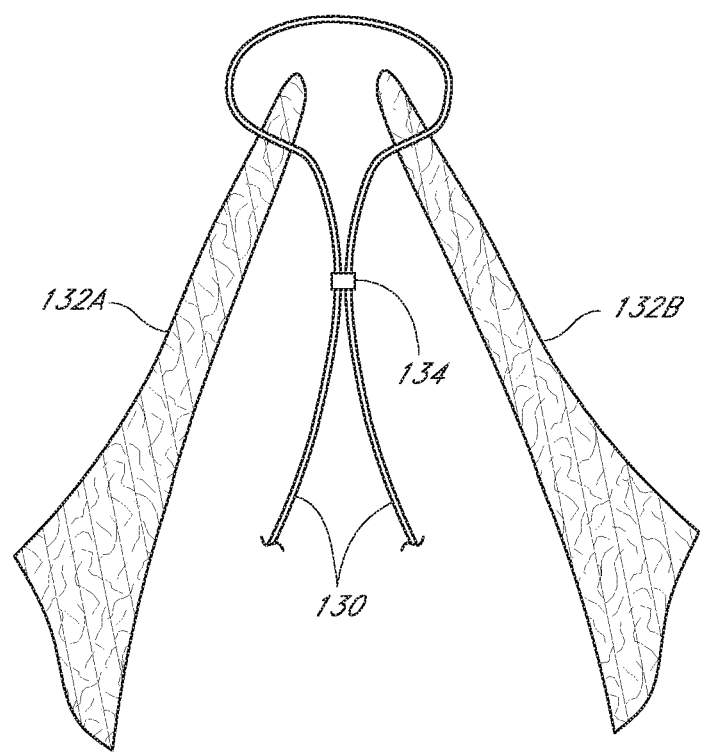
FIG. 15 is a schematic representation as in FIG. 14 showing the suture portions extending through the first and second leaflets and being joined by a knot.

As shown in FIG. 15, after the suturing device 100 has been withdrawn, the suture portions 130 extend from the leaflets 132. The suture portions 130 can be pulled to draw the first leaflet 132A and the second leaflet 132B towards one another. The suture portions 130 can then be secured together to limit movement of the leaflets 132A, 132B relative to one another, as illustrated in FIG. 15 for example. In some embodiments, the sutures 130 can hold a portion of the leaflets 132A, 132B in contact with one another. In other embodiments, the sutures 130 merely hold the leaflets 132A, 132B in closer proximity to one another than they had previously been. The suture portions 130 can be secured together by tying a knot 134 according to any known method or by applying a knot 134, such as described in U.S. Patent Publication No. 2007/0010829 A1, published Jan. 11, 2007, which is hereby incorporated by reference herein in its entirety and is considered a part of this specification. The suture portions 130 can be secured together exterior to the body or within the body. Any excess portion of sutures 130 can be trimmed. In some embodiments, one or more pledgets can be attached to the suture portions 130, either before or after the knot is tied or applied, and located distal and/or proximal to the knot 134.

Figure 16:
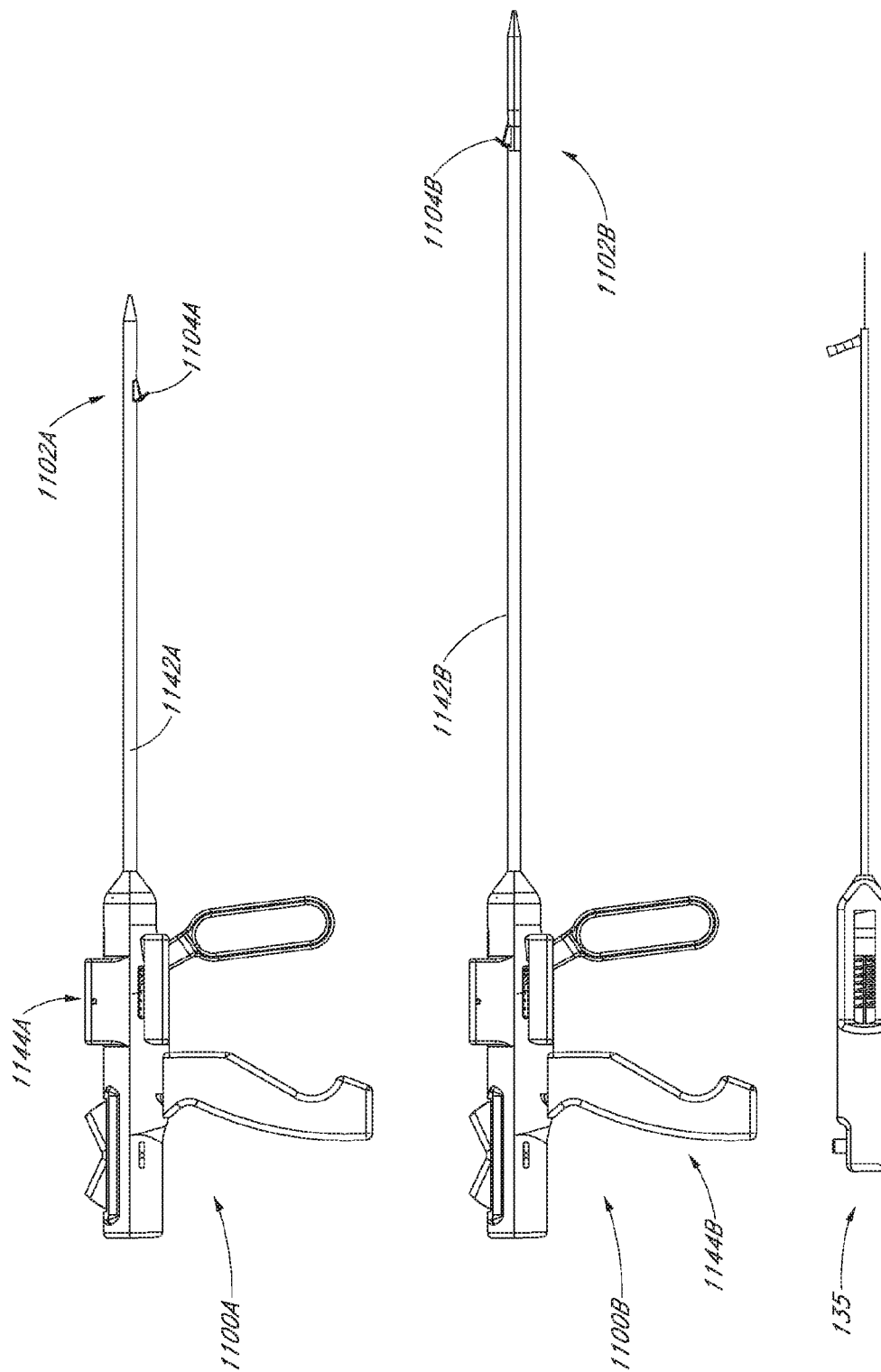
FIG. 16 is a plan view of an embodiment of a suturing device system with two suturing devices and a suture joining device.

FIG. 16 illustrates an embodiment of a system of devices that can be used to suture an anatomical valve, such as a heart valve. In some embodiments, the device can be included in a system of devices used to suture an anatomical valve, such as the system illustrated in FIG. 16. The system of FIG. 16 includes two suturing devices 1100A,B, each of which can comprise a distal assembly 1102A,B, a single suture clasp arm 1104A,B, and a single suture catch mechanism 1106A,B (shown in FIGS. 21 and 25). Further description herein of either suturing device 1100A or 1100B may omit the letter A or B following the reference number, as it will be appreciated that the components described can refer to either device.

The devices can be substantially similar but with at least the exception that the single suture clasp arm 1104 of each suturing device is oriented generally opposite that of the other suturing device with respect to their handles 1144. As illustrated, the devices have elongate bodies of differing lengths, but in other embodiments the elongate bodies can be substantially the same length. The system can also include a suture joining device 135, which can be used to apply a knot to two or more suture ends or otherwise join two or more suture ends. Further details regarding the device for joining sutures are provided in U.S. Patent Application Publication No. 2011/0190793, published on Aug. 4, 2011, which is hereby incorporated by reference herein in its entirety and should be considered as part of this specification. Additionally, description of a device for joining sutures can be found below, and with respect to FIGS. 117-119.

The suturing devices 1100A,B can comprise an elongate body 1142 to facilitate manipulation of the suture clasp arm 1104 and the suture catch mechanism (not visible) from a remote location. For example, the elongate body can comprise one or more lumens to accommodate a length of suture, or one or more actuator rods for manipulating the suture clasp arm 1104 and the suture catch mechanism, or both.

Figure 17:
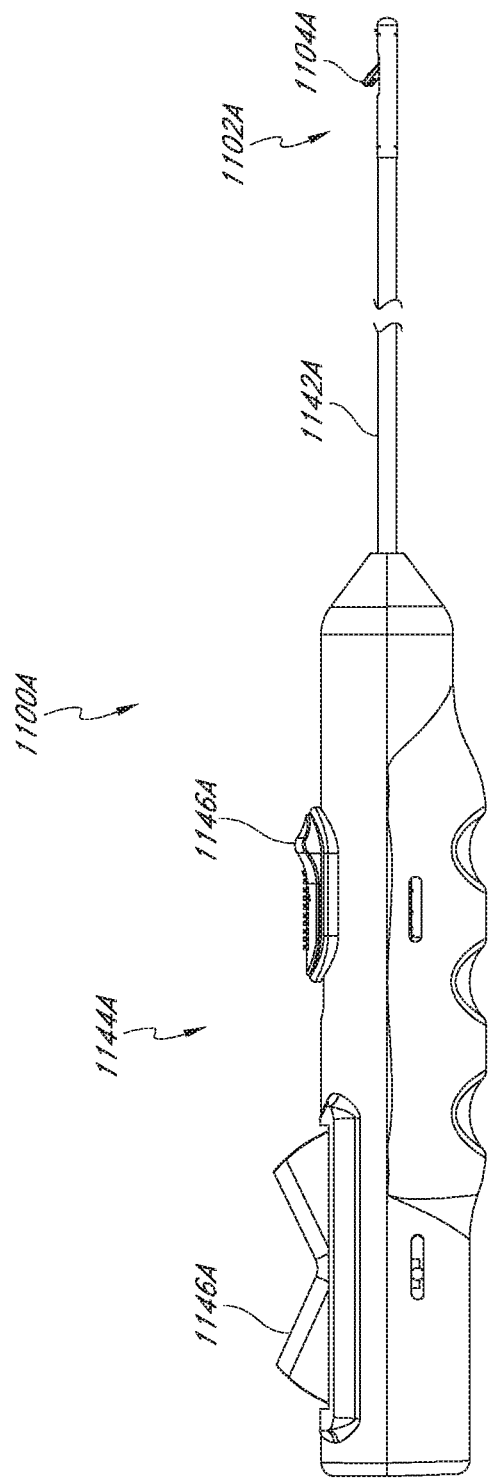
FIG. 17 is a plan view of an embodiment of a suturing device with a suture clasp arm in an extended position.

The suturing devices 1100A,B can comprise a handle 1144 with one or more actuators and/or pulls 1146 for moving the suture clasp arm 1104 and the suture catch mechanism 1106. In various embodiments, the handle can be of different shapes and configures, such as the handles of FIG. 16, or the handle illustrated in FIG. 17. Further details regarding handles and associated components, including actuator rods, are provided in U.S Patent Application Publication No. 2008/0269786, published on Oct. 30, 2008, which is hereby incorporated by reference herein in its entirety and is considered a part of this specification.

Figure 18:
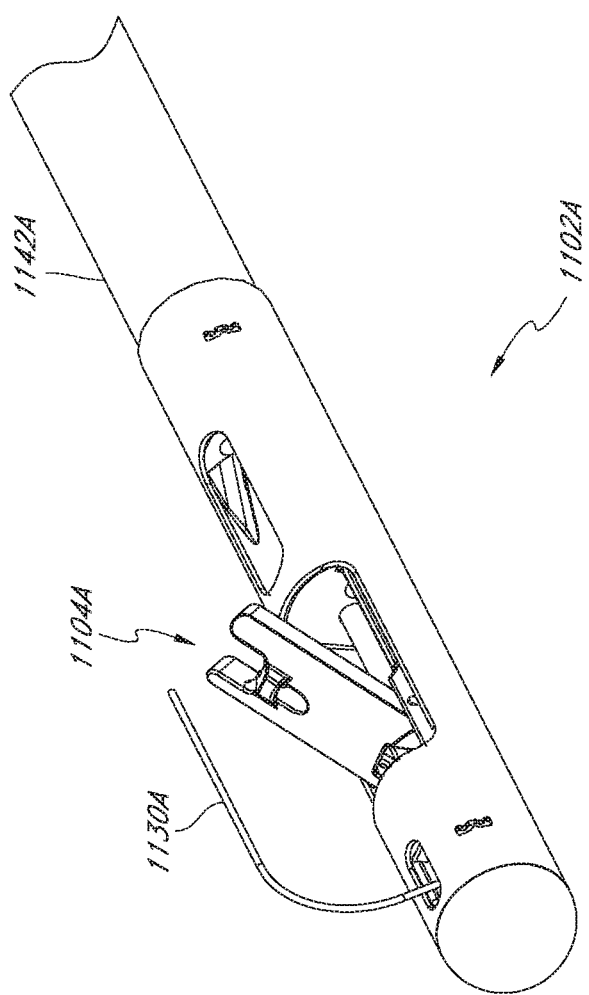
FIG. 18 is an enlarged perspective view of the distal end of the suturing device of FIG. 17 with the suture clasp arm in an extended position.

FIG. 18 illustrates a distal assembly 1102A of one of the suturing devices 1100A with the suture clasp arm 1104A in an extended position. In some embodiments, the suture clasp arm 1104A can pivot about an axis located at a distal end of the suture clasp arm 1104A to move the suture clasp arm 1104A from a retracted position to an extended position, as illustrated in FIG. 18. The same description can apply to the other suturing device 1100B.

FIGS. 19-27 illustrate a method according to one embodiment for suturing an anatomical valve, such as edge-to-edge repair of a mitral valve. Although the illustrated method involves two devices 1100A,B, each having a single suture clasp arm 1104 and a single suture catch mechanism 1106, the illustrated method can also be practiced using a single suturing device 1100 having more than one arm 1104 and more than one suture catch mechanism 1106, as described further below.

Figure 19:
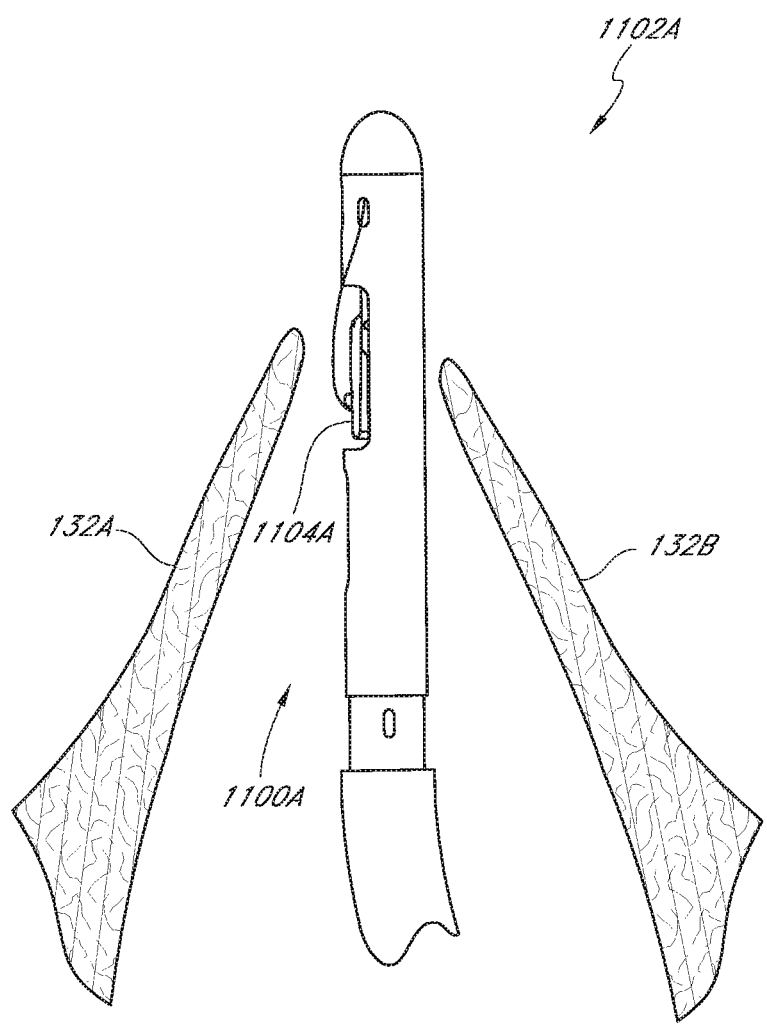
FIG. 19 is a schematic representation an embodiment of a first suturing device positioned in a passage through a valve.

The distal end of a first suturing device 1100A can be positioned between leaflets 132 of a valve, as shown in FIG. 19. The device 1100A can be advanced through the vasculature to the desired position using any of the access routes discussed above, and with or without a guide wire. For example, the device 1100A can be advanced through the inferior vena cava into right atrium and through the septum and positioned in the passage through the mitral valve 8 (FIG. 2).

Figure 20:
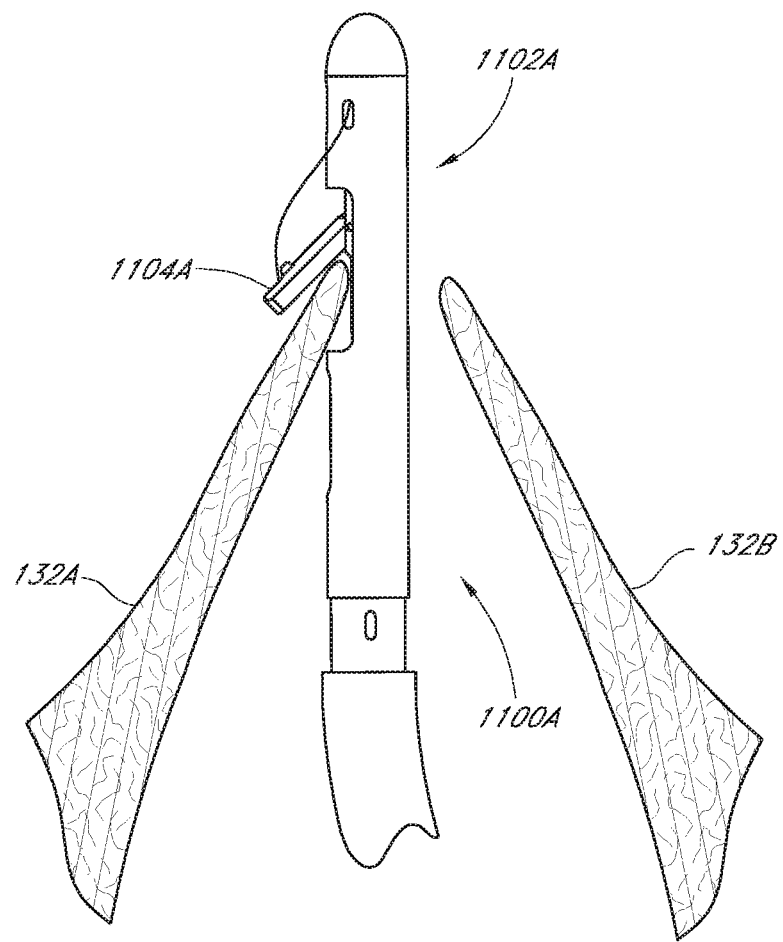
FIG. 20 is a schematic representation as in FIG. 19 with a suture clasp arm positioned around a first leaflet of the valve.

The suturing device 1100A can be advanced to allow a suture clasp arm 1104A to extend from the distal assembly 1102A. The suture clasp arm 1104A can then be extended and the device 1100A can be retracted until the suture clasp arm 1104A extends around a first leaflet 132A of the valve, as shown in FIG. 20.

Figure 21:
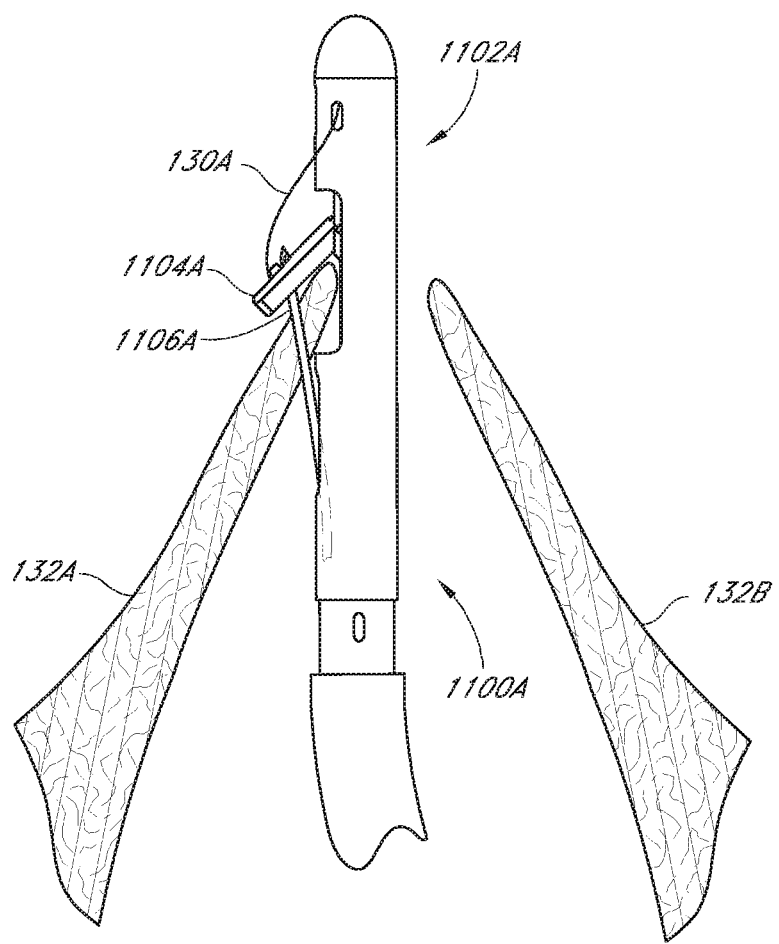
FIG. 21 is a schematic representation as in FIG. 20 showing a suture catch mechanism engaging the suture clasp arm.

Once the suture clasp arm 1104A has been properly positioned around the first leaflet 132A, the suture catch mechanism 1106A can be advanced from the distal assembly 1102A to penetrate the first leaflet 132A and engage the suture portion 130A held by the suture clasp arm 1104A, as illustrated in FIG. 21. In some embodiments, the suture clasp arm 1104A can be moved to the retracted position to securely hold a portion of the first leaflet 132A between the arm 1104A and the elongate body, for example, before the suture catch mechanism 1106A is advanced through the first leaflet 132A to engage the suture end, as described above.

Figure 22:
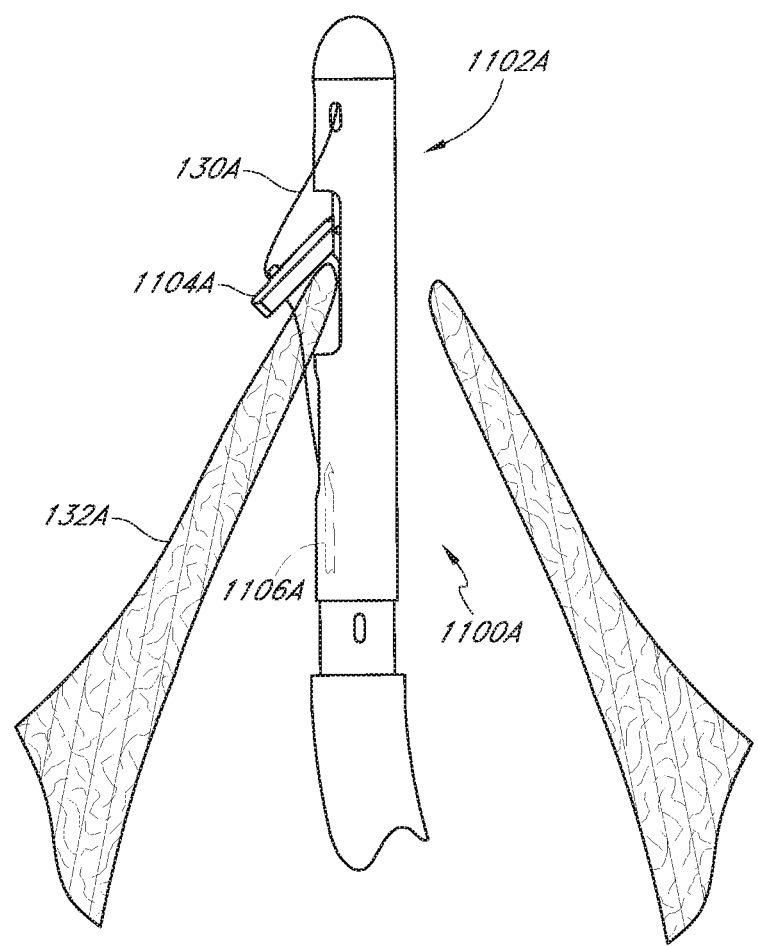
FIG. 22 is a schematic representation as in FIG. 21 showing the suture catch mechanism and a suture portion retracted through the first leaflet.

After the suture portion 130A has been engaged, the suture catch mechanism 1106A and engaged suture portion 130A are then retracted through the tissue of the first leaflet 132A into the distal assembly 1102A, as shown in FIG. 22. The device 1100A can be advanced slightly so that the suture clasp arm 1104A can be moved to the retracted position without pinching the first leaflet 132A. The first suturing device 1100A can then be withdrawn from the valve.

Figure 23:
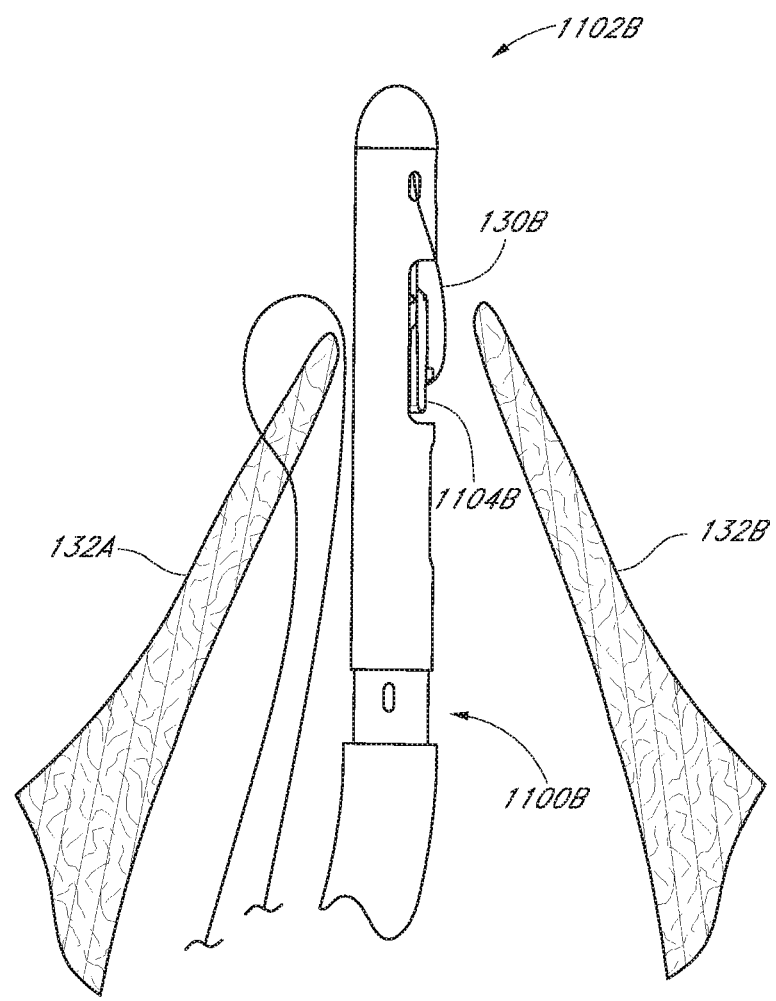
FIG. 23 is a schematic representation as in FIG. 22 showing a second suturing device positioned in the passage through the valve.
Figure 24:
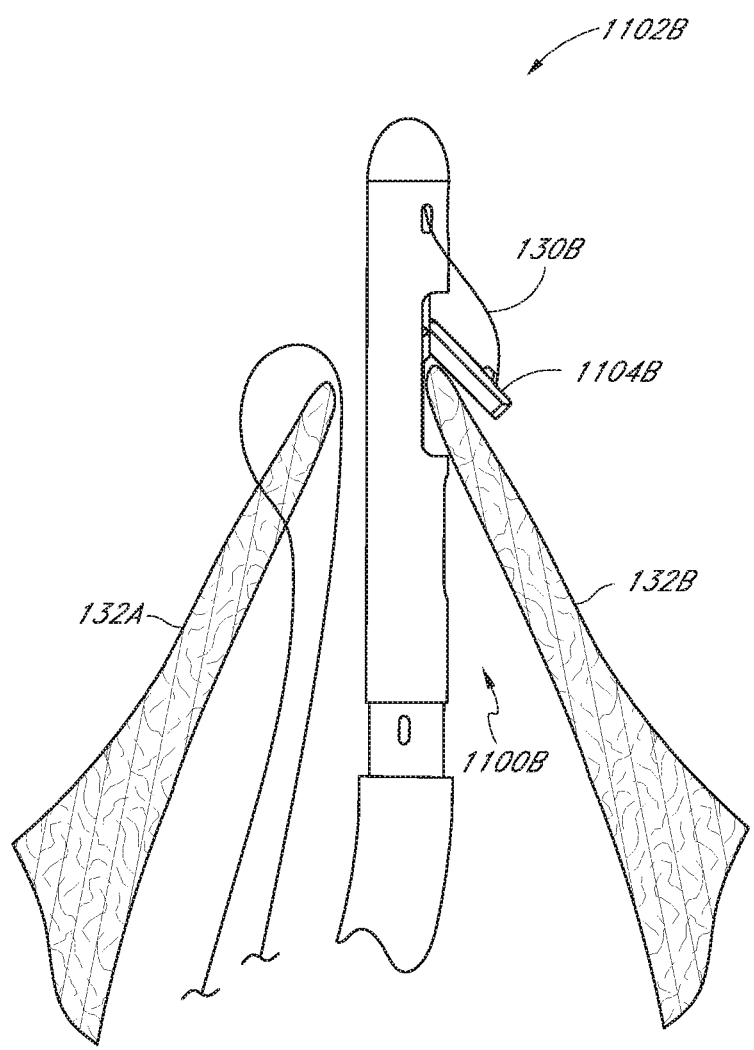
FIG. 24 is a schematic representation as in FIG. 23 with the suture clasp arm positioned around a second leaflet of the valve.

A second suturing device 1100B can then be advanced into the heart and positioned between the leaflets 132A, 132B of the valve, as shown in FIG. 23. The suture clasp arm 1104B can then be extended and the device 1100B can be advanced such that the suture clasp arm 1104B extends around the tip of the second leaflet 132B, as shown in FIG. 24.

Figure 25:
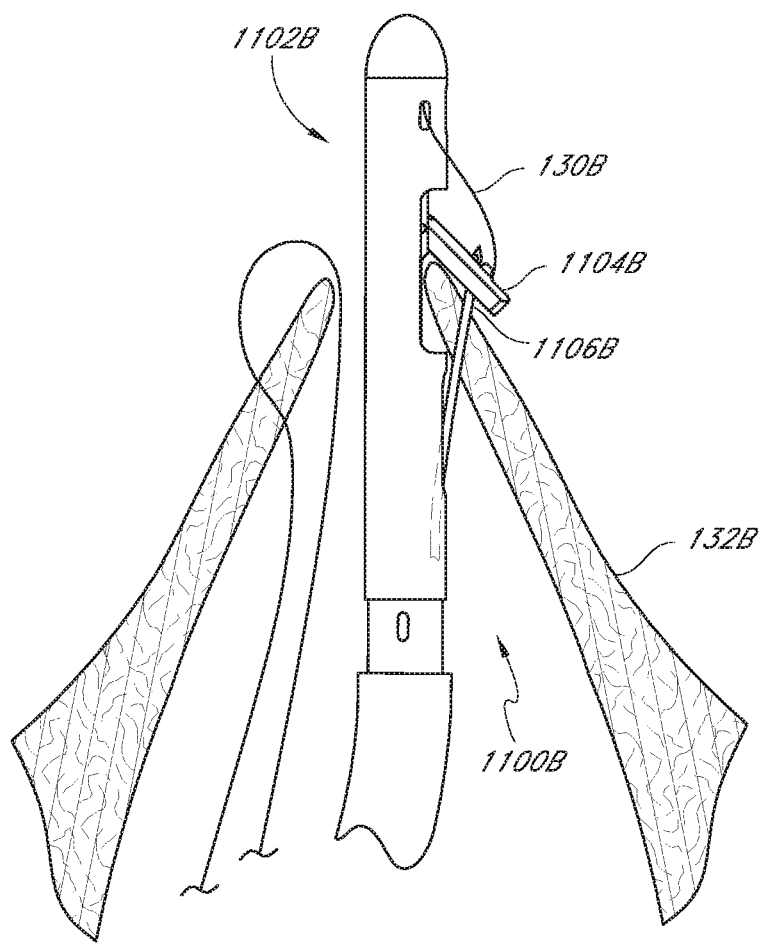
FIG. 25 is a schematic representation as in FIG. 24 showing a suture catch mechanism engaging the suture clasp arm.

Once the suture clasp arm 1104B has been properly positioned around the second leaflet 132B, the suture catch mechanism 1106B can be advanced from the distal assembly 1102B to penetrate the second leaflet 132B and engage the suture portion 130B held by the suture clasp arm 1104B, as illustrated in FIG. 25. As noted above with respect to the first leaflet 132A, in some embodiments, the suture clasp arm 1104B can be moved to the retracted position to securely hold a portion of the second leaflet 132B between the arm 1104B and the distal assembly 1102B before the suture catch mechanism 1106B is advanced through the second leaflet 132B to engage the suture portion 130B.

Figure 26:
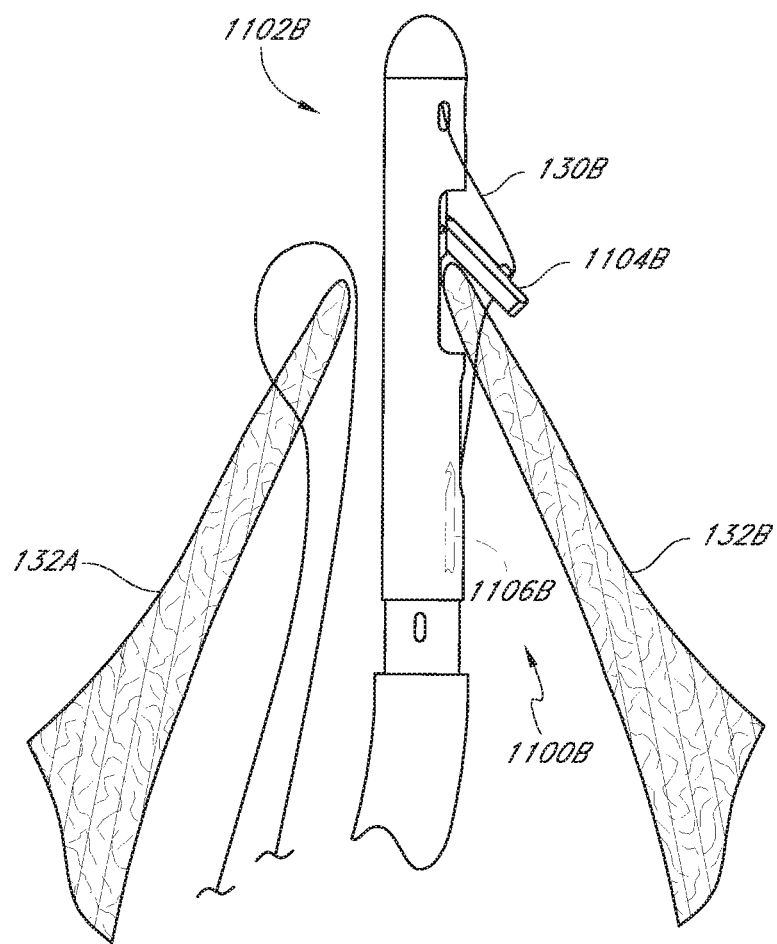
FIG. 26 is a schematic representation as in FIG. 25 showing the suture catch mechanism and a suture portion retracted through the second leaflet.

After the suture portion 130B has been engaged, the suture catch mechanism 1106B and engaged suture portion 130B are then retracted through the tissue of the second leaflet 132B into the distal assembly 1102B, as illustrated in FIG. 26. The suture clasp arm 1104B can then be closed after slightly advancing the device 1100B to avoid pinching the second leaflet 132B as the arm 1104B is closed. Once the suture clasp arm 1104B is closed, the suturing device 1100B can be withdrawn from the patient's heart.

Figure 27:
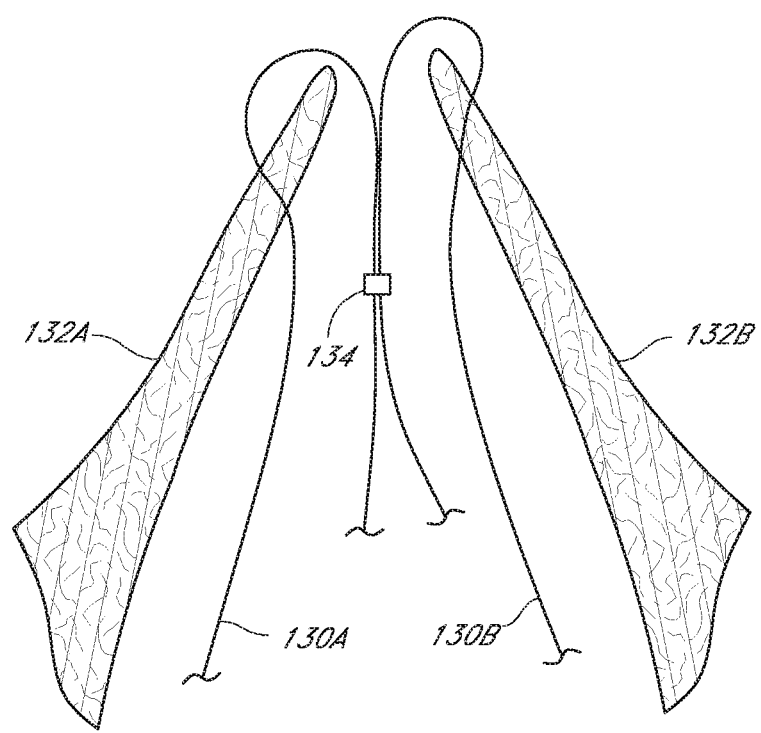
FIG. 27 is a schematic representation as in FIG. 26 showing the suture portions extending through the first leaflet and the second leaflet and being joined by a first knot.

As shown in FIG. 27, after the suturing device 1100B has been withdrawn, the suture portions 130A,B will extend proximally from the leaflets 132A, 132B. The suture portions 130A,B can then be secured together, as illustrated in FIG. 27, by tying a knot 134 according to any known method or by applying a knot 134. In some embodiments, one or more pledgets can be attached to the suture portions 130A,B, either before or after the knot is tied or applied, and located distal and/or proximal to the knot 134. The suture portions 130A,B can be secured together exterior to the body or within the body. Any excess portion of sutures 130 can be trimmed. The suture portions 130A,B can then be pulled to draw the first leaflet 132A and the second leaflet 132B towards one another. A second knot can then be tied or applied to the sutures 130 to limit movement of the leaflets 132A, 132B relative to one another, as described above. In some embodiments, the sutures 130 can hold a portion of the leaflets 132A, 132B in contact with one another. In other embodiments, the sutures 130 merely hold the leaflets 132A, 132B in closer proximity to one another than they had previously been.

When a device having a plurality of arms and a plurality of suture catch mechanisms is used, the device can be configured to place a single suture 130 through both the first leaflet 132A and the second leaflet 132B. The single suture 130 can be placed through the first and second leaflets 132 either simultaneously or sequentially. In some embodiments, the suture portions 130 can be pulled to draw the first leaflet 132A and the second leaflet 132B towards one another without applying a knot to the suture 130 beforehand. Accordingly, a single knot 134 can be applied to the suture 130 to hold the leaflets 132A, 132B in proximity to one another.

Figure 28:
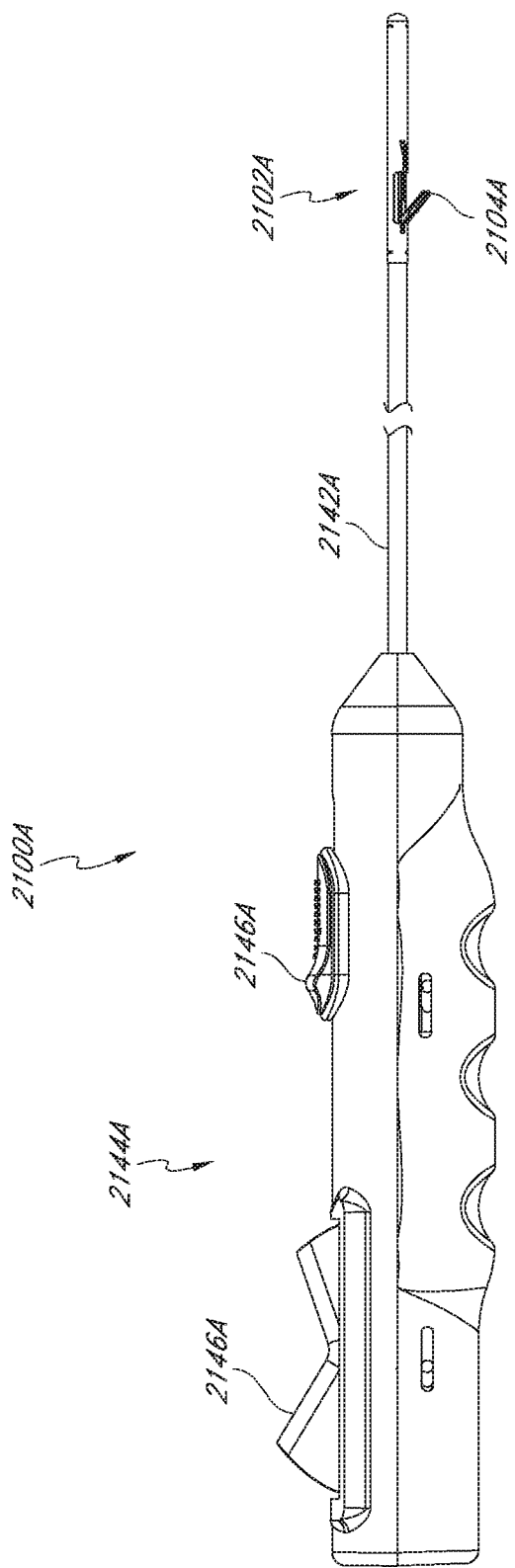
FIG. 28 is a plan view of an embodiment of a suturing device with a suture clasp arm in an extended position.
Figure 29:
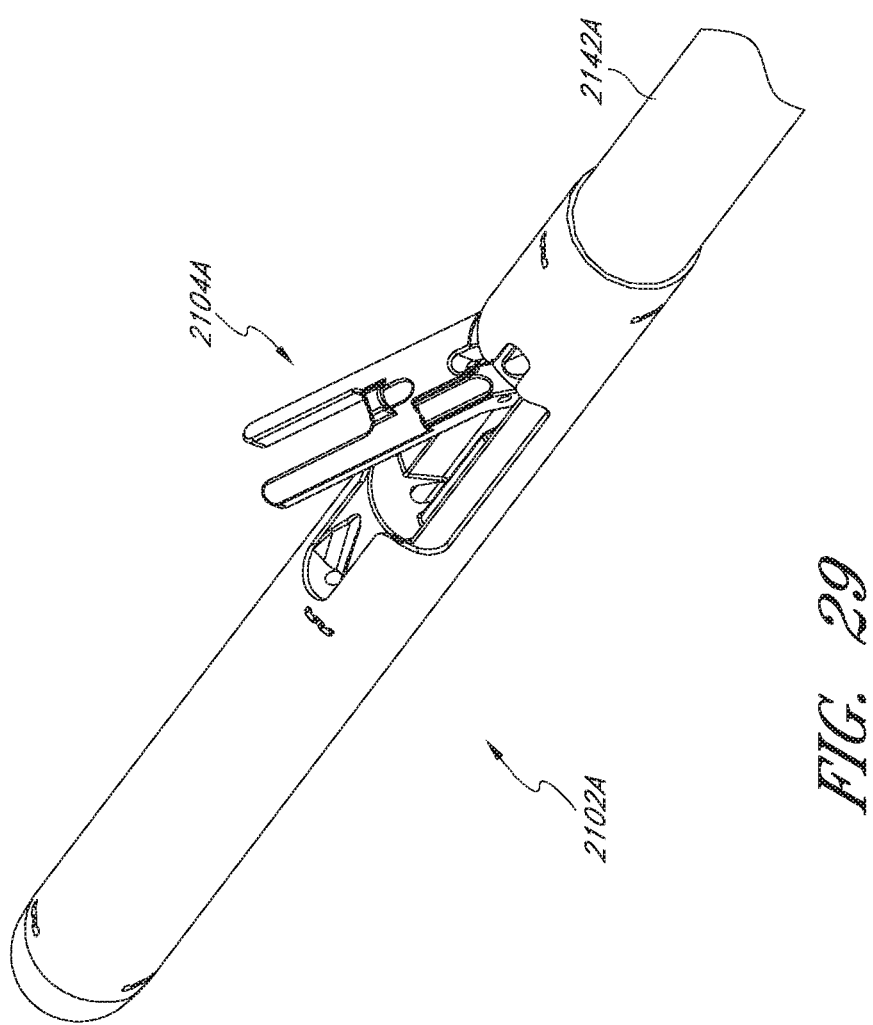
FIG. 29 is an enlarged perspective view of the distal end of the suturing device of FIG. 28 with the suture clasp arm in an extended position.

FIGS. 28 and 29 illustrate an embodiment of a suturing device 2100A that can be used to suture an anatomical valve, such as a heart valve. The suture device 2100A illustrated in FIGS. 28 and 29 is similar is some respects to the suturing devices illustrated and described above. For example, the suturing device 2100A of FIGS. 28 and 29, like the suturing device 1100 of FIGS. 17 and 18, can comprise a distal assembly 2102A, a single suture clasp arm 2104A, and a single suture catch mechanism 2106A.

As illustrated in FIGS. 28 and 29, the suturing device 2100A can comprise an elongate body 2142A to facilitate manipulation of the suture clasp arm 2104A and the suture catch mechanism 2106A from a remote location. For example, the elongate body can comprise one or more lumens to accommodate a length of suture, or one or more actuator rods for manipulating the suture clasp arm 2104A and the suture catch mechanism 2106A, or both. The suturing device 2100A can comprise a handle with one or more actuators and/or pulls 2146A for moving the suture clasp arm 2104A and the suture catch mechanism 2106A. Further details regarding handles and associated components, including actuator rods, are provided in U.S Patent Application Publication No. 2008/0269786, published on Oct. 30, 2008, which is hereby incorporated by reference herein in its entirety and is considered a part of this specification.

In some embodiments, the suture clasp arm 2104A can pivot about an axis located at a proximal end of the suture clasp arm 2104A when the suture clasp arm 2104A is in a retracted position, as illustrated in FIGS. 28 and 29.

A method of suturing anatomical valves, such as edge-to-edge repair of a mitral valve, is illustrated in FIGS. 30-37. Although the illustrated method involves two devices 2100A,B, each having a single suture clasp arm 2104A,B and a single suture catch mechanism 2106A,B, the illustrated method can also be practiced using a device 2100 having more than one arm 2104 and more than one suture catch mechanism 2106, as discussed above, for example.

Figure 30:
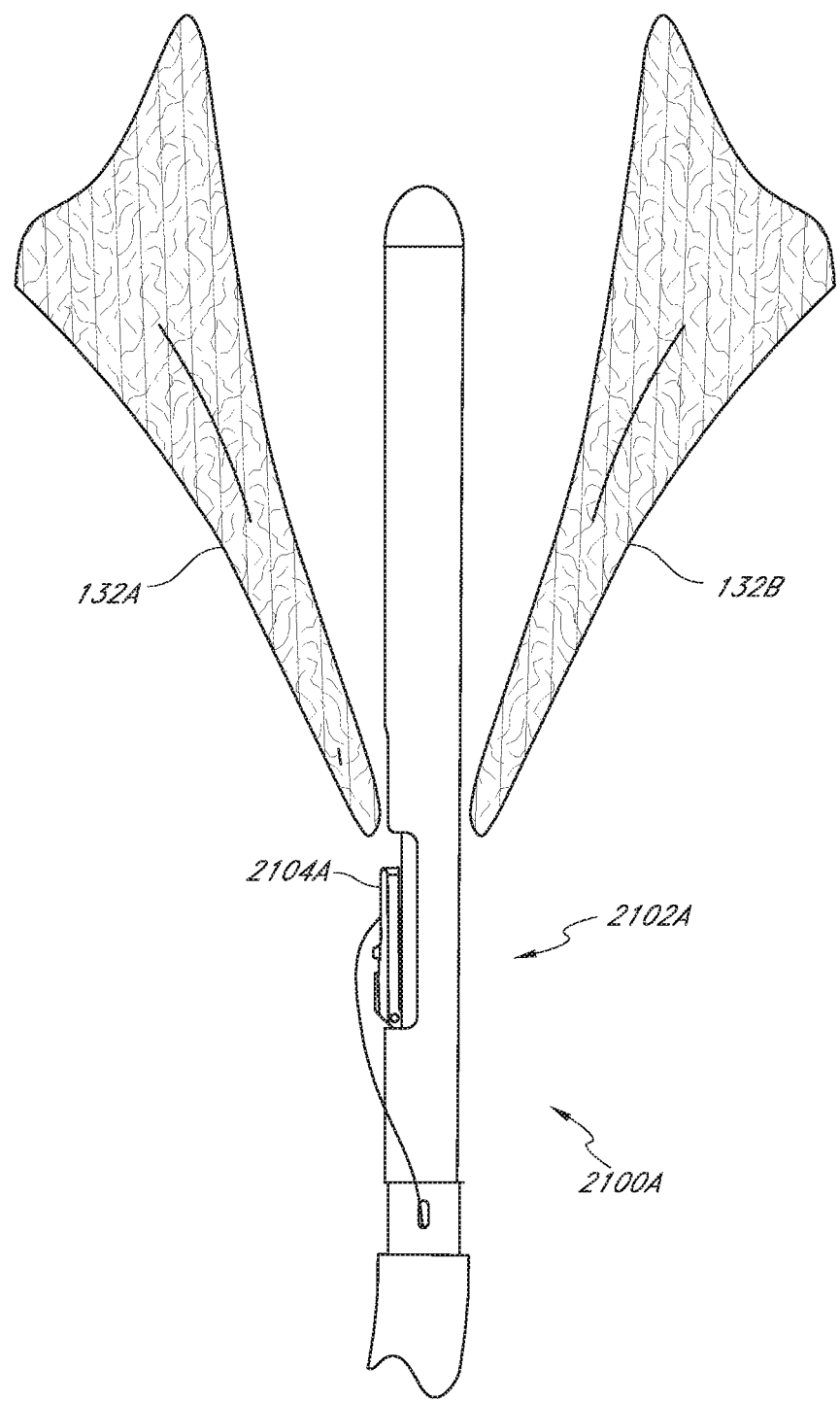
FIG. 30 is a schematic representation of an embodiment of a first suturing device positioned in a passage through a valve.

The distal end of a first suturing device 2100A can be positioned between leaflets 132 of a valve, as shown in FIG. 30. The device 2100A can be advanced through the vasculature to the desired position using any of the access routes discussed above, and with or without a guide wire. For example, the device 2100A can be advanced through a subclavian artery into the aorta to position the device 2100A in the passage through the aortic valve 4 (FIG. 1). Alternatively, the device 2100A can be inserted through a puncture or small incision 9 in the heart to position the device 2100A in the passage through the mitral valve 8, as shown in FIG. 2. Such a puncture can be located at or near the apex of the heart 7.

Figure 31:
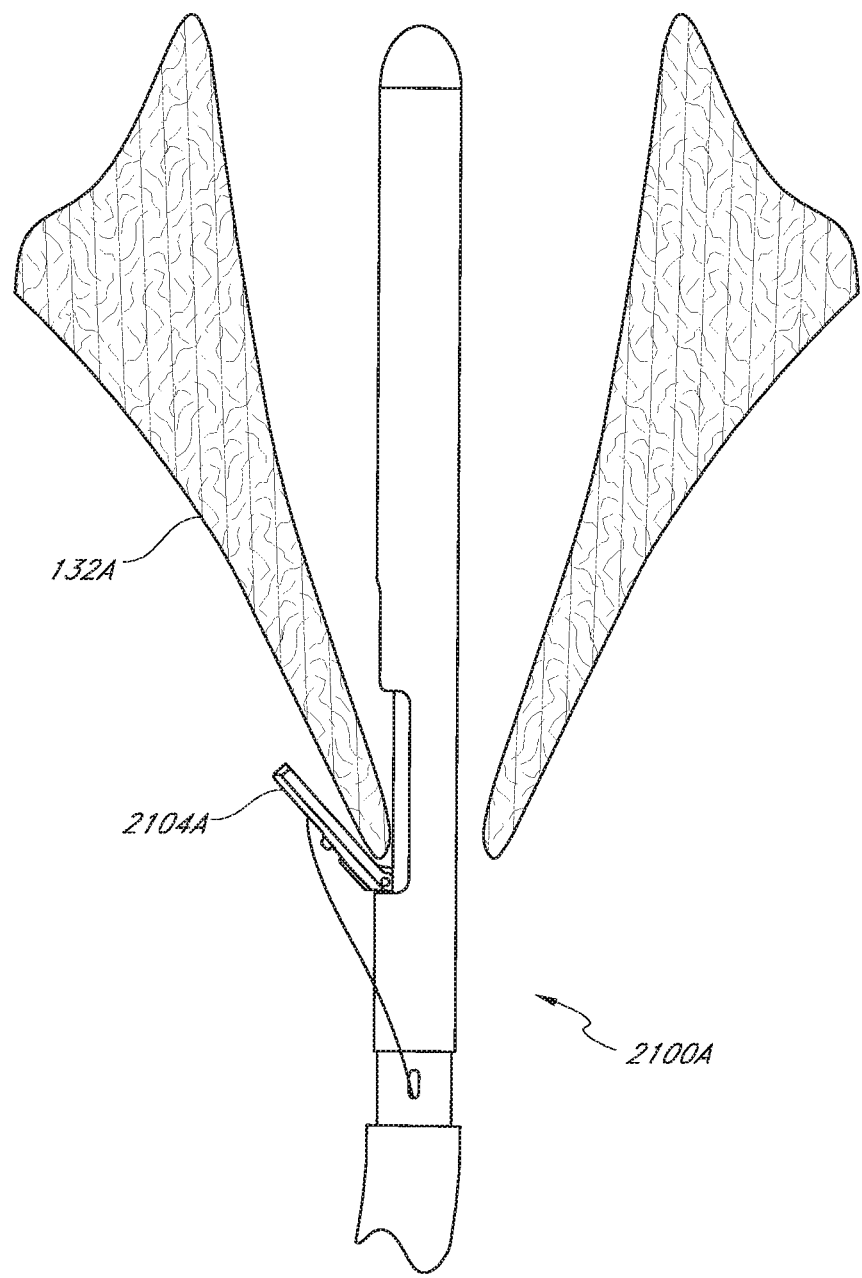
FIG. 31 is a schematic representation as in FIG. 30 with a suture clasp arm positioned around a first leaflet of the valve.

As illustrated in FIG. 30, the suturing device 2100A can be positioned to allow a suture clasp arm 2104A to extend from the distal assembly 2102A. The suture clasp arm 2104A can then be extended and the device 2100A can be advanced until the suture clasp arm 2104A extends around a first leaflet 132A of the valve, as shown in FIG. 31.

Figure 32:
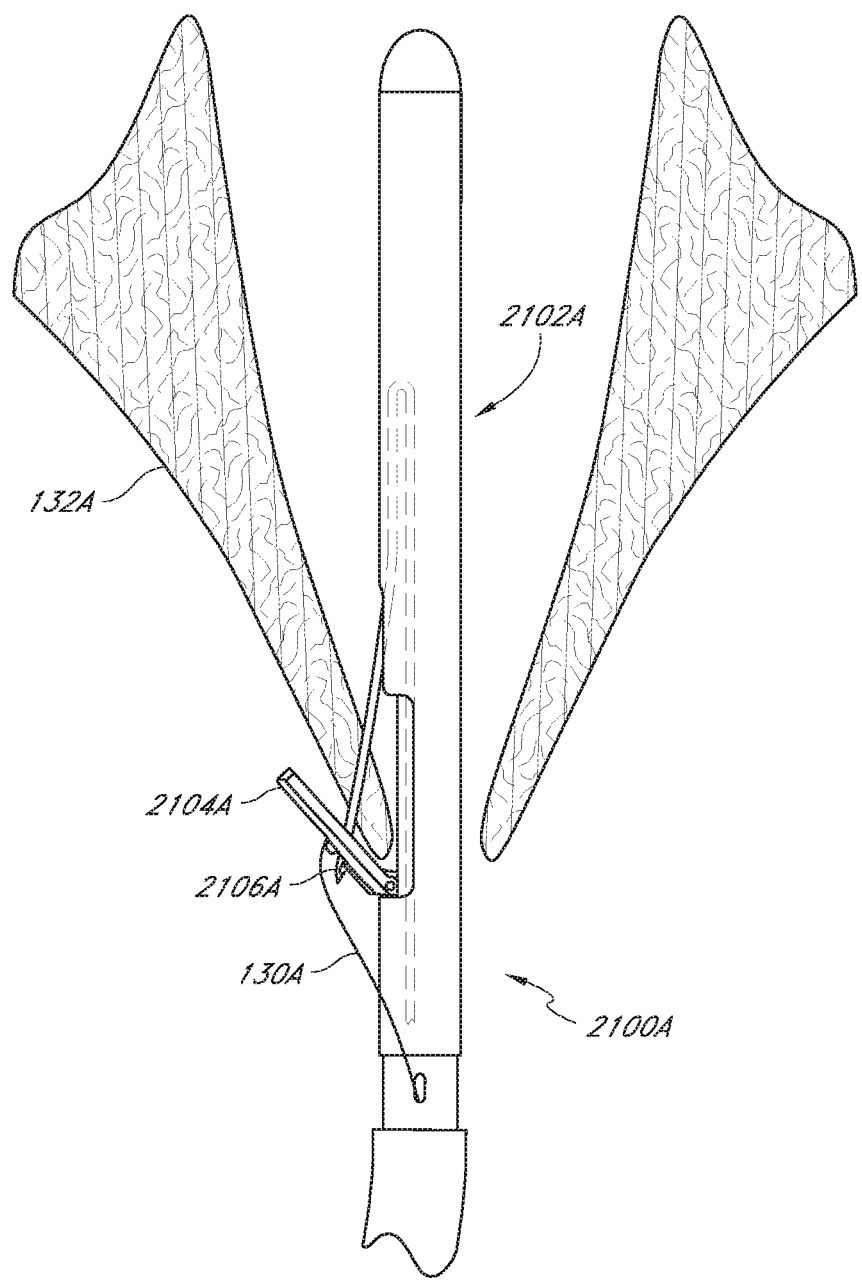
FIG. 32 is a schematic representation as in FIG. 31 showing a suture catch mechanism engaging the suture clasp arm.

Once the suture clasp arm 2104A has been properly positioned around the first leaflet 132A, the suture catch mechanism 2106A can be advanced from the distal assembly 2102A to penetrate the first leaflet 132A and engage the suture portion 130A held by the suture clasp arm 2104A, as illustrated in FIG. 32. In some embodiments, the suture clasp arm 2104A can be moved to the retracted position to securely hold a portion of the first leaflet 132A between the arm 2104A and the distal assembly 2102A before the suture catch mechanism 2106A is advanced through the first leaflet 132A to engage the suture end, as described above, for example.

Figure 33:
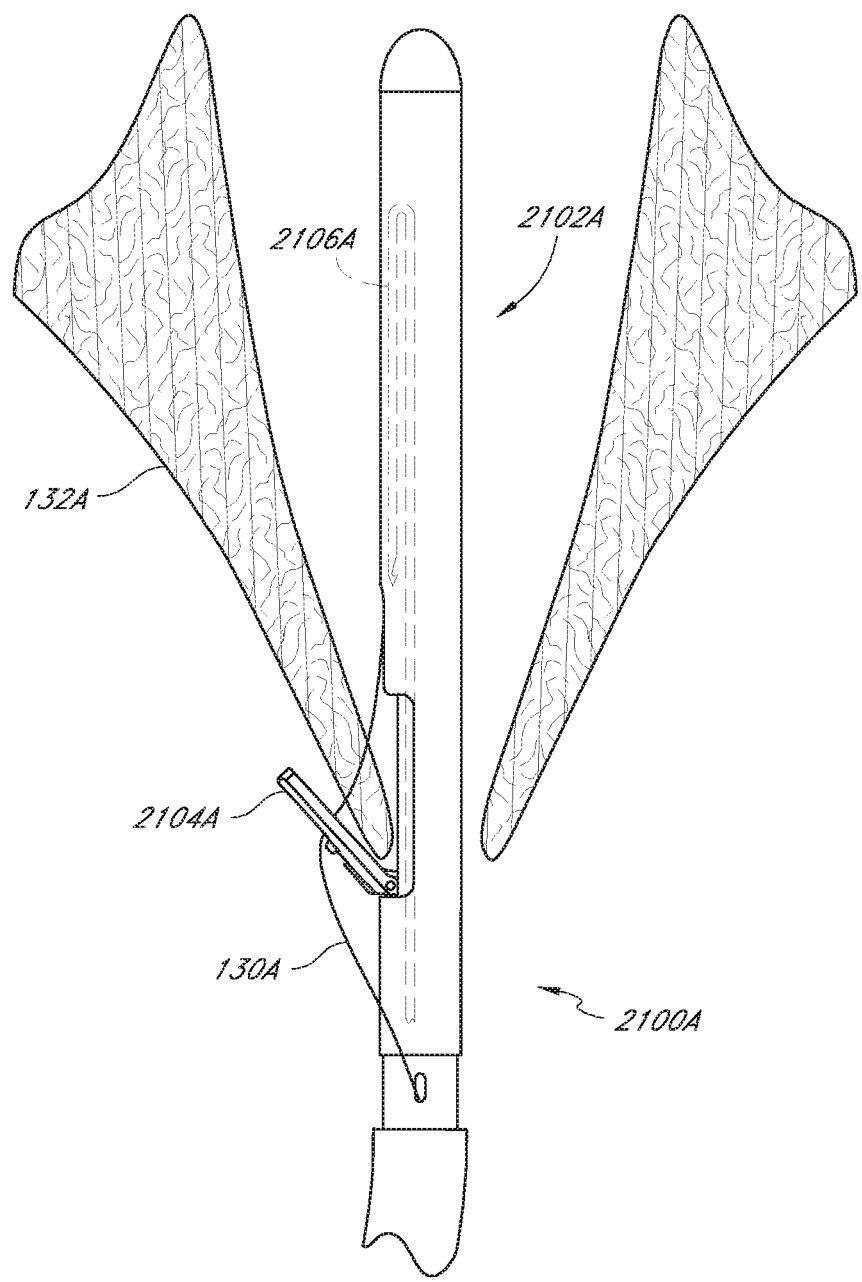
FIG. 33 is a schematic representation as in FIG. 32 showing the suture catch mechanism and a suture portion retracted through the first leaflet.

As shown in FIG. 33, once the suture portion 130A has been engaged, the suture catch mechanism 2106A and engaged suture portion 130A are then retracted through the tissue of the first leaflet 132A into the distal assembly 2102A. The device 2100A can be retracted slightly so that the suture clasp arm 2104A can be moved to the retracted position without pinching the first leaflet 132A. The first suturing device 2100A can then be withdrawn from the valve.

Figure 34:
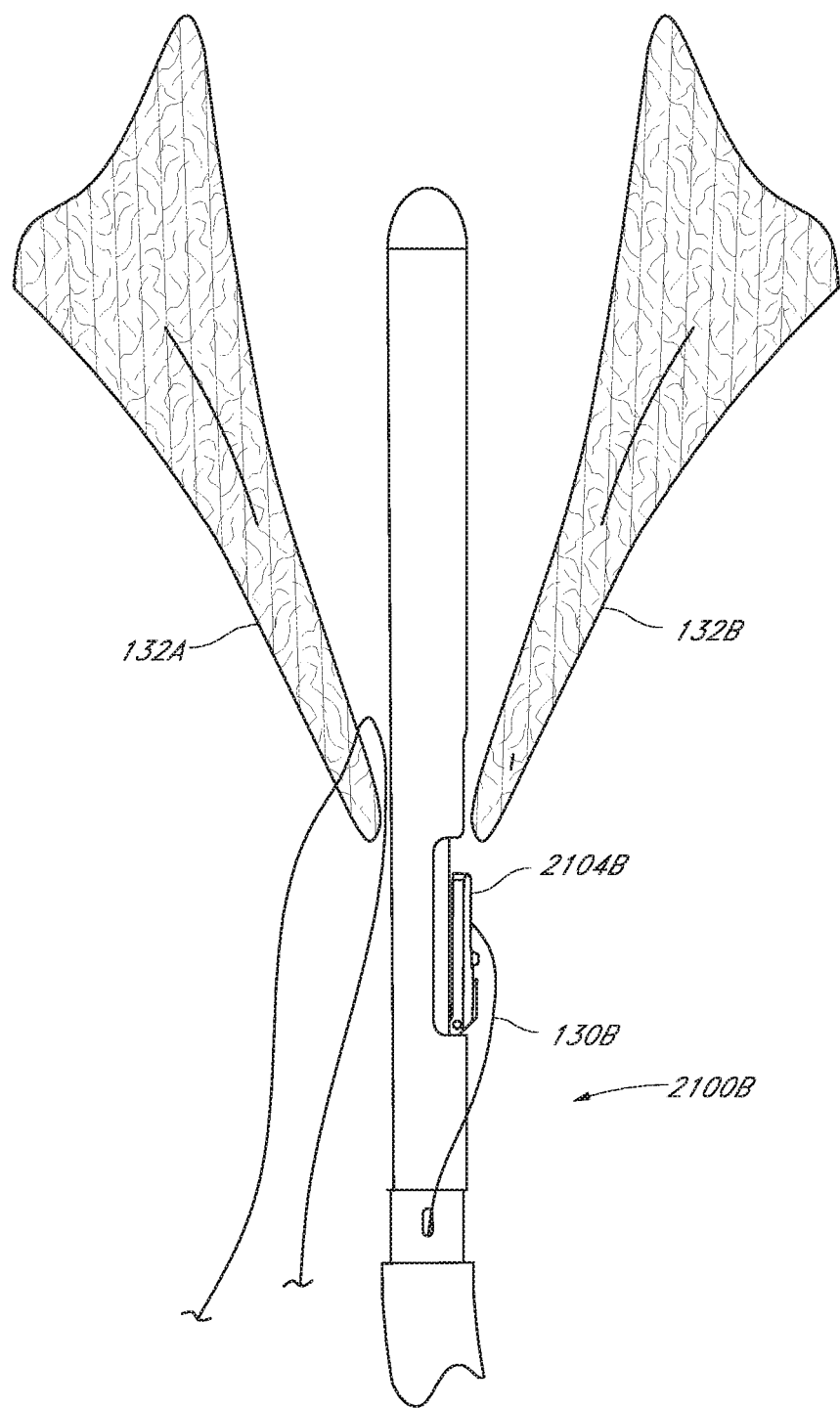
FIG. 34 is a schematic representation as in FIG. 33 showing a second suturing device positioned in the passage through the valve so as to permit a suture clasp arm to extend from the second suturing device.
Figure 35:
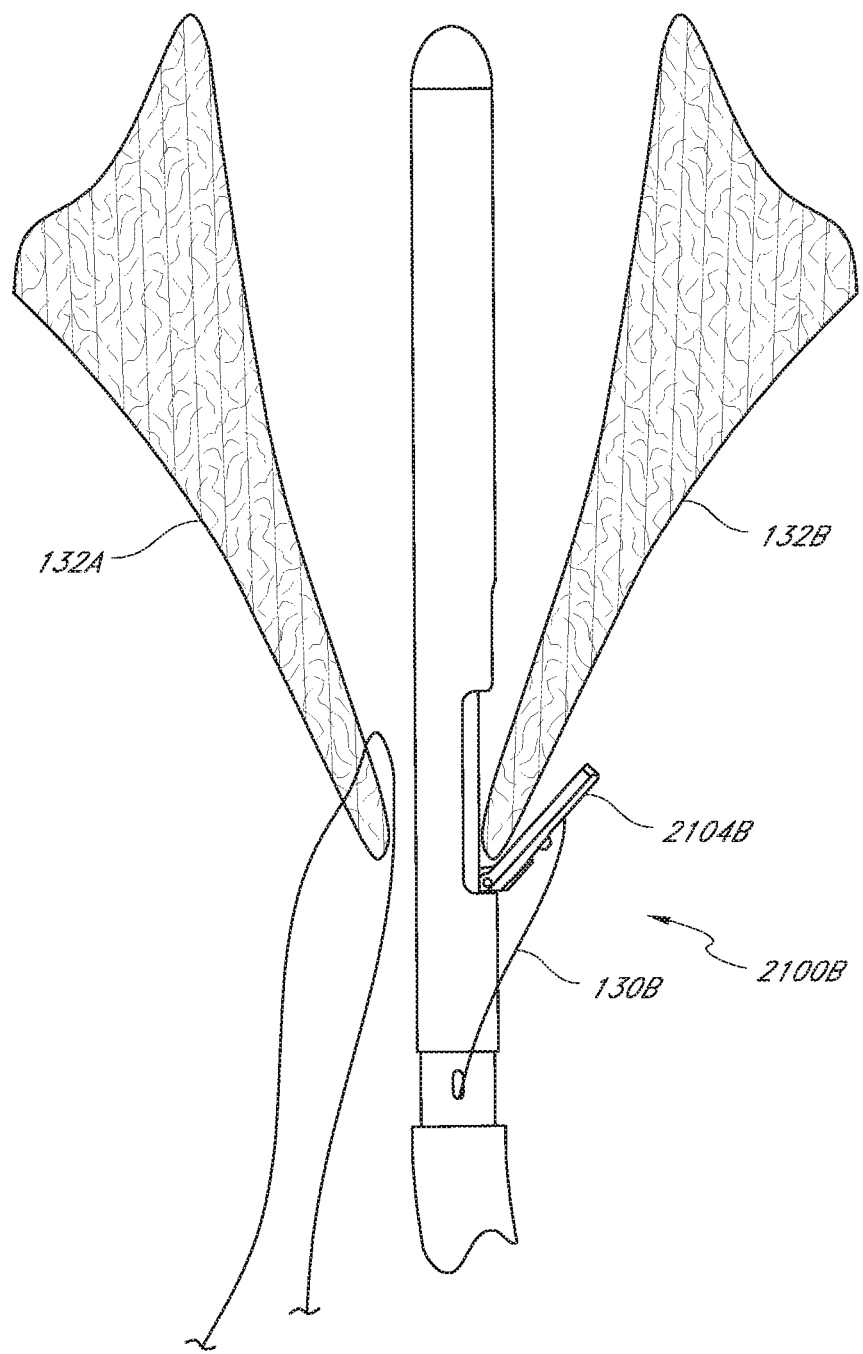
FIG. 35 is a schematic representation as in FIG. 34 with the suture clasp arm positioned around a second leaflet of the valve.

A second suturing device 2100B can then be advanced into the heart and positioned between the leaflets 132A, 132B of the valve, as shown in FIG. 34. The suture clasp arm 2104B can then be extended and the device 2100B can be advanced such that the suture clasp arm 2104B extends around the tip of the second leaflet 132B, as shown in FIG. 35.

Figure 36:
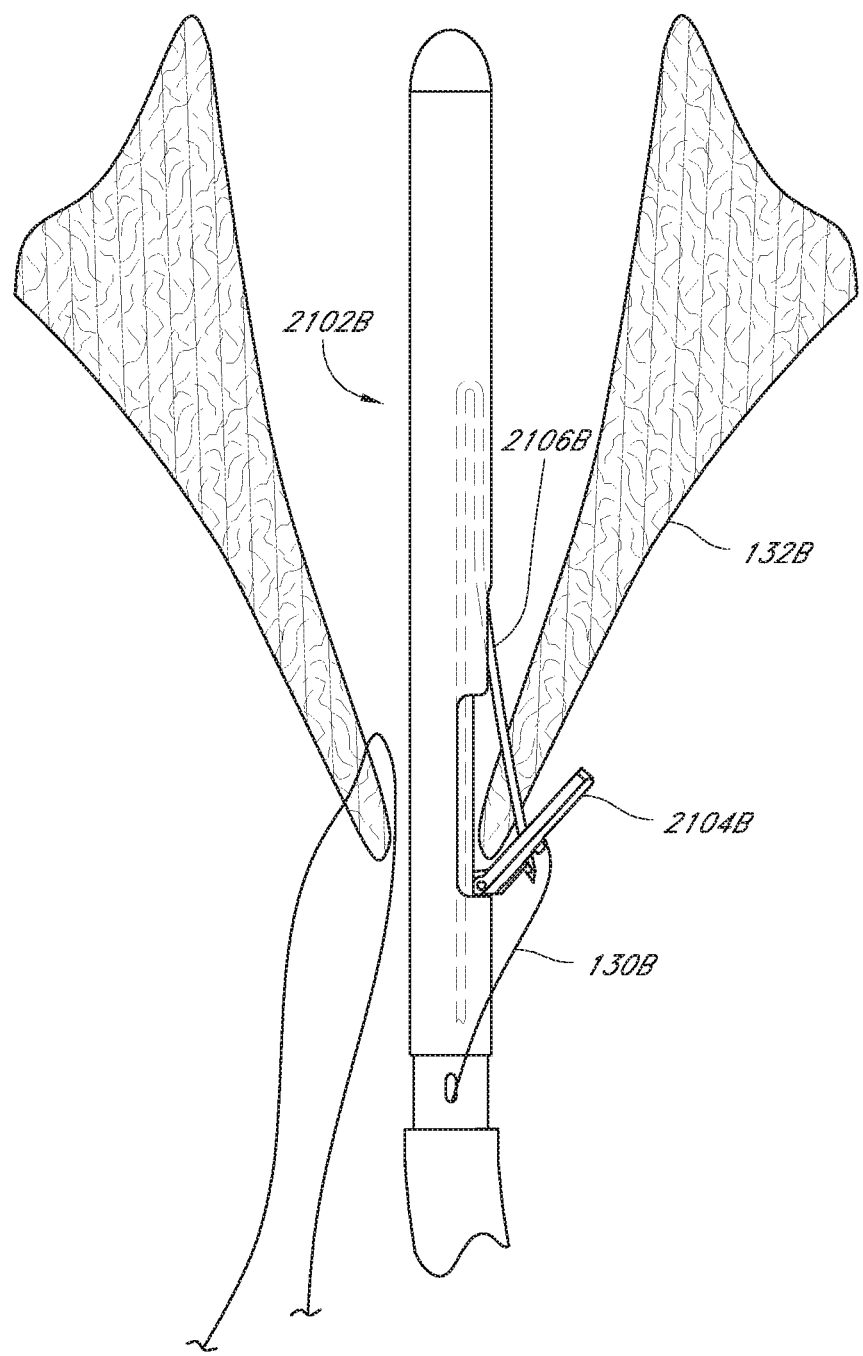
FIG. 36 is a schematic representation as in FIG. 35 showing a suture catch mechanism engaging the suture clasp arm.

In the illustrated embodiment, once the suture clasp arm 2104B has been properly positioned around the second leaflet 132B, the suture catch mechanism 2106B can be advanced from the distal assembly 2102B to penetrate the second leaflet 132B and engage the suture portion 130B held by the suture clasp arm 2104B, as illustrated in FIG. 36. As noted above with respect to the first leaflet 132A, in some embodiments, the suture clasp arm 2104B can be moved to the retracted position to securely hold a portion of the second leaflet 132B between the arm 2104B and the distal assembly 2102B before the suture catch mechanism 2106B is advanced through the second leaflet 132B to engage the suture portion 130B.

Figure 37:
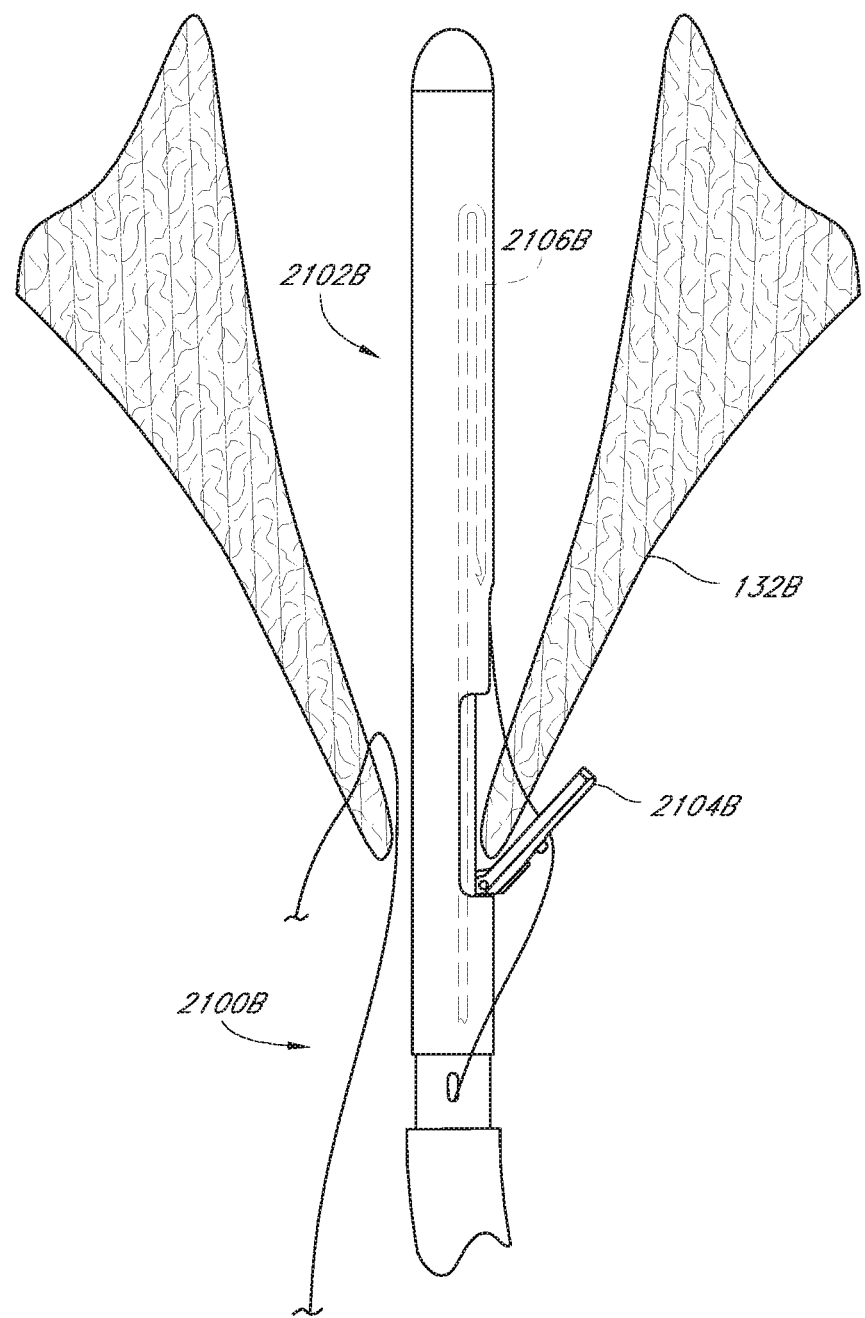
FIG. 37 is a schematic representation as in FIG. 36 showing the suture catch mechanism and a suture portion retracted through the second leaflet.

After the suture portion 130B has been engaged, the suture catch mechanism 2106B and engaged suture portion 130B are then retracted distally through the tissue of the second leaflet 132B into the distal assembly 2102B, as illustrated in FIG. 37. The suture clasp arm 2104B can then be closed after slightly retracting the device 2100B to avoid pinching the second leaflet 132B. Once the suture clasp arm 2104B is closed, the suturing device 2100B can be withdrawn from the patient's heart.

Figure 38A:
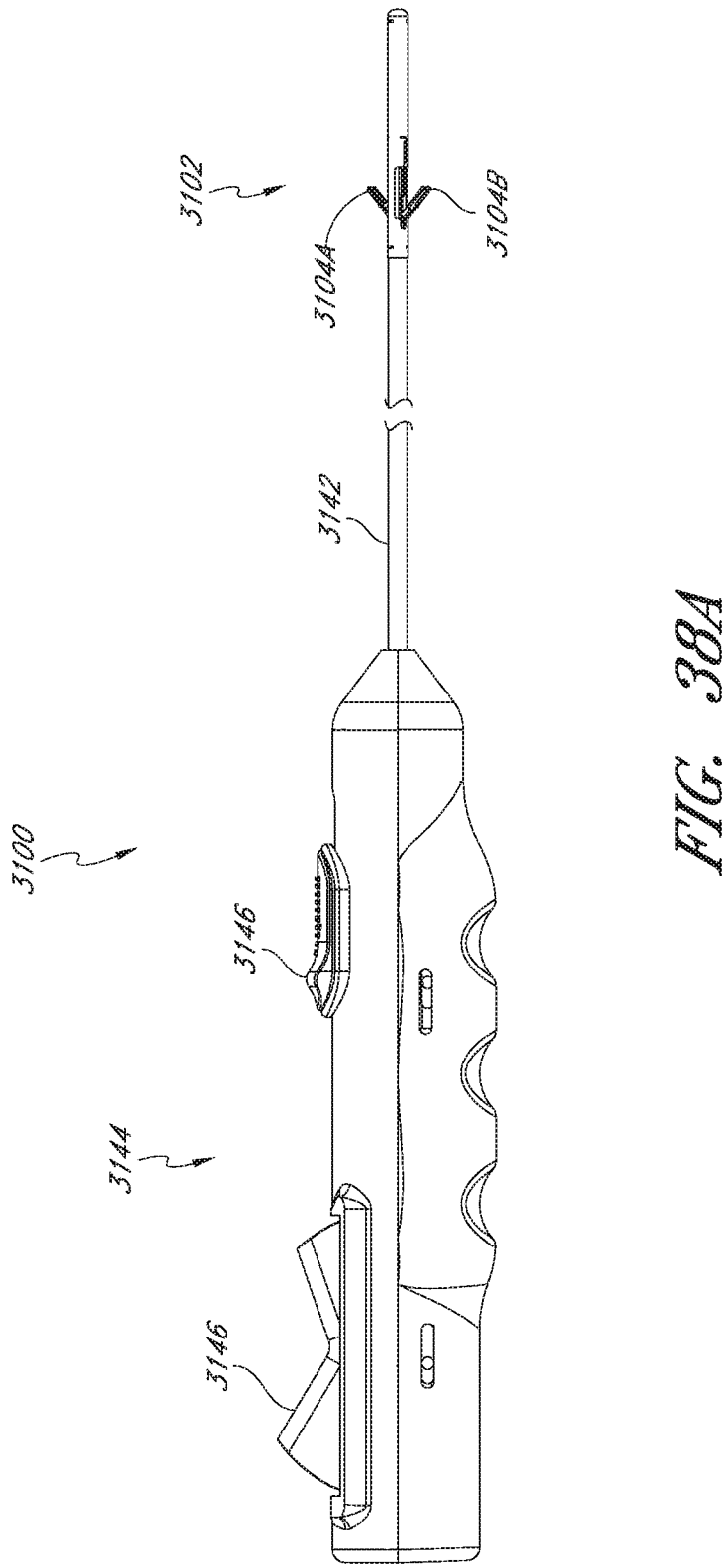
FIG. 38A is a plan view of an embodiment of a suturing device with two suture clasp arms in an extended position.
Figure 38B:
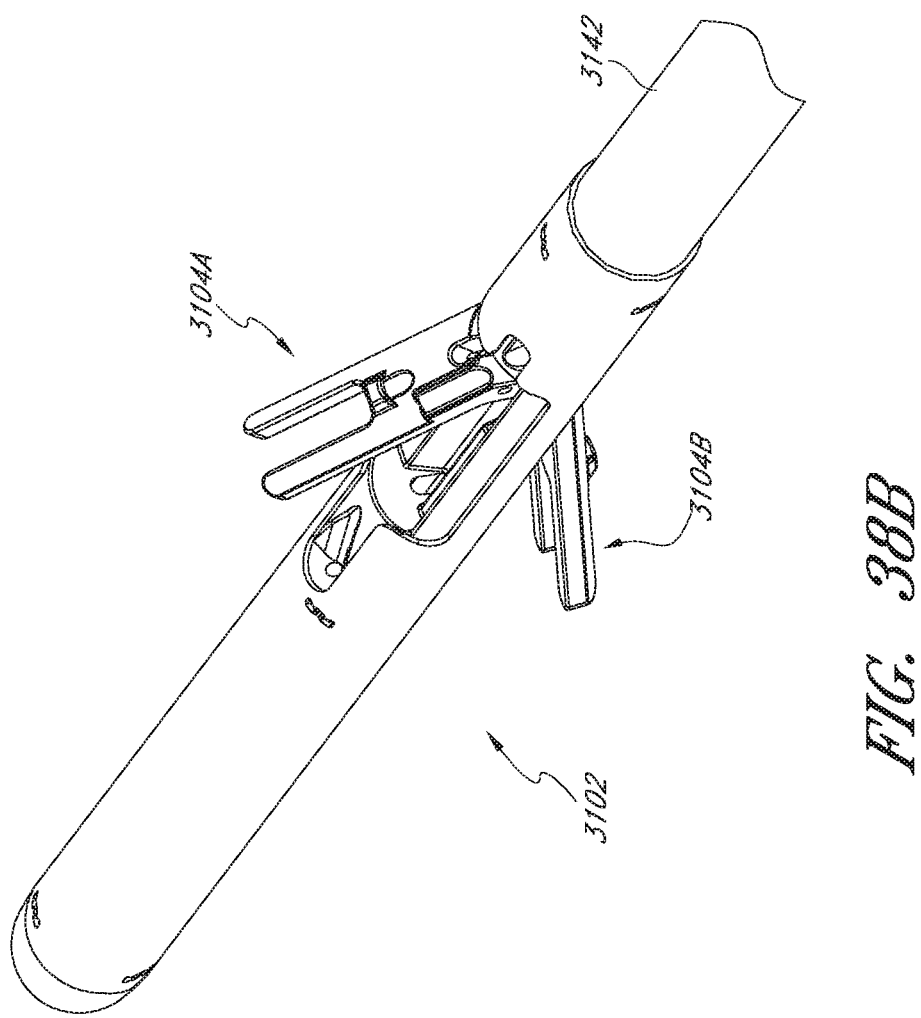
FIG. 38B is an enlarged perspective view of the distal end of the suturing device of FIG. 38A with the suture clasp arms in an extended position.

In some embodiments, a suturing device 3100 can have a plurality of arms 3104. In some embodiments, the arms can be spaced at varying intervals around the circumference of the elongate body. In some embodiments, a plurality of arms can extend from one side of the elongate body and a corresponding plurality of arms can extend from an opposite side of the elongate body. FIGS. 38A and 38B illustrate a view of a suturing device 3100 having two arms 3104A,B. As illustrated, the arms are spaced approximately 180 degrees from each other about the elongate body 3142. In some embodiments, the suturing device can have two suture catch mechanisms 3106A,B, one associated with each arm. The device can be designed so that the plurality of arms is deployed simultaneously, and that the plurality of suture catch mechanisms is deployed simultaneously. Alternatively, the device can be designed so that each arm and each suture catch mechanism can be deployed separately. In some embodiments, the suturing device can be used as a system with a suture joining device 135, as discussed above with respect to FIG. 16. Many aspects of the suturing device can function substantially the same as aspects of the device described with respect to FIGS. 28-37. Unless discussed otherwise, components can be considered to have substantially the same function and operate in substantially the same manner as similarly labeled components described with respect to FIGS. 28-37. As a non-limiting example, the device can comprise a distal assembly 3102 and a handle with one or more actuators and/or pulls 3146 for moving the suture clasp arms 3104 and deploying the suture catch mechanisms 3106.

Figure 39A:
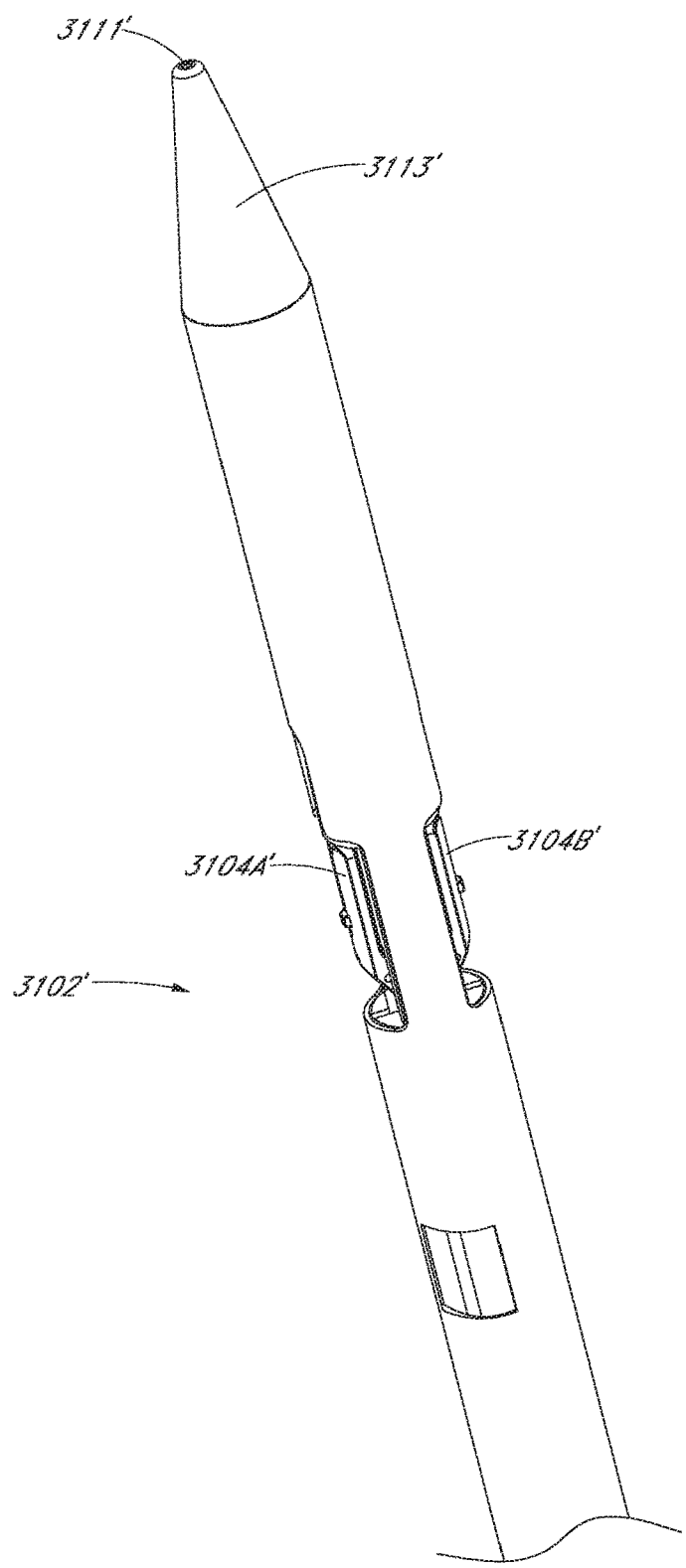
FIG. 39A is an enlarged perspective view of a distal end of an embodiment of a suturing device with two suture clasp arms in a retracted position.
Figure 39B:
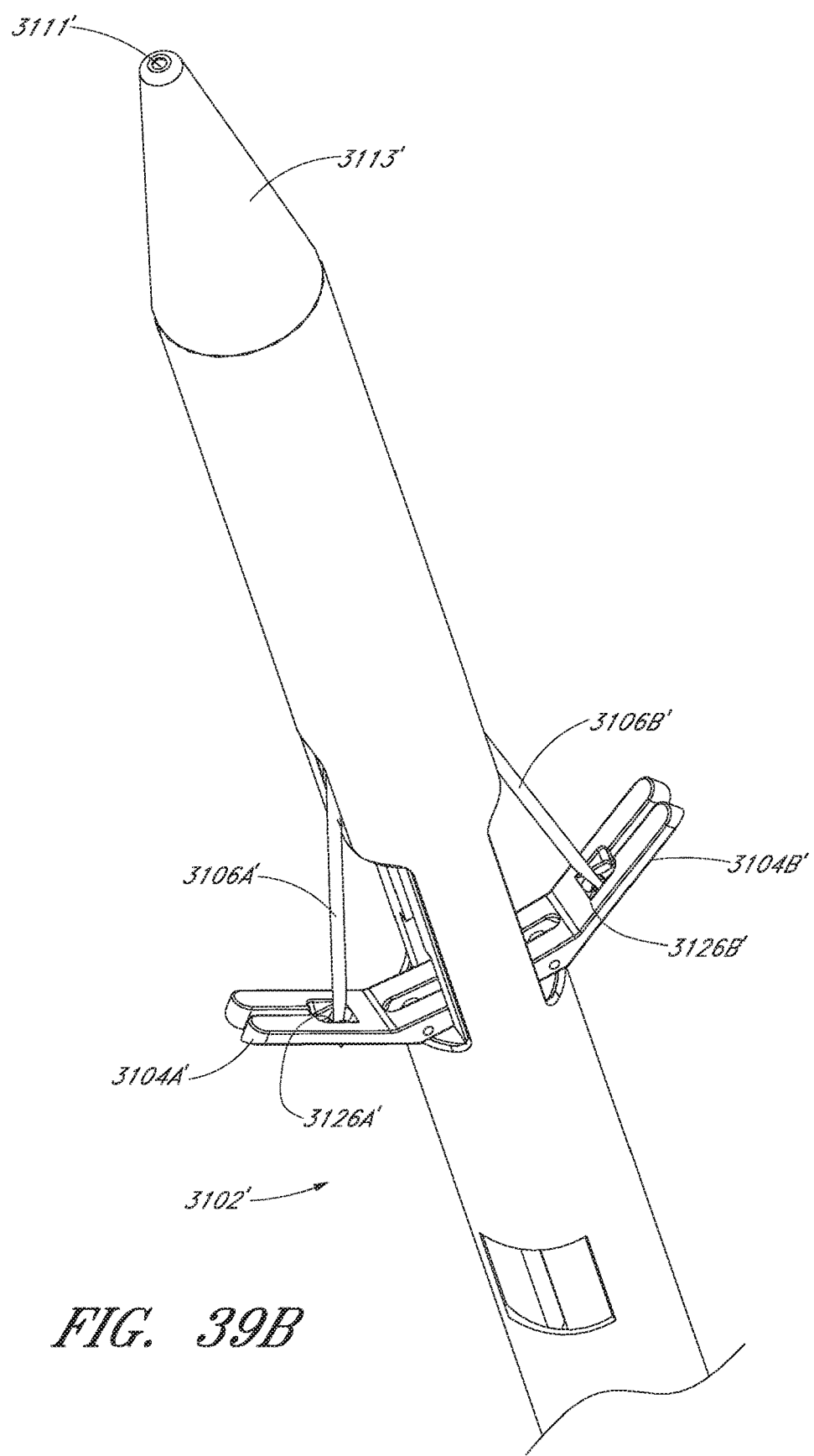
FIG. 39B is an enlarged perspective view of the distal end of the suture device of FIG. 39A with the suture clasp arms in an extended position.

In some embodiments, a suturing device can have a distal assembly 3102' as seen in FIGS. 39A and 39B. FIG. 39A illustrates a device with two suture arms 3104A',B' that are in a retracted position. In FIG. 39B, both suture arms 3104A',B' are in an extended position, and suture catch mechanisms 3106A',B' have extended through the corresponding arms at suture clasps 3126A',B'. In some embodiments, the arms can extend and retract simultaneously or in sequence, and in some embodiments the suture catch mechanisms can extend and retract simultaneously or in sequence. Also as illustrated, in some embodiments a suturing device can comprise a tapered portion 3113' at a distal end and/or a guide wire lumen 3111' that can be used if the device advances over a guide wire.

Figure 40:
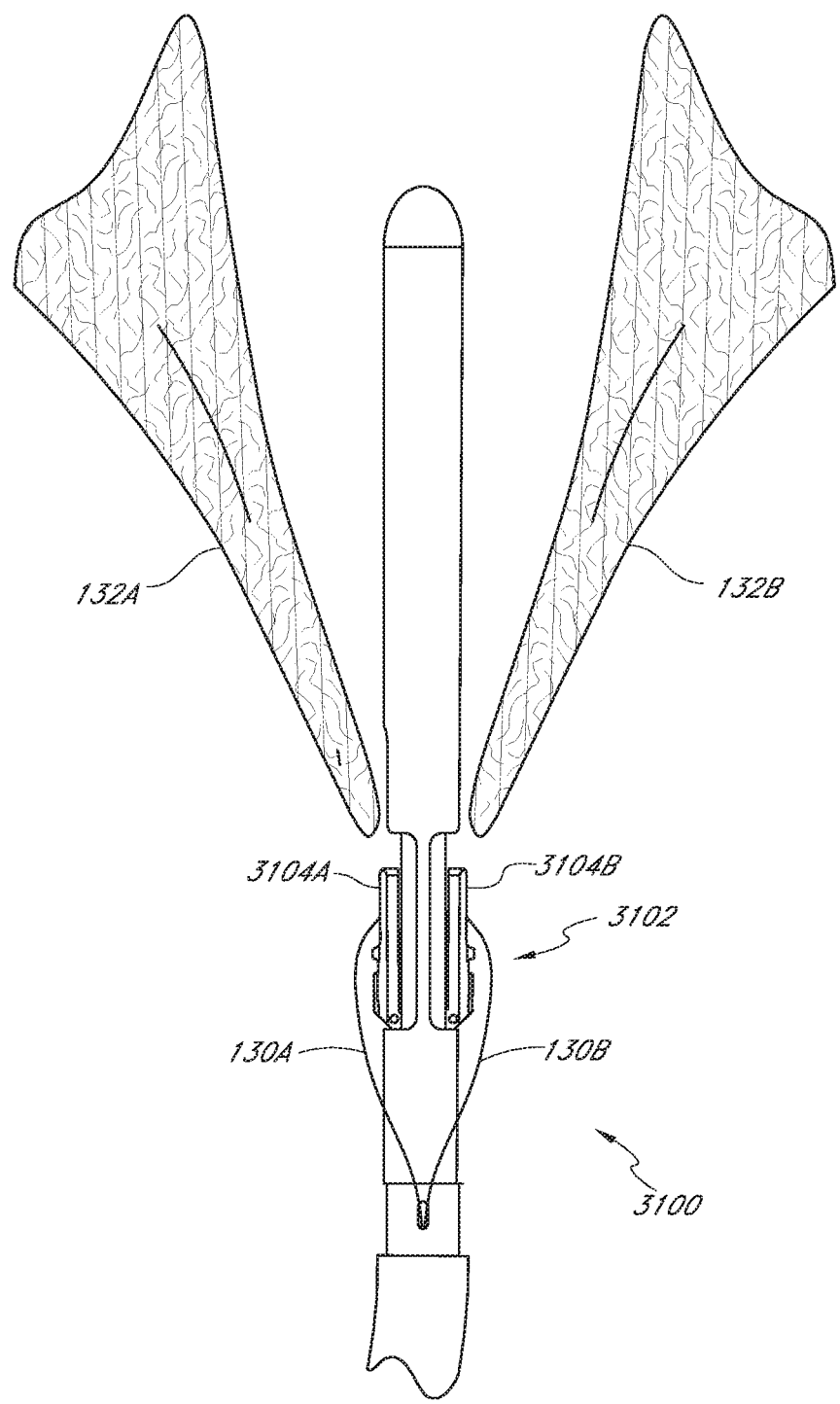
FIG. 40 is a schematic representation of an embodiment of a suturing device positioned in a passage through a valve.

A method of suturing anatomical valves, such as edge-to-edge repair of a mitral valve, with a dual arm suturing device is illustrated in FIGS. 40-47. The method is described with reference to the suturing device 3100 of FIGS. 38A and 38B, but any dual arm suturing device can be used, such as one with a distal assembly as described with reference to FIGS. 39A and 39B. The suturing device 3100 can be advanced to a desired position between leaflets 132 of a valve, as shown in FIG. 40, by any of the methods discussed above with reference to the method of FIGS. 30-37, and with or without a guide wire. In the embodiment illustrated, the suturing device 3100 may be delivered transapically into the left ventricle, and delivered so that the distal end of the device extends through the mitral valve into the left atrium. However, the device can also be designed for an approach to pass through the septum between the right and left atrium, through the mitral valve and into the left ventricle. The locations and configurations of the suture clasp arms 3104 and the suture catch mechanisms 3106 may be appropriately designed based on the desired method of approach and based on the desired location to be sutured. For example, while the arms 3104 in the embodiment of FIG. 40 are shown proximal to the suture catch mechanisms 3106, in a different device the arms 3104 may be located distal to the suture catch mechanisms.

Figure 41:
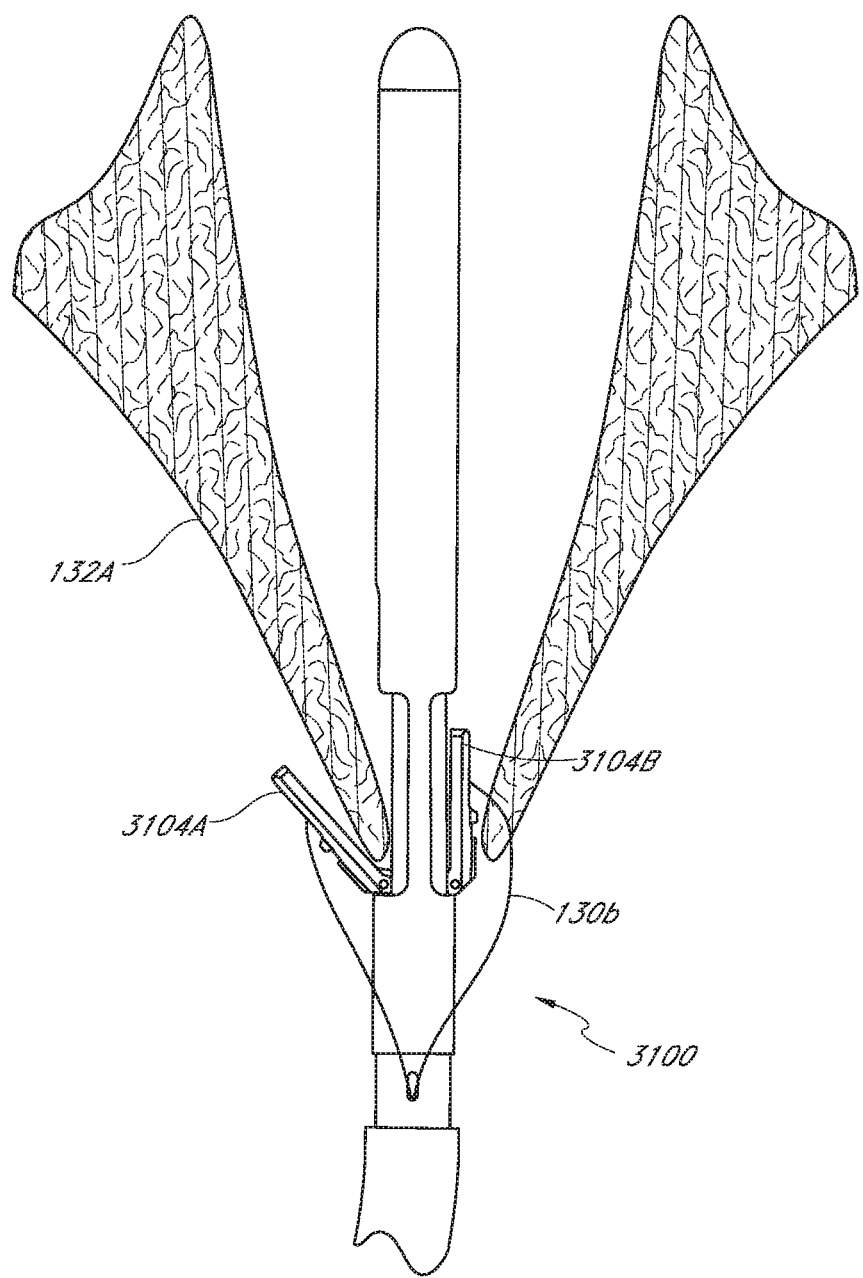
FIG. 41 is a schematic representation as in FIG. 40 with a suture clasp arm positioned around a first leaflet of the valve.

For suturing a mitral valve as shown in FIG. 40, the device can be positioned such that at least one of the suture clasp arms, a first arm 3104A, can be extended from the device, and the device can be advanced until the first arm 3104A extends around or adjacent to a first leaflet of the valve 132A, as shown in FIG. 41. Accordingly, when suturing the mitral valve, the arm 3104A can be positioned on a proximal side, or the ventricular side, of the leaflet 132A. The arm 3104A carries an end of a suture portion 130A. FIG. 40 shows arm 3104A being deployed independently of arm 3104B, but in other embodiments, both arms can be deployed together.

Figure 42:
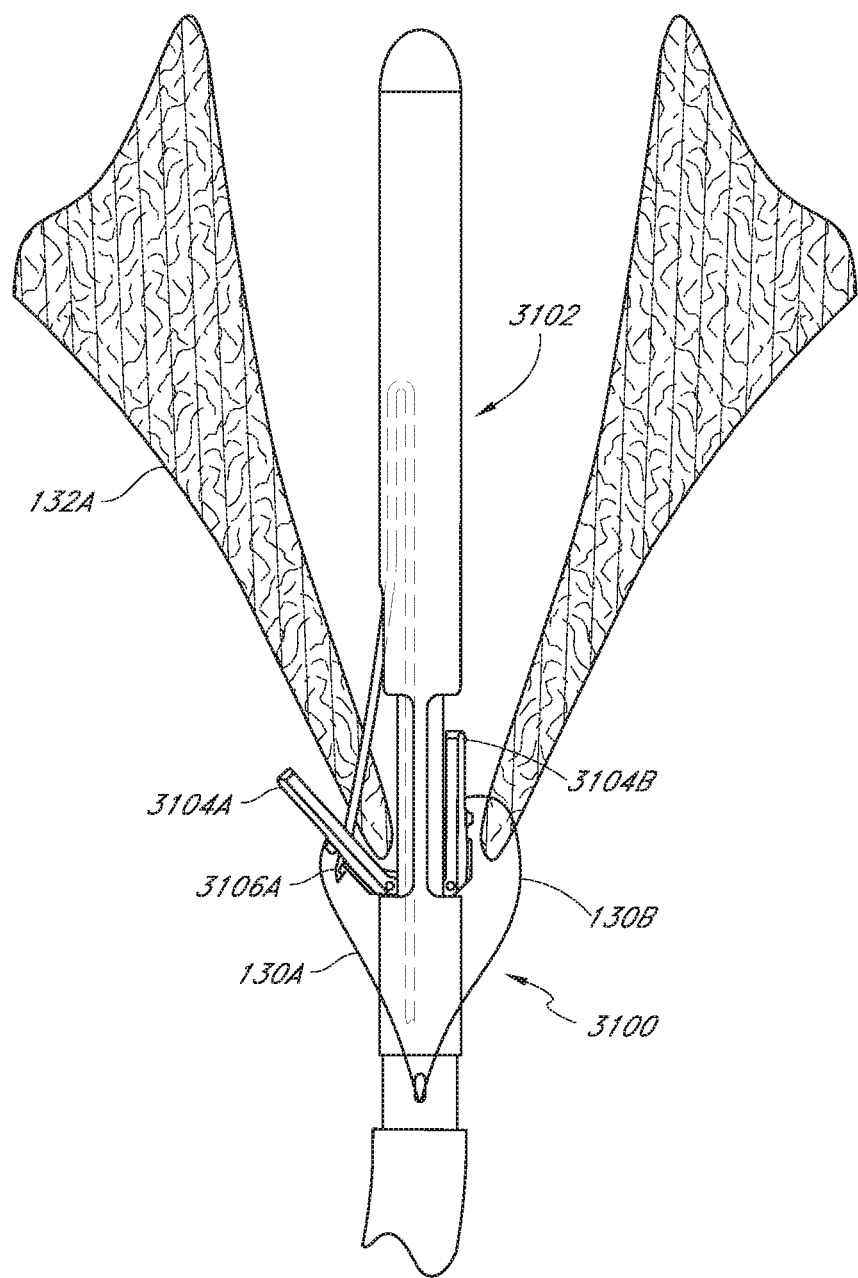
FIG. 42 is a schematic representation as in FIG. 41 showing a suture catch mechanism engaging the suture clasp arm.

As described with respect to FIG. 32, once the first suture clasp arm 3104A is properly positioned, the suture catch mechanism 3106A can be advanced from the distal assembly 3102 from a location distal to the leaflet 132A (or on the atrial side of the leaflet, for a mitral valve procedure) to penetrate the first leaflet 132A and engage the suture portion 130A held by the first suture clasp arm 3104A, as illustrated in FIG. 42. In some embodiments, the first suture clasp arm 3104A can be moved to the retracted position to securely hold a portion of the first leaflet 132A between the first arm 3104A and the distal assembly 3102 before the suture catch mechanism 3106A is advanced through the first leaflet 132A to engage the suture end.

Figure 43:
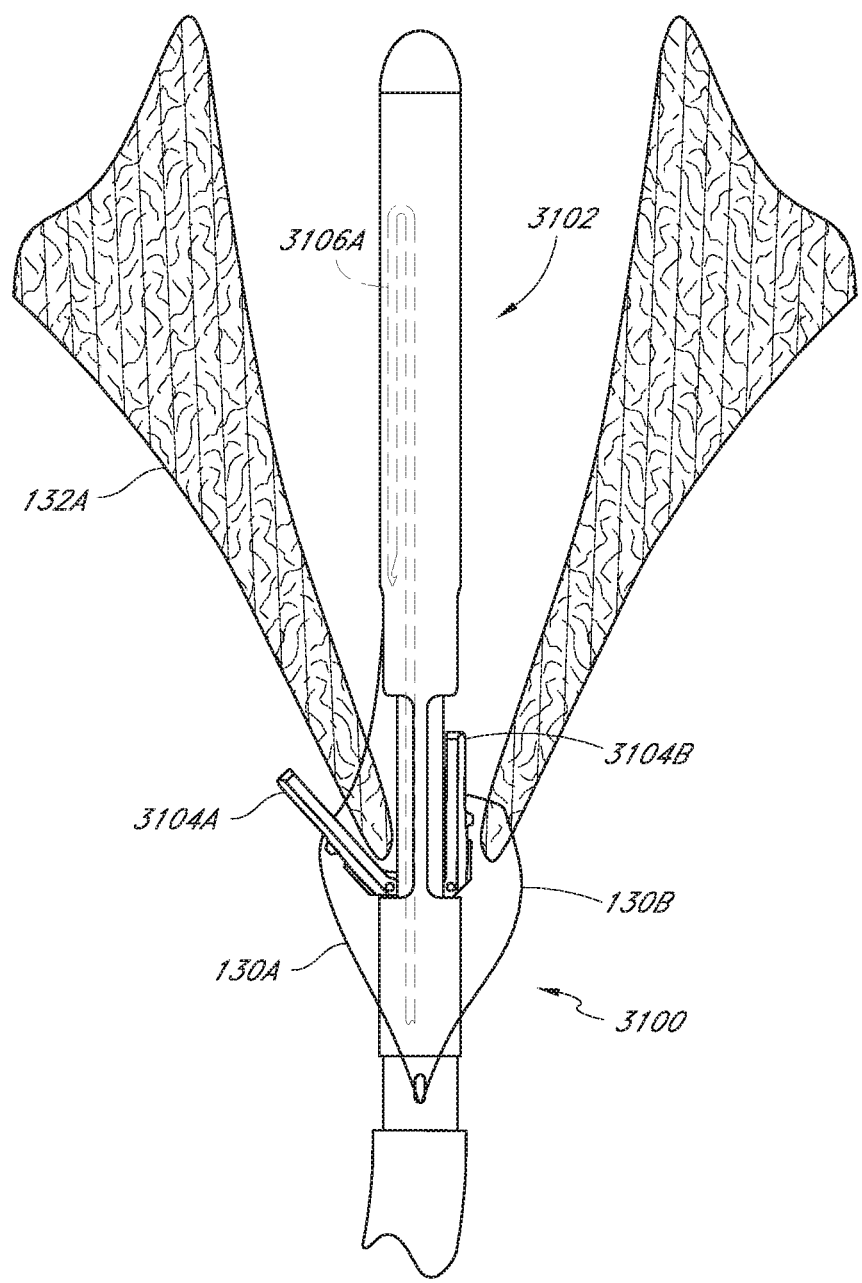
FIG. 43 is a schematic representation as in FIG. 42 showing the suture catch mechanism and a suture portion retracted through the first leaflet.
Figure 44:
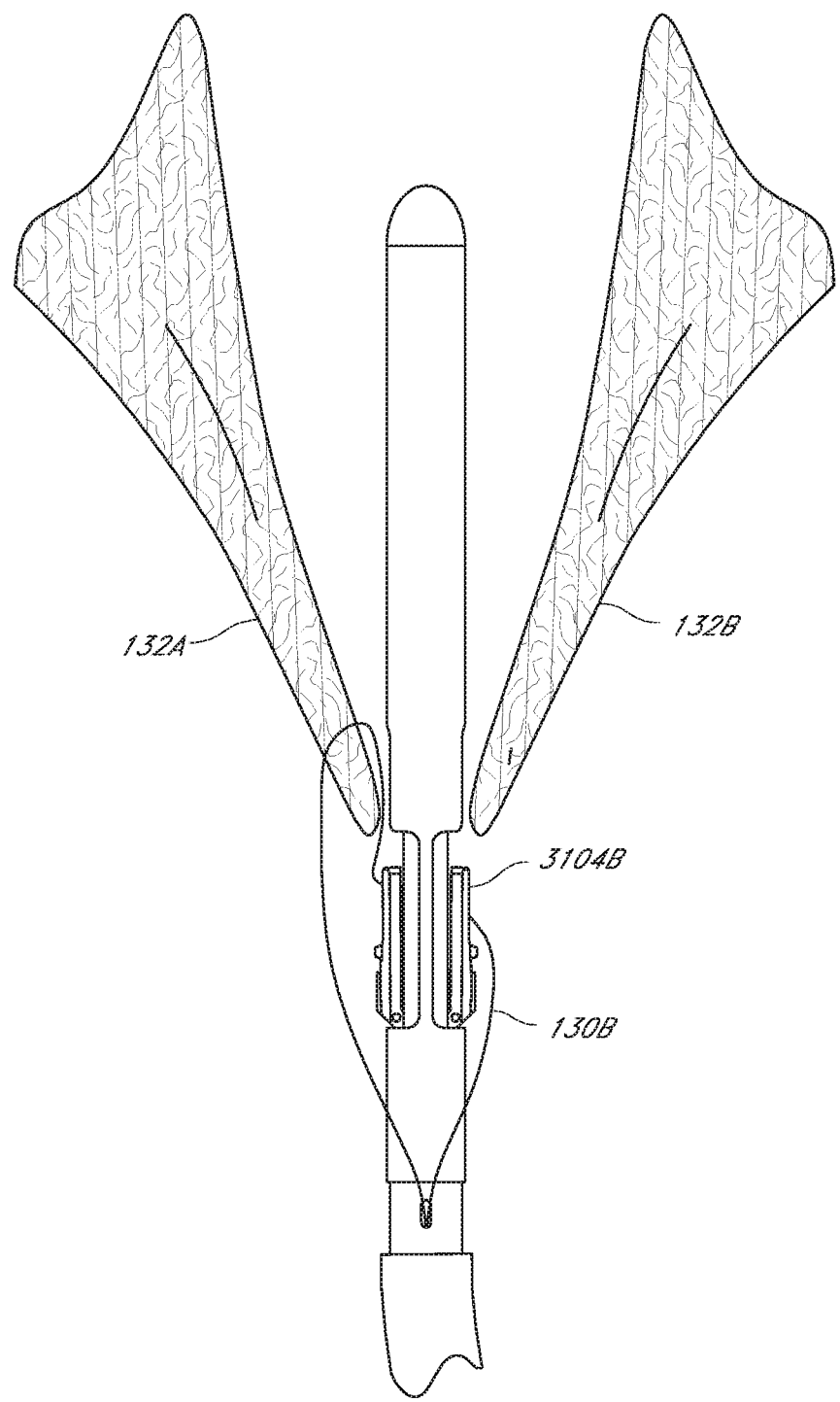
FIG. 44 is a schematic representation as in FIG. 43 showing the suturing device positioned in the passage through the valve so as to permit a second suture clasp arm to extend from the suturing device.

As shown in FIG. 43, once the suture portion 130A has been engaged, the suture catch mechanism 3106A and engaged suture portion 130A are then retracted through the tissue of the first leaflet 132A into the distal assembly 3102. The device 3100 can be retracted slightly so that the first suture clasp arm 3104A can be moved to the retracted position without pinching the first leaflet 132A, as illustrated in FIG. 44. The suturing device 3100 can then be retracted at least far enough to allow the second suture clasp arm 3104B to extend from the device.

Figure 45:
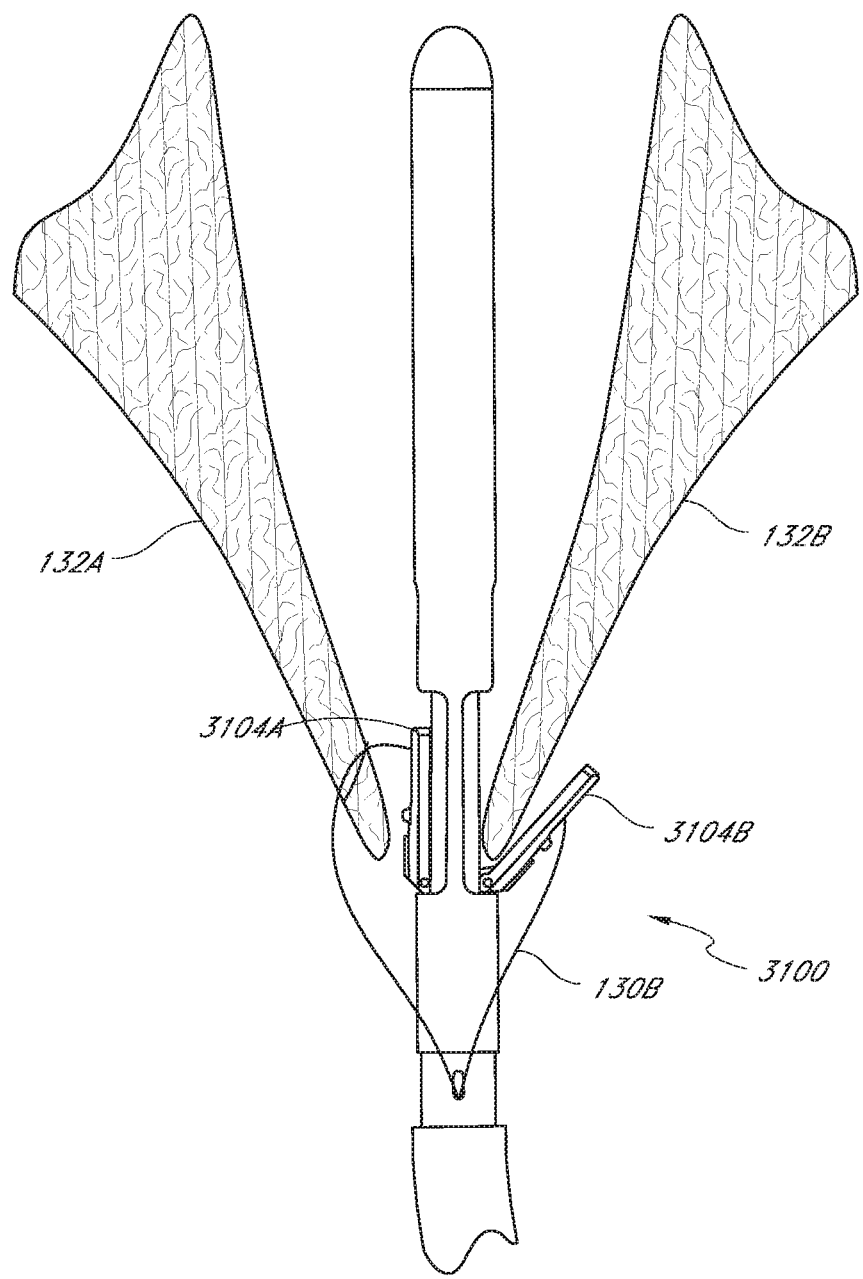
FIG. 45 is a schematic representation as in FIG. 44 with the suture clasp arm positioned around a second leaflet of the valve.

As illustrated in FIG. 45, the second suture clasp arm 3104B can extend from the device and the device can be advanced, and moved laterally if necessary, such that the second suture clasp arm 3104B extends around the tip of the second leaflet 132B. In some embodiments, the second suture clasp arm 3104B can extend before or while the first arm 3104A is retracted.

Figure 46:
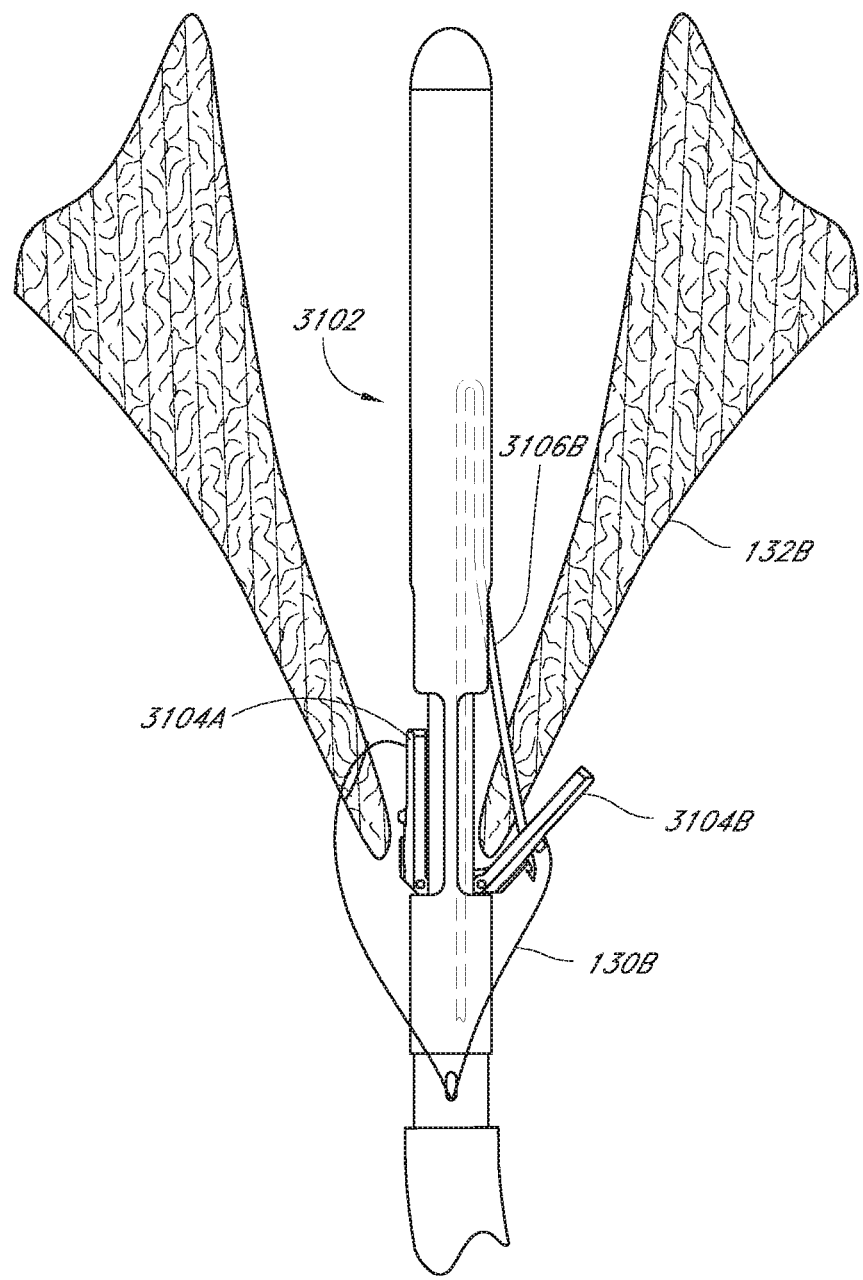
FIG. 46 is a schematic representation as in FIG. 45 showing a suture catch mechanism engaging the suture clasp arm.

As with the first arm 3104A, once the second suture clasp arm 3104B has been properly positioned around the second leaflet 132B, a suture catch mechanism 3106B can be advanced from the distal assembly 3102 to penetrate the second leaflet 132B and engage the suture portion 130B held by the suture clasp arm 3104B, as illustrated in FIG. 46. As noted above with respect to the first leaflet 132A, in some embodiments, the suture clasp arm 3104B can be moved to the retracted position to securely hold a portion of the second leaflet 132B between the arm 3104B and the distal assembly 3102 before the suture catch mechanism 3106B is advanced through the second leaflet 132B to engage the suture portion 130B. In some embodiments, the suture catch mechanism can be the same catch mechanism as the one used with the first arm 104A. In the illustrated embodiment, the suture portions 130A,B are portions of separate sutures, but in some embodiments the suture portions 130A,B can be portions of the same suture.

Figure 47:
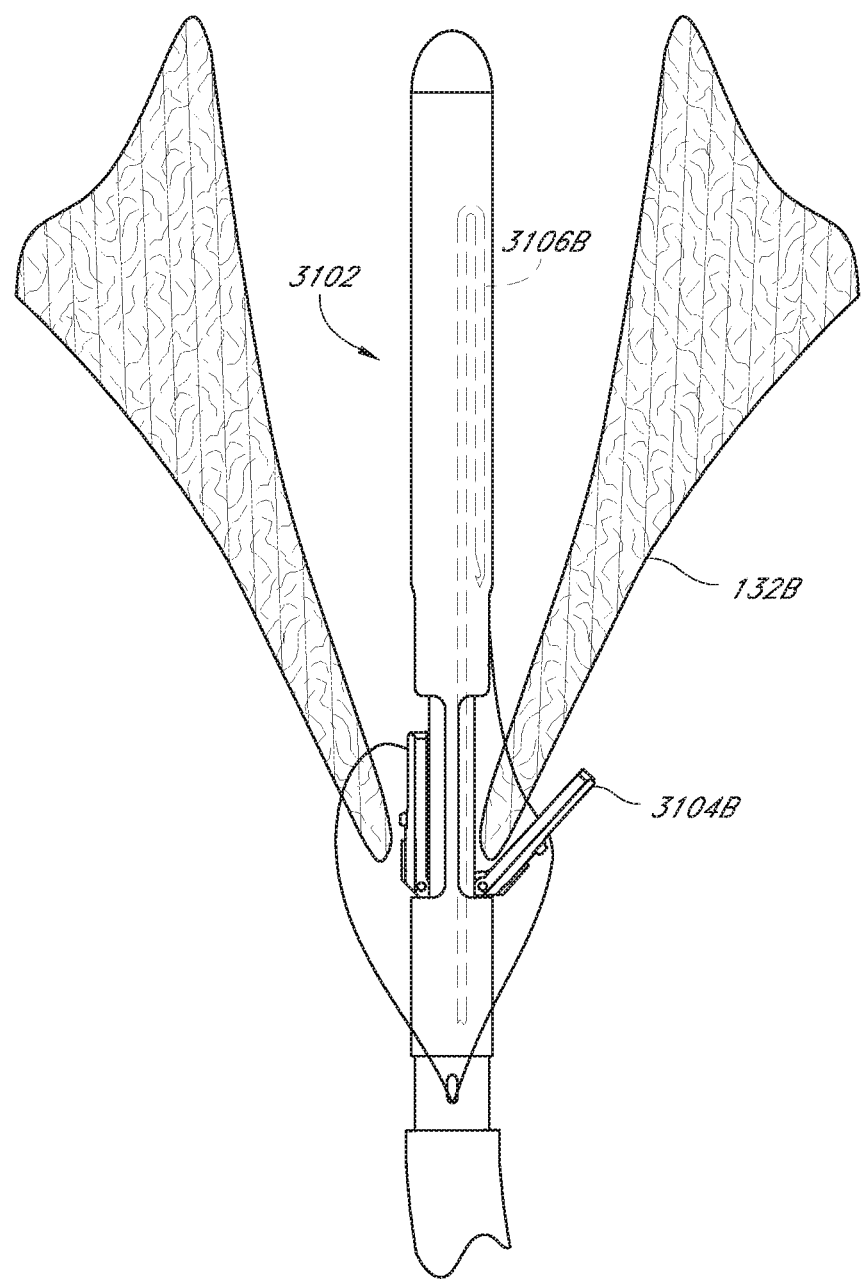
FIG. 47 is a schematic representation as in FIG. 46 showing the suture catch mechanism and a suture portion retracted through the second leaflet.

After the suture portion 130B has been engaged, the suture catch mechanism 3106B and engaged suture portion 130B are then retracted distally through the tissue of the second leaflet 132B into the distal assembly 3102, as illustrated in FIG. 47. The suture clasp arm 3104B can then be closed after slightly retracting the device 3100 to avoid pinching the second leaflet 132B. Once the suture clasp arm 3104B is closed, the suturing device 3100 can be withdrawn from the patient's heart.

Figure 48:
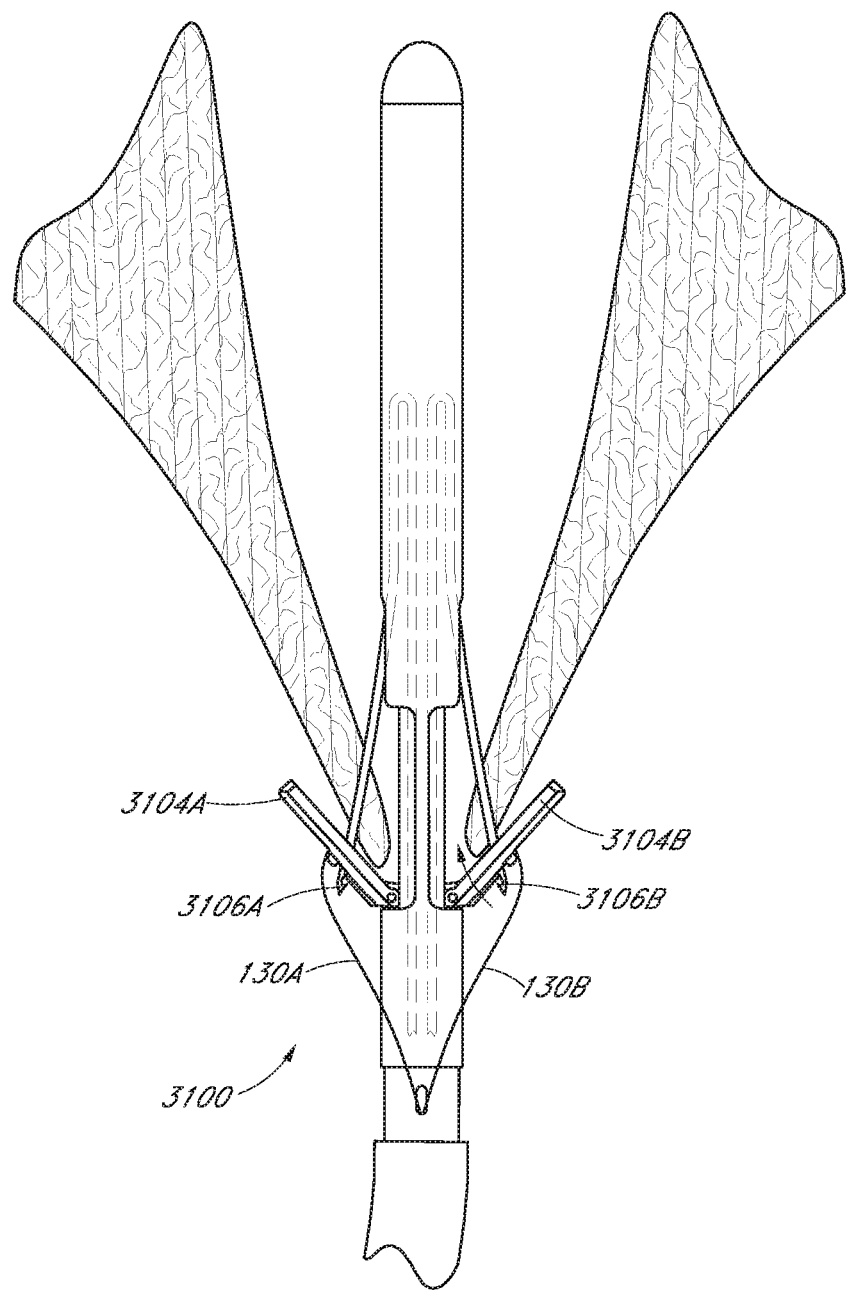
FIG. 48 is a schematic representation of an embodiment of a suturing device positioned in a passage through a valve with a first suture clasp arm positioned around a first leaflet of the valve, and a second suture clasp arm positioned around a second leaflet of the valve.

In some embodiments, the first suture clasp arm 3104A and the second suture clasp arm 3104B can both be extended from the device at substantially the same time and extend around opposite tips of the leaflets 132A, 132B, as illustrated in FIG. 48. In other embodiments, the clasp arms can be extended at the same time, but with one having extended before the other. Also as illustrated, suture catch mechanisms can be advanced through the suture clasp arms 3104A, 3104B at substantially the same time. In other embodiments, both clasp arms can extend around the leaflets but the suture catch mechanisms can advance one before the other.

Methods for Drawing Sutured Leaflets Closer Together

Figure 49:
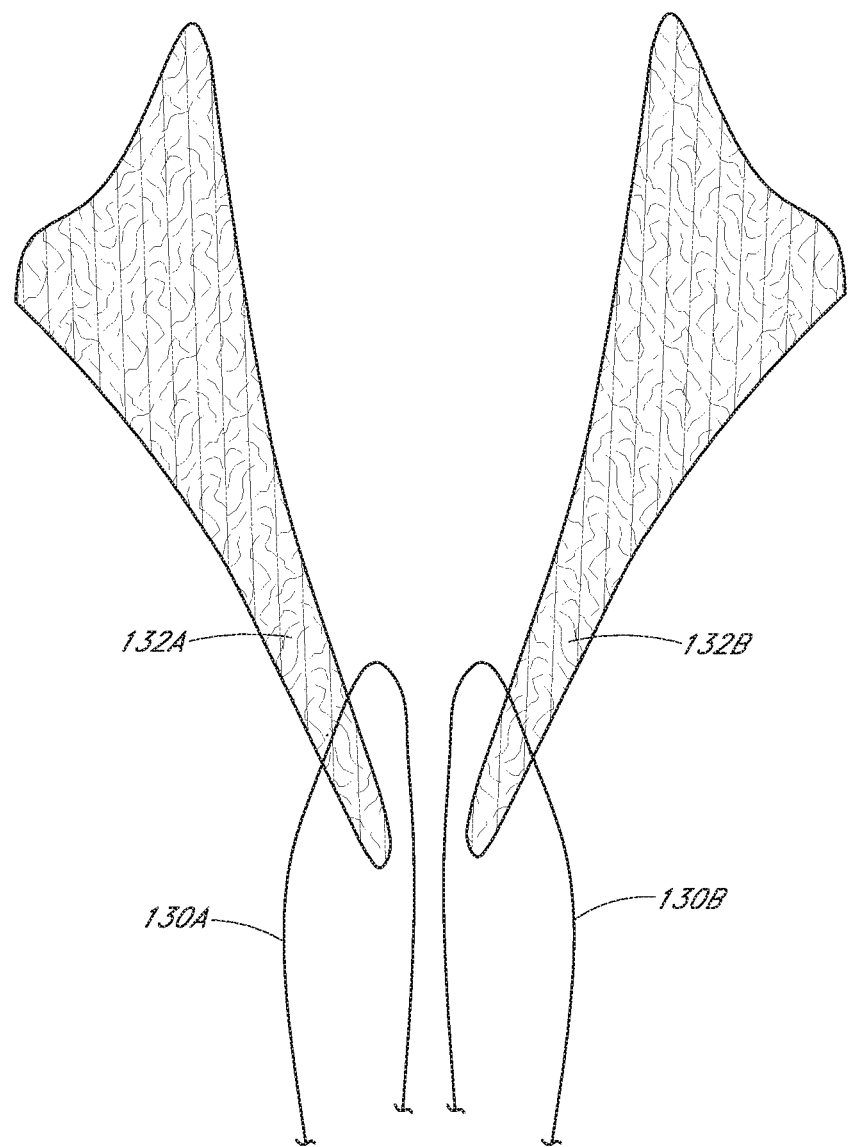
FIG. 49 is a schematic representation as in FIG. 47 or 48 showing the suture portions extending through the first leaflet and the second leaflet.

As shown in FIG. 49, after one or more of the suturing devices has been withdrawn, the suture portions 130A, 130B will extend proximally from the leaflets 132A, 132B. The methods for drawing sutured leaflets closer together described herein with respect to FIGS. 49-59 can apply equally to orientations, such as that of FIG. 15, reflected in embodiments where suturing devices take different access routes to a valve. Additionally, for all methods described herein, one or more pledgets can be attached to the suture portion(s), either before or after a knot is tied or applied, and located distal and/or proximal to the knot. FIG. 49 illustrates four strands of suture portion extending from the leaflets, which can comprise either a single suture if the arms described above were carrying the same suture, or two separate sutures, one sutured to each leaflet, if the arms described above were carrying their own suture. If the four strands illustrated in FIG. 49 are part of the same suture, the ends of the suture may be pulled from outside of the body to apply tension to the suture and draw the leaflets together. The suture portions can be secured together by tying a knot, applying a knot or otherwise joining the suture portions together according to known methods.

Figure 50:
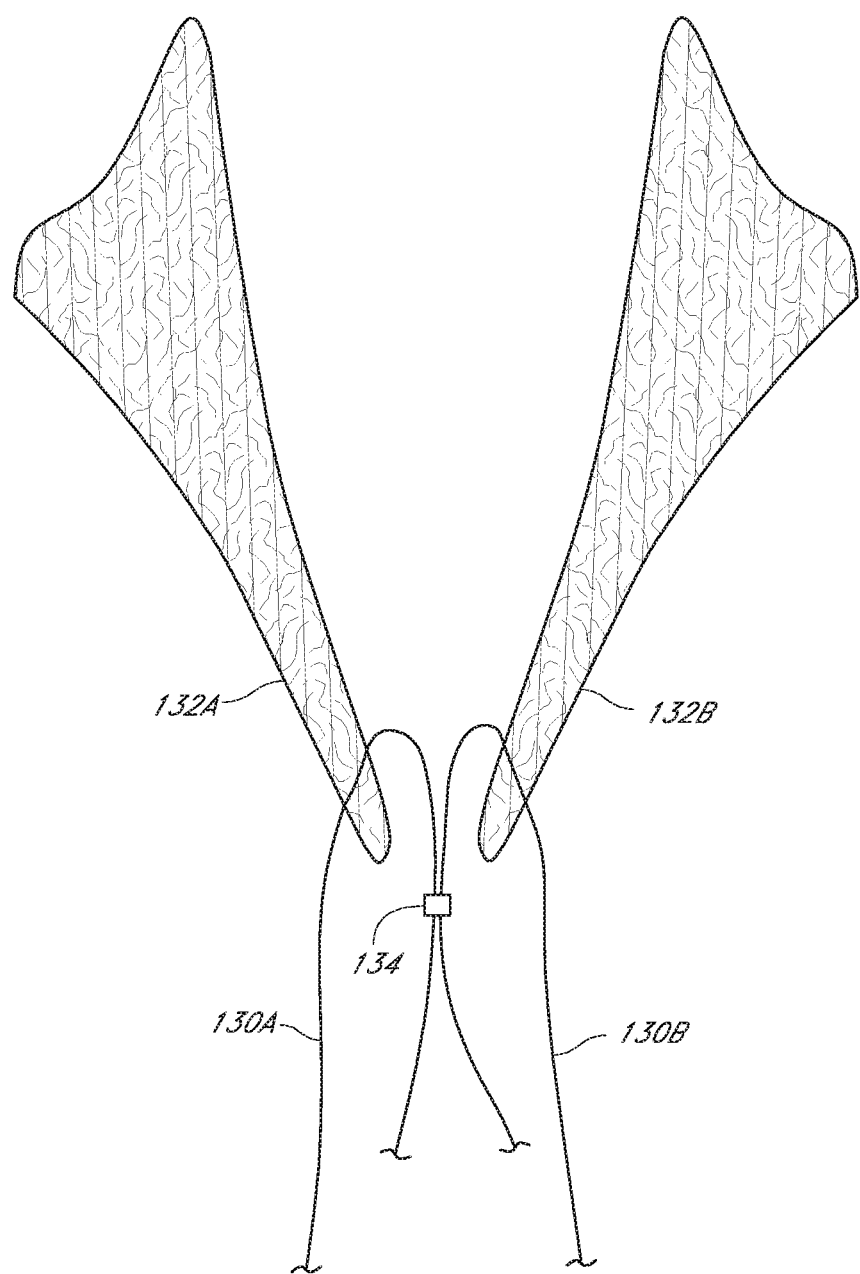
FIG. 50 is a schematic representation as in FIG. 49 showing the suture portions extending through the first leaflet and the second leaflet and being joined by a first knot.
Figure 51:
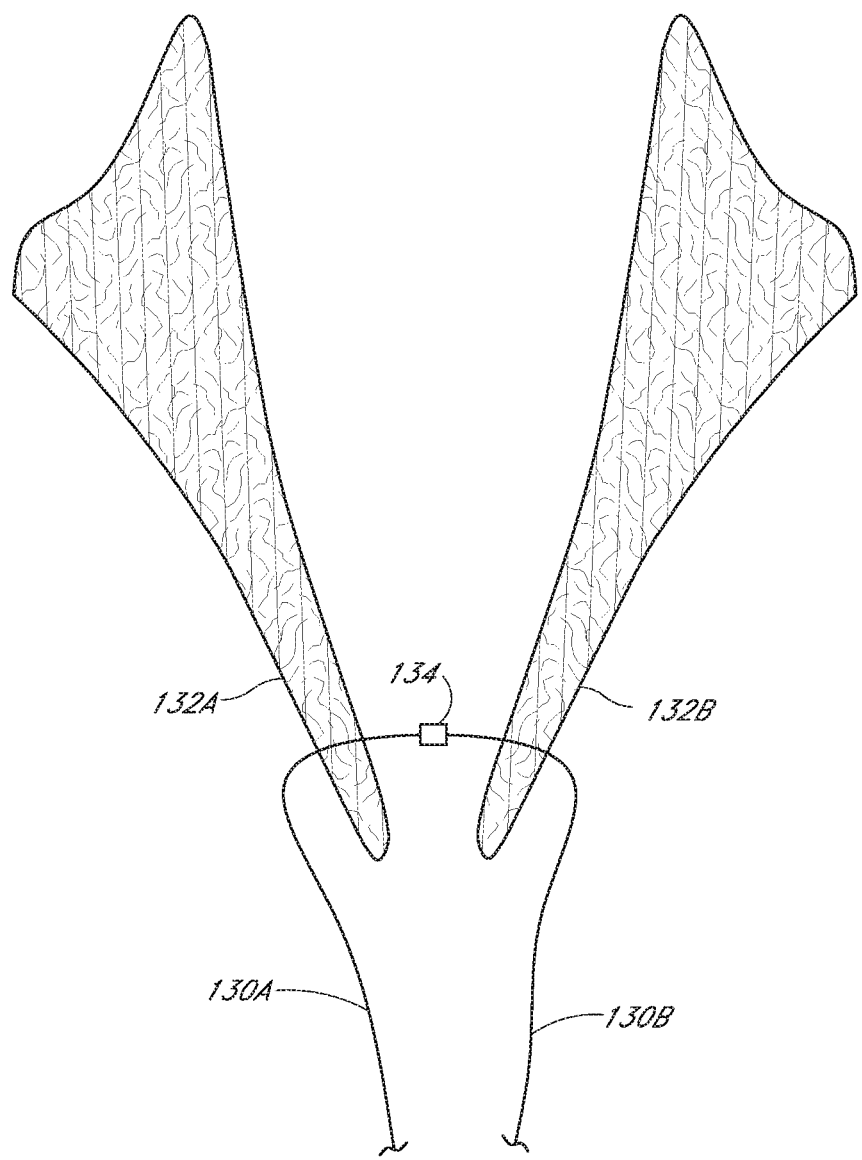
FIG. 51 is a schematic representation as in FIG. 50 showing the suture portions extending through the first leaflet and the second leaflet and being joined by a first knot that has been pulled between the leaflets.

In some embodiments, for example where two separate sutures are sutured to the leaflets 132A and 132B, two ends of the separate sutures can then be secured together, as illustrated in FIG. 50, by tying a knot 134 according to any known method or by applying a knot 134. The suture portions 130A,B can be secured together exterior to the body or within the body. Any excess portion of sutures can be trimmed. In some embodiments, the free ends of the suture portions 130A,B can then be pulled to draw the first leaflet 132A and the second leaflet 132B towards one another, with the knot or joined portion between the leaflets as illustrated in FIG. 51. A second knot can then be tied or applied to the sutures 130A,B to limit movement of the leaflets 132A,B relative to each other.

Figure 52:
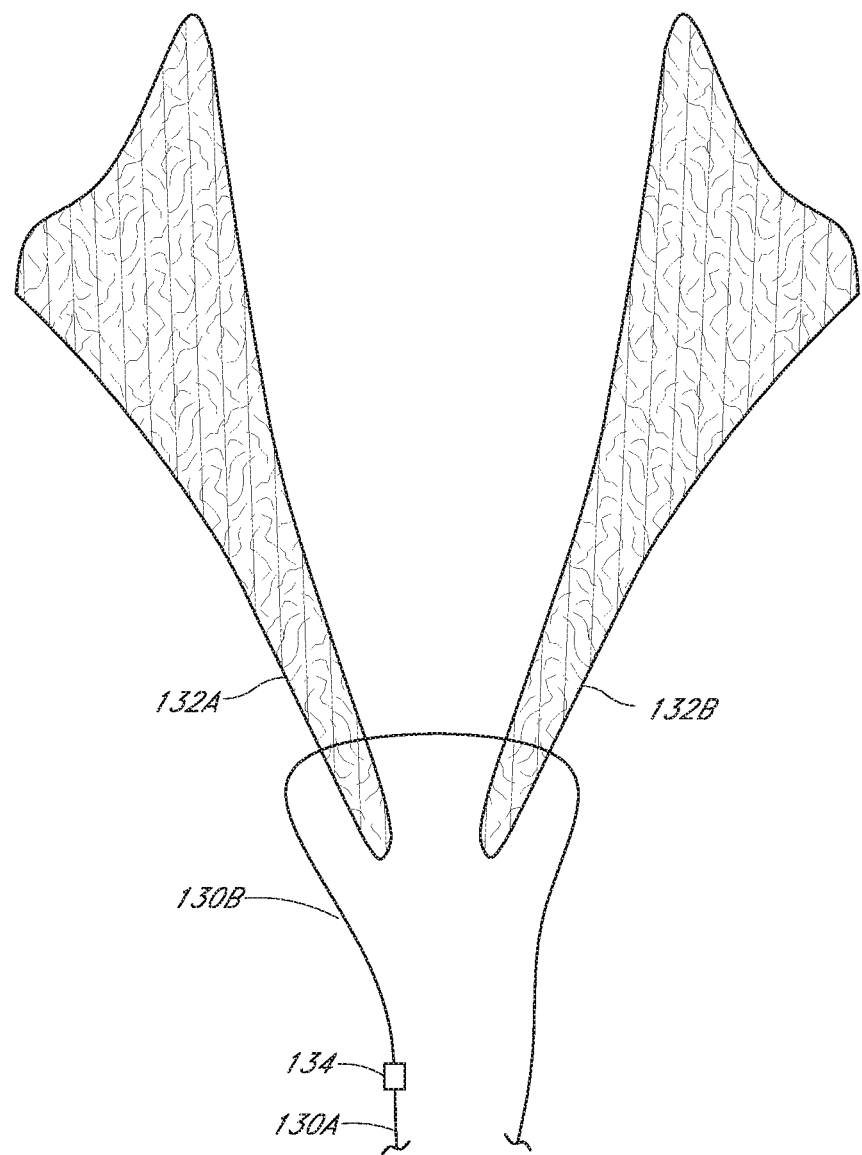
FIG. 52 is a schematic representation as in FIG. 51 showing the suture portions extending through the first leaflet and the second leaflet and being joined by a first knot that has been pulled through one of the leaflets.

In some embodiments, after the knot has 134 has been applied and positioned as shown in FIG. 51, just one of the free ends can be pulled initially, drawing the knot through one of the leaflets and out of the body, as illustrated in FIG. 52. This leaves a single suture passing through the leaflets. The two portions of the single suture can then be pulled to draw the first leaflet and second leaflet towards each other and a second knot can be tied or applied to the two portions.

Figure 53:
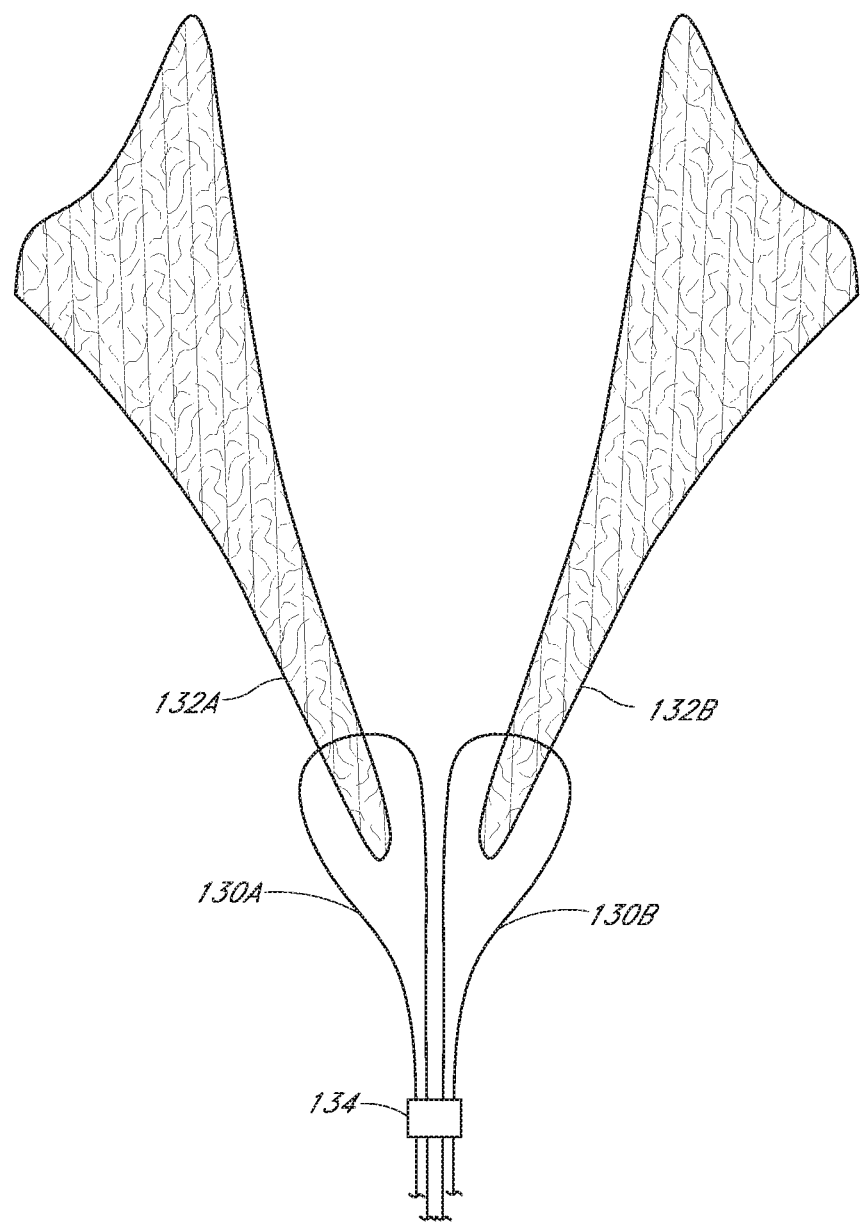
FIG. 53 is a schematic representation as in FIG. 49 showing the suture portions extending through the first leaflet and the second leaflet and being joined by a first knot.

In some embodiments, where two separate sutures and four suture portions extend from the leaflets, rather than initially securing two ends of the suture portions together, all four portions can be secured together according to any of the methods discussed herein, as illustrated in FIG. 53.

In some embodiments, where a single suture is positioned through the leaflets or a pair of sutures is positioned through the leaflets such as shown in FIGS. 51 and 52, one end of the suture can be secured to a second suture, the second suture can be drawn through the leaflets by pulling on the first suture, and a knot can be tied or applied to the second suture. In this embodiment, a first suture placed by the suturing device can be utilized to guide a second suture or another piece of material across the leaflets. The second suture or other piece of material is, in some embodiments, thicker or stronger than the first suture. In some embodiments, the second piece of material has a greater surface area to engage tissue, which can advantageously minimize dissection of tissue.

To accomplish placement of the second suture or additional piece of material in the place of the first suture, the second suture or other piece of material can be attached to one end or a first portion of the already placed suture. The first suture can be attached to the second suture or other piece of material by forming a knot by any known manner, or by otherwise joining them, for example, by welding the material together.

Thereafter, the other end or a second portion of the first suture can be pulled away from the leaflets. This causes the thicker suture to be drawn through the tissue and across the leaflets into the same position where the first suture(s) was placed. After the thicker suture has been pulled across the leaflets, the ends of the second suture or piece of material will in one embodiment be outside of the body.

The second suture or other piece of material can be detached from the original suture, and if the original suture has not already been removed from the patient, it can then be removed. With the ends of the second suture or other piece of material extending from the opening and out of the patient, that suture or material can be secured together by tying a knot according to any known method or by applying a knot, such as described in U.S. Patent Publication No. 2007/0010829 A1, published Jan. 11, 2007, which is hereby incorporated by reference herein in its entirety and is considered a part of this specification.

In some embodiments, once the suture or other material is used to draw the leaflets closer together and the knot is made or applied, the suture or other material can hold a portion of the leaflets 132A, 132B in contact with one another. In other embodiments, the suture or other material merely hold the leaflets 132A, 132B in closer proximity to one another than they had previously been.

When a suturing device having two arms 3104 and two suture catch mechanisms 3106 is used, as discussed with reference to FIGS. 38A-48, the device 3100 can be configured to place a single suture 130 through both the first leaflet 132A and the second leaflet 132B, either simultaneously or sequentially. In some such embodiments, the suture portions 130 can be pulled to draw the first leaflet 132A and the second leaflet 132B towards one another without applying a knot to the suture 130 beforehand. Accordingly, a single knot 134 can be applied to the suture 130 to hold the leaflets 132A, 132B in proximity to one another.

Figure 54:
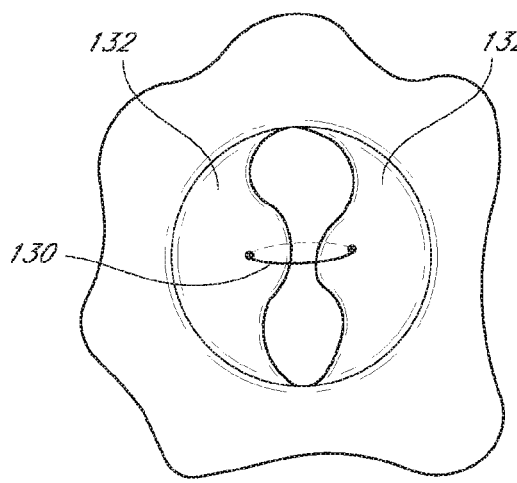
FIG. 54 illustrates placement of suture through a bicuspid valve near a central portion of each leaflet.
Figure 55:
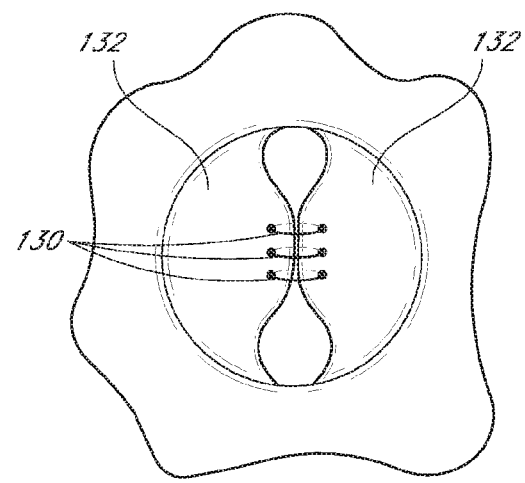
FIG. 55 illustrates placement of three sutures through a bicuspid valve near a central portion of each leaflet.
Figure 56:
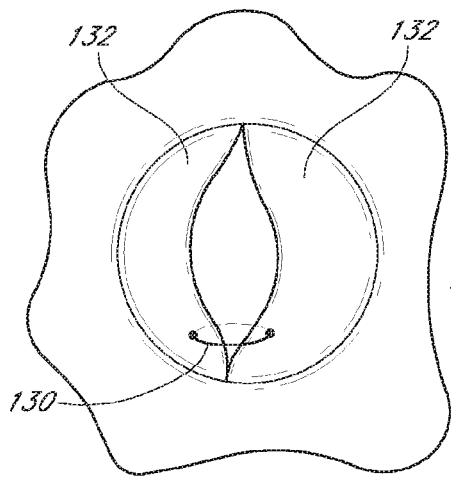
FIG. 56 illustrates placement of suture through a bicuspid valve at locations spaced from the center of each leaflet.
Figure 57:
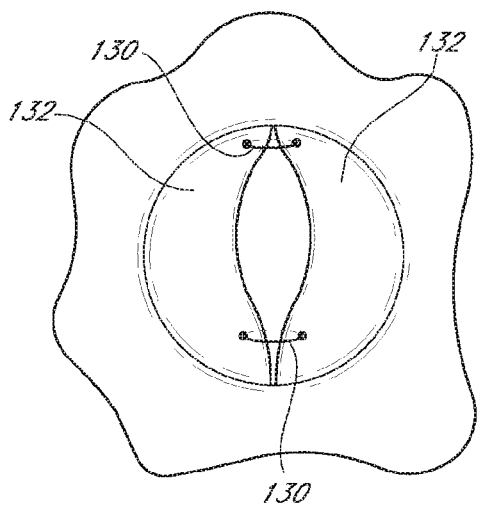
FIG. 57 illustrates placement of suture through a bicuspid valve at multiple locations spaced from the center of each leaflet.
Figure 58:
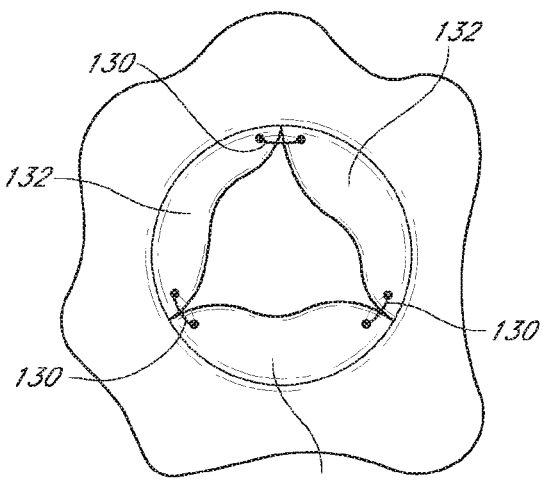
FIG. 58 illustrates placement of suture through a tricuspid valve.

The suture or sutures 130 can be placed through the leaflets 132 at locations selected by the physician to treat a problem of a particular valve. For example, in some embodiments, a suture or sutures 130 can be passed through the leaflets 132 at locations in or near a central region of the leaflets 132, as illustrated in FIG. 54. FIG. 55 illustrates an embodiment in which three sutures 130 have been passed through the leaflets 132 in a central region of the leaflets. In some embodiments, a suture or sutures 130 can be passed through a portion of the leaflets 132 that is in proximity to a periphery of the valve, as illustrated in FIG. 56. In some embodiments, sutures 130 can be applied to multiple locations between two leaflets 132, as illustrated in FIG. 57. In some embodiments, sutures 130 can be applied to multiple locations between more than two leaflets 132, as illustrated in FIG. 58 with respect to a tricuspid valve.

Figure 59:
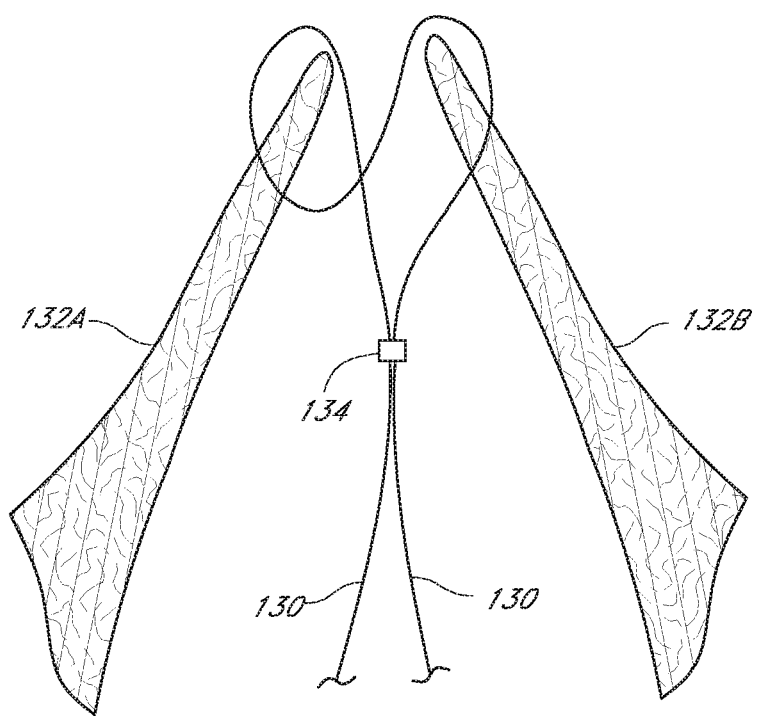
FIG. 59 illustrates placement of suture through a valve.
Figure 60:
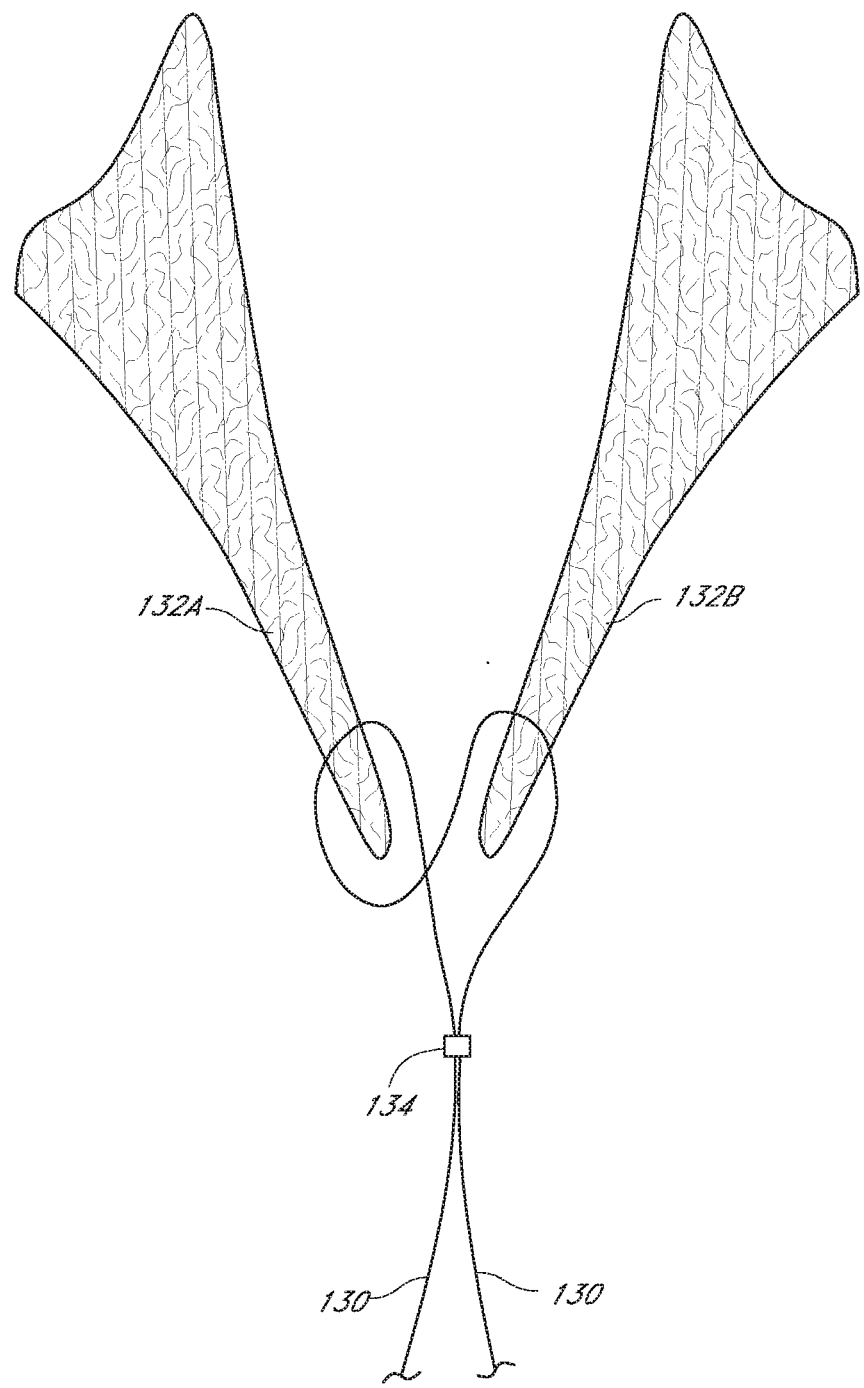
FIG. 60 illustrates placement of suture through a valve.

FIGS. 59 and 60 illustrate other manners of placing suture through leaflets of a valve. In some embodiments, suture can be placed as shown in FIG. 59 or 60 using the devices illustrated in FIGS. 17-18 and 28-29. The devices can be introduced through the same or different access routes. For example, one device can be introduced to the heart through the vasculature while another device is introduced transapically. In some embodiments, a first suture can be placed through a first leaflet by a first device 1100 as illustrated in FIGS. 19-22 and a second suture can be placed through a second leaflet by a second device 2100 as illustrated in FIGS. 30-33. The second suture can be placed before the first suture in some embodiments. In embodiments involving the placement of multiple sutures, the multiple sutures can be joined with a single knot or with multiple knots. Further information regarding devices and methods for placing suture as shown in FIGS. 59 and 60 is provided in U.S Patent Application Publication No. 2008/0269786, published on Oct. 30, 2008, and, in particular, the embodiments described in association with FIGS. 10I-L, 27-28B, 36-39A-K.

Devices and Methods for Techniques Other than Valve Repair

Figure 61:
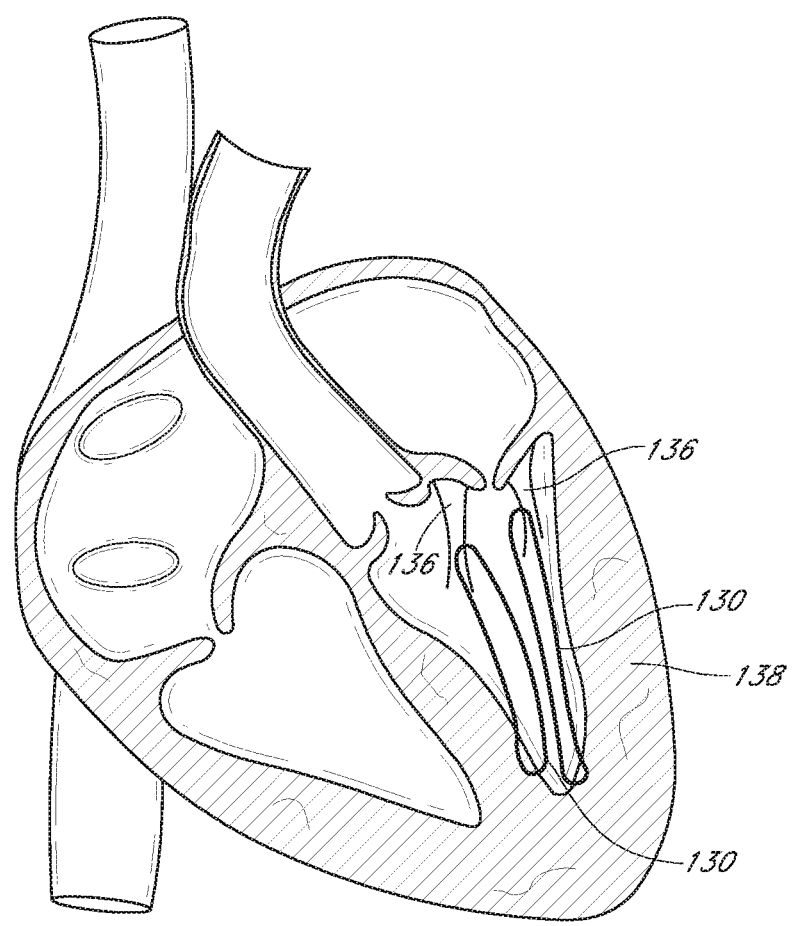
FIG. 61 illustrates placement of suture through chordae tendineae and myocardium.

The devices and methods described and referenced herein can be used to perform other techniques for valve repair. For example, the devices and methods described above can be used to apply a suture to one or more of the chordae tendineae 136 and myocardium 138, as illustrated in FIG. 61, to restore tension to chordae tendineae that have been come elongated. In some embodiments, the applied suture can be used as a guide suture to deliver a second suture or other material (e.g. artificial chordae) through the chordae, as described above. The devices and methods described above can be used to suture a patch to natural or surgically-created openings in leaflets. The devices and methods described above can be used to attach a ring around the outside of the malfunctioning valve. The devices and methods described above can be used to suture prosthetics to the heart.

Figure 62:
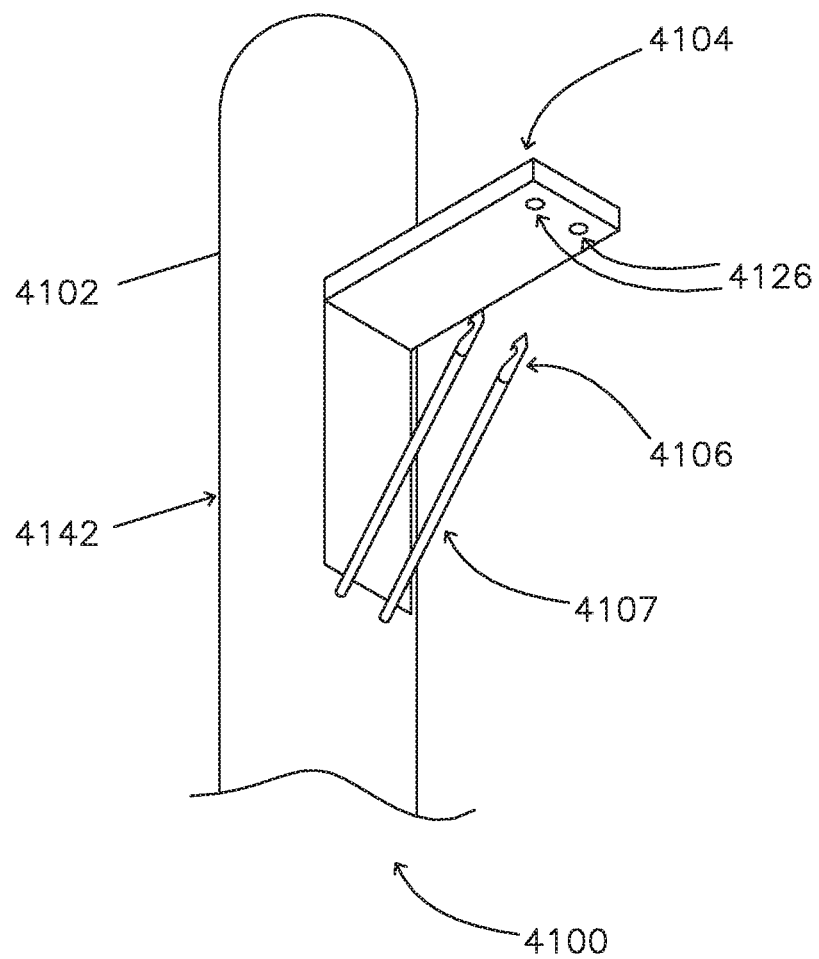
FIG. 62 is a schematic perspective view of an embodiment of a suturing device comprising two needles and a single arm having two suture mounts.

Further Embodiments of Additional Suturing Devices, Such as for Suturing a Base of A Valve FIG. 62 is a schematic perspective view of an exemplifying embodiment of a distal end 4102 of a suturing device 4100 that can be used to suture an anatomical valve, such as a heart valve. The suturing device 4100 can comprise two suture catch mechanisms 4106 and a single arm 4104 located in proximity to a distal end 4102 of an elongate body 4142. The arm is configured for movement between a retracted position and an extended position. In some embodiments, the arm can be moved between the retracted and extended position by rotation around an end of the arm that is pivotally coupled to the elongate body 4142. In other embodiments, the arms can be advanced along their length out of an opening in the elongate body 4142, as shown and described in U.S. Pat. No. 6,911,034, issued on Jun. 28, 2005, which is hereby incorporated by reference herein in its entirety and is considered a part of this specification.

In the embodiment of FIG. 62, the single arm 4104 comprises two suture clasps or mounts 4126 in proximity to a free end of the arm 4104. In some embodiments, the arm 4104 can comprise more than two suture clasps 4126. The suture clasps 4126 can be located at or near the free end of the arm 4104. The arm 4104 of this embodiment is sufficiently long to be able to position the suture clasps 4126 at or near a base of a heart valve, such as the mitral valve for example. The arm 4104 illustrated in FIG. 62 extends generally orthogonally to a longitudinal axis of the elongate body 4142.

The suture clasps 4126 of the arm 4104 are spaced from one another by a distance. The distance between the suture clasps can vary among different embodiments. The magnitude of separation corresponds generally to the magnitude of separation between locations of suture placement in the tissue. The magnitude of separation between the suture clasps can be varied depending on the desired use.

In the exemplifying embodiment of FIG. 62, the two suture catch mechanisms 4106 are illustrated as needles. The needles can be operated simultaneously in some embodiments and sequentially in other embodiments. As described in connection with the preceding embodiments, the suture catch mechanisms can be deployed and retracted to retrieve suture portions 130 that are releasably held by the arm 4104 (see FIGS. 65-68). Although the embodiment illustrated in FIG. 62 comprises two needles, the suturing device can comprise more than two needles in some embodiments. The arm(s) 4104 will typically be configured to have the same number of suture mounts as the number of suture catch mechanisms, with each suture mount releasably carrying a suture portion.

The exemplifying embodiment of FIG. 62 also includes protective members 4107 (also described herein as "needle arms"). The protective members 4107 are configured to inhibit contact between a distal end of the suture catch mechanisms and surrounding tissue during at least a portion of the deployment of the needles. In general, the protective members protect the tissue surrounding the suturing device 4100 from damage by the suture catch mechanisms 4106 as the suture catch mechanisms are moved from their retracted positions to the locations of the valve where the suture portions are to be passed through the valve.

As illustrated in FIG. 62, in embodiments comprising a plurality of suture catch mechanisms, the suturing device can have a separate protective member corresponding to each suture catch mechanism. In other embodiments, the suturing device can have a single protective member configured to protect surrounding tissue from two or more suture catch mechanisms at the same time.

In some embodiments, such as that of FIG. 62, the protective members can have a generally sleeve-like configuration to generally surround the suture catch mechanisms 4106. The protective members can entirely surround a circumference of the suture catch mechanisms in some embodiments. In other embodiments, the protective members can merely partially surround a circumference of the suture catch mechanisms. For example, whether surrounding one or more suture catch mechanisms, the protective member can in some embodiments have a generally U-shaped cross-section with the opening in the protective member being oriented to face the elongate body when the protective member is extended. In some embodiments, a protective member can completely surround more than one needle in a single lumen.

The protective members preferably extend over the distal ends of the suture catch mechanisms, extend beyond the distal ends of the suture catch mechanisms, or both.

Figure 63:
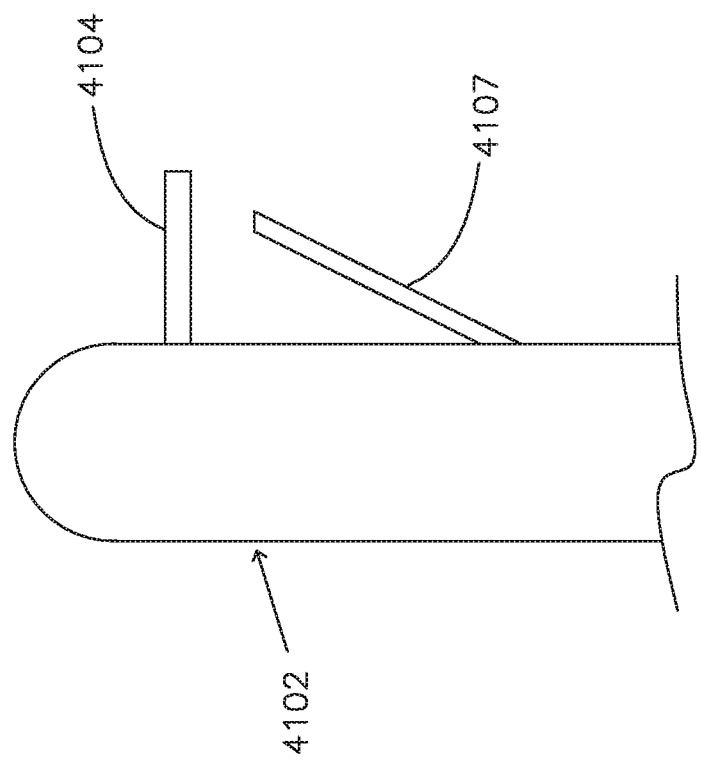
FIG. 63 is a schematic side view of the suturing device of FIG. 62 with the arm extended and a protective member extended.

The protective members 4107 of the exemplifying embodiment of FIG. 62 can be moved between a retracted position and an extended position. As illustrated in FIG. 63, the protective member 4107 can be extended from the elongate body 4142 in advance of the corresponding suture catch mechanism 4106 such that the distal end of the suture catch mechanism is not exposed to the surrounding tissue as the suture catch mechanism is moved toward the location of the valve to be sutured.

Figure 64:
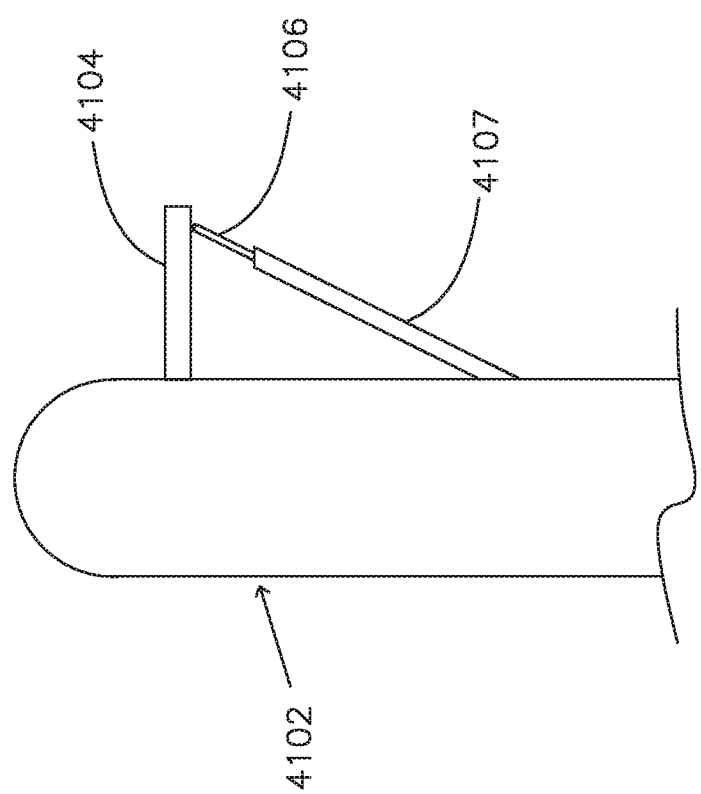
FIG. 64 is a schematic side view of the suturing device of FIGS. 62 and 63 with a needle extended through the protective member.

In some embodiments, the suture catch mechanism 4106 can be advanced toward the location for suture placement and the arm 4104 once the protective member 4107 has been advanced to the location for suture placement, as illustrated in FIG. 64 for example. After the suture catch mechanism has retrieved the suture portion from the arm as discussed in connection with the foregoing embodiments, the suture catch mechanism 4106 and the protective member 4107 can be retracted into the elongate body 4142 with the suture portion 130. The protective members can be placed generally at the location to be sutured before the needles are moved from their retracted positions in some embodiments. In other embodiments, the needles can be moved toward their deployed positions while the protective members are extended. For example, the distal end of the protective member can be located beyond a distal end of the corresponding needle as both are advanced. In this example, once the distal end of the protective member has been placed generally at the location to be sutured, the distal end of the needle can then be advanced beyond the distal end of the protective member to penetrate the tissue of the valve.

When a plurality of suture catch mechanisms 4106 are advanced toward the arm 4104 simultaneously, the protective members 4107 may also be advanced simultaneously. Alternatively, the protective members 4107 may be sequentially advanced even though the suture catch mechanisms are advanced simultaneously. The protective members 4107 can, in some embodiments, be advanced simultaneously, although the suture catch mechanisms are advanced sequentially. The use of multiple suture catch mechanisms per arm, as well as the use of the protective member, can be incorporated into any of the devices described herein, including the edge-to-edge repair devices previously described.

FIGS. 65-70 schematically illustrate use of the suturing device 4100 of FIGS. 62-64 according to an embodiment. The valve shown in FIGS. 65-70 can be a mitral valve 8 and the suturing device can be inserted into the valve via a transapical opening, or using any of the access routes discussed above, with or without a guide wire. Although reference is made to the mitral valve in connection with FIGS. 65-70, the description can apply to valves other than the mitral valve.

As illustrated in FIG. 65, the distal assembly 4102 of the suturing device 4100 is advanced into the passage through the mitral valve 8. The distal assembly 4102 is advanced sufficiently far through the passage to permit the arm 4104 to be opened without damaging surrounding tissue. Once the arm 4104 is extended, the suturing device is retracted through the passage such that the free end of the arm 4104 is adjacent a base of the valve as illustrated in FIG. 66. A protective member 4107 is then advanced to position the distal end of the protective member 4107 at or near a base of the valve. A leaflet 132 of the valve can be posited between the arm 4104 and the protective member in some embodiments, such as that illustrated in FIG. 66. Once the protective member has been advanced, the suture catch mechanism 4106 is advanced through the tissue of the valve to engage the arm 4104 as illustrated in FIG. 67.

FIG. 68 is a schematic a partial cross-sectional view of the arm 4104, the suture catch mechanisms 4106, and the valve of FIG. 67 taken along line 68-68. Although FIG. 68 illustrates both needles positioned through the tissue at the same time, such an arrangement may not occur in some embodiments, for example when a first needle is deployed and retracted before a second need is deployed.

The suture catch mechanisms 4106 are retracted through the tissue with the suture portions 130 into the elongate body 4142. The protective members 4107 can be retracted into the elongate body 4142 before, after, or with the suture catch mechanisms 4106. FIG. 69 illustrates the suture portions 130 positioned through the valve with the suturing device 100 being withdrawn from the valve.

With the suture portions 130 positioned through the valve, the suture portions are tightened to draw together the locations of suture penetration. As illustrated in FIG. 70, the sutures are then secured together by tying or other methods as described above or in the patents incorporated by reference, which form a part of this specification.

Figure 71:
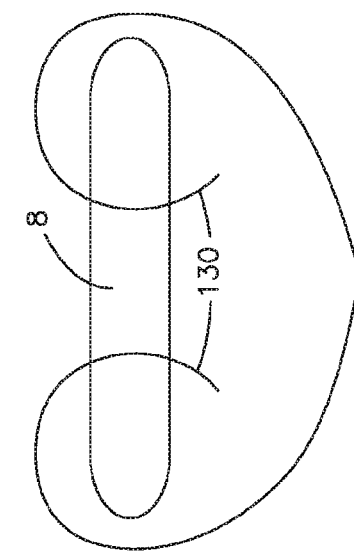
FIG. 71 is a schematic partial cross-sectional view of an arm, a needle, and a valve similar to FIG. 68, except the arm comprises a single suture mount and a single needle is illustrated.

In another embodiment, a suturing device 5100 of a configuration similar to that of FIGS. 62-64 may be used, except that the arm 5104 comprises a single suture clasp 5126 rather than a plurality of suture clasps 5126. As illustrated in FIG. 71, when a device having an arm 5104A with a single suture clasp is used, the suturing device is positioned at least partially in the mitral valve 8 as illustrated and described in connection with FIGS. 65-67. FIG. 71 is a schematic partial cross-sectional view of an arm, a needle, and a valve taken along line 68-68 in FIG. 67 according to an embodiment employing a suturing device having an arm comprising a single suture mount. As illustrated in FIG. 71, the arm 5104A has been positioned on a first side of the valve and a suture catch mechanism 5106A has passed through the tissue of the valve from a second side of the valve. The suture catch mechanism 5106A is then retracted to position the suture portion 130 through the valve as illustrated in FIG. 72.

Figure 72:
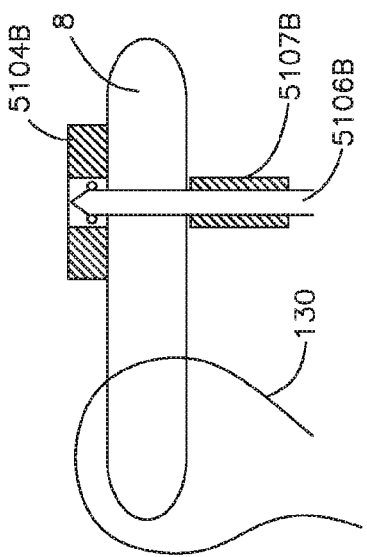
FIG. 72 is a schematic partial cross-sectional view as in FIG. 71 with a first suture portion positioned through the valve and a second arm and a second needle illustrated in the process of placing a second suture portion through a second location in the valve.

A second arm 5104B is then positioned to place a second suture portion at a location spaced from the first location as illustrated in FIG. 72. The second arm can be attached to the same elongate body 5142 as the first arm 5104A in some embodiments. In other embodiments, the second arm can be attached to a second device of similar or identical configuration to the prior device. If a second device is employed, it may be introduced into the mitral valve according to the steps described above in connection with FIGS. 65-67 and 71 and a second suture portion is placed through the valve as the suture catch mechanism 106 is retracted through the valve.

Figure 73:
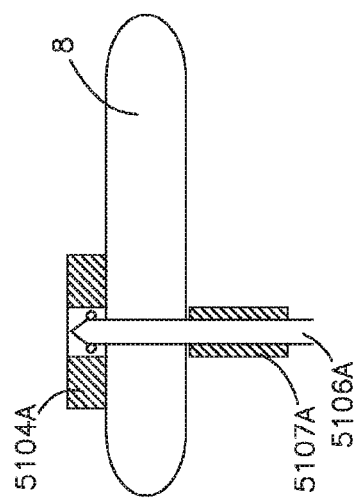
FIG. 73 is a schematic representation as in FIG. 72 with two suture portions positioned through the valve and first ends of the suture portions being secured together.
Figure 74:
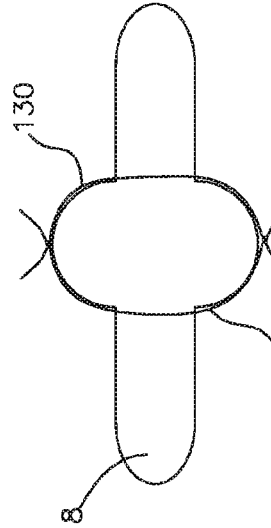
FIG. 74 is a schematic representation as in FIG. 73 with the second suture ends having been pulled to draw the secured first ends toward a first side of the valve.
Figure 75:
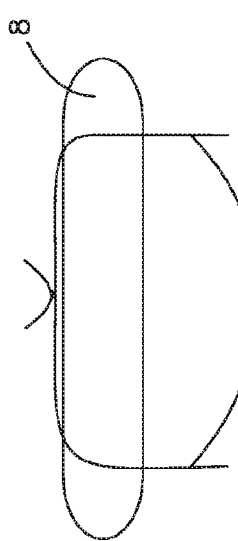
FIG. 75 is a schematic representation as in FIG. 74 with the second suture ends secured together.

FIG. 73 illustrates two separate suture portions positioned through the tissue of the valve 8. Also as illustrated in FIG. 73, first ends of the suture portions 130 are then secured together by knotting or other means, such as described above or in the patents incorporated by reference, which form a part of this specification. The second ends of the suture portions 130 are then pulled to draw the suture portions through the tissue and position the secured first ends of the suture portions adjacent one side of the tissue, as illustrated in FIG. 74. The suture portions 130 are tightened to draw together the locations of suture penetration through the tissue and secured together, as illustrated in FIG. 75

Figure 76:
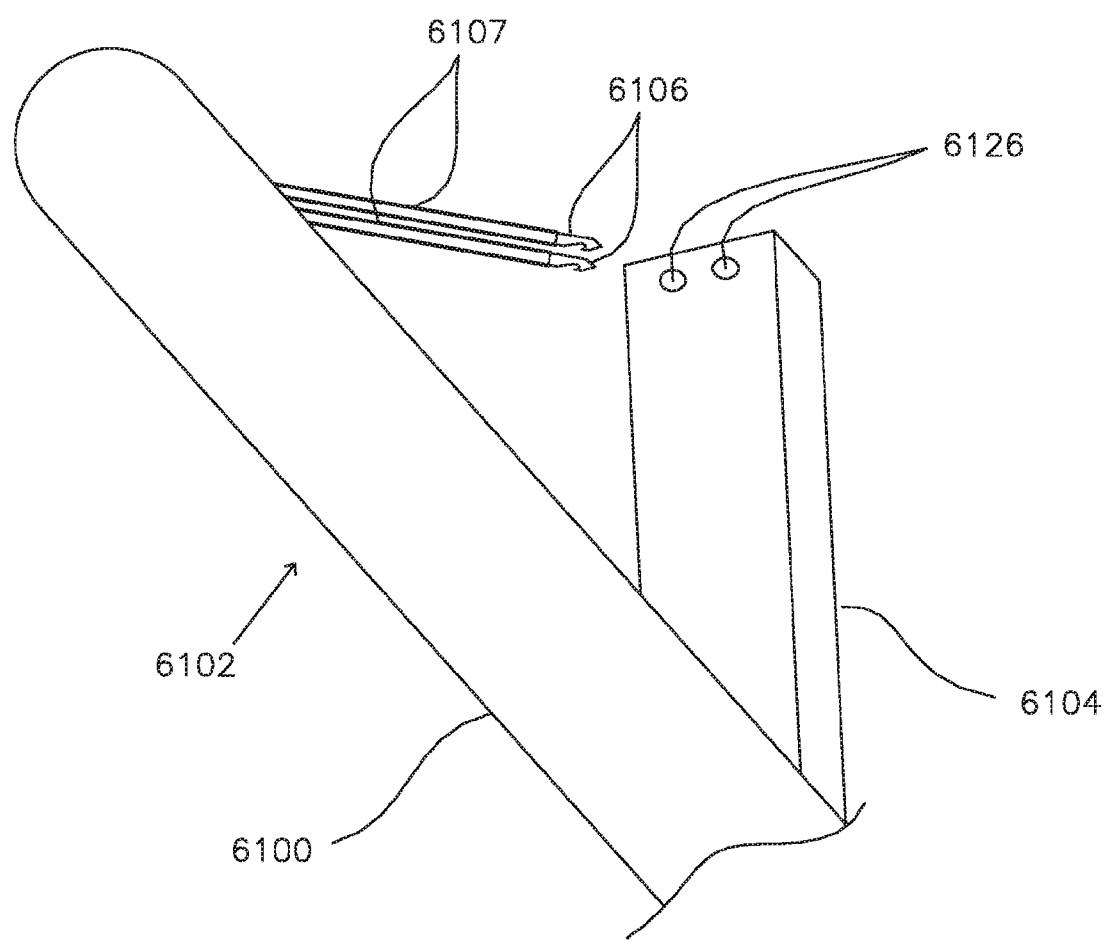
FIG. 76 is a schematic perspective view of an embodiment of a suturing device comprising two needles and a single arm having two suture mounts, the two needles being located distally of the arm and configured for proximal movement to engage the arm.

FIG. 76 is a schematic perspective view of an exemplifying embodiment of a suturing device comprising a two suture catch mechanisms 6106 and a single arm 6104 located in proximity to a distal end of an elongate body 6142. The suturing device illustrated in FIG. 76 is similar to the suturing device of FIG. 62, except (1) the suture catch mechanisms 6106 of suturing device of FIG. 76 are located distally of the arm 6104 and configured to be moved proximally from the retracted position to the deployed position, (2) the arm 6104 of the embodiment of FIG. 76 extends distally and outwardly from the elongate body 6142 such that an angle between the arm 6104 and a longitudinal axis of the elongate body 6142 is less than 90°, and (3) other changes to the device of FIG. 76 compared to the device of FIG. 62 resulting from the first two differences as will be understood from the foregoing embodiments.

FIGS. 77-79 schematically illustrate use of the suturing device 6100 of FIG. 76 according to an embodiment. The valve shown in FIGS. 77-79 can be a mitral valve 8 and the suturing device can be inserted into the valve via access through the inferior vena cava and the atrial septum, with or without a guide wire. Although reference is made to the mitral valve in connection with FIGS. 77-79, the accompanying description can apply to valves other than the mitral valve.

As illustrated in FIG. 77, the distal assembly 6102 of the suturing device 6100 is advanced into the passage through the mitral valve 8. The arm 6104 is extended from the elongate body 6142 and the suturing device is advanced through the passage such that the free end of the arm 6104 is adjacent a base of the valve as illustrated in FIG. 77. A protective member 6107 is then advanced to position the distal end of the protective member 6107 at or near a base of the valve. A leaflet 132 of the valve can be posited between the arm 6104 and the protective member in some embodiments, such as that illustrated in FIG. 78. Once the protective member has been advanced, the suture catch mechanism 6106 is advanced through the tissue of the valve to engage the arm 6104 as illustrated in FIG. 79.

Two suture portions are then passed through the valve tissue essentially in the same manner illustrated and described in connection with FIGS. 68-70. In embodiments wherein an arm of the suturing device comprises only a single suture mount, the suture portions can be placed through the valve tissue in essentially the same manner illustrated and described in connection with FIGS. 71-75.

Figure 80:
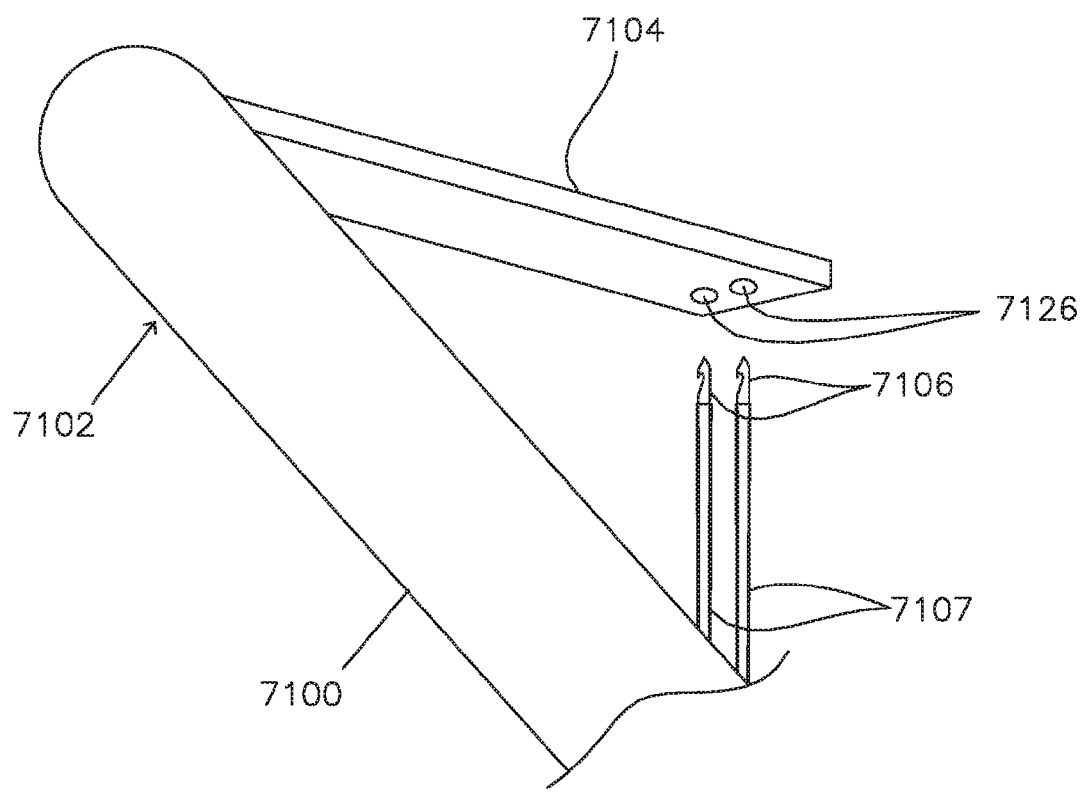
FIG. 80 is a schematic perspective view of a suturing device comprising two needles and a single arm having two suture mounts, the two needles being located proximally of the arm and configured for distal movement to engage the arm, and the arm having an extended position in which the arm is oriented at an angle of less than 90° relative to a longitudinal axis of the suturing device.

FIG. 80 is a schematic perspective view of an exemplifying embodiment of a suturing device comprising two suture catch mechanisms 7106 and a single arm 7104 located in proximity to a distal end of an elongate body 7142. The suturing device illustrated in FIG. 80 is similar to the suturing device of FIG. 76, except the suture catch mechanisms 7106 of suturing device of FIG. 80 are located proximally of the arm 7104 and configured to be moved distally from the retracted position to the deployed position and the suturing device of FIG. 80 includes other changes compared to the device of FIG. 76 resulting from the arrangement of the arm and suture catch mechanisms as will be understood from the foregoing embodiments.

Figure 83:
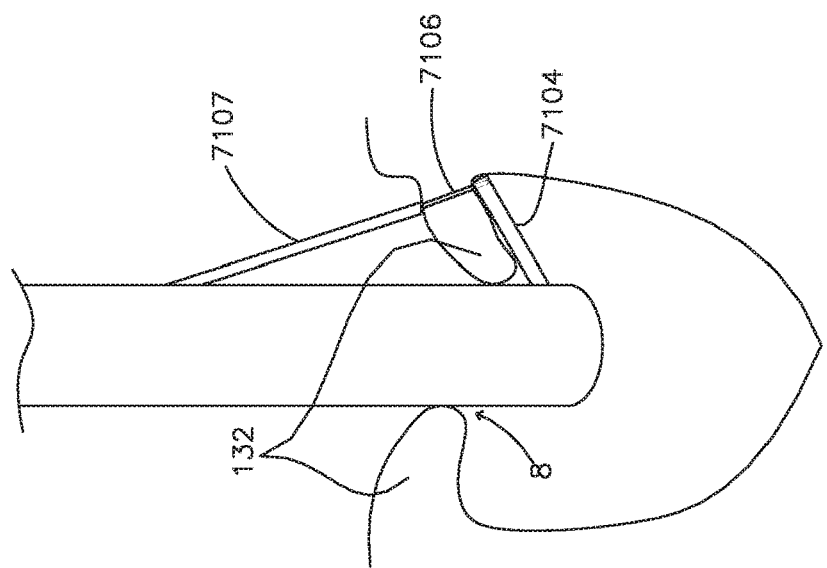
FIG. 83 is a schematic representation as in FIG. 82 with a needle being advanced through the protective member to engage the arm.
Figure 82:
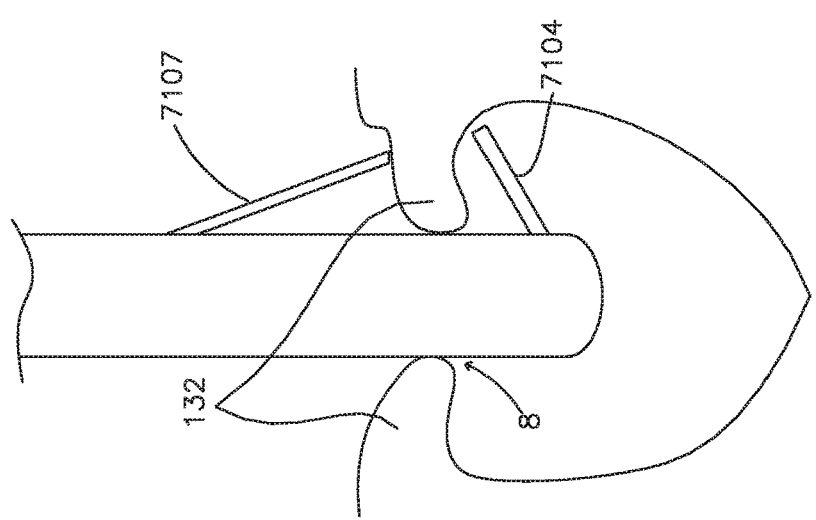
FIG. 82 is a schematic representation as in FIG. 81 with a protective member extended.
Figure 81:
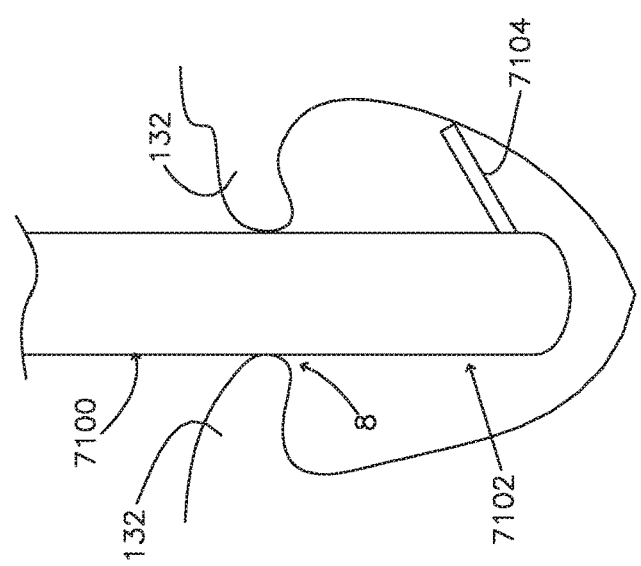
FIG. 81 is a schematic representation of the suturing device of FIG. 80 being positioned in a passage of a valve, such as a mitral valve such as by access through the inferior vena cava and the atrial septum, with the arm extended.

FIGS. 81-83 schematically illustrate use of the suturing device 7100 of FIG. 80 according to an embodiment. The valve shown in FIGS. 81-83 can be a mitral valve 8 and the suturing device can be inserted into the valve via access through the inferior vena cava and the atrial septum, with or without a guide wire. Although reference is made to the mitral valve in connection with FIGS. 81-83, the accompanying description can apply to valves other than the mitral valve.

As illustrated in FIG. 81, the distal assembly 7102 of the suturing device 7100 is advanced into the passage through the mitral valve 8. The distal assembly 7102 is advanced sufficiently far through the passage to permit the arm 7104 to be opened without damaging surrounding tissue. Once the arm 7104 is extended, the suturing device is retracted through the passage such that the free end of the arm 7104 is adjacent a base of the valve as illustrated in FIG. 82. A protective member 7107 is then advanced to position the distal end of the protective member 7107 at or near a base of the valve. A leaflet 132 of the valve can be posited between the arm 7104 and the protective member in some embodiments, such as that illustrated in FIG. 82. Once the protective member has been advanced, the suture catch mechanism 7106 is advanced through the tissue of the valve to engage the arm 7104 as illustrated in FIG. 83.

Two suture portions are then passed through the valve tissue essentially in the same manner illustrated and described in connection with FIGS. 68-70, except that the positions of the arm and the suture catch mechanisms have been exchanged relative to the valve. In embodiments wherein an arm of the suturing device comprises only a single suture mount, the suture portions can be placed through the valve tissue in essentially the same manner illustrated and described in connection with FIGS. 71-75, except that the positions of the arm and the suture catch mechanisms have been exchanged relative to the valve.

Figure 84:
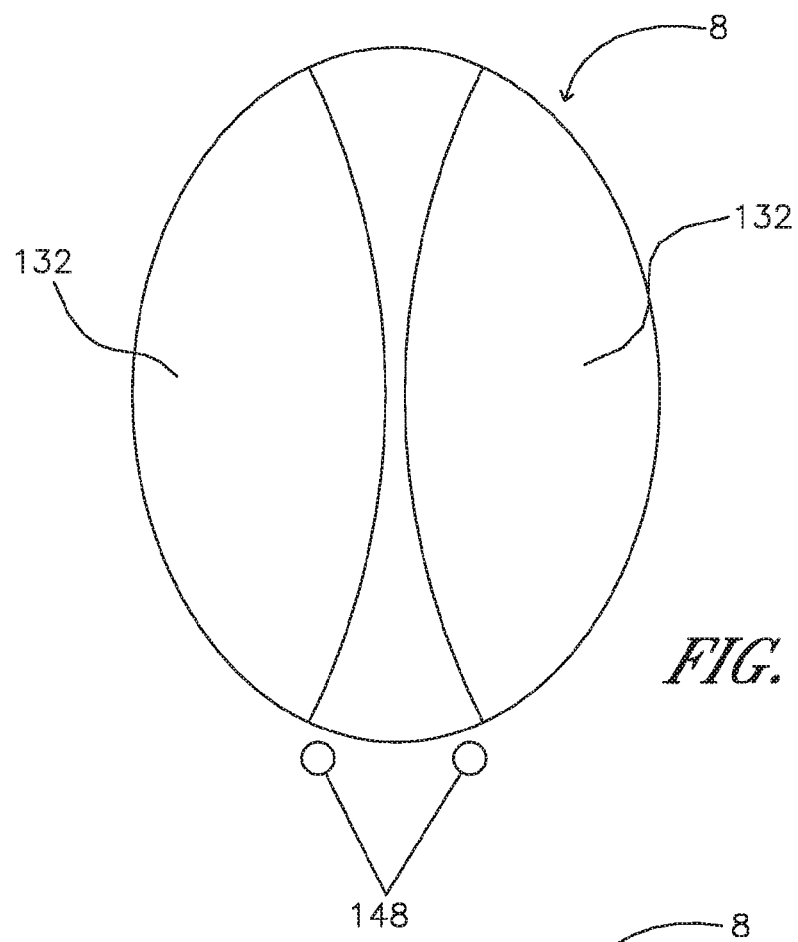
FIG. 84 is a schematic representation of suture placement locations according to an embodiment.
Figure 85:
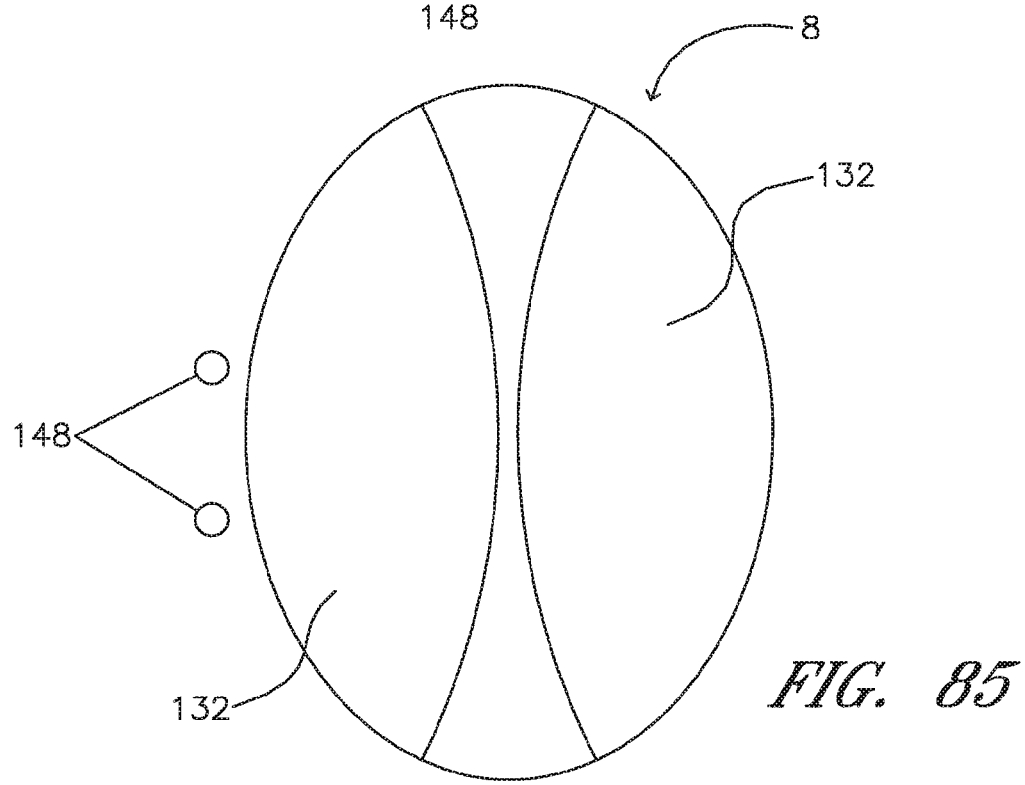
FIG. 85 is a schematic representation of suture placement locations according to an embodiment.

Using the methods illustrated and described in connection with FIGS. 65-75, 77-79, and 81-83 sutures can be passed through a variety of locations near a base of a valve. For example, FIGS. 84 and 85 schematically illustrate locations 148 where suture can be placed in a valve. As illustrated in FIG. 84, the suture can be placed through valve tissue at locations 148 generally between adjacent leaflets 132. Alternatively or additionally, sutures may be placed through locations 148 at or near a base of a leaflet 132 approximately at the middle of the leaflet 132 as illustrated in FIG. 85. The devices and methods illustrated and described in connection with FIGS. 65-75, 77-79, and 81-83 can be used to perform other procedures, such as attachment of a ring around the outside of the malfunctioning valve and attachment of prosthetic devices to tissue. The protective member or needle arm described above can also be utilized in the embodiments of the suturing device described above for suturing valves, such as edge-to-edge suturing of mitral valves. In such embodiments, the needle arms may be deployed to a position that pinches the leaflet between the suture clasp arm and the needle arm. The suture catch mechanism or needle may then be advanced from out of the needle arm, through tissue of the leaflet, and into engagement with the suture end held by the suture clasp arm.

Although methods have been described for suturing valve tissue using a suturing device having an arm with a single suture mount and using a suturing device with multiple suture mounts in a single arm, other embodiments can employ a suturing device comprising an arm having more than two suture clasps and a corresponding number of needles configured to retrieve suture portions from each of the suture clasps.

Figure 86:
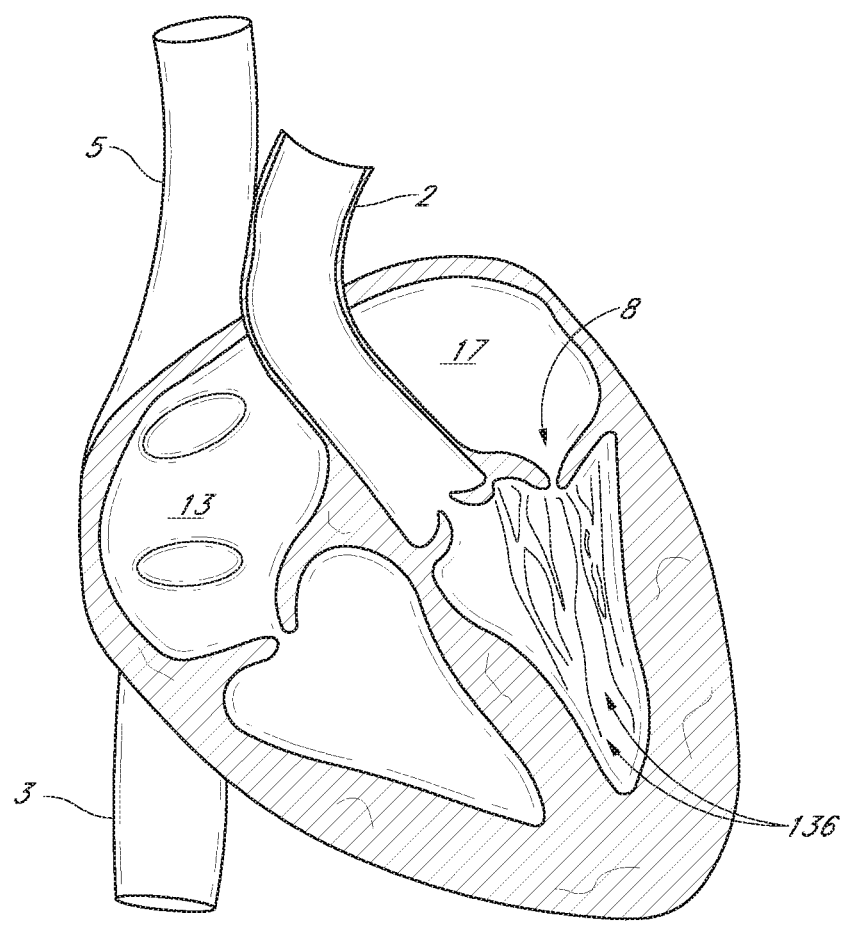
FIG. 86 is a schematic illustration of a human heart showing the chordae tendineae.

FIG. 86 schematically illustrates the chordae tendineae in the left ventricle of a human heart. Positioning the arms of a suturing device on a side of a valve (e.g., the atrial side) opposite the chordae tendineae can facilitate protection of the chordae tendineae from damage and facilitate the procedure by avoiding tangling of the arms with the chordae tendineae. Protection members (also described herein as "needle arms"), such as those described herein above and below, can help avoid damage to the chordae tendineae by suture catch mechanisms, such as needles for example, located on the same side of the valve as the chordae tendineae (e.g., the ventricular side).

Figure 88:
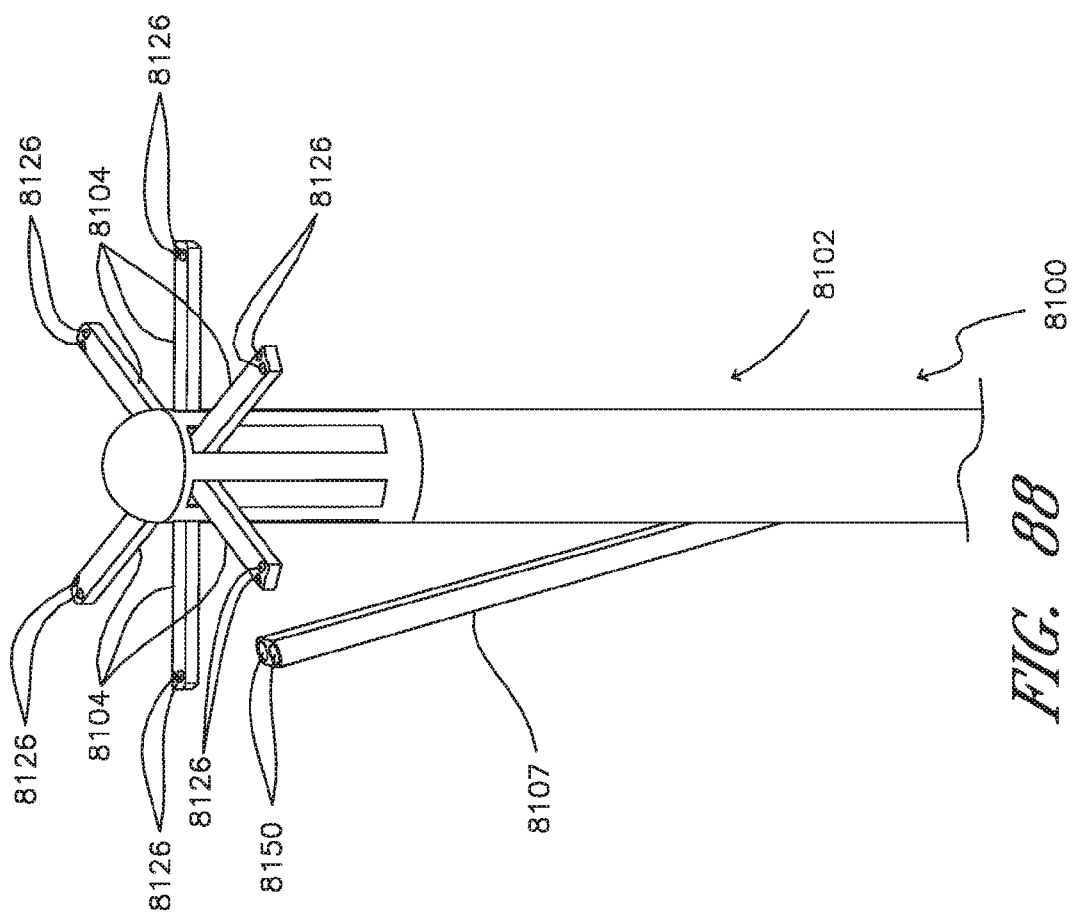
FIG. 88 is a schematic illustration of the suturing device of FIG. 87 with six arms extended, with each arm having two suture mounts, and a protective member extended.
Figure 87:
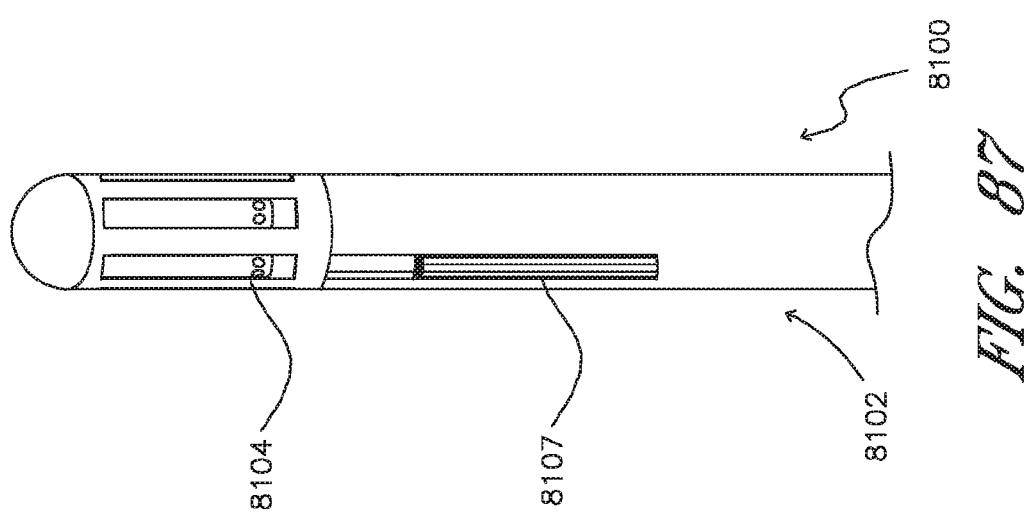
FIG. 87 is a schematic perspective view of an embodiment of a suturing device.

Suturing Devices and Methods Having a Plurality of Arms, Such as for Suturing a Base of a Valve FIGS. 87 and 88 illustrate an exemplifying embodiment of a suturing device 8100 having an elongate body and comprising more than one suture arm 8104 at the distal end of the elongate body, with each arm having two suture clasps 8126. Such embodiments can facilitate performance of annuloplasty. The illustrated embodiment comprises six arms 8104, with each arm having two suture mounts 8126, the arms extending perpendicular to a longitudinal axis of the elongate body. Each of the illustrated suture mounts releasably carries a suture portion for retrieval by a suture catch mechanism. Other embodiments can comprise fewer arms or more arms than 6. In some embodiments, the device can comprise a single arm. In some embodiments, the arm(s) can rotate about the elongate body.

The arms illustrated in FIG. 88 are sized to allow the suture mount to be placed at or near a base of the valve when the body of the device is placed in an opening of the valve. In some embodiments, the arms are sized and configured such that each of the suture mounts on all of the arms are at or in proximity of the base of the valve when the device is in a valve and the arms have been deployed. For example, the arms can each have a length of about 1.5 cm and the suture mounts can be located at or near an outermost point of the arms. In other embodiments, the arms may be longer or shorter than 1.5 cm. Various embodiments can have arms of different lengths to accommodate the size of the particular valve to be sutured and the anatomy of the intended patient.

The embodiment of FIGS. 87 and 88 comprises 12 suture catch mechanisms (not illustrated), one for each suture mount of the device. The suture catch mechanisms can be of the type described above and in the patents incorporated by reference (which form a part of this specification), such as needles for example. These needles may be located in carriers in a portion of the elongate body proximal to the arms, arranged circumferentially around the elongate body to correspond in location to the suture mounts on the ends of the arms. The suture catch mechanisms may be actuated by a user to move in a proximal-to-distal direction, extending outwardly away from the elongate body to penetrate through tissue and into engagement with the suture mounts. Proximal retraction of the suture catch mechanism carries suture away from the arms through the tissue and back into the arms. The suture catch mechanisms can be operated independently of each other, or can be operated in groups in some embodiments. For example, two or more needles can be operated simultaneously in some embodiments. Other embodiments are contemplated where there are fewer needles than suture mounts provided on the device, but additional needles can be loaded and reloaded as desired to penetrate through tissue and retrieve suture. In certain embodiments, needles can be housed in a carrier that is rotatable around the circumference of the elongate body to position the needles in the desired location relative to the suture mounts.

The suturing device illustrated in FIGS. 87 and 88 comprises a protection member 8107 that is configured to protect surrounding tissue, e.g. chordae tendineae, from movement of the suture catch mechanisms. The protection member illustrated in FIGS. 87 and 88 is an elongate body comprising two lumens 8150 extending through a length of the protection member, although the protection member can comprise other numbers of lumens in some embodiments, as discussed above.

The protection member 8107 of this embodiment is configured to move between a retracted position parallel to a longitudinal axis of the elongate body and an outwardly extending, deployed position. The protection member is also configured to rotate about the longitudinal axis of the suturing device while the protection member is in the retracted position, the deployed position, and locations between the retracted position and the deployed position in order to point the protection member toward a desired arm. In some embodiments, the protection member is configured to rotate about the suturing device only when the protection member is in a selected one or more positions, e.g. fully-retracted position, fully-deployed position, or selected position between full retraction and full deployment.

In some embodiments, the protection member and a cooperating portion of the suturing device can be configured with detents to assist a user in determining when the protection member is aligned with a suture catch mechanism and arm as the protection member rotates. In alternative embodiments, rather than having a single rotating protection member, multiple protection members may be provided, for example, one per arm, having a number of lumens corresponding to the number of suture mounts in each arm.

The suturing device illustrated in FIGS. 87 and 88 can be used to suture a valve without stopping the beating of the heart. In some embodiments, suturing of the heart while beating can allow the effect of suture placement on valve operation to be observed during the procedure, thereby allowing the procedure to be tailored to the needs of the particular valve by placing only those sutures required to repair the valve. For example, if the desired repair of the valve has not been achieved by the placement of initial sutures, continued use of the same device or additional devices may be employed through the same access path (e.g., through a transapical opening) until the procedure is observed to be successful on the beating heart. Once the practitioner observes this success, any access path which has been created to perform the procedure (e.g., the transapical opening) can be closed.

Figure 89:
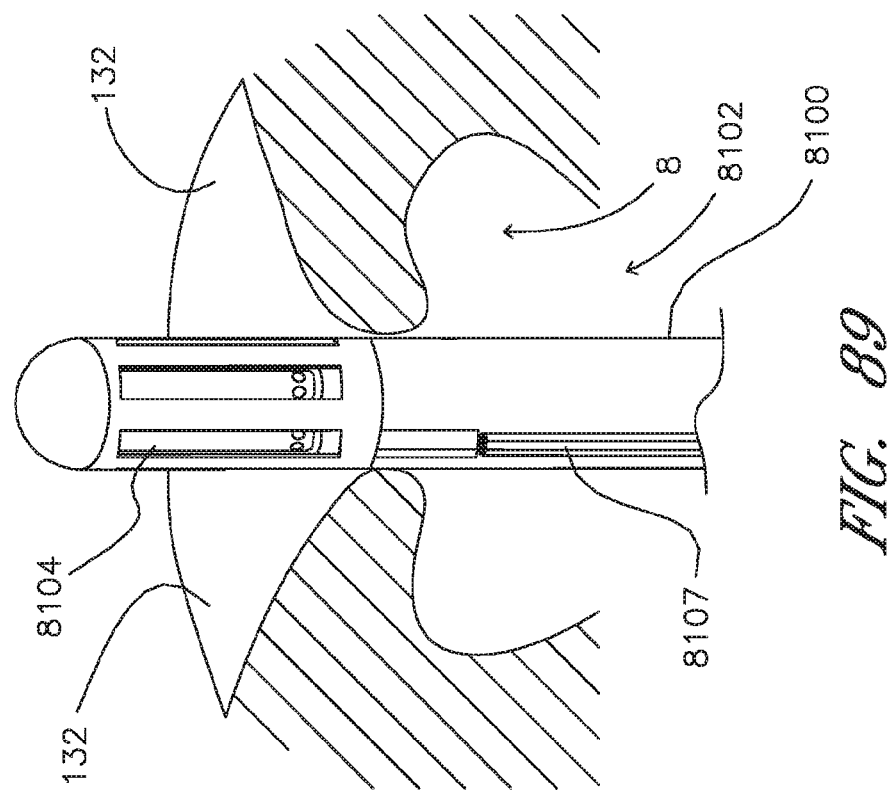
FIG. 89 is a schematic representation of the suturing device of FIGS. 87 and 88 positioned in a passage through a valve, such as the mitral valve via transapical entry.

FIGS. 89-94 schematically illustrate a method of suturing using the device of FIGS. 87 and 88, and more specifically illustrates a method of performing a valve annuloplasty on a beating heart. As illustrated in FIG. 89, a distal end 8102 of the suturing device 8100 is positioned in the passage through the valve, such as the mitral valve 8, using any of the access routes discussed above, and with or without a guide wire. The device is advanced through the valve a sufficient distance to allow the arms 8104 to be deployed without damage to the valve or walls of the heart.

Figure 90:
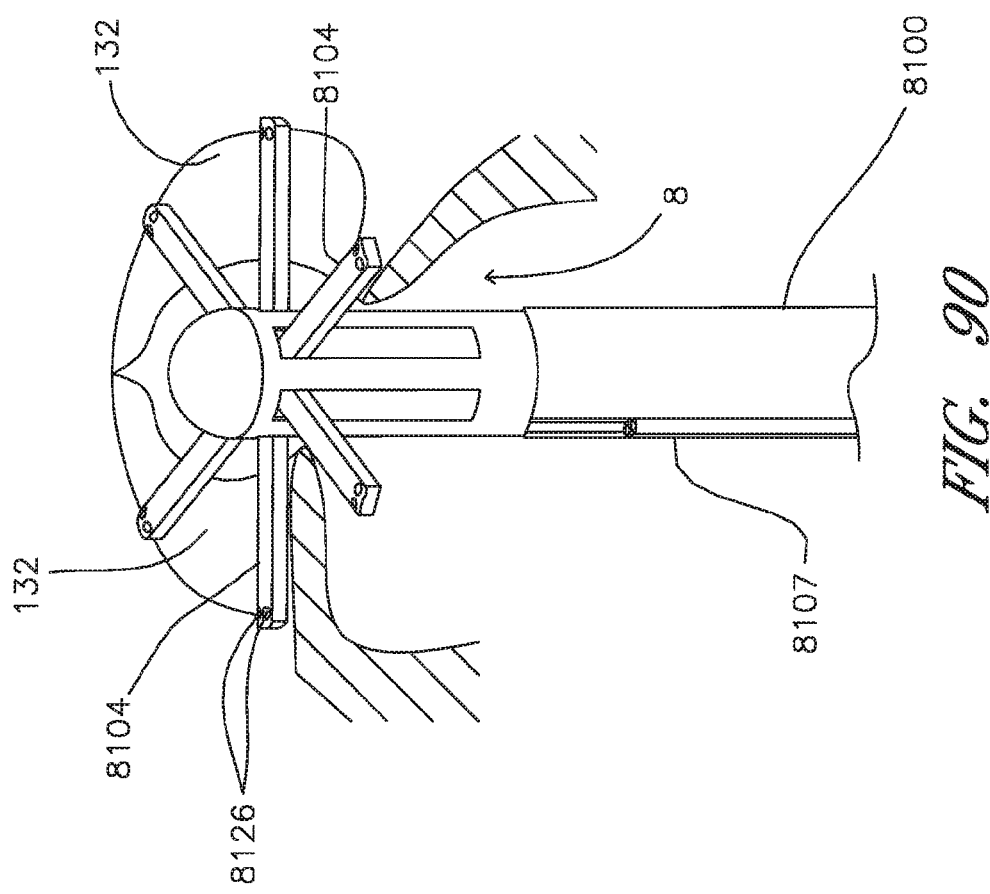
FIG. 90 is a schematic representation as in FIG. 89 with the arms extended.
Figure 92:
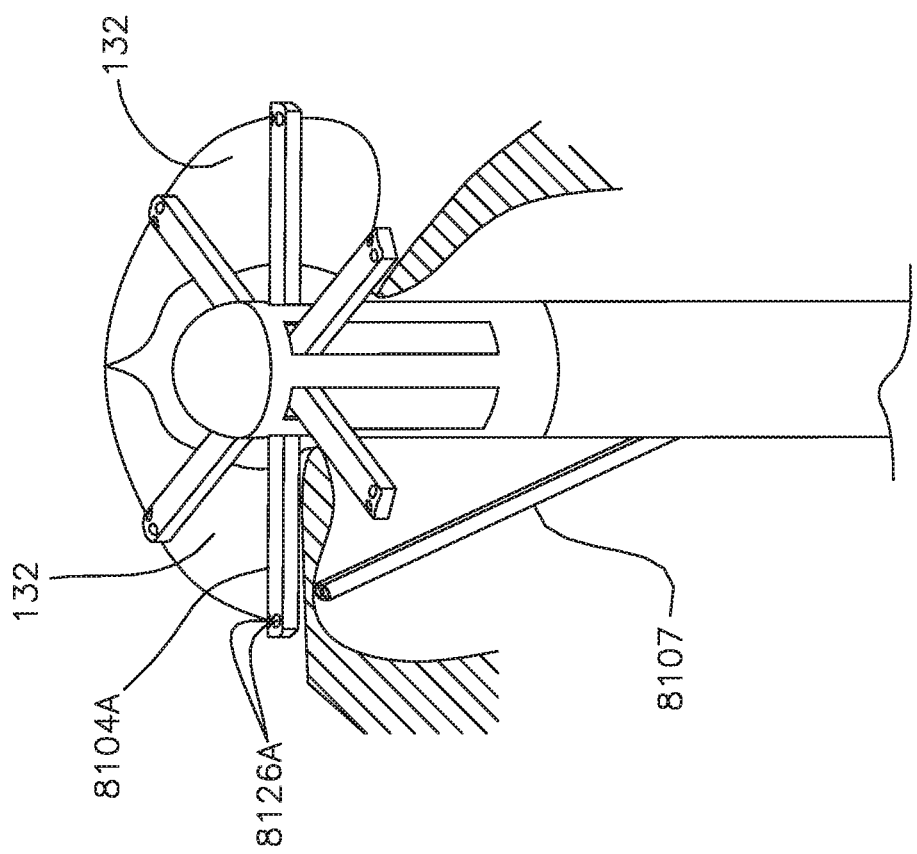
FIG. 92 is a schematic representation as in FIG. 91 with the protective member positioned for movement of a needle through the protective member to engage a first arm.
Figure 91:
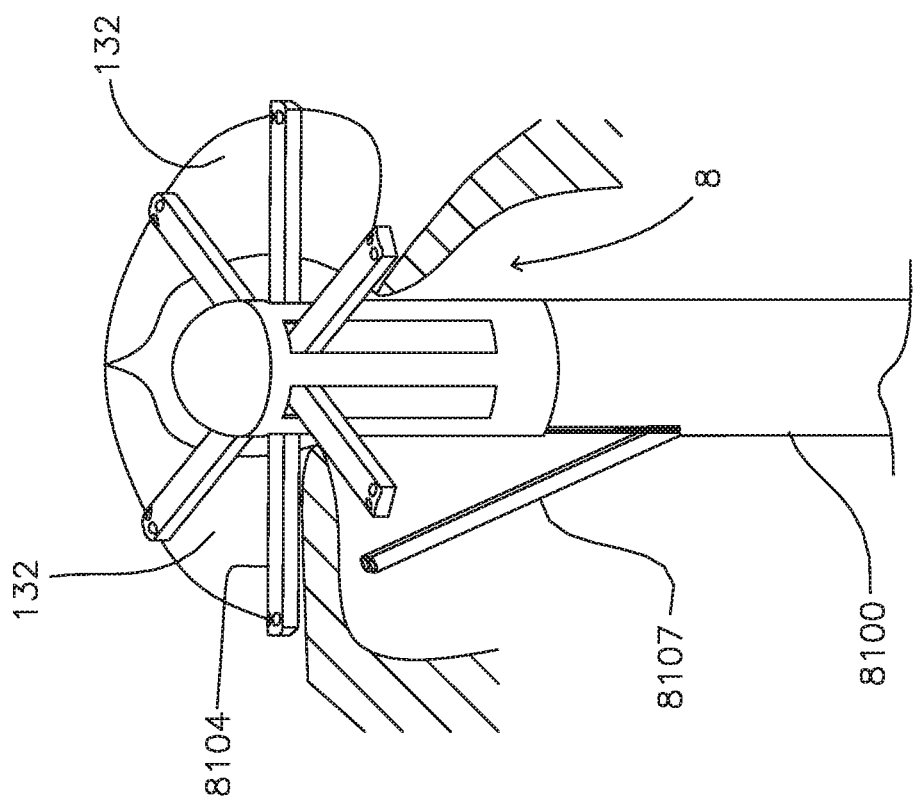
FIG. 91 is a schematic representation as in FIG. 90 with the protective member extended.
Figure 94:
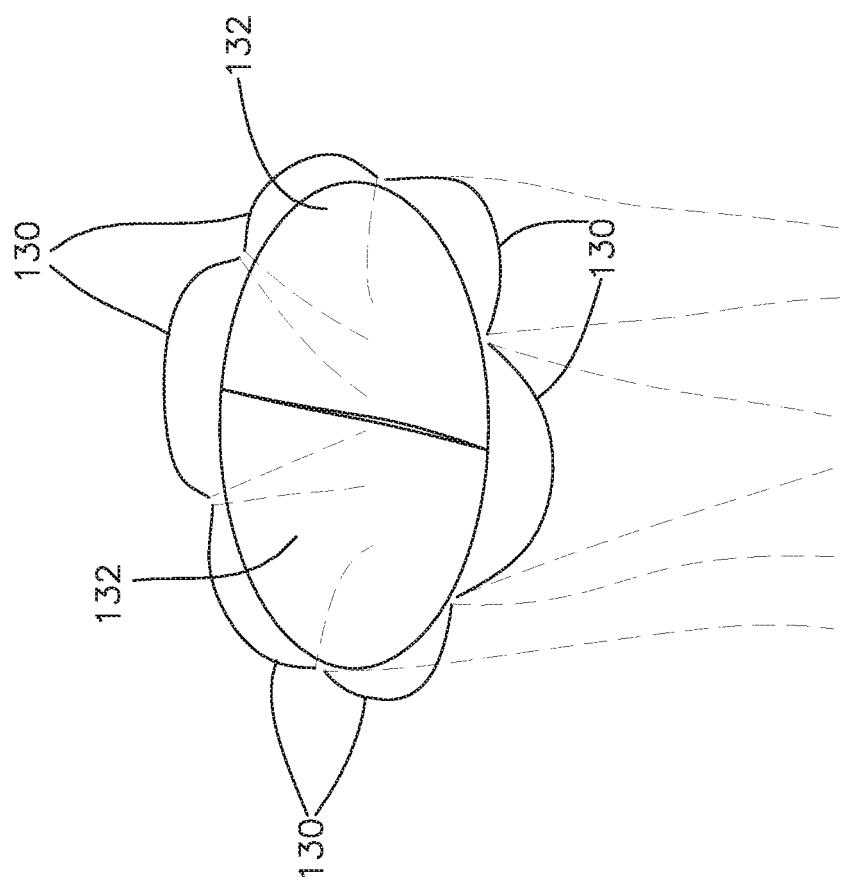
FIG. 94 is a schematic representation as in FIG. 93, with suture portions passed through 12 locations in the valve.

FIGS. 89-94 are illustrated to schematically represent transapical access of the device to the mitral valve 8. However, as discussed herein, other access routes can be used and other valve can be sutured. In FIG. 89, the valve is shown in cross section along a plane passing through a longitudinal axis of the suturing device 8100. In FIGS. 90-92, the valve is shown in cross section on two planes, which both intersect the longitudinal axis of the suturing device 8100. A first plane extends along the arm 8104 which is illustrated at approximately a 9 o'clock position from the elongate body of the suturing device. The second plane extends along the arm 8104 which is illustrated at approximately a 5 o'clock position relative to the elongate body of the suturing device. Thus, five of the arms 8104 are illustrated in FIGS. 90-92 as generally overlying leaflets 132 of the valve, with a portion of one of the leaflets which underlies the sixth arm being hidden from view. In FIG. 91, the planes of cross section of the valve pass generally through the longitudinal axis of the suturing device and extend generally along the arms 8104 which are illustrated at the 5 o'clock and 7 o'clock positions such that all six of the illustrated arms are shown generally overlying the leaflets 132 of the valve 8. The chordae tendineae are omitted from view in FIGS. 89-94.

Once the arms have been extended, the device 8100 can be retracted through the valve 8 to place the ends of the arms at or near the base of the valve 8, as illustrated in FIG. 90. In certain embodiments, the length of the arms will not correspond exactly with the size of the valve. In such embodiments, two of the arms may be placed in a desired location with respect to the base of the valve where sutures are desired to be placed. The protective member 8107 is then moved from the retracted position toward the deployed position as illustrated in FIG. 91.

Figure 93:
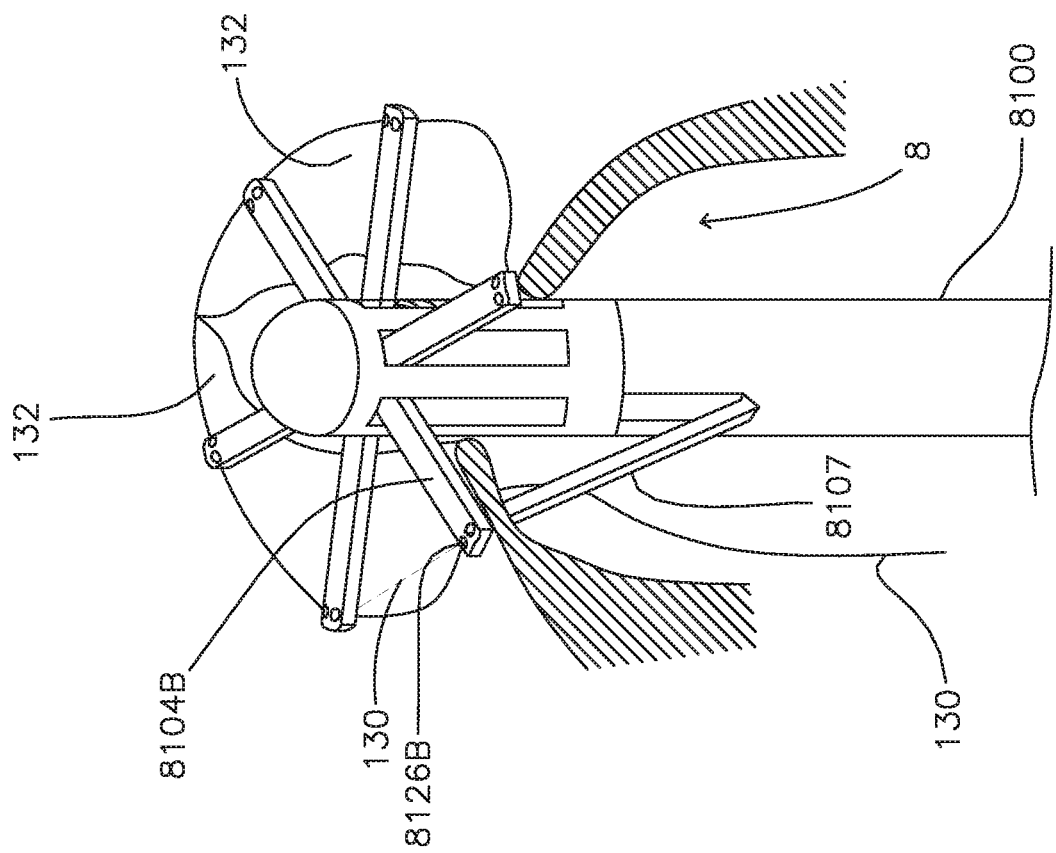
FIG. 93 is a schematic representation as in FIG. 92 with the protective member positioned for movement of a needle through the protective member to engage a second arm.

As shown in FIG. 91, the protective member 8107 when deployed can be moved to positions located angularly between the suture arms 8104. In other embodiments, the protective member 8107 when deployed can be positioned at a rotational orientation relative to the body of the suturing device 8100 that is aligned with at least one of the suture mounts of a suture arm. The ability to move the protective member between the arms can be advantageous in some embodiments. For example, movement of the protective member between the arms can allow the protective member to be rotated about the device between a positioned aligned with a first arm 8104A, as illustrated in FIG. 92, and a position aligned with a second arm 8104B, as illustrated in FIG. 93, without damage to the chordae tendineae. This feature can also help avoid tangling of the protection member 8107 with the chordae tendineae as a reduced number of instances of deployment and retraction occur.

In one embodiment, the protective member 8107 is first deployed and positioned in alignment with a suture mount 8126 of the first arm 8104A, as shown in FIG. 92. The end of the protective member 8107 may be located near the end of the arm 8104A, but on the opposite side of tissue of valve 132. In some embodiments, the end of the protective member 8107 is positioned a few millimeters away from the arm 8104A. In other embodiments, this distance may be adjustable. A first suture catch mechanism, such as a needle, can be deployed through one of the lumens of the protective member 8107, through tissue of valve 132, and into the suture mount 8126A of the first arm 8104A. Retraction of the suture catch mechanism carries a first suture end portion through the tissue of valve 132 and into the elongate body.

With the suture catch mechanism retracted and the protective member 8107 deployed, the protective member can be rotated into alignment with a suture mount of the second arm 8104B, as shown in FIG. 93, for example. A second suture catch mechanism, such as a needle, can be deployed through the other of the lumens of the protective member 8107, through tissue of valve 132, and into the suture mount 8126B of the second arm. This suture mount of the second arm preferably holds the second end of the suture mounted in the first arm. Retraction of the suture catch mechanism carries the second suture end portion through the tissue of valve 132 and into the elongate body. The suturing device at this point has desirably placed a suture along the circumference of the valve at an angular distance corresponding to the angular distance between the ends of the two adjacent suture arms.

At this point in the procedure only one of the suture mounts from the first arm and the second arm has been used, preferably the suture mounts closest to the corresponding adjacent arm. The protection member 8107 may then be retracted and rotated to a location between another pair of arms, such as the second arm and the third arm. The device 8100 may also be desirably repositioned such that the second and third arms may be positioned as needed at the base of the valve 132. The steps discussed in connection with FIGS. 90-93 are then repeated to place a second suture through two additional locations in the valve. In embodiments wherein these steps are repeated for each of the pairs of adjacent suture arms, six sutures 130 may be positioned through the valve as illustrated schematically in FIG. 94. Opposing ends of each suture can then be tightened and secured together by any known method, such as those described herein.

In some embodiments, methods similar to those described in connection with FIGS. 89-94 can be used to attached a prosthetic device to cardiac tissue.

Suturing Devices and Methods Having Two Arms, Such as for Suturing a Base of a Valve FIGS. 95-97 illustrate an embodiment of a suturing device 9100 that can be used to suture an anatomical valve, such as a heart valve. For example, the suturing device 9100 (as well as similar devices described above) can be used to perform an annuloplasty by plication, where suture(s) are applied to a section of a valve and the suture(s) is tightened to reduce the size of the valve to remodel the valve. The suturing device 9100 illustrated in FIGS. 95-97 is similar in some respects to suturing devices illustrated and described above. For example, the suturing device can comprise an elongate body 9142 and a distal assembly 9102 that can have one or more suture arms 9104, as in the suturing device of FIGS. 87 and 88 described above. As illustrated, the suturing device has only a single suture mount 9126 on each suture arm 9104, although in some embodiments it can have multiple suture mounts 9126 on each arm 9104. As described above, the suture mounts 9126 can be configured to releasably hold a suture portion.

In some embodiments, the suturing device can have multiple suture arms 9104 and multiple protective members or needle arms 9107. In the illustrated embodiments, the device has two suture arms 9104A,B and a single needle arm 9107. The configuration and deployment of the arms, as well as other features and ways of operating the suturing device, may be as shown and described in the U.S. Pat. No. 6,911,034, the entirety of which is hereby incorporated by reference. The suture arms can be positioned near a distal end of the device, and the needle arm can be positioned proximally to the suture arms, as illustrated in FIGS. 95-97. The suture arms and the needle arm can each have a retracted position in which they are retracted within the elongate body, as illustrated in FIG. 96. Each suture arm can also have an extended position in which the suture arm rotates about one end and extends away from the elongate body. In some embodiments, the arms 9104A,B can extend perpendicular to a longitudinal axis of the elongate body when in the extended position. The needle arm can also be deployed to an extended position, in which the needle arm extends away from the elongate body and toward a distal end of the elongate body. FIG. 97 illustrates an embodiment where both suture arms and the needle arm are in the extended position.

Figure 98:
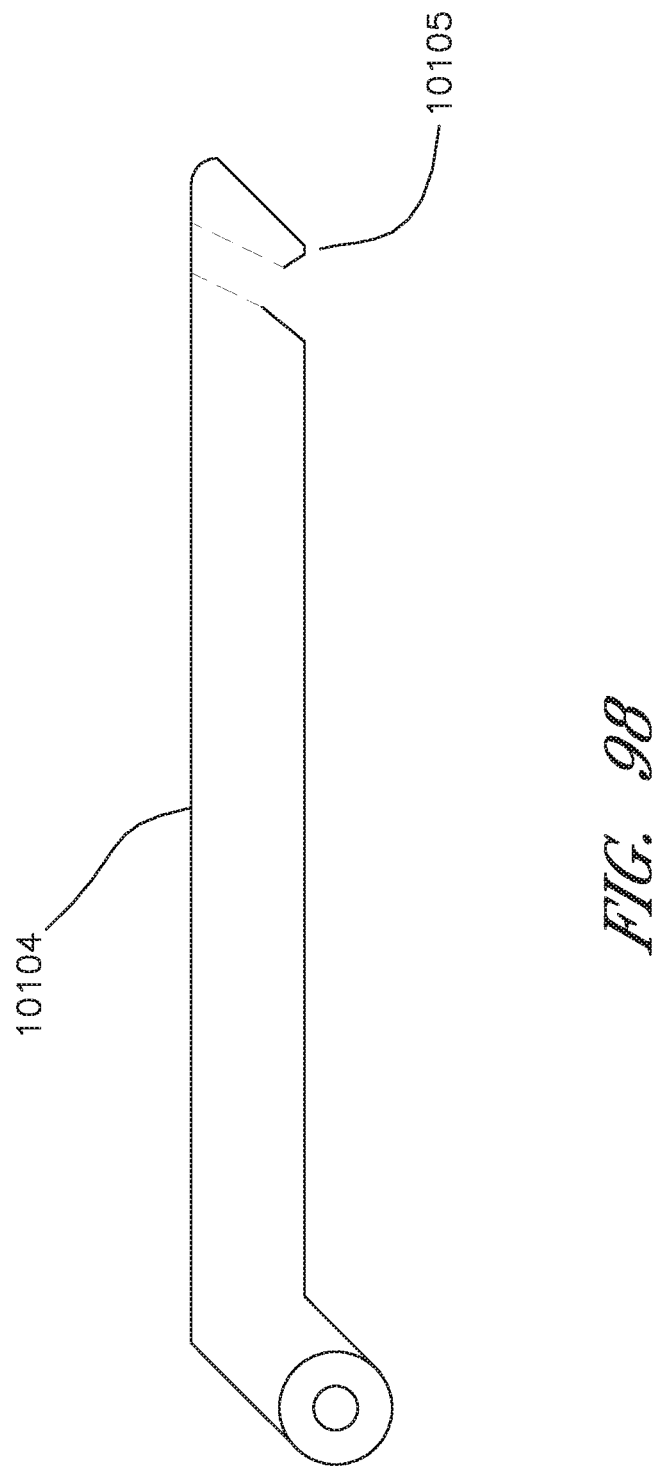
FIG. 98 is a cross sectional view of an embodiment of a suture arm.

As described above, various embodiments can have arms 9104A,B of different lengths to accommodate the size of the particular valve to be sutured and the anatomy of the intended patient. In some embodiments, the arms are sized and configured such that each of the suture mounts on the arms are at or in proximity of the base of a valve when the device is in the valve and the arms have been deployed. In some embodiments, when the arms have been deployed and the suture mounts are at or in proximity of the base of a valve, the needle arm can be on an opposite side of the valve. In some embodiments, the needle arm in its extended position can extend into alignment with a suture mount of a suture arm, but with the valve between them. Additionally, in some embodiments a suture arm can comprise a sharp edge 10105, or any hook, point, needle tip, knurling, or other roughening at a distal end on a surface that faces toward a proximal end of the elongate body when the suture arm is extended, as illustrated in FIG. 98. The sharp edge or other roughening can help retain the suture arm in a position against tissue of an anatomic valve.

Also as described above, the needle arm 9107 can be configured to protect surrounding tissue from movement of a suture catch mechanism, which in some embodiments can be a needle 9106. The needle arm can comprise one or more lumens 9150 through which one or more needles 9106 can pass. In the illustrated embodiment of FIG. 97, the needle arm has two lumens, each of which can be associated with a needle 9106 and a suture mount 9126.

In some embodiments, the needle arm can rotate around the elongate body. As illustrated in FIG. 97, the needle arm can extend between the two suture arms 9104A,B. In FIG. 99, the needle arm has rotated into alignment with one of the suture arms 9104A and a suture mount 9126A. FIG. 99 illustrates a cross sectional view of a section of the elongate body with the suture arm 9104A and the protection member 9107 in their extended positions, and the needle arm aligned with the suture arm 9104A. As illustrated, a needle 9106 is positioned within the needle arm 9107. In some embodiments, the needle 9106 can be positioned within the needle arm before the needle arm is deployed to its extended position.

In some embodiments, the elongate body can comprise a rotating sleeve 9160, which can surround an inner cylinder, and which can house the needle 9106 and the needle arm 9107 when the needle arm is in the retracted position. As illustrated, when the needle arm is in its extended position the needle runs through the rotating sleeve, exits the rotating sleeve into a gap, and then enters the needle arm. In some embodiments, the needle can run directly into the needle arm without passing first to a gap between the rotating sleeve and the needle arm. In some embodiments, discussed in more detail below, at least part of the needle can be within an extrusion. In some embodiments, the extrusion can be located only within the needle arm. In some embodiments, the extrusion can extend from the needle arm when the needle arm is in its extended position into the rotating sleeve.

When the needle arm begins to move into the extended position from a retracted position within the rotating sleeve it first moves distally until it engages extension surface 9164. The extension surface angles the needle arm away from the elongate body, such that as the needle arm continues to move forward it moves both away from the elongate body and toward a distal end of the elongate body. In some embodiments, the extension surface 9164 can be at approximately a 45 degree angle. In some embodiments, the needle arm can extend at approximately a 45 degree angle. In other embodiments, the extension surface can be at an angle less than or greater than 45 degrees, and the needle arm can be at an angle less than or greater than 45 degrees. As the needle arm is retracted, it can engage against retraction surface 9166 which can guide the needle arm back into its retracted position within the rotating sleeve 9160. In some embodiments, the retraction surface can comprise a gap that can allow a needle and/or extrusion to pass through it.

In some embodiments, the rotating sleeve 9160 can be configured to rotate about a longitudinal axis of the elongate body. In some embodiments, in addition to being able to rotate, the rotating sleeve can move proximally or distally along the inner cylinder. As the rotating sleeve rotates, the needle arm can rotate with it. As described with respect to FIGS. 87 and 88, the sleeve and needle arm, in various embodiments, can be configured to rotate while the needle arm is in the retracted positioned, the extended position, and/or in locations between the retracted position and the extended position in order to point the needle arm toward a desired arm. In some embodiments, when the needle arm is pointed toward a desired arm a gap of greater than or equal to 3 millimeters (or about 3 millimeters) and/or less than or equal to 5 millimeters (or about 5 millimeters) can exist between the needle arm and the suture arm. In some embodiments, the needle arm can point between two arms and a gap of greater than or equal to 3 millimeters (or about 3 millimeters) and/or less than or equal to 5 millimeters (or about 5 millimeters) can exist between the needle arm and a plane on which the two arms lie.

In some embodiments, the elongate body can have one or more detents 9162, which can be positioned such that as the rotating sleeve rotates it can engage a detent when the needle arm is in alignment with a suture arm 9104. In some embodiments, the detent or detents can be configured such that as the rotating sleeve engages with the detent the sleeve moves distally. In some embodiments, this can be achieved by creating a bayonet connection between the sleeve and the detent(s). The distal motion of the rotating sleeve can drive the needle arm distally, and can be configured such that the needle arm engages tissue of the valve, pinching the valve between the tissue and the suture arm. If the needle arm rotates back, the rotating sleeve can disengage the detent, moving proximally and releasing the valve. In some embodiments, the needle arm can move distally as it comes into alignment with a suture arm, but does not pinch the valve. In some embodiments, the needle arm can move distally as it comes into alignment with a suture arm, but can rotate back without moving proximally.

Pinching the valve can help facilitate suturing a valve without stopping the beating of the heart, because it can help ensure desired placement of sutures. As discussed above, suturing of the heart while beating can allow the effect of suture placement on valve operation to be observed during the procedure, thereby allowing the procedure to be tailored to the needs of the particular valve by placing only those sutures required to repair the valve. For example, if the desired repair of the valve has not been achieved by the placement of initial sutures, continued use of the same device or additional devices may be employed through the same access path (e.g., through a transapical opening) until the procedure is observed to be successful on the beating heart. Once the practitioner observes this success, any access path which has been created to perform the procedure (e.g., the transapical opening) can be closed.

FIG. 100 illustrates a view of the suturing device from a distal end. As illustrated, the first and second suture arms 9104A,B have been extended and extend away from the elongate body at approximately 90 degrees from each other. In some embodiments, the suture arms can be positioned at less than 90 degrees from each other, and in other embodiments the suture arms can be positioned at more than 90 degrees from each other. The distance 9127 between the suture mounts 9126A,B can define the initial width of a suture or other element that can be tightened when performing an annuloplasty. In some embodiments, the distance 9127 can be greater than or equal to 10 millimeters (or about 10 millimeters) and/or less than or equal to 15 millimeters (or about 15 millimeters). Also illustrated in FIG. 100 is a guide wire 10 and a guide wire lumen 9111 through which the guide wire can pass. As discussed above, in some embodiments the device can advance over a guide wire to reach a location within the heart.

FIG. 101 illustrates a cross sectional view of a distal end of a needle arm 9107. In some embodiments, the needle arm can have one or more channels through which needles can pass. In some embodiments, as illustrated, a needle arm can have one or more extrusions 9170 positioned within one or more channels of the needle arm. The extrusion can be configured to receive a needle 9106, as illustrated. In some embodiments, the needle arm can have one or more of a draft 9174, a tunnel 9172, and/or a suture retaining area 9176, with the extrusion extending only as far as the draft 9174. The draft 9174 can guide a needle into the tunnel 9172, which can help ensure that the needle is aligned to pass through a suture clasp or mount 9126 and receive a section of a suture. The suture retaining area 9176 can be of a size sufficient to house both a needle and a portion of suture caught by the needle. In some embodiments, the needle 9106 can be pre-loaded to the illustrated position, extending through the extrusion and through the tunnel 9172, before a needle arm is deployed to an extended position. In some embodiments, the needle can be pre-loaded into other positions within the needle arm and/or extrusion, such as within the extrusion but short of the tunnel. The needle 9106 as illustrated in FIG. 101 (or in any of the embodiments described elsewhere herein) may have a hook at its distal end to engage a portion of suture held by arm 9104A or 9104B. Sutures as described herein (or elsewhere in the specification) may have ends that are flattened with a hole formed therein for engaging the needle, as described in the U.S. Pat. No. 7,090,686, the entirety of which is hereby incorporated by reference.

In some embodiments, the needle arm can have a single extrusion 9170 with one or more lumens 9150. FIG. 102 illustrates a top view of an extrusion 9170 with two lumens 9150 configured to hold two needles 9106. In some embodiments, the needle arm can have multiple extrusions, each extrusion associated with one or more needles. In some embodiments, the needle arm can have a draft, tunnel, and/or a suture retaining area as described above for each lumen and/or needle. In FIG. 102, the extrusion has parallel sides and rounded corners. In other embodiments, the extrusion or extrusions can be square, rounded, ovular, or of any shape that can fit within a needle arm. The various embodiments and configurations of an extrusion or extrusions can be used with any protective member ("needle arm") discussed in the present application.

FIGS. 103-112 illustrate schematically one method of using a suturing device to perform an annuloplasty. The illustrated procedure represents transapical access of the device to the mitral valve 8, although as discussed herein other access routes can be used, including routes by which the device enters the valve from the atrial side, and other valves can be sutured. The device can also access the valve with or without a guide wire. The valve is shown without surrounding tissue, and in FIG. 103 a distal end of the device has been inserted through the valve, with the suture arms 9104A,B and needle arm 9107 in the retracted position. The needle arm is positioned approximately equidistant between the two arms, although in some embodiments the needle arm can be positioned closer to one arm or the other. Also illustrated schematically are chordae tendineae 133 extending from the ventricle side of the valve.

The suture arms can be placed in their extended positions, as illustrated in FIG. 104. In some embodiments they can reach their extended position simultaneously, and in some embodiments one arm can begin to extend or reach the extended position before the other arm begins to extend. With the suture arms extended, the device can be retracted until the arms engage tissue of the valve, as illustrated in FIG. 105. As illustrated, the suture mounts 9126A,B are along a base of the valve on the same leaflet. In some embodiments, the arms do not extend all the way to the base of the valve, and in some embodiments each arm can be over a different leaflet.

Figure 107:
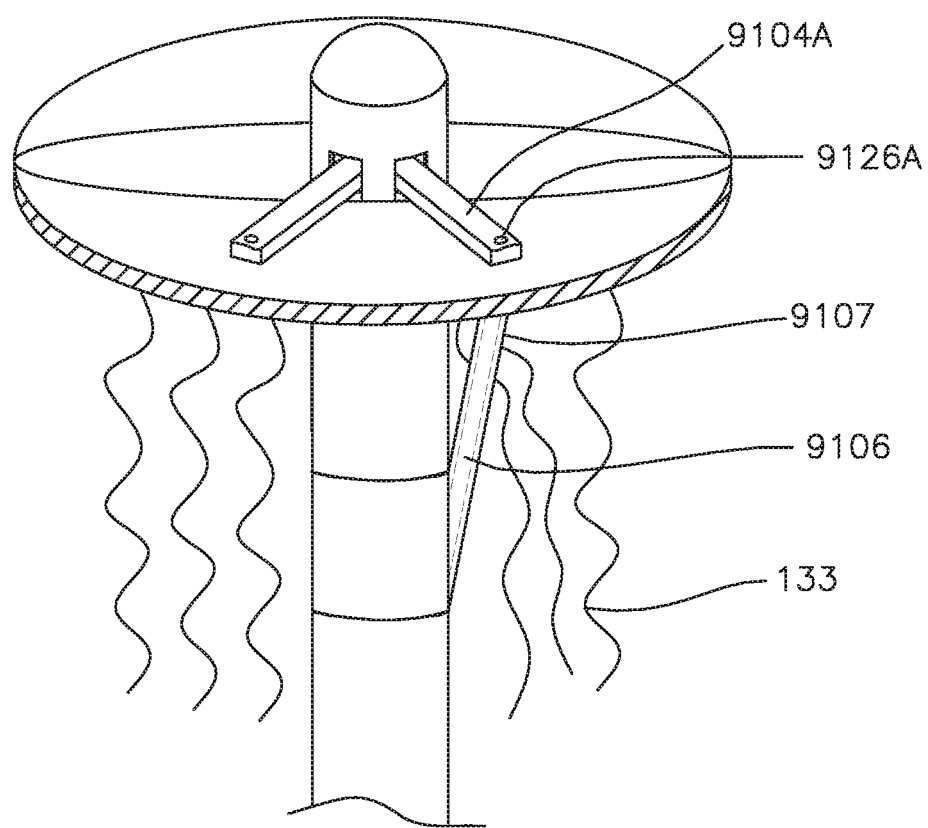
FIG. 107 is a schematic representation as in FIG. 106 with the protective member positioned for movement of a needle through the protective member to engage a first arm.

Either before, after, or while the suture arms are extending or the device is retracted such that the suture arms can engage tissue of the valve, the needle arm can be deployed to an initial extended position, such as past the chordae, for example. FIG. 106 illustrates the needle arm in the extended position and the suture arms in place on the valve. The needle arm 9107 can then rotate toward a first arm 9104A until it is aligned with the arm, as illustrated in FIG. 107. As discussed above, in some embodiments, when the needle arm is aligned with the arm it can extend distally and pinch the valve between the suture arm and the needle arm. In other embodiments, there can be a gap between the needle arm and the valve.

As the needle arm rotates, it can displace chordae tendineae 133 positioned between the needle arm and the first arm. One advantage of having the needle arm positioned initially equidistant between the two arms 9104A,B is that it minimizes the distance that the needle arm may need to travel to reach each arm, which can minimize stress on any displaced chordae. The needle arm when extended is preferably positioned between adjacent chordae tendineae, such that movement of the needle arm between the first and second arms does not cause the needle arm to tangle with the chordae tendineae.

Figure 108:
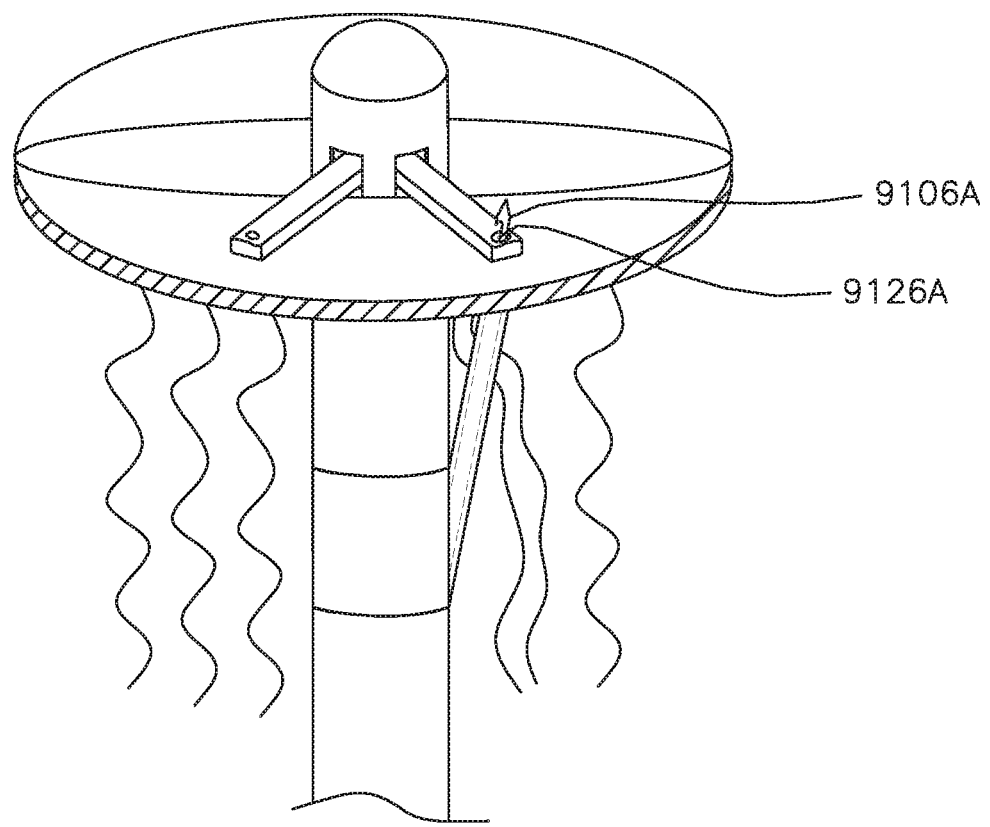
FIG. 108 is a schematic representation as in FIG. 107 with the needle engaging a first arm.
Figure 109:
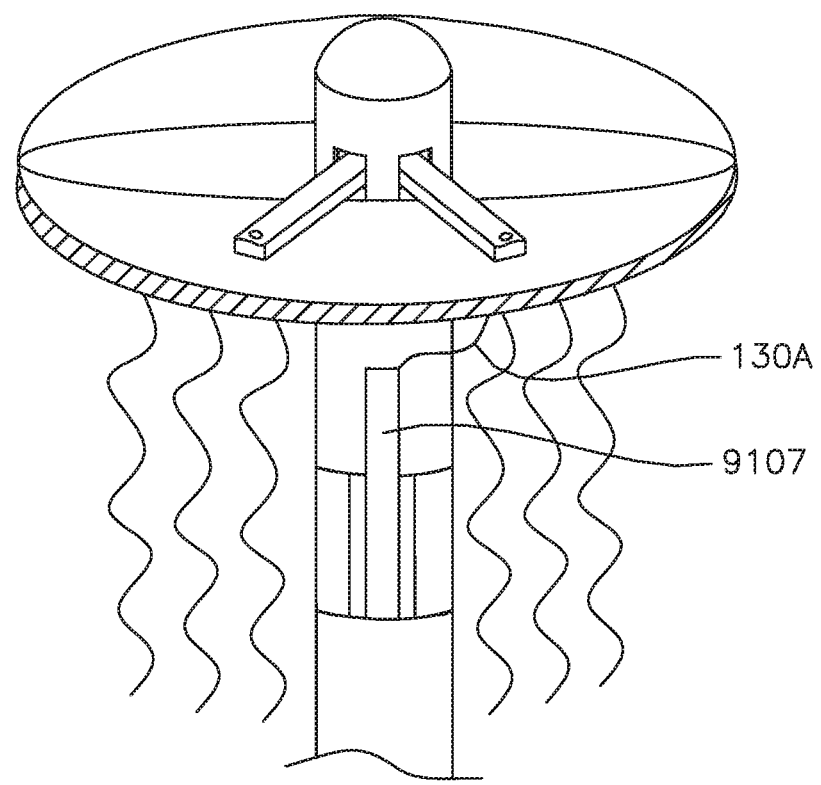
FIG. 109 is a schematic representation as in FIG. 108 with the needle arm in a position between the two suture arms.

Once the needle arm is aligned with the suture arm, a needle 9106A can be extended out of the needle arm and through the suture mount 9126A, as illustrated in FIG. 108. As discussed above, retraction of the needle can carry a first suture end portion from the suture mount, through tissue of the valve, and into the elongate body. The needle arm can then rotate back to its initial extended position, bringing a length of suture 130A with it, as illustrated in FIG. 109.

Figure 110:
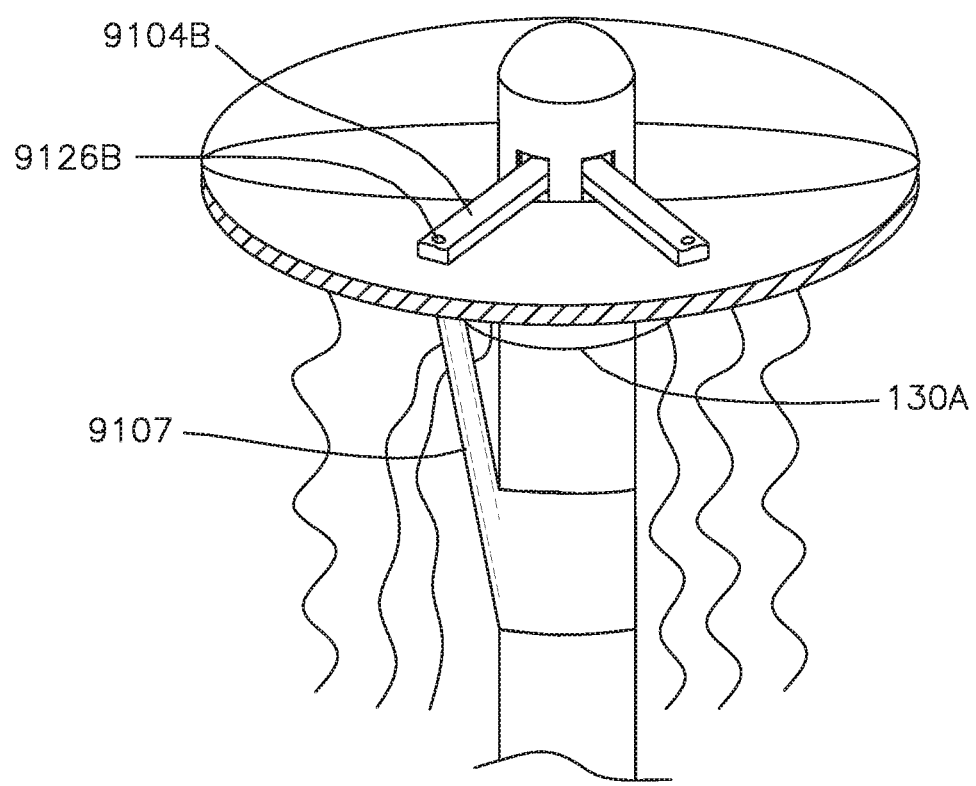
FIG. 110 is a schematic representation as in FIG. 109 with the protective member positioned for movement of a needle through the protective member to engage a second arm.

From the initial extended position, the needle arm 9107 can rotate toward second arm 9104B until it is aligned with the arm, as illustrated in FIG. 110. In some embodiments, the needle arm can pinch the valve tissue against the arm, as discussed above. Also as discussed above, and as illustrated, the needle arm can displace chordae tendineae 133 positioned between the needle arm and the second arm 9104B.

Figure 111:
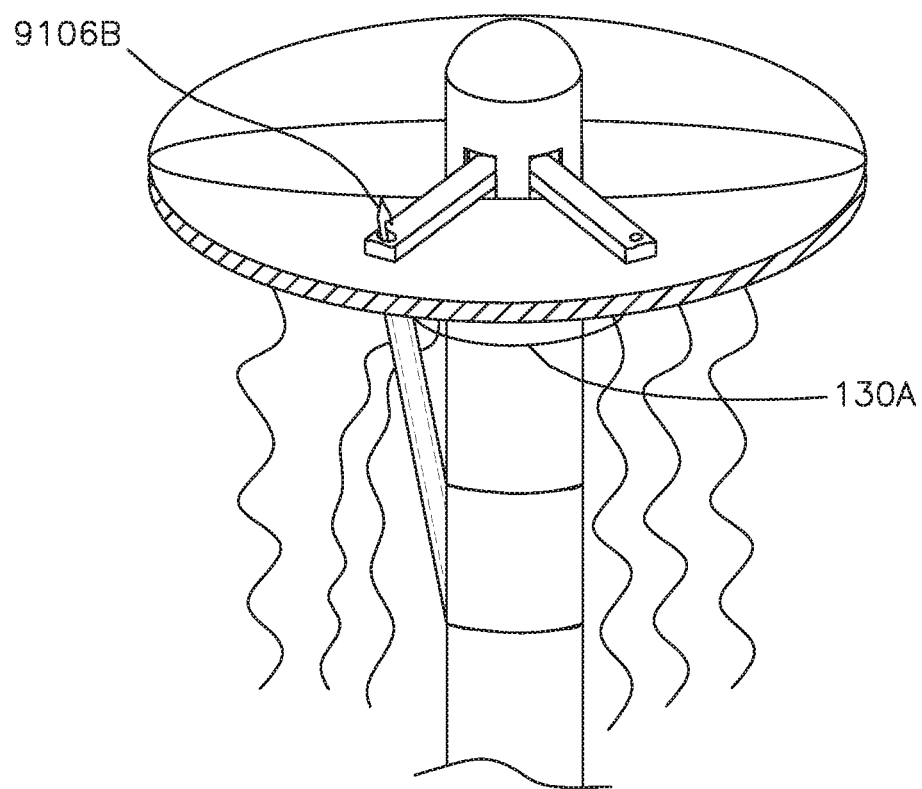
FIG. 111 is a schematic representation as in FIG. 110 with the needle engaging a second arm.
Figure 112:
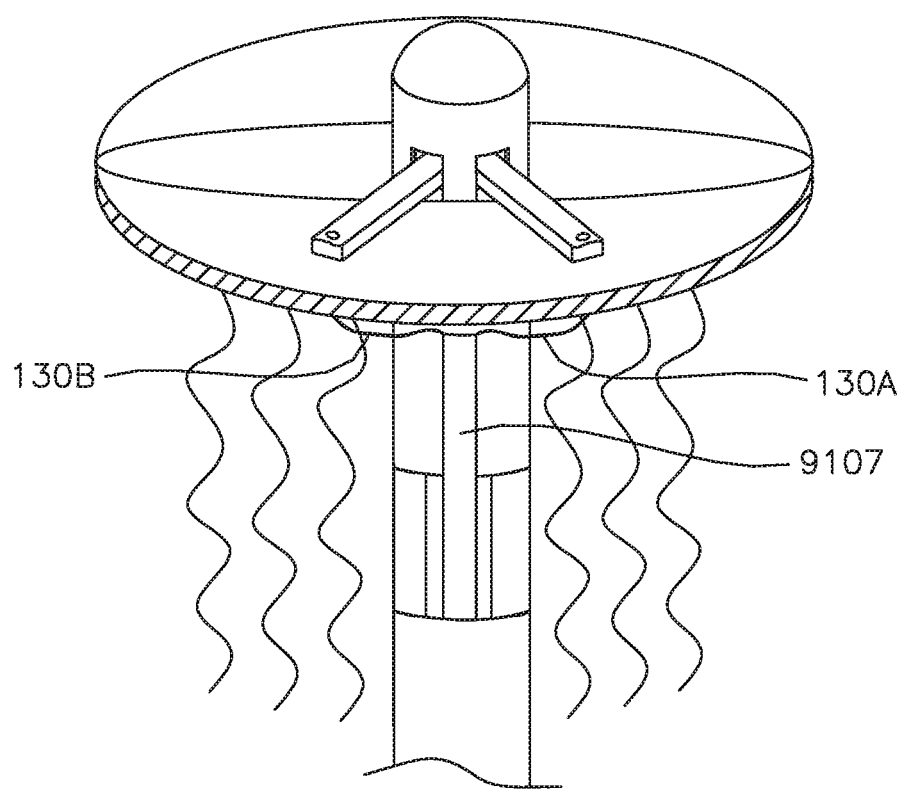
FIG. 112 is a schematic representation as in FIG. 111 with the needle arm in a position between the two suture arms.

A separate needle 9106B can extend through the needle arm and through the suture mount, as illustrated in FIG. 111, and then retract into the elongate body with a second suture end portion. The needle arm can then return to its initial extended position, as illustrated in FIG. 112, with a length of suture extending from each arm through the valve and into the needle arm. In some embodiments, the elongate body can have an initial detent that informs a user when the needle arm has returned to its initial extended position.

The suture arms and the needle arm can retract into the elongate body. In some embodiments, the needle arm and/or the suture arms can retract into the elongate body before the needle arm returns to the initial extended position, or without the needle arm returning to the initial extended position. Once the needle arm and suture arms are retracted, the device can be removed from the valve and the heart, leaving the suture lengths running through the valve.

Figure 113:
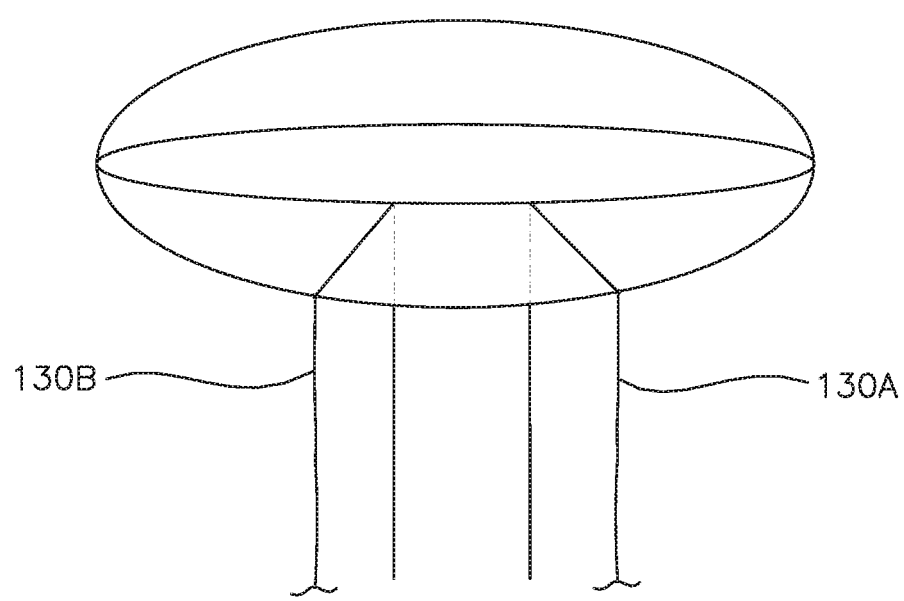
FIG. 113 is a schematic representation as in FIG. 112, with suture portions passed through two locations in the valve.
Figure 114:
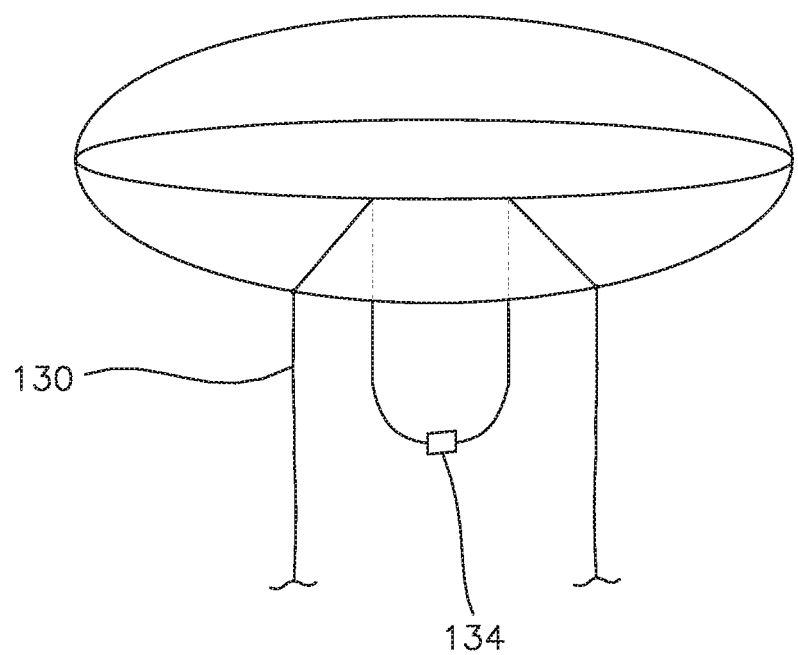
FIG. 114 is a schematic representation as in FIG. 112, showing the suture portions passing through two locations in the valve and being joined by a first knot.

In some embodiments, the two suture end portions can be parts of separate sutures, as illustrated in FIG. 113. The two suture ends that pass through the gap in the valve can be secured together by tying a knot 134 according to any known method or by applying a knot 134, such as described in U.S. Patent Publication No. 2007/0010829 A1, published Jan. 11, 2007, which is hereby incorporated by reference herein in its entirety and is considered a part of this specification. FIG. 114 illustrates the sutures after they have been joined together. In some embodiments, the two suture end portions can be ends of the same suture, and it is not necessary to secure the two suture ends together as seen in FIG. 113.

One or more of the loose suture ends can then be pulled, as described with reference to FIGS. 50 and 51, bringing the suture against the valve. The remaining ends can be tightened and tied according to any of the methods described above, such as FIGS. 69 and 70 and accompanying description, to thereby draw together the locations of suture penetration. In some embodiments, as described above, the initial distance between the set of suture penetrations can be greater than or equal to 10 millimeters (or about 10 millimeters) and/or less than or equal to 15 millimeters (or about 15 millimeters). In some embodiments, the distance between the set of suture penetrations can be tightened to a second distance greater than or equal to 6 millimeters (or about 6 millimeters) and/or less than or equal to 8 millimeters (or about 8 millimeters). The connection between the set of suture penetrations can be referred to as a plication, and in some embodiments multiple plications can be inserted into the valve with the suturing device. The plications can be positioned and sized to reshape the valve according to a desired treatment goal.

Figure 116:
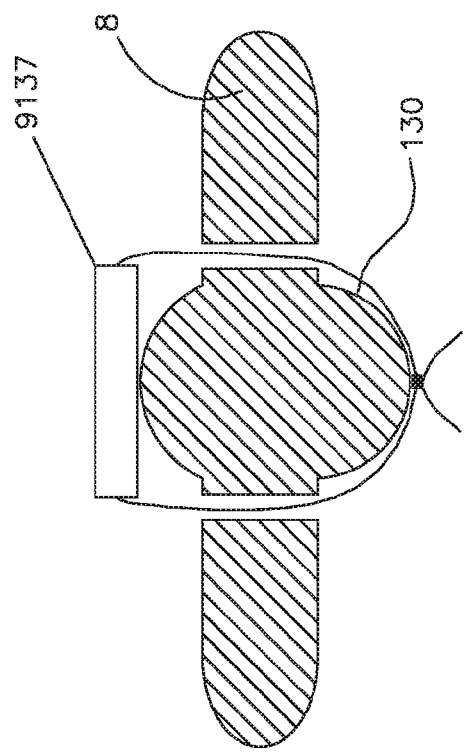
Figure 115:
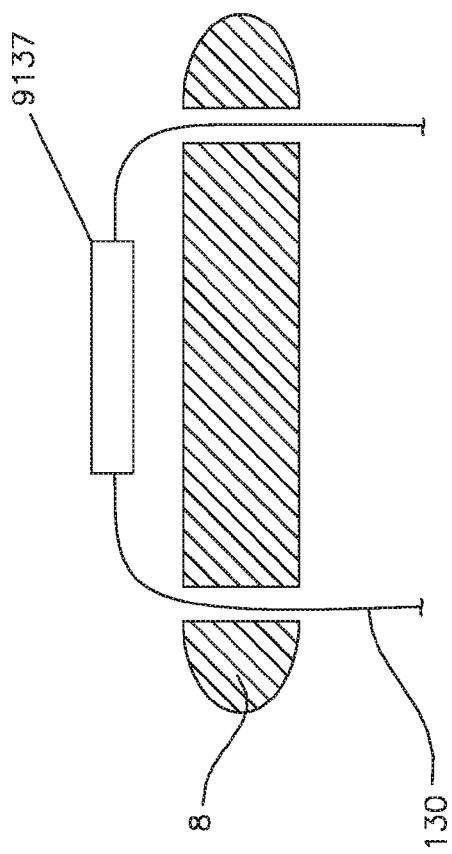

In some embodiments, a tube 9137 can be inserted over the suture, as illustrated in FIG. 115, which is a cross sectional view of a valve with a plication. The tube can be made of metal or a plastic, such as polypropylene, and can be straight or curved. In embodiments where the two suture end portions are part of separate sutures, the tube can be inserted over one of the suture ends that pass through the gap in the valve before the suture ends are secured together. In some embodiments, the tube 9137 can be secured to the two free ends of separate sutures that pass through the gap in the valve, rather than sliding loosely over the joined sutures. The loose ends can then be pulled until the tube sits against or is near the valve. In embodiments where the two suture end portions are part of the same suture, the tube can be inserted over and/or attached to the suture before the suture is attached to the device, or in some embodiments the tube can be attached to the suture after the suture is attached to the device. The tube can be set to a desired length and can help control the distance that the locations of suture penetration are drawn together, as illustrated in FIG. 116. In some embodiments, a pledget can be used instead of a tube. With the tube or pledget in place, a knot can be applied on the opposite side of the valve, as illustrated in FIG. 116.

In some embodiments, in order to maintain consistent tightening among multiple plications, or to monitor the tightening of a single plication, a strain gauge can be connected to the suture. In some embodiments, a strain gauge can be built into the handle of the device. The plication can be tightened until the strain gauge indicates a desired value. In some embodiments, a first plication can be tightened to a desired distance, and the value measured by a strain gauge recorded. Subsequent plications can then be tightened to approximately the same reading of the strain gauge.

Because the chordae were pushed aside as the needle arm rotated between the two suture arms, the suture on the ventricle side can run in a generally direct route between the suture penetrations. This can help prevent unnecessary strain on chordae that could result if the suture took a circuitous path around chordae as it ran from one suture penetration to the next. Tightening the suture could pull the suture tight against the base of one or more chordae, potentially damaging the chordae.

Example Device for Applying Knots

Figure 117:
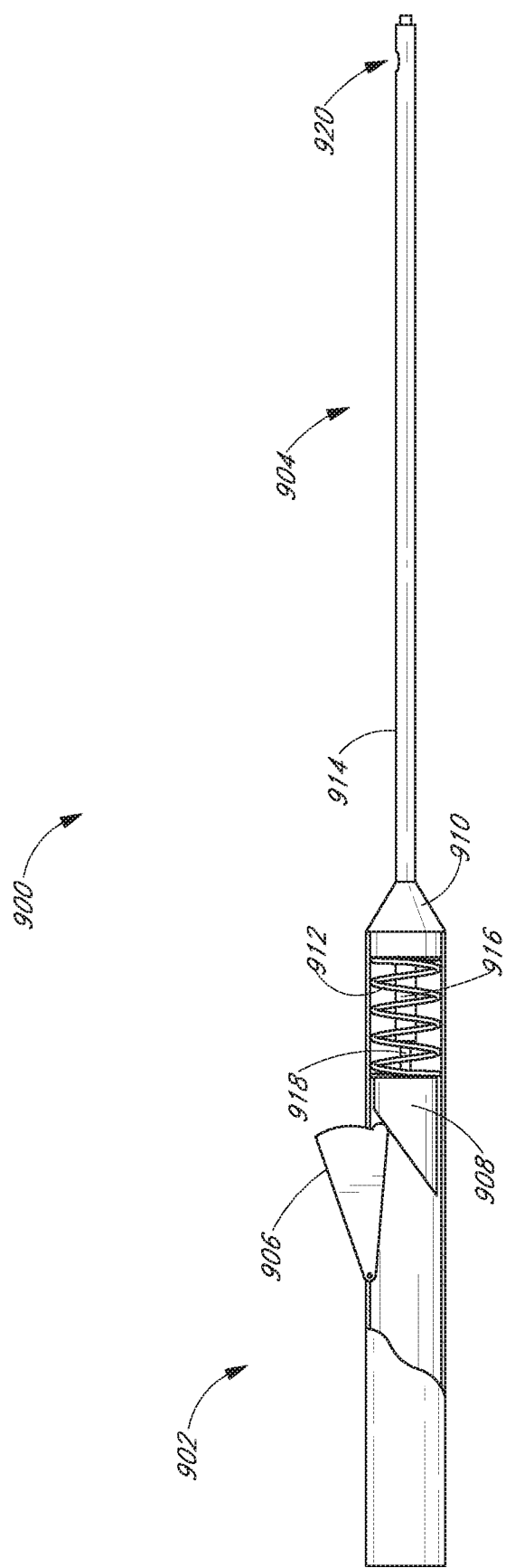

Varying embodiments described herein rely on joining one or more sutures together. The following description relates to devices and methods of joining sutures. FIG. 117 illustrates one embodiment of a knot placement device 900 that can be used to apply a knot to the suture portion 130. The knot placement device 900 can include a handle 902 and a shaft 904 extending distally from the handle. The handle 902 can include an elongate tubular body extending from a proximal end to a distal end, and can include an actuator 906 and a distal end portion 910. The handle 902 can further comprise a cam 908 and a spring 912, shown in its rest position, disposed between the cam 908 and end portion 910. The actuator 906 can be a thumb or finger button in contact with the cam 908. End portion 910 can be fixedly attached to an outer tube 914 by glue, press fit, injection molding, or other suitable means known to one of ordinary skill in the art. An intermediate tube 916 can be concentrically and slidably disposed within the outer tube 914. A push rod 918 can be concentrically and slidably disposed within the intermediate tube 916 and fixedly attached to the cam 908. It should be appreciated that it is contemplated that the knot placement device 900 does not necessarily comprise an intermediate tube 916; however its inclusion provides certain benefits.

Depression of the actuator 906 causes the cam 908 to move distally, compressing the spring 912, thereby moving the push rod 918. After traveling for a certain desired distance, the cam 908 engages a proximal end of the intermediate tube 916, causing the intermediate tube 916 to also move distally. Upon release of the actuator 906, the spring 912 expands to move the cam 908 and the push rod 918 proximally. In the illustrated embodiment, the intermediate tube 916 can be freely slidable over the push rod 918.

In one embodiment, not shown, the cam 908 can include a detent in the surface which contacts the actuator 906. The detent can signal to the user a specific degree of advancement of the push rod 918, the intermediate tube 916, or both. For example, the detent can signal that the push rod has been advanced sufficiently far to insert the plug into the knot body, as described below. The detent can also indicate travel up until, but not including, the point at which the cam 908 engages the intermediate tube 916. The detent can be shaped so as to prevent the actuator 906 from returning to its original position. The cam can comprise multiple detents to indicate multiple increments of travel. To return the actuator to its initial position, the actuator and cam can include a mechanism such that after the actuator can be fully depressed, the actuator can automatically return to its initial position. Alternatively, the actuator can have a locked configuration, either at one of the detents or in a fully depressed configuration, and the handle can include a mechanism by which a second actuator can be used to release the cam and actuator to return to their initial positions.

In one embodiment, not shown, the intermediate tube 916 can comprise a keyway and the outer tube 914, the end portion 910, or both can comprise a key. Alternatively, the intermediate tube 916 can comprise a key and the outer tube 914, the end portion 910, or both can comprise a keyway. Providing such a key and keyway can be used to keep the intermediate tube 916 aligned with the outer tube. Other embodiments are contemplated to maintain rotational alignment of the intermediate tube, such as rotationally fixing the intermediate tube relative to the push rod. Providing such a key and keyway can also be used to constrain the range of sliding movement of the intermediate tube 916.

Figure 118:
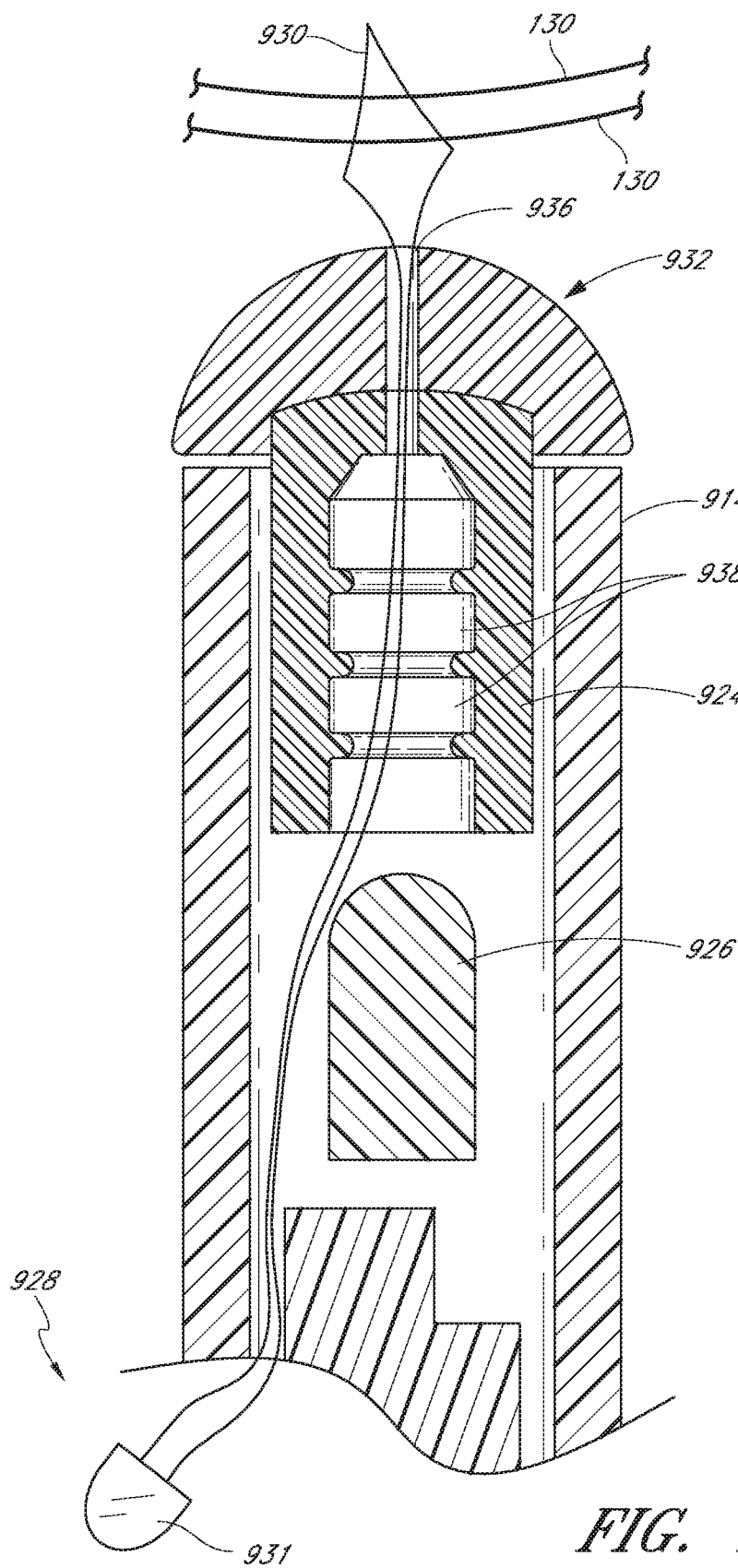

As shown in FIG. 118, a knot, comprising a knot body 924 and a plug 926, can be disposed within the outer tube 914 at its distal end. In another embodiment, the knot body can include an atraumatic tip 932. The tip 932 can be rounded and have an outer diameter about the same as that of the outer tube 914. The tip can also include a flat transition 934 as well. The tip 932 can be integrally formed with the knot body 924 or can be separately attached. As illustrated, the tip 932 can have an aperture 936 extending axially through the tip, opening to the cavity inside the knot body. When the knot is delivered into a patient as described above, the atraumatic tip prevents damage to the patient.

Alternatively, the fit between the knot body 924 and the outer tube 914 cannot retain the knot body 924 in the outer tube 914. The knot body 924 can be at the distal end of the outer tube 914, and can protrude slightly distal to the distal end of outer tube 914. The plug 926 can be positioned proximal to the knot body 924, and can be slidably disposed within the intermediate tube 916, having a distal end located proximally from the knot body and distally from the push rod 918. The plug 926 has an outer dimension configured to be inserted into an inner cavity of the knot body 924. The intermediate tube 916 can be sized and positioned such that its distal end can abut knot body 924.

As shown in FIG. 118, the outer tube 914 can include a side hole 920 near its distal end. The intermediate tube 916 can include a slot (not shown) extending proximally from its distal end, forming a C-shaped cross section. At a proximal end of the slot, a sharpened cutting surface can be provided to cut suture 130, as described below. The slot can also be spaced from the distal end of the intermediate tube, such that the distal end of the tube still forms a complete circle in cross-section. The outer tube 914, intermediate tube 916 and push rod 918 can be made of any suitable material, including but not limited to metals, plastics, and a combination of metals and plastics.

As shown in FIG. 118, in a preloaded configuration, the knot placement device 900 can include a threader 928 comprising a tab 931 and a looped wire 930 passing through the side hole 920 in the outer tube 914. The wire 930 extends through the slot 122 located in the intermediate tube 916, and through knot body 924, exiting through opening 936 at the distal end of the knot body 924. The threader 928 can be used to load the suture into the knot placement device as described below. The threader 928 also prevents the knot body 924 from escaping from the placement device 900 when the knot body can be provided with an outer dimension of the same or smaller size than the inner wall of the outer tube 914.

With reference to FIG. 118, the knot body 924 can be generally tubular and comprise a proximal end, a distal end, and a longitudinal axis. The knot body 924 further defines an inner cavity and can include an opening 936 at its distal end. The knot body can be of a generally constant inner diameter and outer diameter. Alternatively, the inner diameter, the outer diameter, or both can generally taper along the longitudinal axis of the knot body. Alternatively, the inner diameter, the outer diameter, or both can generally taper along a portion of the longitudinal axis and can be of a generally constant inner diameter, outer diameter or both over a portion of the longitudinal axis.

The opening 936 at the distal end of the knot body can, in some embodiments, be of a reduced diameter relative to an inner cavity of the knot body 924. The knot body also can include an opening at the proximal end. The opening at the proximal end can, in some embodiments, be of a reduced diameter relative to an inner cavity of the knot body 924. The knot body can further comprise protrusions 938 extending from the inner surface of the knot body 924 toward the longitudinal axis. Protrusions 938 can be formed as rings as illustrated, or as spirals, spikes, bumps, or other suitable structures or combinations of structures.

Referring to FIG. 118, in one embodiment, the knot body 924 can be located distally from the plug 926 within the outer tube 914. The plug can be sized to be inserted into the inner cavity of the knot body 924, and can have a tapered configuration. Alternatively, the plug 926 can have a constant cross-section over a majority of its length, with a tapered, chamfered or rounded distal end for facilitating insertion into the knot body 924. The outer dimension of the plug 926 can be slightly larger than the inner dimension of the cavity of the knot body 924, such that when the plug is inserted into the cavity, a relatively secure fit can be provided between the two. The protrusions 938 within the knot body further facilitate the relative securement. The plug 926 can also comprise indentations, not shown, for receiving the protrusions 938 to secure the plug 926 more surely in the knot body 924. Other embodiments are contemplated wherein protrusions can be formed on the plug 926 with or without indentations formed in the inner cavity of the knot body 924. It is also contemplated that in some embodiments both the plug 926 and the knot body 924 can comprise protrusions and indentations, respectively. In certain embodiments, insertion of the plug 926 into the knot body 924 can cause the knot body 924 to slightly expand. Both the knot and the knot body can be formed of any suitable resilient materials, and in one embodiment, can be made from the same material as the suture, more preferably polypropylene.

Figure 119:
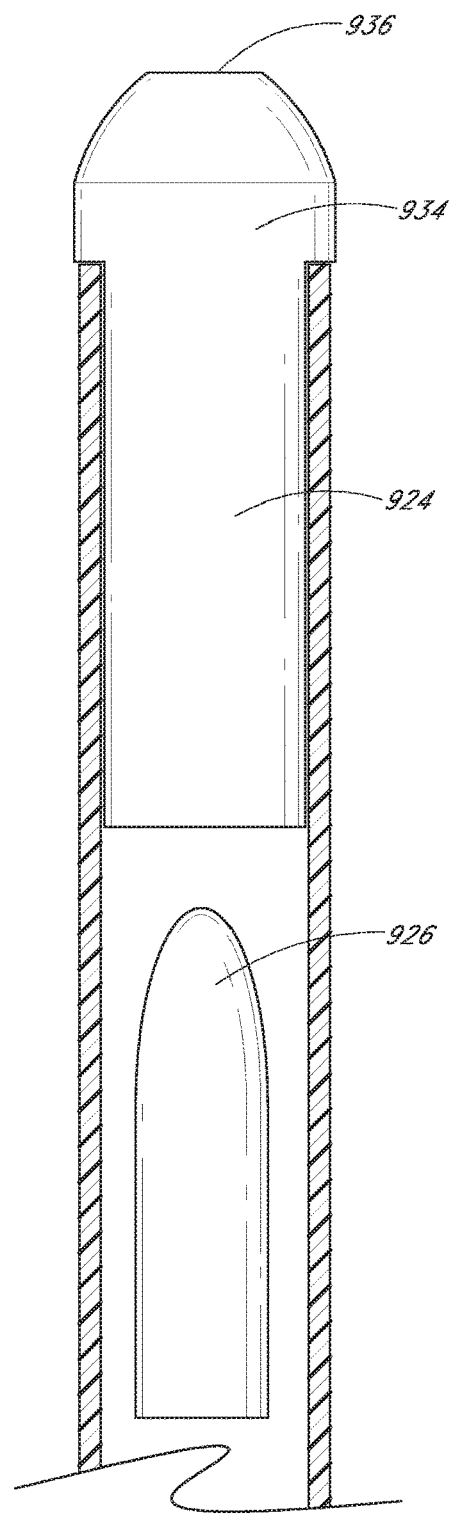

FIGS. 118-119 illustrate one embodiment for placing a knot utilizing the knot placement device 900 described above. A pair of sutures ends 130 can be passed through the loop 930 of threader 928. The threader can be preloaded into the knot placement device 900 as described above. The tab 931 of threader 928 can be pulled proximally to dispose suture 130 in the device. Suture 130 can be held in tension, by hand or otherwise, while the device 900 can be advanced until the knot body 924 or shaft 904 contacts at least one tissue portion. The actuator 906 can be depressed to advance the push rod 918, thereby forcing the plug 926 distally into the knot body 924 and trapping suture 130 there between the plug 926 and the knot body 924. The actuator can be further depressed until the cam 908 contacts the proximal end of intermediate tube 916, causing the intermediate tube 916 to contact knot body 924 and eject the knot from the shaft 904. Advancement of intermediate tube 916 can also cause cutting surface to sever suture 130 where it extends out of opening. The knot placement device can then be removed, leaving the knot in place against the tissue portions.

In one embodiment, the knot can be ejected from the shaft 904 while leaving the sutures 130 un-severed. For example, the knot can be ejected before the cutting surface reaches the suture 130. In another embodiment, no intermediate tube can be provided, and the suture can be cut manually.

In an embodiment including the intermediate tube, the device 900 can be configured such that the distal ends of the outer tube 914, intermediate tube 916, and the push rod 918 lie generally flush relative to one another and can be held relatively in position. This position can be held, for example, by depressing the actuator until it rests in a detent in cam 908. The detent can signal to the user that the plug 926 has been inserted into knot body 924, but also that the sutures 130 have not been cut. At such time, the placement device can be used to further advance the knot against tissue portions using the distal end surface of the shaft. The actuator can be further depressed to advance the push rod 918 and intermediate tube 916 to sever sutures 130.

The actuator 906 and cam 908 can also be provided with locking mechanisms that prevent the actuator 906 from returning to its original position. Further details are provided in U.S. Patent Application Publication No. 2006/0069397, published on Mar. 30, 2006, the entirety of which is hereby incorporated by reference herein. Such an embodiment can be advantageous to hold the push rod flush with the distal end of the outer tube to provide a surface that can be utilized to further advance and position the knot against tissue portions.

It will be appreciated that other embodiments can be contemplated without use of the intermediate tube, but can still be capable of severing the suture. For example, the push rod can be provided with portions of differing diameter. A distal, smaller diameter can be sized to engage the plug 926 to push the plug into the knot body 924. A proximal, larger diameter can be provided on the push rod, which can include a sharpened surface at the transition between the larger and smaller diameter sections. Once the smaller portion of the push rod pushes the plug 926 into the knot body 924, the larger portion of the push rod can engage the knot body 924 to push the knot out of the placement device, while the sharpened surface on the push rod can sever the suture.

In the embodiment described above, when the knot body 924 and the plug 926 as described above are secured together, suture portions extending through the inner cavity of the knot body will be fixedly secured therein, forming a knot. It will be appreciated that many other embodiments can be possible for forming a knot, including various other shapes and configurations for the knot body and plug, as well as embodiments wherein only one component can be used to provide securement relative to a suture. It will also be appreciated that in those embodiments in which the knot can include a knot body and plug, the plug can be located within the shaft proximally from the knot body or the knot body can be located within the shaft proximally from the plug.

After the procedure within the heart is complete, any path that has been opened to provide access for entry of the suturing device to the body (e.g., the transapical opening) can be closed. Additional details regarding closure of transapical openings are provided in U.S. Patent Publication No. 2011/0190793 A1, entitled METHODS AND APPARATUSES FOR SUTURING OF CARDIAC OPENINGS, which is hereby incorporated by reference herein in its entirety and forms a part of this specification.

Although the foregoing description of the preferred embodiments has shown, described and pointed out the fundamental novel features of the invention, it will be understood that various omissions, substitutions, and changes in the form of the detail of the apparatus as illustrated as well as the uses thereof, may be made by those skilled in the art, without departing from the spirit of the invention. For example, while the suturing device is described with respect to suturing a valve of a patient's heart, it is further envisioned that the suturing device could be used to close or reduce a variety of other tissue openings, lumens, hollow organs or natural or surgically created passageways in the body. The suturing device can have any suitable number of arms, such as two or four or more, and any given arm can have one or more suture clasps or openings.

What is claimed is:

1. A suturing device, comprising:
   an elongate member comprising a distal end;
   at least two arms connected with the elongate member near the distal end, each of the at least two arms configured to move between a retracted position and an extended position, each arm comprising at least one suture mount located near a free end of the arm and configured to releasably retain a suture portion, wherein the free ends of the at least two arms in their extended positions are spaced apart from each other;
   at least two needles connected with the elongate body and positioned proximal to the at least two arms, each of the needles configured to move between a retracted position and a deployed position to retrieve the suture portion retained in the at least one suture mount of one of the at least two arms when the needle is moved from the retracted position to the deployed position and returned to the retracted position; and
   at least two protective members, each protective member configured to inhibit contact between a distal end of one of the at least two needles and surrounding tissue during at least a portion of the movement of the needle from its retracted position toward its deployed position, wherein each protective member is configured to house one needle and move between a retracted position and a deployed position, wherein moving the protective member from its retracted position to its deployed position aligns the protective member with one of the deployed free ends of one of the at least two arms.

2. The suturing device of claim 1, wherein each of the at least two protective members points distally and at an angle with respect to the elongate member when in its deployed position.

3. The suturing device of claim 1, wherein each protective member is configured to move between its retracted position and its deployed position before the needle housed within the protective member is deployed.

4. The suturing device of claim 1, wherein each protective member is configured to move between its retracted position and its deployed position while the needle housed within the protective member is deployed.

5. The suturing device of claim 1, wherein the at least two arms extend at an angle of approximately 90 degrees with respect to the elongate member when the arms are extended.

6. The suturing device of claim 1, wherein the two or more needles are deployed sequentially.

7. The suturing device of claim 1, wherein the two or more needles are deployed simultaneously.

8. The suturing device of claim 1, wherein the at least two protective members extend at an angle of less than 90 degrees with respect to the elongate member when the at least two protective members are in the deployed position.

9. The suturing device of claim 1, wherein the at least two protective members extend at an angle of approximately 45 degrees with respect to the elongate member when the at least two protective members are in the deployed position.

10. The suturing device of claim 1, wherein the at least two arms extend at approximately 90 degrees from each other when the arms are extended.

11. The suturing device of claim 1, wherein a distal end of the elongate member comprises an opening to a guidewire lumen through which a guidewire is configured to pass.

12. The suturing device of claim 1, wherein when each protective member aligns with the one of the deployed free ends of one of the at least two arms, the protective member is configured to extend distally and pinch a valve between the one of the at least two arms and the protective member.

13. The suturing device of claim 1, wherein when each protective member moves from the retracted position to the deployed position, the protective member moves both radially away from the elongate body and distally toward a distal end of the elongate member.

14. The suturing device of claim 1, wherein when each protective member moves from the retracted position to the deployed position, the protective member is configured to rotate about the elongate member.

15. The suturing device of claim 1, wherein each protective member comprises two needle lumens.

* * * * *